US009638692B2

(12) United States Patent
Manuguerra et al.

(10) Patent No.: US 9,638,692 B2
(45) Date of Patent: May 2, 2017

(54) MULTIPLEX IMMUNO SCREENING ASSAY

(71) Applicant: INSTITUT PASTEUR, Paris (FR)

(72) Inventors: Jean-Claude Manuguerra, Paris (FR); Jessica Vanhomwegen, Paris (FR); Philippe Despres, La Garenne-Colombes (FR); Sylvie Paulous, Sarcelles (FR)

(73) Assignee: INSTITUT PASTEUR, Paris (FR)

( * ) Notice: Subject to any disclaimer, the term of this patent is extended or adjusted under 35 U.S.C. 154(b) by 152 days.

(21) Appl. No.: 13/883,339

(22) PCT Filed: Dec. 10, 2012

(86) PCT No.: PCT/EP2012/074986
§ 371 (c)(1),
(2) Date: May 3, 2013

(87) PCT Pub. No.: WO2013/083847
PCT Pub. Date: Jun. 13, 2013

(65) Prior Publication Data

US 2014/0274762 A1 Sep. 18, 2014

Related U.S. Application Data

(60) Provisional application No. 61/642,924, filed on May 4, 2012.

(30) Foreign Application Priority Data

Dec. 9, 2011 (WO) .......................... EP2011/072387

(51) Int. Cl.
*G01N 33/53* (2006.01)
*C12Q 1/70* (2006.01)
(Continued)

(52) U.S. Cl.
CPC ..... *G01N 33/54306* (2013.01); *G01N 33/564* (2013.01); *G01N 33/6845* (2013.01)

(58) Field of Classification Search
CPC ............ C07K 2319/20; C07K 2319/60; G01N 33/531
See application file for complete search history.

(56) References Cited

U.S. PATENT DOCUMENTS 4,358,388 A 11/1982 Daniel et al.
4,654,267 A 3/1987 Ugelstad et al.
(Continued)

FOREIGN PATENT DOCUMENTS

EP 1204869 B1 5/2002
WO 84/01153 A1 3/1984
(Continued)

OTHER PUBLICATIONS

Margison and Santibanez-Koref (BioEssays vol. 24, pp. 255-266, 2002).*
(Continued)

*Primary Examiner* — Janet L Andres
*Assistant Examiner* — M. Franco Salvoza
(74) *Attorney, Agent, or Firm* — Arrigo, Lee & Guttman LLP

(57) ABSTRACT

The present invention provides kits and assay methods for the early detection of pathogens, precise identification of the etiologic agent, and improved disease surveillance. More specifically, the present invention discloses an immunoassay leading to the rapid and simultaneous detection of antibodies to a wide range of infectious pathogens in biological fluids of infected patients. This immunoassay involves the covalent and oriented coupling of fusion proteins comprising an AGT enzyme and a viral antigen on an identifiable solid support (e.g. fluorescent microspheres), said support being
(Continued)

Figure 1:
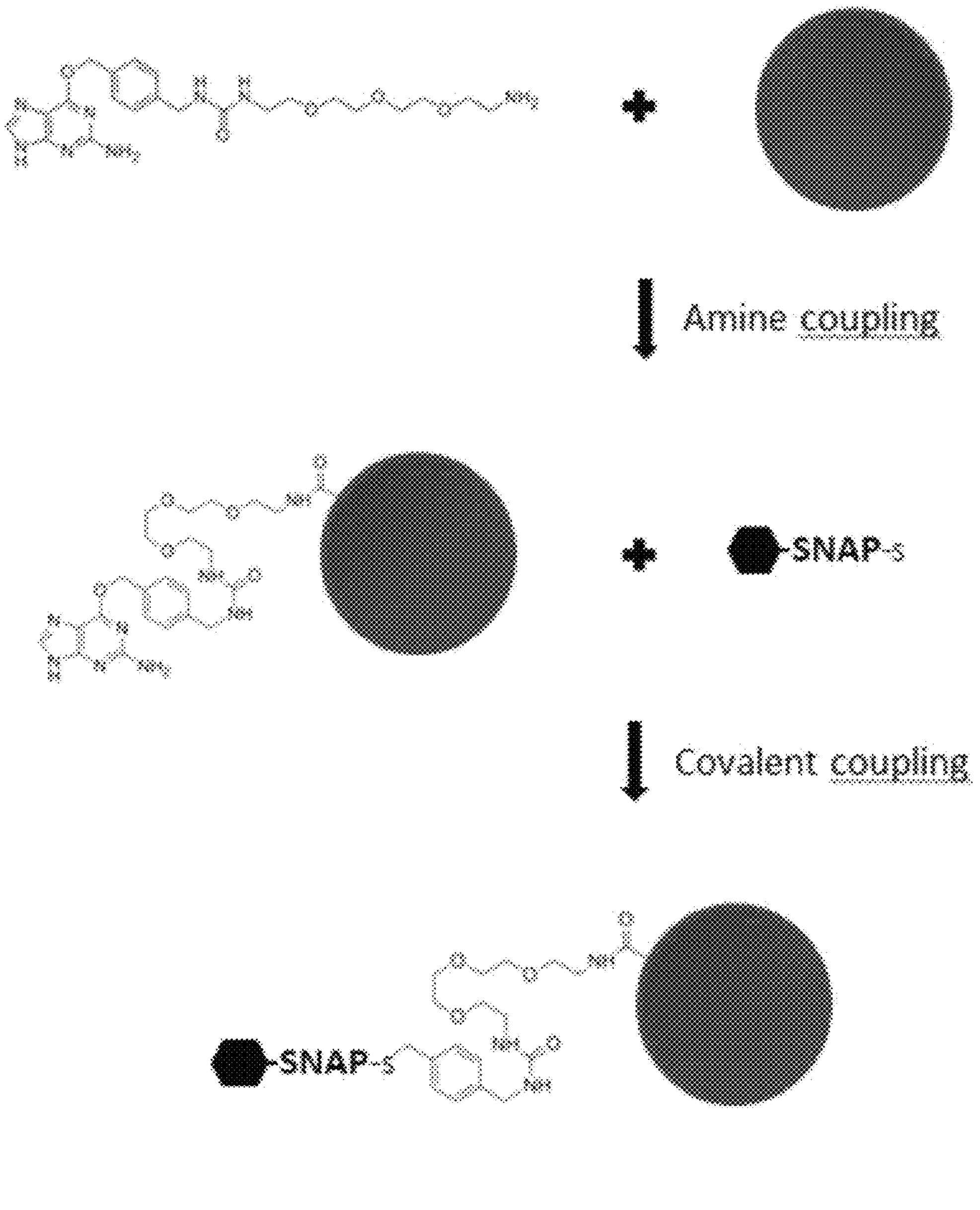

previously coated with an AGT substrate. This coupling is mediated by the irreversible reaction of the AGT enzyme on its substrate. The thus obtained antigen-coupled microspheres show enhanced capture of specific antibodies as compared to antigen-coupled microspheres produced by standard amine coupling procedures. The methods of the invention possess the ability to multiplex, minimize the amount of biological sample, and have enhanced sensitivity and specificity toward target antibodies as compared with classical ELISA or Radio-Immunoprecipitation assays.

13 Claims, 12 Drawing Sheets

(51) Int. Cl.

| | |
|---|---|
| ***A61K 39/00*** | (2006.01) |
| ***G01N 33/543*** | (2006.01) |
| ***G01N 33/564*** | (2006.01) |
| ***G01N 33/68*** | (2006.01) |

(56) References Cited

U.S. PATENT DOCUMENTS

| | | | | |
|---|---|---|---|---|
| 4,774,265 | A | 9/1988 | Ugelstad et al. | |
| 5,320,944 | A | 6/1994 | Okada et al. | |
| 5,356,713 | A | 10/1994 | Charmot et al. | |
| 5,459,127 | A | 10/1995 | Felgner et al. | |
| 5,736,330 | A | 4/1998 | Fulton | |
| 5,817,514 | A * | 10/1998 | Li | C07K 16/40 435/338 |
| 5,879,926 | A | 3/1999 | Lemoine et al. | |
| 5,981,180 | A | 11/1999 | Chandler et al. | |
| 6,057,107 | A | 5/2000 | Fulton | |
| 6,268,222 | B1 | 7/2001 | Chandler et al. | |
| 6,449,562 | B1 | 9/2002 | Chandler et al. | |
| 6,514,295 | B1 | 2/2003 | Chandler et al. | |
| 6,524,793 | B1 | 2/2003 | Chandler et al. | |
| 6,528,165 | B2 | 3/2003 | Chandler | |
| 6,682,907 | B1 | 1/2004 | Charneau et al. | |
| 7,939,284 | B2 * | 5/2011 | Johnsson | G01N 33/531 435/15 |
| 2004/0115130 | A1 * | 6/2004 | Johnsson | G01N 33/531 424/1.69 |
| 2006/0166268 | A1 | 7/2006 | Grus et al. | |
| 2006/0292651 | A1 * | 12/2006 | Juillerat | C12N 9/1085 435/15 |
| 2010/0009872 | A1 | 1/2010 | Eid et al. | |

FOREIGN PATENT DOCUMENTS

| | | | | |
|---|---|---|---|---|
| WO | 87/02670 A1 | 5/1987 | | |
| WO | 95/02059 A1 | 1/1995 | | |
| WO | 95/18863 A1 | 7/1995 | | |
| WO | 95/21931 A1 | 8/1995 | | |
| WO | 96/17823 A1 | 7/1996 | | |
| WO | 96/25508 A1 | 8/1996 | | |
| WO | 99/55892 A1 | 11/1999 | | |
| WO | 01/27300 A1 | 4/2001 | | |
| WO | 02/083937 A2 | 10/2002 | | |
| WO | WO 02/083937 A2 * | 10/2002 | | C12Q 1/48 |
| WO | 2004/031404 A1 | 4/2004 | | |
| WO | 2004/031405 A1 | 4/2004 | | |
| WO | WO 2004/031404 A1 * | 4/2004 | | C12Q 1/48 |
| WO | 2005/085470 A1 | 9/2005 | | |
| WO | 2010/107433 A1 | 9/2010 | | |

OTHER PUBLICATIONS

Juillerat et al. (ChemBioChem 2005, vol. 6, pp. 1263-1269).*
Mullapudi et al. (Journal of Biochem., 2000, vol. 351, pp. 393-402).*
Kindermann et al. (JACS, 2003, vol. 125, pp. 7810-7811).*
Andresen et al., Deciphering the Antibodyome—Peptide Arrays for Serum Antibody Biomarker Diagnostics, Antibody Biomarker Diagnostics, Current Proteomics, Bentham Science, Publishers, GB, vol. 6, No. 1, Apr. 1, 2009 (Apr. 1, 2009), pp. 1-12.
Avrameas S., Natural autoantibodies: from 'horror autotoxicus' to 'gnothi seauton', Immunol. Today, May 1991;12(5):154-9.
Bond et al., The *Drosophila melanogaster* Actin 5C Gene Uses Two Transcription Initiation Sites and Three Polyadenylation Sites to Express Multiple mRNA Species, Mol. Cell. Biol. 6:2080 (1986).
Brecht et al, SNAP-tag(TM): Self-Labeling Protein tag for medium throughput and HTS assay formats, Poster P7016 Booth 345, Sep. 19, 2006 (Sep. 19, 2006), SBS 12th Annual Conference and Exhibition, Advancing Drug Discovery: From Better Hits to Better Candidates Sep. 17-21, 2006—Seattle, WA, USA.
Brinster et al., Regulation of metallothionein-thymidine kinase fusion plasmids injected into mouse eggs, Nature, 296:39-42, 1982.
Damoiseaux et al., Synthesis and Applications of Chemical Probes for Human O6-Alkylguanine-DNA Alkyltransferase, Chembiochem. 4:285-287, 2001.
Daniels D.S. et al., Active and alkylated human AGT structures: a novel zinc site, inhibitor and extrahelical base binding, EMBO J. 19: 1719-1730, 2000.
Engin et al., Benzylguanine Thiol Self-Assembled Monolayers for the Immobilization of SNAP-tag Proteins on Microcontact-Printed Surface Structures, Langmuir, vol. 26, No. 9, May 4, 2010 (May 4, 2010), pp. 6097-6101.
Felgner et al., Lipofection: A highly efficient, lipid-mediated DNA-transfection procedure, Proc. Natl. Acad. Sci. U.S.A., 84:7413-7417, 1987.
Hellwig et al., Plant cell cultures for the production of recombinant proteins, Nat. Biotechnol.2004; 22 (11):1415-22.
Juillerat et al., Directed Evolution of O6-Alkylguanine-DNA Alkyltransferase for Efficient Labeling of Fusion Proteins with Small Molecules In Vivo, Chemistry ET Biology, vol. 10, 313-317, 2003.
Kim et al., Competitive ELISA for the detection of Antibodies to Rift Valley Fever Virus in Goats and Cattle, The Journal of Veterinary Medical Science, 2011.
Kindermann M. et al., Covalent and Selective Immobilization of Fusion Proteins, Journal of the American Chemical Society, vol. 125, No. 26, Jul. 2, 2003 (Jul. 2, 2003), pp. 7810-7811.
Kolpe et al., Display of enterovirus 71 VP1 on baculovirus as a type II transmembrane protein elicits protective B and T cell responses in immunized mice, Virus Research 2012; 168:64-72.
Kufer, et al., Covalent immobilization of recombinant fusion proteins with hAGT for single molecule force spectroscopy, European Biophysics Journal, vol. 35, No. 1, Dec. 1, 2005 (Dec. 1, 2005), pp. 72-78.
Lastowski-Perry et al., Nucleotide Sequence and Expressionof a *Drosophila Metallothionein*, J.Biol. Chem. 260:1527 (1985).
Lim et al., The nuclear targeting and nuclear retention properties of a human DNA repair protein 06-methylguanine-DNA methyltransferase are both required for its nuclear localization: the possible implications, EMBO J. 15: 4050-4060, 1996.
Machy et al., Gene transfer from targeted liposomes to specific lymphoid cells by electroporation, Proc. Natl. Acad. Sci. U.S.A., 85:8027-8031, 1988.
Miller and Rosman, Improved Retroviral Vectors for Gene Transfer and Expression, Biotechniques, 7:980-990, 1992.
Neuman De Vegvar et al., Microarray profiling of antiviral antibodies for the development of diagnostics, vaccines, and therapeutics, Clinical Immunology, vol. 111, No. 2, May 1, 2004 (May 1, 2004), pp. 196-201.
Pan et al., Fusion of Two Malaria Vaccine Candidate Antigens Enhances Product Yield, Immunogenicity, and Antibody-Mediated Inhibition of Parasite Growth In Vitro, The Journal of Immunology, 2004, 172:6167-6174.
Robinson et al., Autoantigen microarrays for multiplex characterization of autoantibody responses, Nature Medicine, vol. 8, No. 3, Mar. 1, 2002 (Mar. 1, 2002), pp. 295-301.

(56) References Cited

OTHER PUBLICATIONS

Sivakolundu et al., Serological diagnosis of leptospiral uveitis by HbpA IgG Elisa, Journal of Medical Microbiology, 61:1681-1687, 2012.
Wibley J.E.A. et al., Crystal structure of the human O6-alkylguanine-DNA alkyltransferase, Nucleic Acids Research, 2000, vol. 28, No. 2, 393-401.
Williams et al., Introduction of foreign genes into tissues of living mice by DNA-coated microprojectiles, Proc. Natl. Acad. Sci. U.S. A., 88:2726-2730, 1991.
Wilson et al., Hepatocyte-directed Gene Transfer in Vivo Leads to Transient Improvement of Hypercholesterolemia in Low Density Lipoprotein Receptor-deficient Rabbits, The Journal of Biological Chemistry, vol. 267, No. 2, Issue of Jan. 15, pp. 963-967,1992.
Wong et al., Detection of Human Anti-Flavivirus Antibodies with a West Nile Virus Recombinant Antigen Microsphere Immunoassay, Journal of Clinical Microbiology 42, No. 1 (Jan. 2004): 65-72.
Wu and Wu, Receptor-mediated Gene Delivery and Expression in Viuo, J. Biol. Chem., 263:14621-14624, 1988.
Xu-Welliver et al., Role of Codon 160 in the Sensitivity of Human O6-Alkylguanine-DNA Alkyltransferase to O6-Benzylguanine, Biochemical Pharmacology 58: 1279-85, 1999.
Zimmerman et al., Multivariate statistical comparison of autoantibody-repertoires (Western blots) by discriminant analysis, Electrophoresis Jun. 1995;16(6):941-7.
USPTO, Office Action in U.S. Appl. No. 14/396,841, Apr. 14, 2016.

* cited by examiner

A

B

SEQUENCE LISTING

```
<160> NUMBER OF SEQ ID NOS: 153

<210> SEQ ID NO 1
<211> LENGTH: 238
<212> TYPE: PRT
<213> ORGANISM: homo sapiens

<400> SEQUENCE: 1

Met Leu Gly Gln Pro Ala Pro Leu Glu Arg Phe Ala Ser Arg Arg Pro
1               5                   10                  15

Gln Val Leu Ala Val Arg Thr Val Cys Asp Leu Val Leu Gly Lys Met
            20                  25                  30

Asp Lys Asp Cys Glu Met Lys Arg Thr Thr Leu Asp Ser Pro Leu Gly
        35                  40                  45

Lys Leu Glu Leu Ser Gly Cys Glu Gln Gly Leu His Glu Ile Lys Leu
    50                  55                  60

Leu Gly Lys Gly Thr Ser Ala Ala Asp Ala Val Glu Val Pro Ala Pro
65                  70                  75                  80

Ala Ala Val Leu Gly Gly Pro Glu Pro Leu Met Gln Cys Thr Ala Trp
                85                  90                  95

Leu Asn Ala Tyr Phe His Gln Pro Glu Ala Ile Glu Glu Phe Pro Val
            100                 105                 110

Pro Ala Leu His His Pro Val Phe Gln Gln Glu Ser Phe Thr Arg Gln
        115                 120                 125

Val Leu Trp Lys Leu Leu Lys Val Val Lys Phe Gly Glu Val Ile Ser
    130                 135                 140

Tyr Gln Gln Leu Ala Ala Leu Ala Gly Asn Pro Lys Ala Ala Arg Ala
145                 150                 155                 160

Val Gly Gly Ala Met Arg Gly Asn Pro Val Pro Ile Leu Ile Pro Cys
                165                 170                 175

His Arg Val Val Cys Ser Ser Gly Ala Val Gly Asn Tyr Ser Gly Gly
            180                 185                 190

Leu Ala Val Lys Glu Trp Leu Leu Ala His Glu Gly His Arg Leu Gly
        195                 200                 205

Lys Pro Gly Leu Gly Gly Ser Ser Gly Leu Ala Gly Ala Trp Leu Lys
    210                 215                 220

Gly Ala Gly Ala Thr Ser Gly Ser Pro Pro Ala Gly Arg Asn
225                 230                 235


<210> SEQ ID NO 2
<211> LENGTH: 193
<212> TYPE: PRT
<213> ORGANISM: artificial
<220> FEATURE:
<223> OTHER INFORMATION: Amino acid sequence of SNAP

<400> SEQUENCE: 2

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45
```

-continued

```
Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu


<210> SEQ ID NO 3
<211> LENGTH: 404
<212> TYPE: DNA
<213> ORGANISM: Dengue virus 1

<400> SEQUENCE: 3

taggcgcgcc agggtccctg gagggaggtg gcgggtctct gactttaaaa gggatgtcat      60

atgtgatgtg cacaggctca tttaagctag agaaggaagt ggctgagacc cagcatggaa     120

ctgtcctagt gcaggttaaa tacgaaggaa cagatgcgcc atgcaagatc cccttttcga     180

cccaagatga gaaaggagtg acccagaatg ggagattgat aacagccaat cccatagtta     240

ctgacaaaga aaaaccaatc aacattgaga cagaaccacc ttttggtgag agctacatca     300

tagtaggggc aggtgaaaaa gctttgaaac taagctggtt caagaaagga agcagcatag     360

ggaaaggagg tggccatcac catcaccatc actgatgacc ggtt                      404


<210> SEQ ID NO 4
<211> LENGTH: 404
<212> TYPE: DNA
<213> ORGANISM: Dengue virus 2

<400> SEQUENCE: 4

taggcgcgcc agggtccctg gagggaggtg gcgggtctct acagctcaaa ggaatgtcat      60

attctatgtg tacaggaaag tttaaagttg tgaaggaaat agcagaaaca caacatggaa     120

caatagttct cagagtacaa tatgaagggg acggttctcc gtgcaagatc ccttttgaaa     180

taatggattt ggaaaaaaga catgtcttag gtcgcttgat cacagtcaac ccaattgtta     240

cagaaataga cagcccagtc aacatagaag cagaacctcc attcggagac agctacatca     300

ttataggagt agaaccggga caactgaagc tcagctggtt taagaaagga agttccattg     360

gccaaggagg tggccatcac catcaccatc actgatgacc ggtt                      404


<210> SEQ ID NO 5
<211> LENGTH: 401
<212> TYPE: DNA
<213> ORGANISM: Dengue virus 3
```

<400> SEQUENCE: 5
taggcgcgcc agggtccctg gagggaggtg gcgggtctga actcaagggg atgagctatg 60
caatgtgctt gaatacctt gtgttgaaga aagaagtctc cgaaacgcag catgggacaa 120
tactcattaa ggttgagtac aaaggggaag atgcaccttg caagattcct ttctccacag 180
aggatggaca agggaaagcc cacaatggta gactgatcac agccaaccca gtggttacta 240
agaaggagga gcctgtcaac attgaggctg aacctccttt tggggaaagc aacatagtga 300
ttggagttgg agacaaagcc ttgaaaatta actggtacaa gaagggaagc tcgattggga 360
agggaggtgg ccatcaccat caccatcact gatgaccggt t 401

<210> SEQ ID NO 6
<211> LENGTH: 401
<212> TYPE: DNA
<213> ORGANISM: Dengue virus 4

<400> SEQUENCE: 6
taggcgcgcc agggtccctg gagggaggtg gcgggtctag aatcaaggga atgtcataca 60
cgatgtgctc aggaaagttc tcaattgaca aagagatggc agaaacacag catgggacaa 120
cagtggtgaa agtcaagtat gaaggtgctg gagctccgtg taaagtcccc atagagatac 180
gagatgtaaa taaggaaaaa gtggttgggc gtgtcatctc atccacccct ctagctgaga 240
ataccaacag tgtgaccaac atagaactgg aacccccctt tggggacagt tacatagtca 300
taggtgttgg gaacagtgca ttgacactcc attggttcag gaaaggaagt tctattggca 360
agggaggtgg ccatcaccat caccatcact gatgaccggt t 401

<210> SEQ ID NO 7
<211> LENGTH: 398
<212> TYPE: DNA
<213> ORGANISM: West Nile Virus

<400> SEQUENCE: 7
taggcgcgcc aggaggtggc gggtctcagt tgaagggaac aacctatggc gtctgttcaa 60
aggctttcaa gtttcttggg actcccgcag acacaggtca cggcactgtg gtgttggaat 120
tgcagtacac tggcacggat ggaccttgca aagttcctat ctcgtcagtg gcttcattga 180
acgacctaac gccagtgggc agattggtca ctgtcaaccc ttttgtttca gtggccacgg 240
ccaacgctaa ggtcctgatt gaattggaac caccctttgg agactcatac atagtggtgg 300
gcagaggaga acaacagatc aatcaccatt ggcacaagtc tggaagcagc attggcaaag 360
gaggtggcca tcaccatcac catcactgat gaccggtt 398

<210> SEQ ID NO 8
<211> LENGTH: 410
<212> TYPE: DNA
<213> ORGANISM: Yellow fever virus

<400> SEQUENCE: 8
taggcgcgcc agggtccctg gagggaggtg gcgggtcttc agctttgaca ctcaagggga 60
catcctacaa aatgtgcact gacaaaatgt cttttgtcaa gaacccaact gacactggcc 120
atggcactgt tgtgatgcag gtgaaagtgc caaaaggagc cccctgcaag attccagtga 180
tagtagctga tgatcttaca gcggcaatca ataaaggcat tttggttaca gttaacccca 240
tcgcctcaac caatgatgat gaagtgctga ttgaggtgaa cccacctttt ggagacagct 300
acattatcgt tgggacagga gattcacgtc tcacttacca gtggcacaaa gagggaagct 360
caataggaaa gggaggtggc catcaccatc accatcactg atgaccggtt 410

<210> SEQ ID NO 9
<211> LENGTH: 410
<212> TYPE: DNA
<213> ORGANISM: Japanese encephalitis virus

<400> SEQUENCE: 9
taggcgcgcc agggtccctg gagggaggtg gcgggtctgc tctgaaaggc acaacctatg 60
gcatgtgtac agaaaaattc tcgttcgcga aaaatccggc ggacactggt cacggaacag 120
ttgtcattga actctcctac tctgggagtg atggcccctg caaaattccg attgtctccg 180
tcgcgagcct caatgacatg actcctgttg ggcggctggt gacagtgaac ccctttgtcg 240
cggcttccag tgccaactca aaggtgctgg tcgagatgga acccccctttc ggagactcct 300 atatcgtggt tggaagggga gacaagcaga tcaaccacca ttggcacaga gctggaagca 360
cgctgggcaa gggaggtggc catcaccatc accatcactg atgaccggtt 410

<210> SEQ ID NO 10
<211> LENGTH: 397
<212> TYPE: DNA
<213> ORGANISM: Zika virus

<400> SEQUENCE: 10
gcgcgccagg aggtggcggg tctcttagat tgaagggcgt gtcatactcc ttgtgtaccg 60
cagcgttcac attcaccaag atcccggctg aaacactgca cgggacagtc acagtggagg 120
tacagtacgc agggacagat ggaccctgca aggttccagc tcagatggcg gtggacatgc 180
aaactctgac cccagttggg aggctgataa ccgctaaccc tgtaatcact gaaagcactg 240
agaactctaa gatgatgctg gaacttgatc caccatttgg ggactcttac attgtcatag 300
gagtcgggga gaagaagatc acccatcact ggcacaggag tggcagcacc attggaaaag 360
gaggtggcca tcaccatcac catcactgat gaccggt 397

<210> SEQ ID NO 11
<211> LENGTH: 385
<212> TYPE: DNA
<213> ORGANISM: Wesselbron virus

<400> SEQUENCE: 11
gcgcgccagg aggtggcggg ctcatcctga aaggttcaac ctactcaatg tgcaaaagag 60
ggatgtcctt tgctaagcaa ccagttgaga cagaccatgg aacagcagtg atgcagataa 120
aagttacaac tggagctccg tgcagaattc cagtgattgc agcagattcc atggcgggaa 180
cagaaaaccg tggaagcgtc atcacaacca atcctattgc tgcgtcaaac aatgatgaag 240
tgttggtgga gatcagtcca ccatttggag agagttacat catcgttggt aatggagatg 300
ataaacttac ataccactgg caaagatcag gaagcaccat cgggaatgga ggtggccatc 360
accatcacca tcactgatga ccggt 385

<210> SEQ ID NO 12
<211> LENGTH: 397
<212> TYPE: DNA
<213> ORGANISM: Rocio virus

<400> SEQUENCE: 12
gcgcgccagg aggtggcggg tctctcaaaa tcaaagggtc aacatacctg atgtgcaagg 60

-continued

```
acaaatttgc ttttgccaag aacccagttg acacaggaca cggcacaatc gtgacggagg    120

tacagtacgc tggttctgat gggccatgca ggattccaat caccatgacc gagaacctac    180

atgatctcac tcccatcgga cgattggtga cggtcaatcc atttgttccc tcatccgaga    240

cggcacaaaa aattttgatt gaactcgagc ccccctttgg gacatccttc atactggtgg    300

gtacaggtcc caaccaggtg aaataccagt ggcataagtc tggtagtgtg atcggaaaag    360

gaggtggcca tcaccatcac catcactgat gaccggt                             397
```

<210> SEQ ID NO 13
<211> LENGTH: 397
<212> TYPE: DNA
<213> ORGANISM: Murray encephalitis virus

<400> SEQUENCE: 13

```
gcgcgccagg aggtggcggg tctttgaaac tgaaaggaac cacttatggg atgtgcacag     60

aaaaatttac tttctcaaag aatccagccg acaccggaca tggcacggta gtactagaac    120

tgcagtacac cgggagtgat ggaccatgca aaattccaat atcctctgta gcaagtctca    180

atgacatgac gcctgtcgga agaatggtga cagctaatcc atatgtagct tcatcaactg    240

ccaatgctaa agttctggtg gagattgaac caccccttcgg agactcatac attgtggtag    300

gcaggggaga caagcagatc aatcaccact ggcataagga gggtagttca attggcaaag    360

gaggtggcca tcaccatcac catcactgat gaccggt                             397
```

<210> SEQ ID NO 14
<211> LENGTH: 397
<212> TYPE: DNA
<213> ORGANISM: Saint-Louis encephalitis virus

<400> SEQUENCE: 14

```
gcgcgccagg aggtggcggg tctgttaaaa tcaaggggac gacatatggt atgtgtgact     60

ctgctttcac cttcagcaag aaccctgctg acacagggca tgggacagtg atcgtggaac    120

tgcagtacac tggaagcaac ggaccatgcc gggttcccat ttctgtgact gcaaacctca    180

tggacttgac accagttgga agactggtca cggtcaatcc ctttattagc acagggggag    240

cgaacaacaa ggtcatgatc gaagttgaac cacccctttgg cgactcttac atcgtcgtcg    300

gaagaggcac cacccagatc aactaccact ggcacaaaga gggaagcagc attgggaagg    360

gaggtggcca tcaccatcac catcactgat gaccggt                             397
```

<210> SEQ ID NO 15
<211> LENGTH: 579
<212> TYPE: DNA
<213> ORGANISM: artificial
<220> FEATURE:
<223> OTHER INFORMATION: DNA encoding original SNAP (normal G/C content)

<400> SEQUENCE: 15

```
agatctgaca aagactgcga aatgaagcgc accaccctgg atagccctct gggcaagctg     60

gaactgtctg ggtgcgaaca gggcctgcac gagatcaagc tgctgggcaa aggaacatct    120

gccgccgacg ccgtggaagt gcctgcccca gccgccgtgc tgggcggacc agagccactg    180

atgcaggcca ccgcctggct caacgcctac tttcaccagc ctgaggccat cgaggagttc    240

cctgtgccag ccctgcacca cccagtgttc cagcaggaga gctttacccg ccaggtgctg    300

tggaaactgc tgaaagtggt gaagttcgga gaggtcatca gctaccagca gctggccgcc    360

ctggccggca atcccgccgc caccgccgcc gtgaaaaccg ccctgagcgg aaatcccgtg    420
```

```
cccattctga tcccctgcca ccgggtggtg tctagctctg gcgccgtggg gggctacgag    480

ggcgggctcg ccgtgaaaga gtggctgctg gcccacgagg gccacagact gggcaagcct    540

gggctgggtc ctgcaggtat aggcgcgcca gggtcccta                           579
```

<210> SEQ ID NO 16
<211> LENGTH: 235
<212> TYPE: PRT
<213> ORGANISM: artificial
<220> FEATURE:
<223> OTHER INFORMATION: mutated N protein of schmallenberg virus

<400> SEQUENCE: 16

```
Asp Ile Ser Ser Gln Phe Ile Phe Glu Asp Val Pro Gln Arg Asn Ala
1               5                   10                  15

Ala Thr Phe Asn Pro Glu Val Gly Tyr Val Ala Phe Ile Gly Lys Tyr
            20                  25                  30

Gly Gln Gln Leu Asn Phe Gly Val Ala Arg Val Phe Phe Leu Asn Gln
        35                  40                  45

Lys Lys Ala Lys Met Val Leu His Lys Thr Ala Gln Pro Ser Val Asp
    50                  55                  60

Leu Thr Phe Gly Gly Val Lys Phe Thr Val Val Asn Asn His Phe Pro
65                  70                  75                  80

Gln Tyr Val Ser Asn Pro Val Pro Asp Asn Ala Ile Thr Leu His Arg
                85                  90                  95

Met Ser Gly Tyr Leu Ala Arg Trp Ile Ala Asp Thr Cys Lys Ala Ser
            100                 105                 110

Val Leu Lys Leu Ala Glu Ala Ser Ala Gln Ile Val Met Pro Leu Ala
        115                 120                 125

Glu Val Lys Gly Cys Thr Trp Ala Asp Gly Tyr Thr Met Tyr Leu Gly
    130                 135                 140

Phe Ala Pro Gly Ala Glu Met Phe Leu Asp Ala Phe Asp Phe Tyr Pro
145                 150                 155                 160

Leu Val Ile Glu Met His Arg Val Leu Lys Asp Asn Met Asp Val Asn
                165                 170                 175

Phe Met Lys Lys Val Leu Arg Gln Arg Tyr Gly Thr Met Thr Ala Glu
            180                 185                 190

Glu Trp Met Thr Gln Lys Ile Thr Glu Ile Lys Ala Ala Phe Asn Ser
        195                 200                 205

Val Gly Gln Leu Ala Trp Ala Lys Ser Gly Phe Ser Pro Ala Ala Arg
    210                 215                 220

Thr Phe Leu Gln Gln Phe Gly Ile Asn Ile Pro
225                 230                 235
```

<210> SEQ ID NO 17
<211> LENGTH: 707
<212> TYPE: DNA
<213> ORGANISM: artificial
<220> FEATURE:
<223> OTHER INFORMATION: Mutated DNA sequence encoding the N protein of
      schmallenberg virus

<400> SEQUENCE: 17

```
gatatctcaa gccaattcat ttttgaagat gtaccacaac ggaatgcagc tacatttaac     60

ccggaggtcg ggtatgtggc atttattggt aagtatgggc aacaactcaa cttcggtgtt    120

gctagagtct tcttcctcaa ccagaagaag gccaagatgg tcctacataa gacggcacaa    180
```

-continued

```
ccaagtgtcg atcttacttt tggtggggtc aaatttacag tggttaataa ccattttccc    240

caatatgtct caaatcctgt gccagacaat gccattacac ttcacaggat gtcaggttat    300

ctagcacgtt ggattgctga tacatgcaag gctagtgtcc tcaaactagc tgaagctagt    360

gctcagattg tcatgcccct tgctgaggtt aagggatgca cctgggccga tggttataca    420

atgtatcttg gatttgcacc tggggccgaa atgttccttg atgcttttga cttctatcca    480

ctagttattg aaatgcatag ggtcctcaag gacaatatgg atgtaaattt tatgaaaaaa    540

gtcctccgcc aacgctatgg aacaatgact gctgaagaat ggatgactca gaaaataaca    600

gaaataaaag ctgcttttaa ttctgttgga cagcttgcct gggccaaatc tggattctct    660

cctgctgcta gaaccttctt gcagcaattc ggtatcaaca tcccggg                707


<210> SEQ ID NO 18
<211> LENGTH: 211
<212> TYPE: PRT
<213> ORGANISM: mus musculus

<400> SEQUENCE: 18

Met Ala Glu Thr Cys Lys Met Lys Tyr Ser Val Leu Asp Ser Pro Leu
1               5                   10                  15

Gly Lys Met Glu Leu Ser Gly Cys Glu Arg Gly Leu His Gly Ile Arg
            20                  25                  30

Leu Leu Ser Gly Lys Thr Pro Asn Thr Asp Pro Thr Glu Ala Pro Ala
        35                  40                  45

Thr Pro Glu Val Leu Gly Gly Pro Glu Gly Val Pro Glu Pro Leu Val
    50                  55                  60

Gln Cys Thr Ala Trp Leu Glu Ala Tyr Phe Arg Glu Pro Ala Ala Thr
65                  70                  75                  80

Glu Gly Leu Pro Leu Pro Ala Leu His His Pro Val Phe Gln Gln Asp
                85                  90                  95

Ser Phe Thr Arg Gln Val Leu Trp Lys Leu Leu Lys Val Val Lys Phe
            100                 105                 110

Gly Glu Thr Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
    130                 135                 140

Ile Leu Ile Pro Cys His Arg Val Val Arg Ser Asp Gly Ala Ile Gly
145                 150                 155                 160

His Tyr Ser Gly Gly Gly Gln Ala Val Lys Glu Trp Leu Leu Ala His
                165                 170                 175

Glu Gly Ile Pro Thr Gly Gln Pro Ala Ser Lys Gly Leu Gly Leu Thr
            180                 185                 190

Gly Thr Trp Leu Lys Ser Ser Phe Glu Ser Thr Ser Ser Glu Pro Ser
        195                 200                 205

Gly Arg Asn
    210


<210> SEQ ID NO 19
<211> LENGTH: 209
<212> TYPE: PRT
<213> ORGANISM: Rattus norvegicus

<400> SEQUENCE: 19

Met Ala Glu Ile Cys Lys Met Lys Tyr Thr Val Leu Asp Ser Pro Leu
1               5                   10                  15
```

-continued

```
Gly Lys Ile Glu Leu Ser Gly Cys Glu Arg Gly Leu His Gly Ile Arg
            20                  25                  30

Phe Leu Ser Gly Lys Thr Pro Asn Thr Asp Pro Thr Glu Ala Pro Ala
        35                  40                  45

Cys Pro Glu Val Leu Gly Gly Pro Glu Gly Val Pro Glu Pro Leu Val
    50                  55                  60

Gln Cys Thr Ala Trp Leu Glu Ala Tyr Phe His Glu Pro Ala Ala Thr
65                  70                  75                  80

Glu Gly Leu Pro Leu Pro Ala Leu His His Pro Val Phe Gln Gln Asp
                85                  90                  95

Ser Phe Thr Arg Gln Val Leu Trp Lys Leu Leu Lys Val Val Lys Phe
            100                 105                 110

Gly Glu Met Val Ser Tyr Gln Gln Leu Ala Ala Leu Ala Gly Asn Pro
        115                 120                 125

Lys Ala Ala Arg Ala Val Gly Gly Ala Met Arg Ser Asn Pro Val Pro
    130                 135                 140

Ile Leu Ile Pro Cys His Arg Val Ile Arg Ser Asp Gly Ala Ile Gly
145                 150                 155                 160

Asn Tyr Ser Gly Gly Gly Gln Thr Val Lys Glu Trp Leu Leu Ala His
                165                 170                 175

Glu Gly Ile Pro Thr Gly Gln Pro Ala Ser Lys Gly Leu Gly Leu Ile
            180                 185                 190

Gly Ser Trp Leu Lys Pro Ser Phe Glu Ser Ser Ser Pro Lys Pro Ser
        195                 200                 205

Gly


<210> SEQ ID NO 20
<211> LENGTH: 963
<212> TYPE: DNA
<213> ORGANISM: artificial
<220> FEATURE:
<223> OTHER INFORMATION: DNA sequence coding for SNAP - linker - DEN1
      EDIII - linker- Histag

<400> SEQUENCE: 20

agatctgaca aagactgcga aatgaagcgc accaccctgg atagccctct gggcaagctg     60

gaactgtctg ggtgcgaaca gggcctgcac gagatcaagc tgctgggcaa aggaacatct    120

gccgccgacg ccgtggaagt gcctgcccca gccgccgtgc tgggcggacc agagccactg    180

atgcaggcca ccgcctggct caacgcctac tttcaccagc ctgaggccat cgaggagttc    240

cctgtgccag ccctgcacca cccagtgttc cagcaggaga gctttacccg ccaggtgctg    300

tggaaactgc tgaaagtggt gaagttcgga gaggtcatca gctaccagca gctggccgcc    360

ctggccggca atcccgccgc caccgccgcc gtgaaaaccg ccctgagcgg aaatcccgtg    420

cccattctga tcccctgcca ccgggtggtg tctagctctg gcgccgtggg gggctacgag    480

ggcgggctcg ccgtgaaaga gtggctgctg gcccacgagg gccacagact gggcaagcct    540

gggctgggtc ctgcaggtat aggcgcgcca gggtccctgg agggaggtgg cgggtctctg    600

actttaaaag ggatgtcata tgtgatgtgc acaggctcat ttaagctaga gaaggaagtg    660

gctgagaccc agcatggaac tgtcctagtg caggttaaat acgaaggaac agatgcgcca    720

tgcaagatcc ccttttcgac ccaagatgag aaaggagtga cccagaatgg gagattgata    780

acagccaatc ccatagttac tgacaaagaa aaaccaatca acattgagac agaaccacct    840

tttggtgaga gctacatcat agtaggggca ggtgaaaaag ctttgaaact aagctggttc    900
```

aagaaaggaa gcagcatagg gaaaggaggt ggccatcacc atcaccatca ctgatgaccg 960
gtt 963

<210> SEQ ID NO 21
<211> LENGTH: 316
<212> TYPE: PRT
<213> ORGANISM: artificial
<220> FEATURE:
<223> OTHER INFORMATION: SNAP - linker - DEN1 EDIII - linker- Histag

<400> SEQUENCE: 21

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Gly Lys Gly Thr Ser Ala Ala Asp Ala Val Glu Val Pro Ala
35 40 45

Pro Ala Ala Val Leu Gly Gly Pro Glu Pro Leu Met Gln Ala Thr Ala
50 55 60

Trp Leu Asn Ala Tyr Phe His Gln Pro Glu Ala Ile Glu Glu Phe Pro
65 70 75 80

Val Pro Ala Leu His His Pro Val Phe Gln Gln Glu Ser Phe Thr Arg
85 90 95

Gln Val Leu Trp Lys Leu Leu Lys Val Val Lys Phe Gly Glu Val Ile
100 105 110

Ser Tyr Gln Gln Leu Ala Ala Leu Ala Gly Asn Pro Ala Ala Thr Ala
115 120 125

Ala Val Lys Thr Ala Leu Ser Gly Asn Pro Val Pro Ile Leu Ile Pro
130 135 140

Cys His Arg Val Val Ser Ser Ser Gly Ala Val Gly Gly Tyr Glu Gly
145 150 155 160

Gly Leu Ala Val Lys Glu Trp Leu Leu Ala His Glu Gly His Arg Leu
165 170 175

Gly Lys Pro Gly Leu Gly Pro Ala Gly Ile Gly Ala Pro Gly Ser Leu
180 185 190

Glu Gly Gly Gly Gly Ser Leu Thr Leu Lys Gly Met Ser Tyr Val Met
195 200 205

Cys Thr Gly Ser Phe Lys Leu Glu Lys Glu Val Ala Glu Thr Gln His
210 215 220

Gly Thr Val Leu Val Gln Val Lys Tyr Glu Gly Thr Asp Ala Pro Cys
225 230 235 240

Lys Ile Pro Phe Ser Thr Gln Asp Glu Lys Gly Val Thr Gln Asn Gly
245 250 255

Arg Leu Ile Thr Ala Asn Pro Ile Val Thr Asp Lys Glu Lys Pro Ile
260 265 270

Asn Ile Glu Thr Glu Pro Pro Phe Gly Glu Ser Tyr Ile Ile Val Gly
275 280 285

Ala Gly Glu Lys Ala Leu Lys Leu Ser Trp Phe Lys Lys Gly Ser Ser
290 295 300

Ile Gly Lys Gly Gly Gly His His His His His His
305 310 315

<210> SEQ ID NO 22
<211> LENGTH: 54
<212> TYPE: DNA
<213> ORGANISM: artificial

<220> FEATURE:
<223> OTHER INFORMATION: DNA sequence encoding the ssBiP sequence

<400> SEQUENCE: 22
atgaagttat gcatattact ggccgtcgtg gcctttgttg gcctctcgct cggg 54

<210> SEQ ID NO 23
<211> LENGTH: 66
<212> TYPE: DNA
<213> ORGANISM: artificial
<220> FEATURE:
<223> OTHER INFORMATION: DNA artificial encoding BiP-like signal = insect ssBiP signal peptide + cleavage site DEN1prM signal sequence

<400> SEQUENCE: 23
atgaaactat gtattctact tgcagttgtt gcgttcgtag gattgtcctt acctacagct 60
ctggca 66

<210> SEQ ID NO 24
<211> LENGTH: 22
<212> TYPE: PRT
<213> ORGANISM: artificial
<220> FEATURE:
<223> OTHER INFORMATION: BiP-like signal = insect ssBiP signal peptide + cleavage site DEN1prM signal sequence

<400> SEQUENCE: 24

Met Lys Leu Cys Ile Leu Leu Ala Val Val Ala Phe Val Gly Leu Ser
1 5 10 15

Leu Pro Thr Ala Leu Ala
20

<210> SEQ ID NO 25
<211> LENGTH: 4
<212> TYPE: PRT
<213> ORGANISM: artificial
<220> FEATURE:
<223> OTHER INFORMATION: Amino acid sequence of the spacer

<400> SEQUENCE: 25

Gly Gly Gly Ser
1

<210> SEQ ID NO 26
<211> LENGTH: 12
<212> TYPE: DNA
<213> ORGANISM: artificial
<220> FEATURE:
<223> OTHER INFORMATION: DNA sequence of the spacer

<400> SEQUENCE: 26
ggtggcggat ct 12

<210> SEQ ID NO 27
<211> LENGTH: 6
<212> TYPE: PRT
<213> ORGANISM: artificial
<220> FEATURE:
<223> OTHER INFORMATION: Amino acid sequence of HIS TAG

<400> SEQUENCE: 27

His His His His His His
1 5

<210> SEQ ID NO 28
<211> LENGTH: 18
<212> TYPE: DNA
<213> ORGANISM: artificial
<220> FEATURE:
<223> OTHER INFORMATION: DNA sequence encoding His Tag

<400> SEQUENCE: 28
catcatcatc atcatcat 18

<210> SEQ ID NO 29
<211> LENGTH: 21
<212> TYPE: DNA
<213> ORGANISM: artificial
<220> FEATURE:
<223> OTHER INFORMATION: DNA encoding pro-TEV cleavage site 1

<400> SEQUENCE: 29
gaaaacctgt acttccagag c 21

<210> SEQ ID NO 30
<211> LENGTH: 21
<212> TYPE: DNA
<213> ORGANISM: artificial
<220> FEATURE:
<223> OTHER INFORMATION: DNA encoding pro-TEV cleavage site 2

<400> SEQUENCE: 30
gagaatctat attttcaagg g 21

<210> SEQ ID NO 31
<211> LENGTH: 530
<212> TYPE: DNA
<213> ORGANISM: artificial
<220> FEATURE:
<223> OTHER INFORMATION: SNAP-like sequence G/C low content

<400> SEQUENCE: 31
gacaaagact gcgaaatgaa aagaactaca ttggattcac cacttgggaa gttggaactg 60
agtggatgcg agcaaggatt gcatgaaatt aagctactgg gaaaaggaac ttctgctgct 120
gatgcagttg aagttccagc accagcagct gttcttggag gtcctgagcc cctcatgcaa 180
gccacagcct ggcttaacgc atatttccac cagcctgagg ccattgagga atttccagtc 240
cccgcccttc accatcctgt gtttcagcag gagagcttca cccgccaggt cctgtggaaa 300
ttgctgaagg tggtcaagtt tggtgaagtg atttcatatc agcaacttgc tgcattggcc 360
ggtaaccccg cagctacagc tgccgtgaaa actgctctca gcggaaatcc tgtgcccatc 420
ctgatccctt gtcacagagt cgtttcatct tccggagctg taggtggcta tgaaggagga 480
ctggcagtta aggagtggct gctggctcat gaaggtcata gacttggaaa 530

<210> SEQ ID NO 32
<211> LENGTH: 7
<212> TYPE: PRT
<213> ORGANISM: artificial
<220> FEATURE:
<223> OTHER INFORMATION: Pro-TEV cleavage site 1

<400> SEQUENCE: 32

Glu Asn Leu Tyr Phe Gln Ser
1 5

<210> SEQ ID NO 33
<211> LENGTH: 7

<212> TYPE: PRT
<213> ORGANISM: artificial
<220> FEATURE:
<223> OTHER INFORMATION: Pro-TEV cleavage site 2

<400> SEQUENCE: 33

Glu Asn Leu Tyr Phe Gln Gly
1               5

<210> SEQ ID NO 34
<211> LENGTH: 798
<212> TYPE: DNA
<213> ORGANISM: artificial
<220> FEATURE:
<223> OTHER INFORMATION: Cassette DNA pDeSNAP Univ (BIPlike - SNAPlike-
      proTEV/Histag)

<400> SEQUENCE: 34
gatcgcgagc tagcaccatg aaactatgta ttctacttgc agttgttgcg ttcgtaggat      60
tgtccttacc tacagctctg gcaagatctg acaaagactg cgaaatgaaa agaactacat     120
tggattcacc acttgggaag ttggaactga gtggatgcga gcaaggattg catgaaatta     180
agctactggg aaaaggaact tctgctgctg atgcagttga agttccagca ccagcagctg     240
ttcttggagg tcctgagccc ctcatgcaag ccacagcctg gcttaacgca tatttccacc     300
agcctgaggc cattgaggaa tttccagtcc ccgcccttca ccatcctgtg tttcagcagg     360
agagcttcac ccgccaggtc ctgtggaaat tgctgaaggt ggtcaagttt ggtgaagtga     420
tttcatatca gcaacttgct gcattggccg gtaaccccgc agctacagct gccgtgaaaa     480
ctgctctcag cggaaatcct gtgcccatcc tgatcccttg tcacagagtc gtttcatctt     540
ccggagctgt aggtggctat gaaggaggac tggcagttaa ggagtggctg ctggctcatg     600
aaggtcatag acttggaaag cctgggctgg gtcctgctgg tataggcgcg ccagggtccc     660
taggtggcgg atccgaaaac ctgtacttcc agagcgatat cggaggtgga ggcccgggag     720
agaatctata ttttcaaggg cccggcggag gtagtcacca tcatcaccat cactaatgac     780
cggtgcggcc gcaagctt                                                   798

<210> SEQ ID NO 35
<211> LENGTH: 1439
<212> TYPE: DNA
<213> ORGANISM: artificial
<220> FEATURE:
<223> OTHER INFORMATION: Cassette DNA pDeSNAP Univ +SBV.N (ssBIP -
      SNAPlike- SBV.N- proTEV/Histag)

<400> SEQUENCE: 35
atgaagttat gcatattact ggccgtcgtg gcctttgttg gcctctcgct cgggagatct      60
gacaaagact gcgaaatgaa aagaactaca ttggattcac cacttgggaa gttggaactg     120
agtggatgcg agcaaggatt gcatgaaatt aagctactgg gaaaaggaac ttctgctgct     180
gatgcagttg aagttccagc accagcagct gttcttggag gtcctgagcc cctcatgcaa     240
gccacagcct ggcttaacgc atatttccac cagcctgagg ccattgagga atttccagtc     300
cccgcccttc accatcctgt gtttcagcag gagagcttca cccgccaggt cctgtggaaa     360
ttgctgaagg tggtcaagtt tggtgaagtg atttcatatc agcaacttgc tgcattggcc     420
ggtaaccccg cagctacagc tgccgtgaaa actgctctca gcggaaatcc tgtgcccatc     480
ctgatccctt gtcacagagt cgtttcatct tccggagctg taggtggcta tgaaggagga     540
ctggcagtta aggagtggct gctggctcat gaaggtcata gacttggaaa gcctgggctg     600

-continued

```
ggtcctgctg gtataggcgc gccagggtcc ctaggtggcg gatccgaaaa cctgtacttc    660

cagagcgata tctcaagcca attcattttt gaagatgtac cacaacggaa tgcagctaca    720

tttaacccgg aggtcgggta tgtggcattt attggtaagt atgggcaaca actcaacttc    780

ggtgttgcta gagtcttctt cctcaaccag aagaaggcca agatggtcct acataagacg    840

gcacaaccaa gtgtcgatct tacttttggt ggggtcaaat ttacagtggt taataaccat    900

tttccccaat atgtctcaaa tcctgtgcca gacaatgcca ttacacttca caggatgtca    960

ggttatctag cacgttggat tgctgataca tgcaaggcta gtgtcctcaa actagctgaa   1020

gctagtgctc agattgtcat gccccttgct gaggttaagg gatgcacctg ggccgatggt   1080

tatacaatgt atcttggatt tgcacctggg gccgaaatgt tccttgatgc ttttgacttc   1140

tatccactag ttattgaaat gcatagggtc ctcaaggaca atatggatgt aaattttatg   1200

aaaaaagtcc tccgccaacg ctatggaaca atgactgctg aagaatggat gactcagaaa   1260

ataacagaaa taaaagctgc ttttaattct gttggacagc ttgcctgggc caaatctgga   1320

ttctctcctg ctgctagaac cttcttgcag caattcggta tcaacatccc gggagagaat   1380

ctatattttc aagggcccgg cggaggtagt caccatcatc accatcacta atgaccggt    1439
```

<210> SEQ ID NO 36
<211> LENGTH: 1480
<212> TYPE: DNA
<213> ORGANISM: artificial
<220> FEATURE:
<223> OTHER INFORMATION: Cassette DNA pDeSNAP Univ +SBV.N (BIPlike - SNAPlike-SBV.N -proTEV/Histag)

<400> SEQUENCE: 36

```
tcgcgagcta gcaccatgaa actatgtatt ctacttgcag ttgttgcgtt cgtaggattg     60

tccttaccta cagctctggc aagatctgac aaagactgcg aaatgaaaag aactacattg    120

gattcaccac ttgggaagtt ggaactgagt ggatgcgagc aaggattgca tgaaattaag    180

ctactgggaa aaggaacttc tgctgctgat gcagttgaag ttccagcacc agcagctgtt    240

cttggaggtc ctgagcccct catgcaagcc acagcctggc ttaacgcata tttccaccag    300

cctgaggcca ttgaggaatt tccagtcccc gcccttcacc atcctgtgtt tcagcaggag    360

agcttcaccc gccaggtcct gtggaaattg ctgaaggtgg tcaagtttgg tgaagtgatt    420

tcatatcagc aacttgctgc attggccggt aaccccgcag ctacagctgc cgtgaaaact    480

gctctcagcg gaaatcctgt gcccatcctg atcccttgtc acagagtcgt ttcatcttcc    540

ggagctgtag gtggctatga aggaggactg gcagttaagg agtggctgct ggctcatgaa    600

ggtcatagac ttggaaagcc tgggctgggt cctgctggta taggcgcgcc agggtcccta    660

ggtggcggat ccgaaaacct gtacttccag agcgatatct caagccaatt catttttgaa    720

gatgtaccac aacggaatgc agctacattt aacccggagg tcgggtatgt ggcatttatt    780

ggtaagtatg ggcaacaact caacttcggt gttgctagag tcttcttcct caaccagaag    840

aaggccaaga tggtcctaca taagacggca caaccaagtg tcgatcttac ttttggtggg    900

gtcaaattta cagtggttaa taaccatttt ccccaatatg tctcaaatcc tgtgccagac    960

aatgccatta cacttcacag gatgtcaggt tatctagcac gttggattgc tgatacatgc   1020

aaggctagtg tcctcaaact agctgaagct agtgctcaga ttgtcatgcc ccttgctgag   1080

gttaagggat gcacctgggc cgatggttat acaatgtatc ttggatttgc acctggggcc   1140

gaaatgttcc ttgatgcttt tgacttctat ccactagtta ttgaaatgca tagggtcctc   1200
```

```
aaggacaata tggatgtaaa ttttatgaaa aaagtcctcc gccaacgcta tggaacaatg   1260

actgctgaag aatggatgac tcagaaaata acagaaataa aagctgcttt taattctgtt   1320

ggacagcttg cctgggccaa atctggattc tctcctgctg ctagaacctt cttgcagcaa   1380

ttcggtatca acatcccggg agagaatcta tattttcaag ggcccggcgg aggtagtcac   1440

catcatcacc atcactaatg accggtgcgg ccgcaagctt                         1480


<210> SEQ ID NO 37
<211> LENGTH: 18
<212> TYPE: PRT
<213> ORGANISM: artificial
<220> FEATURE:
<223> OTHER INFORMATION: Amino acid sequence of the ssBiP sequence

<400> SEQUENCE: 37

Met Lys Leu Cys Ile Leu Leu Ala Val Val Ala Phe Val Gly Leu Ser
1               5                   10                  15

Leu Gly


<210> SEQ ID NO 38
<211> LENGTH: 17
<212> TYPE: PRT
<213> ORGANISM: West Nile virus strain IS-98-ST1

<400> SEQUENCE: 38

Met Val Val Phe Val Val Leu Leu Leu Leu Val Ala Pro Ala Tyr Ser
1               5                   10                  15

Leu


<210> SEQ ID NO 39
<211> LENGTH: 5
<212> TYPE: PRT
<213> ORGANISM: Dengue virus

<400> SEQUENCE: 39

Pro Thr Ala Leu Ala
1               5


<210> SEQ ID NO 40
<211> LENGTH: 6
<212> TYPE: PRT
<213> ORGANISM: artificial
<220> FEATURE:
<223> OTHER INFORMATION: Cleavage site of enterokinase

<400> SEQUENCE: 40

Asp Asp Asp Asp Lys Asp
1               5


<210> SEQ ID NO 41
<211> LENGTH: 480
<212> TYPE: PRT
<213> ORGANISM: artificial
<220> FEATURE:
<223> OTHER INFORMATION: Amino acid sequence of
      BiPlike+SNAPlike+proTEV+SBV.N+proTEV+Histag

<400> SEQUENCE: 41

Met Lys Leu Cys Ile Leu Leu Ala Val Val Ala Phe Val Gly Leu Ser
1               5                   10                  15

Leu Pro Thr Ala Leu Ala Arg Ser Asp Lys Asp Cys Glu Met Lys Arg
            20                  25                  30
```

-continued

```
Thr Thr Leu Asp Ser Pro Leu Gly Lys Leu Glu Leu Ser Gly Cys Glu
        35                  40                  45

Gln Gly Leu His Glu Ile Lys Leu Leu Gly Lys Gly Thr Ser Ala Ala
    50                  55                  60

Asp Ala Val Glu Val Pro Ala Pro Ala Ala Val Leu Gly Gly Pro Glu
65                  70                  75                  80

Pro Leu Met Gln Ala Thr Ala Trp Leu Asn Ala Tyr Phe His Gln Pro
                85                  90                  95

Glu Ala Ile Glu Glu Phe Pro Val Pro Ala Leu His His Pro Val Phe
            100                 105                 110

Gln Gln Glu Ser Phe Thr Arg Gln Val Leu Trp Lys Leu Leu Lys Val
        115                 120                 125

Val Lys Phe Gly Glu Val Ile Ser Tyr Gln Gln Leu Ala Ala Leu Ala
    130                 135                 140

Gly Asn Pro Ala Ala Thr Ala Ala Val Lys Thr Ala Leu Ser Gly Asn
145                 150                 155                 160

Pro Val Pro Ile Leu Ile Pro Cys His Arg Val Val Ser Ser Ser Gly
                165                 170                 175

Ala Val Gly Gly Tyr Glu Gly Gly Leu Ala Val Lys Glu Trp Leu Leu
            180                 185                 190

Ala His Glu Gly His Arg Leu Gly Lys Pro Gly Leu Gly Pro Ala Gly
        195                 200                 205

Ile Gly Ala Pro Gly Ser Leu Gly Gly Gly Ser Glu Asn Leu Tyr Phe
    210                 215                 220

Gln Ser Asp Ile Ser Ser Gln Phe Ile Phe Glu Asp Val Pro Gln Arg
225                 230                 235                 240

Asn Ala Ala Thr Phe Asn Pro Glu Val Gly Tyr Val Ala Phe Ile Gly
                245                 250                 255

Lys Tyr Gly Gln Gln Leu Asn Phe Gly Val Ala Arg Val Phe Phe Leu
            260                 265                 270

Asn Gln Lys Lys Ala Lys Met Val Leu His Lys Thr Ala Gln Pro Ser
        275                 280                 285

Val Asp Leu Thr Phe Gly Gly Val Lys Phe Thr Val Val Asn Asn His
    290                 295                 300

Phe Pro Gln Tyr Val Ser Asn Pro Val Pro Asp Asn Ala Ile Thr Leu
305                 310                 315                 320

His Arg Met Ser Gly Tyr Leu Ala Arg Trp Ile Ala Asp Thr Cys Lys
                325                 330                 335

Ala Ser Val Leu Lys Leu Ala Glu Ala Ser Ala Gln Ile Val Met Pro
            340                 345                 350

Leu Ala Glu Val Lys Gly Cys Thr Trp Ala Asp Gly Tyr Thr Met Tyr
        355                 360                 365

Leu Gly Phe Ala Pro Gly Ala Glu Met Phe Leu Asp Ala Phe Asp Phe
    370                 375                 380

Tyr Pro Leu Val Ile Glu Met His Arg Val Leu Lys Asp Asn Met Asp
385                 390                 395                 400

Val Asn Phe Met Lys Lys Val Leu Arg Gln Arg Tyr Gly Thr Met Thr
                405                 410                 415

Ala Glu Glu Trp Met Thr Gln Lys Ile Thr Glu Ile Lys Ala Ala Phe
            420                 425                 430

Asn Ser Val Gly Gln Leu Ala Trp Ala Lys Ser Gly Phe Ser Pro Ala
        435                 440                 445
```

Ala Arg Thr Phe Leu Gln Gln Phe Gly Ile Asn Ile Pro Gly Glu Asn
    450                 455                 460

Leu Tyr Phe Gln Gly Pro Gly Gly Gly Ser His His His His His His
465                 470                 475                 480

<210> SEQ ID NO 42
<211> LENGTH: 438
<212> TYPE: PRT
<213> ORGANISM: artificial
<220> FEATURE:
<223> OTHER INFORMATION: Amino acid sequence of the fusion protein
      SNAP+SCHM.N (without BiPlike + HisTag

<400> SEQUENCE: 42

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ser
        195                 200                 205

Gln Phe Ile Phe Glu Asp Val Pro Gln Arg Asn Ala Ala Thr Phe Asn
    210                 215                 220

Pro Glu Val Gly Tyr Val Ala Phe Ile Gly Lys Tyr Gly Gln Gln Leu
225                 230                 235                 240

Asn Phe Gly Val Ala Arg Val Phe Phe Leu Asn Gln Lys Lys Ala Lys
                245                 250                 255

Met Val Leu His Lys Thr Ala Gln Pro Ser Val Asp Leu Thr Phe Gly
            260                 265                 270

Gly Val Lys Phe Thr Val Val Asn Asn His Phe Pro Gln Tyr Val Ser
        275                 280                 285

Asn Pro Val Pro Asp Asn Ala Ile Thr Leu His Arg Met Ser Gly Tyr
    290                 295                 300

Leu Ala Arg Trp Ile Ala Asp Thr Cys Lys Ala Ser Val Leu Lys Leu
305                 310                 315                 320

Ala Glu Ala Ser Ala Gln Ile Val Met Pro Leu Ala Glu Val Lys Gly
                325                 330                 335

```
Cys Thr Trp Ala Asp Gly Tyr Thr Met Tyr Leu Gly Phe Ala Pro Gly
            340                 345                 350

Ala Glu Met Phe Leu Asp Ala Phe Asp Phe Tyr Pro Leu Val Ile Glu
        355                 360                 365

Met His Arg Val Leu Lys Asp Asn Met Asp Val Asn Phe Met Lys Lys
    370                 375                 380

Val Leu Arg Gln Arg Tyr Gly Thr Met Thr Ala Glu Glu Trp Met Thr
385                 390                 395                 400

Gln Lys Ile Thr Glu Ile Lys Ala Ala Phe Asn Ser Val Gly Gln Leu
                405                 410                 415

Ala Trp Ala Lys Ser Gly Phe Ser Pro Ala Ala Arg Thr Phe Leu Gln
            420                 425                 430

Gln Phe Gly Ile Asn Ile
        435


<210> SEQ ID NO 43
<211> LENGTH: 4194
<212> TYPE: DNA
<213> ORGANISM: artificial
<220> FEATURE:
<223> OTHER INFORMATION: pMT/BiP/SNAP-Histag avec cassette DeSNAP Univ

<400> SEQUENCE: 43

tcgcgcgttt cggtgatgac ggtgaaaacc tctgacacat gcagctcccg gagacggtca      60

cagcttgtct gtaagcggat gccgggagca gacaagcccg tcagggcgcg tcagcgggtg     120

ttggcgggtg tcggggctgg cttaactatg cggcatcaga gcagattgta ctgagagtgc     180

accatatgcg gtgtgaaata ccgcacagat gcgtaaggag aaaataccgc atcaggcgcc     240

attcgccatt caggctgcgc aactgttggg aagggcgatc ggtgcgggcc tcttcgctat     300

tacgccagct ggcgaaaggg ggatgtgctg caaggcgatt aagttgggta acgccagggt     360

tttcccagtc acgacgttgt aaaacgacgg ccagtgccag tgaattttaa cgttgcagga     420

caggatgtgg tgcccgatgt gactagctct ttgctgcagg ccgtcctatc ctctggttcc     480

gataagagac ccagaactcc ggccccccac cgcccaccgc cacccccata catatgtggt     540

acgcaagtaa gagtgcctgc gcatgcccca tgtgccccac caagagtttt gcatcccata     600

caagtcccca aagtggagaa ccgaaccaat tcttcgcggg cagaacaaaa gcttctgcac     660

acgtctccac tcgaatttgg agccggccgg cgtgtgcaaa agaggtgaat cgaacgaaag     720

acccgtgtgt aaagccgcgt ttccaaaatg tataaaaccg agagcatctg gccaatgtgc     780

atcagttgtg gtcagcagca aaatcaagtg aatcatctca gtgcaactaa aggggggatc     840

cgatctcaat atgaagttat gcatattact ggccgtcgtg gcctttgttg gcctctcgct     900

cgggagatct gacaaagact gcgaaatgaa aagaactaca ttggattcac cacttgggaa     960

gttggaactg agtggatgcg agcaaggatt gcatgaaatt aagctactgg gaaaaggaac    1020

ttctgctgct gatgcagttg aagttccagc accagcagct gttcttggag gtcctgagcc    1080

cctcatgcaa gccacagcct ggcttaacgc atatttccac cagcctgagg ccattgagga    1140

atttccagtc cccgcccttc accatcctgt gtttcagcag gagagcttca cccgccaggt    1200

cctgtggaaa ttgctgaagg tggtcaagtt tggtgaagtg atttcatatc agcaacttgc    1260

tgcattggcc ggtaaccccg cagctacagc tgccgtgaaa actgctctca gcggaaatcc    1320

tgtgcccatc ctgatccctt gtcacagagt cgtttcatct tccggagctg taggtggcta    1380

tgaaggagga ctggcagtta aggagtggct gctggctcat gaaggtcata gacttggaaa    1440
```

gcctgggctg ggtcctgctg gtataggcgc gccagggtcc ctaggtggcg gatccgaaaa 1500
cctgtacttc cagagcgata tcggaggtgg aggcccggga gagaatctat attttcaagg 1560
gcccggcgga ggtagtcacc atcatcacca tcactaatga ccggtcatca tcaccatcac 1620
cattgagttt aaacccgctg atcagcctcg actgtgcctt ctaaggcctg agctcgctga 1680
tcagcctcga tcgaggatcc agacatgata agatacattg atgagtttgg acaaaccaca 1740
actagaatgc agtgaaaaaa atgctttatt tgtgaaattt gtgatgctat tgctttattt 1800
gtaaccatta taagctgcaa taaacaagtt aacaacaaca attgcattca ttttatgttt 1860
caggttcagg gggaggtgtg ggaggttttt taaagcaagt aaaacctcta caaatgtggt 1920
atggctgatt atgatcagtc gacctgcagg catgcaagct tggcgtaatc atggtcatag 1980
ctgtttcctg tgtgaaattg ttatccgctc acaattccac acaacatacg agccggaagc 2040
ataaagtgta aagcctgggg tgcctaatga gtgagctaac tcacattaat tgcgttgcgc 2100
tcactgcccg ctttccagtc gggaaacctg tcgtgccagc tgcattaatg aatcggccaa 2160
cgcgcgggga gaggcggttt gcgtattggg cgctcttccg cttcctcgct cactgactcg 2220
ctgcgctcgg tcgttcggct gcggcgagcg gtatcagctc actcaaaggc ggtaatacgg 2280
ttatccacag aatcagggga taacgcagga aagaacatgt gagcaaaagg ccagcaaaag 2340
gccaggaacc gtaaaaaggc cgcgttgctg gcgtttttcc ataggctccg cccccctgac 2400
gagcatcaca aaaatcgacg ctcaagtcag aggtggcgaa acccgacagg actataaaga 2460
taccaggcgt ttccccctgg aagctccctc gtgcgctctc ctgttccgac cctgccgctt 2520
accggatacc tgtccgcctt tctcccttcg ggaagcgtgg cgctttctca tagctcacgc 2580
tgtaggtatc tcagttcggt gtaggtcgtt cgctccaagc tgggctgtgt gcacgaaccc 2640
cccgttcagc ccgaccgctg cgccttatcc ggtaactatc gtcttgagtc caacccggta 2700
agacacgact tatcgccact ggcagcagcc actggtaaca ggattagcag agcgaggtat 2760
gtaggcggtg ctacagagtt cttgaagtgg tggcctaact acggctacac tagaaggaca 2820
gtatttggta tctgcgctct gctgaagcca gttaccttcg gaaaaagagt tggtagctct 2880
tgatccggca aacaaaccac cgctggtagc ggtggttttt ttgtttgcaa gcagcagatt 2940
acgcgcagaa aaaaaggatc tcaagaagat cctttgatct tttctacggg gtctgacgct 3000
cagtggaacg aaaactcacg ttaagggatt ttggtcatga gattatcaaa aaggatcttc 3060
acctagatcc ttttaaatta aaaatgaagt tttaaatcaa tctaaagtat atatgagtaa 3120
acttggtctg acagttacca atgcttaatc agtgaggcac ctatctcagc gatctgtcta 3180
tttcgttcat ccatagttgc ctgactcccc gtcgtgtaga taactacgat acgggagggc 3240
ttaccatctg gccccagtgc tgcaatgata ccgcgagacc cacgctcacc ggctccagat 3300
ttatcagcaa taaaccagcc agccggaagg gccgagcgca gaagtggtcc tgcaacttta 3360
tccgcctcca tccagtctat taattgttgc cgggaagcta gagtaagtag ttcgccagtt 3420
aatagtttgc gcaacgttgt tgccattgct acaggcatcg tggtgtcacg ctcgtcgttt 3480
ggtatggctt cattcagctc cggttcccaa cgatcaaggc gagttacatg atcccccatg 3540
ttgtgcaaaa aagcggttag ctccttcggt cctccgatcg ttgtcagaag taagttggcc 3600
gcagtgttat cactcatggt tatggcagca ctgcataatt ctcttactgt catgccatcc 3660
gtaagatgct tttctgtgac tggtgagtac tcaaccaagt cattctgaga atagtgtatg 3720
cggcgaccga gttgctcttg cccggcgtca atacgggata ataccgcgcc acatagcaga 3780
actttaaaag tgctcatcat tggaaaacgt tcttcggggc gaaaactctc aaggatctta 3840
ccgctgttga gatccagttc gatgtaaccc actcgtgcac ccaactgatc ttcagcatct 3900
tttactttca ccagcgtttc tgggtgagca aaaacaggaa ggcaaaatgc cgcaaaaaag 3960
ggaataaggg cgacacggaa atgttgaata ctcatactct tcctttttca atattattga 4020
agcatttatc agggttattg tctcatgagc ggatacatat ttgaatgtat ttagaaaaat 4080
aaacaaatag gggttccgcg cacatttccc cgaaaagtgc cacctgacgt ctaagaaacc 4140
attattatca tgacattaac ctataaaaat aggcgtatca cgaggccctt tcgt 4194

<210> SEQ ID NO 44
<211> LENGTH: 3458
<212> TYPE: DNA
<213> ORGANISM: artificial
<220> FEATURE:
<223> OTHER INFORMATION: pUC57 with DeSNAP Univ cassette

<400> SEQUENCE: 44
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cgagctcggt acctcgcgaa 420
tgcatctaga tcgagctagc accatgaaac tatgtattct acttgcagtt gttgcgttcg 480
taggattgtc cttacctaca gctctggcaa gatctgacaa agactgcgaa atgaaaagaa 540
ctacattgga ttcaccactt gggaagttgg aactgagtgg atgcgagcaa ggattgcatg 600
aaattaagct actgggaaaa ggaacttctg ctgctgatgc agttgaagtt ccagcaccag 660
cagctgttct tggaggtcct gagcccctca tgcaagccac agcctggctt aacgcatatt 720
tccaccagcc tgaggccatt gaggaatttc cagtccccgc ccttcaccat cctgtgtttc 780
agcaggagag cttcacccgc caggtcctgt ggaaattgct gaaggtggtc aagtttggtg 840
aagtgatttc atatcagcaa cttgctgcat tggccggtaa ccccgcagct acagctgccg 900
tgaaaactgc tctcagcgga aatcctgtgc ccatcctgat cccttgtcac agagtcgttt 960
catcttccgg agctgtaggt ggctatgaag gaggactggc agttaaggag tggctgctgg 1020
ctcatgaagg tcatagactt ggaaagcctg ggctgggtcc tgctggtata ggcgcgccag 1080
ggtccctagg tggcggatcc gaaaacctgt acttccagag cgatatcgga ggtggaggcc 1140
cgggagagaa tctatatttt caagggcccg gcggaggtag tcaccatcat caccatcact 1200
aatgaccggt gcggccgcaa gcttggcgta atcatggtca tagctgtttc ctgtgtgaaa 1260
ttgttatccg ctcacaattc cacacaacat acgagccgga agcataaagt gtaaagcctg 1320
gggtgcctaa tgagtgagct aactcacatt aattgcgttg cgctcactgc ccgctttcca 1380
gtcgggaaac ctgtcgtgcc agctgcatta atgaatcggc caacgcgcgg ggagaggcgg 1440
tttgcgtatt gggcgctctt ccgcttcctc gctcactgac tcgctgcgct cggtcgttcg 1500
gctgcggcga gcggtatcag ctcactcaaa ggcggtaata cggttatcca cagaatcagg 1560
ggataacgca ggaaagaaca tgtgagcaaa aggccagcaa aaggccagga accgtaaaaa 1620
ggccgcgttg ctggcgtttt tccataggct ccgcccccct gacgagcatc acaaaaatcg 1680
acgctcaagt cagaggtggc gaaacccgac aggactataa agataccagg cgtttccccc 1740
tggaagctcc ctcgtgcgct ctcctgttcc gaccctgccg cttaccggat acctgtccgc 1800
ctttctccct tcgggaagcg tggcgctttc tcatagctca cgctgtaggt atctcagttc 1860
ggtgtaggtc gttcgctcca agctgggctg tgtgcacgaa ccccccgttc agcccgaccg 1920
ctgcgcctta tccggtaact atcgtcttga gtccaacccg gtaagacacg acttatcgcc 1980
actggcagca gccactggta acaggattag cagagcgagg tatgtaggcg gtgctacaga 2040
gttcttgaag tggtggccta actacggcta cactagaaga acagtatttg gtatctgcgc 2100
tctgctgaag ccagttacct tcggaaaaag agttggtagc tcttgatccg gcaaacaaac 2160
caccgctggt agcggtggtt tttttgtttg caagcagcag attacgcgca gaaaaaaagg 2220
atctcaagaa gatcctttga tcttttctac ggggtctgac gctcagtgga acgaaaactc 2280
acgttaaggg attttggtca tgagattatc aaaaaggatc ttcacctaga tccttttaaa 2340
ttaaaaatga agttttaaat caatctaaag tatatatgag taaacttggt ctgacagtta 2400
ccaatgctta atcagtgagg cacctatctc agcgatctgt ctatttcgtt catccatagt 2460
tgcctgactc cccgtcgtgt agataactac gatacgggag ggcttaccat ctggccccag 2520
tgctgcaatg ataccgcgag acccacgctc accggctcca gatttatcag caataaacca 2580
gccagccgga agggccgagc gcagaagtgg tcctgcaact ttatccgcct ccatccagtc 2640
tattaattgt tgccgggaag ctagagtaag tagttcgcca gttaatagtt tgcgcaacgt 2700
tgttgccatt gctacaggca tcgtggtgtc acgctcgtcg tttggtatgg cttcattcag 2760
ctccggttcc caacgatcaa ggcgagttac atgatccccc atgttgtgca aaaaagcggt 2820
tagctccttc ggtcctccga tcgttgtcag aagtaagttg gccgcagtgt tatcactcat 2880
ggttatggca gcactgcata attctcttac tgtcatgcca tccgtaagat gcttttctgt 2940
gactggtgag tactcaacca agtcattctg agaatagtgt atgcggcgac cgagttgctc 3000
ttgcccggcg tcaatacggg ataataccgc gccacatagc agaactttaa aagtgctcat 3060
cattggaaaa cgttcttcgg ggcgaaaact ctcaaggatc ttaccgctgt tgagatccag 3120
ttcgatgtaa cccactcgtg cacccaactg atcttcagca tcttttactt tcaccagcgt 3180
ttctgggtga gcaaaaacag gaaggcaaaa tgccgcaaaa aagggaataa gggcgacacg 3240
gaaatgttga atactcatac tcttcctttt tcaatattat tgaagcattt atcagggtta 3300
ttgtctcatg agcggataca tatttgaatg tatttagaaa aataaacaaa taggggttcc 3360
gcgcacattt ccccgaaaag tgccacctga cgtctaagaa accattatta tcatgacatt 3420
aacctataaa aataggcgta tcacgaggcc ctttcgtc 3458

<210> SEQ ID NO 45
<211> LENGTH: 6365
<212> TYPE: DNA
<213> ORGANISM: artificial
<220> FEATURE:
<223> OTHER INFORMATION: pcDNA3 with DeSNAP Univ cassette

<400> SEQUENCE: 45
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240

-continued

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
accatgaaac tatgtattct acttgcagtt gttgcgttcg taggattgtc cttacctaca    960
gctctggcaa gatctgacaa agactgcgaa atgaaaagaa ctacattgga ttcaccactt   1020
gggaagttgg aactgagtgg atgcgagcaa ggattgcatg aaattaagct actgggaaaa   1080
ggaacttctg ctgctgatgc agttgaagtt ccagcaccag cagctgttct tggaggtcct   1140
gagcccctca tgcaagccac agcctggctt aacgcatatt tccaccagcc tgaggccatt   1200
gaggaatttc cagtccccgc ccttcaccat cctgtgtttc agcaggagag cttcacccgc   1260
caggtcctgt ggaaattgct gaaggtggtc aagtttggtg aagtgatttc atatcagcaa   1320
cttgctgcat tggccggtaa ccccgcagct acagctgccg tgaaaactgc tctcagcgga   1380
aatcctgtgc ccatcctgat cccttgtcac agagtcgttt catcttccgg agctgtaggt   1440
ggctatgaag gaggactggc agttaaggag tggctgctgg ctcatgaagg tcatagactt   1500
ggaaagcctg ggctgggtcc tgctggtata ggcgcgccag ggtccctagg tggcggatcc   1560
gaaaacctgt acttccagag cgatatcgga ggtggaggcc cgggagagaa tctatatttt   1620
caagggcccg gcggaggtag tcaccatcat caccatcact aatgaccggt gcggccgcaa   1680
gcttggtacc gagctcggat ccactagtcc agtgtggtgg aattctgcag atatccagca   1740
cagtggcggc cgctcgagtc tagagggccc gtttaaaccc gctgatcagc ctcgactgtg   1800
ccttctagtt gccagccatc tgttgtttgc ccctcccccg tgccttcctt gaccctggaa   1860
ggtgccactc ccactgtcct ttcctaataa aatgaggaaa ttgcatcgca ttgtctgagt   1920
aggtgtcatt ctattctggg gggtggggtg gggcaggaca gcaaggggga ggattgggaa   1980
gacaatagca ggcatgctgg ggatgcggtg ggctctatgg cttctgaggc ggaaagaacc   2040
agctggggct ctagggggta tccccacgcg ccctgtagcg gcgcattaag cgcggcgggt   2100
gtggtggtta cgcgcagcgt gaccgctaca cttgccagcg ccctagcgcc cgctcctttc   2160
gctttcttcc cttcctttct cgccacgttc gccggctttc cccgtcaagc tctaaatcgg   2220
gggctccctt tagggttccg atttagtgct ttacggcacc tcgaccccaa aaaacttgat   2280
tagggtgatg gttcacgtag tgggccatcg ccctgataga cggtttttcg ccctttgacg   2340
ttggagtcca cgttctttaa tagtggactc ttgttccaaa ctggaacaac actcaaccct   2400
atctcggtct attcttttga tttataaggg attttgccga tttcggccta ttggttaaaa   2460
aatgagctga tttaacaaaa atttaacgcg aattaattct gtggaatgtg tgtcagttag   2520
ggtgtggaaa gtccccaggc tccccagcag gcagaagtat gcaaagcatg catctcaatt   2580
agtcagcaac caggtgtgga aagtccccag gctccccagc aggcagaagt atgcaaagca   2640
```

```
tgcatctcaa ttagtcagca accatagtcc cgcccctaac tccgcccatc ccgcccctaa   2700
ctccgcccag ttccgcccat tctccgcccc atggctgact aattttttt atttatgcag    2760
aggccgaggc cgcctctgcc tctgagctat tccagaagta gtgaggaggc ttttttggag   2820
gcctaggctt ttgcaaaaag ctcccgggag cttgtatatc cattttcgga tctgatcagc   2880
acgtgatgaa aaagcctgaa ctcaccgcga cgtctgtcga gaagtttctg atcgaaaagt   2940
tcgacagcgt ctccgacctg atgcagctct cggagggcga agaatctcgt gctttcagct   3000
tcgatgtagg agggcgtgga tatgtcctgc gggtaaatag ctgcgccgat ggtttctaca   3060
aagatcgtta tgtttatcgg cactttgcat cggccgcgct cccgattccg gaagtgcttg   3120
acattgggga attcagcgag agcctgacct attgcatctc ccgccgtgca cagggtgtca   3180
cgttgcaaga cctgcctgaa accgaactgc ccgctgttct gcagccggtc gcggaggcca   3240
tggatgcgat cgctgcggcc gatcttagcc agacgagcgg gttcggccca ttcggaccgc   3300
aaggaatcgg tcaatacact acatggcgtg atttcatatg cgcgattgct gatccccatg   3360
tgtatcactg gcaaactgtg atggacgaca ccgtcagtgc gtccgtcgcg caggctctcg   3420
atgagctgat gctttgggcc gaggactgcc ccgaagtccg gcacctcgtg cacgcggatt   3480
tcggctccaa caatgtcctg acggacaatg gccgcataac agcggtcatt gactggagcg   3540
aggcgatgtt cggggattcc caatacgagg tcgccaacat cttcttctgg aggccgtggt   3600
tggcttgtat ggagcagcag acgcgctact tcgagcggag gcatccggag cttgcaggat   3660
cgccgcggct ccgggcgtat atgctccgca ttggtcttga ccaactctat cagagcttgg   3720
ttgacggcaa tttcgatgat gcagcttggg cgcagggtcg atgcgacgca atcgtccgat   3780
ccggagccgg gactgtcggg cgtacacaaa tcgcccgcag aagcgcggcc gtctggaccg   3840
atggctgtgt agaagtactc gccgatagtg gaaaccgacg ccccagcact cgtccgaggg   3900
caaaggaata gcacgtgcta cgagatttcg attccaccgc cgccttctat gaaaggttgg   3960
gcttcggaat cgttttccgg gacgccggct ggatgatcct ccagcgcggg gatctcatgc   4020
tggagttctt cgcccacccc aacttgttta ttgcagctta taatggttac aaataaagca   4080
atagcatcac aaatttcaca aataaagcat ttttttcact gcattctagt tgtggtttgt   4140
ccaaactcat caatgtatct tatcatgtct gtataccgtc gacctctagc tagagcttgg   4200
cgtaatcatg gtcatagctg tttcctgtgt gaaattgtta tccgctcaca attccacaca   4260
acatacgagc cggaagcata aagtgtaaag cctggggtgc ctaatgagtg agctaactca   4320
cattaattgc gttgcgctca ctgcccgctt tccagtcggg aaacctgtcg tgccagctgc   4380
attaatgaat cggccaacgc gcggggagag gcggtttgcg tattgggcgc tcttccgctt   4440
cctcgctcac tgactcgctg cgctcggtcg ttcggctgcg gcgagcggta tcagctcact   4500
caaaggcggt aatacggtta tccacagaat caggggataa cgcaggaaag aacatgtgag   4560
caaaaggcca gcaaaaggcc aggaaccgta aaaaggccgc gttgctggcg tttttccata   4620
ggctccgccc ccctgacgag catcacaaaa atcgacgctc aagtcagagg tggcgaaacc   4680
cgacaggact ataaagatac caggcgtttc cccctggaag ctccctcgtg cgctctcctg   4740
ttccgaccct gccgcttacc ggatacctgt ccgcctttct cccttcggga agcgtggcgc   4800
tttctcatag ctcacgctgt aggtatctca gttcggtgta ggtcgttcgc tccaagctgg   4860
gctgtgtgca cgaacccccc gttcagcccg accgctgcgc cttatccggt aactatcgtc   4920
ttgagtccaa cccggtaaga cacgacttat cgccactggc agcagccact ggtaacagga   4980
```

```
ttagcagagc gaggtatgta ggcggtgcta cagagttctt gaagtggtgg cctaactacg   5040

gctacactag aagaacagta tttggtatct gcgctctgct gaagccagtt accttcggaa   5100

aaagagttgg tagctcttga tccggcaaac aaaccaccgc tggtagcggt ttttttgttt   5160

gcaagcagca gattacgcgc agaaaaaaag gatctcaaga agatcctttg atcttttcta   5220

cggggtctga cgctcagtgg aacgaaaact cacgttaagg gattttggtc atgagattat   5280

caaaaaggat cttcacctag atccttttaa attaaaaatg aagttttaaa tcaatctaaa   5340

gtatatatga gtaaacttgg tctgacagtt accaatgctt aatcagtgag gcacctatct   5400

cagcgatctg tctatttcgt tcatccatag ttgcctgact ccccgtcgtg tagataacta   5460

cgatacggga gggcttacca tctggcccca gtgctgcaat gataccgcga gacccacgct   5520

caccggctcc agatttatca gcaataaacc agccagccgg aagggccgag cgcagaagtg   5580

gtcctgcaac tttatccgcc tccatccagt ctattaattg ttgccgggaa gctagagtaa   5640

gtagttcgcc agttaatagt ttgcgcaacg ttgttgccat tgctacaggc atcgtggtgt   5700

cacgctcgtc gtttggtatg gcttcattca gctccggttc ccaacgatca aggcgagtta   5760

catgatcccc catgttgtgc aaaaaagcgg ttagctcctt cggtcctccg atcgttgtca   5820

gaagtaagtt ggccgcagtg ttatcactca tggttatggc agcactgcat aattctctta   5880

ctgtcatgcc atccgtaaga tgcttttctg tgactggtga gtactcaacc aagtcattct   5940

gagaatagtg tatgcggcga ccgagttgct cttgcccggc gtcaatacgg gataataccg   6000

cgccacatag cagaacttta aaagtgctca tcattggaaa acgttcttcg gggcgaaaac   6060

tctcaaggat cttaccgctg ttgagatcca gttcgatgta acccactcgt gcacccaact   6120

gatcttcagc atcttttact ttcaccagcg tttctgggtg agcaaaaaca ggaaggcaaa   6180

atgccgcaaa aaagggaata agggcgacac ggaaatgttg aatactcata ctcttccttt   6240

ttcaatatta ttgaagcatt tatcagggtt attgtctcat gagcggatac atatttgaat   6300

gtatttagaa aaataaacaa ataggggttc cgcgcacatt tccccgaaaa gtgccacctg   6360

acgtc                                                               6365
```

<210> SEQ ID NO 46
<211> LENGTH: 476
<212> TYPE: PRT
<213> ORGANISM: artificial
<220> FEATURE:
<223> OTHER INFORMATION: Amino acid sequence of ssBiP+SNAPlike+proTEV+SBV.N+proTEV+Histag (encoded by SEQ ID NO:35)

<400> SEQUENCE: 46

```
Met Lys Leu Cys Ile Leu Leu Ala Val Val Ala Phe Val Gly Leu Ser
1               5                   10                  15

Leu Gly Arg Ser Asp Lys Asp Cys Glu Met Lys Arg Thr Thr Leu Asp
            20                  25                  30

Ser Pro Leu Gly Lys Leu Glu Leu Ser Gly Cys Glu Gln Gly Leu His
        35                  40                  45

Glu Ile Lys Leu Leu Gly Lys Gly Thr Ser Ala Ala Asp Ala Val Glu
    50                  55                  60

Val Pro Ala Pro Ala Ala Val Leu Gly Gly Pro Glu Pro Leu Met Gln
65                  70                  75                  80

Ala Thr Ala Trp Leu Asn Ala Tyr Phe His Gln Pro Glu Ala Ile Glu
                85                  90                  95

Glu Phe Pro Val Pro Ala Leu His His Pro Val Phe Gln Gln Glu Ser
```

-continued

```
            100                 105                 110

Phe Thr Arg Gln Val Leu Trp Lys Leu Leu Lys Val Val Lys Phe Gly
        115                 120                 125

Glu Val Ile Ser Tyr Gln Gln Leu Ala Ala Leu Ala Gly Asn Pro Ala
    130                 135                 140

Ala Thr Ala Ala Val Lys Thr Ala Leu Ser Gly Asn Pro Val Pro Ile
145                 150                 155                 160

Leu Ile Pro Cys His Arg Val Val Ser Ser Ser Gly Ala Val Gly Gly
                165                 170                 175

Tyr Glu Gly Gly Leu Ala Val Lys Glu Trp Leu Leu Ala His Glu Gly
            180                 185                 190

His Arg Leu Gly Lys Pro Gly Leu Gly Pro Ala Gly Ile Gly Ala Pro
        195                 200                 205

Gly Ser Leu Gly Gly Gly Ser Glu Asn Leu Tyr Phe Gln Ser Asp Ile
    210                 215                 220

Ser Ser Gln Phe Ile Phe Glu Asp Val Pro Gln Arg Asn Ala Ala Thr
225                 230                 235                 240

Phe Asn Pro Glu Val Gly Tyr Val Ala Phe Ile Gly Lys Tyr Gly Gln
                245                 250                 255

Gln Leu Asn Phe Gly Val Ala Arg Val Phe Phe Leu Asn Gln Lys Lys
            260                 265                 270

Ala Lys Met Val Leu His Lys Thr Ala Gln Pro Ser Val Asp Leu Thr
        275                 280                 285

Phe Gly Gly Val Lys Phe Thr Val Val Asn Asn His Phe Pro Gln Tyr
    290                 295                 300

Val Ser Asn Pro Val Pro Asp Asn Ala Ile Thr Leu His Arg Met Ser
305                 310                 315                 320

Gly Tyr Leu Ala Arg Trp Ile Ala Asp Thr Cys Lys Ala Ser Val Leu
                325                 330                 335

Lys Leu Ala Glu Ala Ser Ala Gln Ile Val Met Pro Leu Ala Glu Val
            340                 345                 350

Lys Gly Cys Thr Trp Ala Asp Gly Tyr Thr Met Tyr Leu Gly Phe Ala
        355                 360                 365

Pro Gly Ala Glu Met Phe Leu Asp Ala Phe Asp Phe Tyr Pro Leu Val
    370                 375                 380

Ile Glu Met His Arg Val Leu Lys Asp Asn Met Asp Val Asn Phe Met
385                 390                 395                 400

Lys Lys Val Leu Arg Gln Arg Tyr Gly Thr Met Thr Ala Glu Glu Trp
                405                 410                 415

Met Thr Gln Lys Ile Thr Glu Ile Lys Ala Ala Phe Asn Ser Val Gly
            420                 425                 430

Gln Leu Ala Trp Ala Lys Ser Gly Phe Ser Pro Ala Ala Arg Thr Phe
        435                 440                 445

Leu Gln Gln Phe Gly Ile Asn Ile Pro Gly Glu Asn Leu Tyr Phe Gln
    450                 455                 460

Gly Pro Gly Gly Gly Ser His His His His His His
465                 470                 475
```

<210> SEQ ID NO 47
<211> LENGTH: 891
<212> TYPE: DNA
<213> ORGANISM: artificial
<220> FEATURE:
<223> OTHER INFORMATION: Modified DNA sequence encoding enterovirus 71
VP1 (strain JL-AFP-EV71-07-03)

<400> SEQUENCE: 47
ggagataggg tggcagacgt gattgaaagt tccaaaggaa atagtgtgag cagagccctc 60
actcaagctc taccagcacc cacaggtcag aacacacagg tgagcagtca tcgactggat 120
acaggcaagg ttccagcact ccaagctgct gaaattggag catcatcaaa tgctagtgat 180
gagagcatga tcgagacacg ctgtgttctt aactcgcata gcacagctga gaccactctt 240
gatagtttct tcagcagagc ggggttagtt ggagagattg atctccctct tgaaggcaca 300
actaacccaa atggttatgc caactgggac atagatataa caggttacgc gcaaatgcgt 360
agaaaggtgg agctattcac ctacatgcgc tttgatgcag agttcacttt tgttgcgtgc 420
acacccaccg ggaagttgt cccacaattg ctccaataca tgtttgtgcc acctggagcc 480
cctaagccag attccaggga atccctcgca tggcaaactg ccaccaaccc ctcagttttt 540
gtcaagctgt cagaccctcc agcacaagtt tcagtaccat tcatgtcacc tgcgagtgct 600
taccaatggt tttatgacgg ttatcccaca ttcggagaac acaaacagga gaaggatctc 660
gaatatgggg catgtcctaa caacatgatg ggcacgttct cagtgcggac tgtagggacc 720
tccaagtcca agtacccttt agtggttagg atttacatga gaatgaagca cgtcagggcg 780
tggatacctc gcccgatgcg caaccaaaac tacctattca aagccaaccc aaattatgct 840
ggcaactcca ttaagccaac tggtaccagt cgcacagcga tcactactct c 891

<210> SEQ ID NO 48
<211> LENGTH: 1643
<212> TYPE: DNA
<213> ORGANISM: artificial
<220> FEATURE:
<223> OTHER INFORMATION: DNA Sequence of chimeric DeSNAPuniv-EV71.VP1
(ssBiP-SNAPlike- proTEVcleavage site - modified
EV71-VP1-proTEVcleavage site -Histag) for expression in S2 cells

<400> SEQUENCE: 48
atgaagttat gcatattact ggccgtcgtg gtggcctttg ttggcctctc gctcgggaga 60
tctagatctg acaaagactg cgaaatgaaa agaactacat tggattcacc acttgggaag 120
ttggaactga gtggatgcga gcaaggattg catgaaatta agctactggg aaaaggaact 180
tctgctgctg atgcagttga agttccagca ccagcagctg ttcttggagg tcctgagccc 240
ctcatgcaag ccacagcctg gcttaacgca tatttccacc agcctgaggc cattgaggaa 300
tttccagtcc ccgcccttca ccatcctgtg tttcagcagg agagcttcac ccgccaggtc 360
ctgtggaaat tgctgaaggt ggtcaagttt ggtgaagtga tttcatatca gcaacttgct 420
gcattggccg gtaaccccgc agctacagct gccgtgaaaa ctgctctcag cggaaatcct 480
gtgcccatcc tgatcccttg tcacagagtc gtttcatctt ccggagctgt aggtggctat 540
gaaggaggac tggcagttaa ggagtggctg ctggctcatg aaggtcatag acttggaaag 600
cctgggctgg gtcctgctgg tataggcgcg ccagggtccc taggtggcgg atccgaaaac 660
ctgtacttcc agagcgatat cggagatagg gtggcagacg tgattgaaag ttccaaagga 720
aatagtgtga gcagagccct cactcaagct ctaccagcac ccacaggtca gaacacacag 780
gtgagcagtc atcgactgga tacaggcaag gttccagcac tccaagctgc tgaaattgga 840
gcatcatcaa atgctagtga tgagagcatg atcgagacac gctgtgttct taactcgcat 900
agcacagctg agaccactct tgatagtttc ttcagcagag cggggttagt tggagagatt 960
gatctccctc ttgaaggcac aactaaccca aatggttatg ccaactggga catagatata 1020

-continued

```
acaggttacg cgcaaatgcg tagaaaggtg gagctattca cctacatgcg ctttgatgca   1080

gagttcactt ttgttgcgtg cacacccacc ggggaagttg tcccacaatt gctccaatac   1140

atgtttgtgc cacctggagc ccctaagcca gattccaggg aatccctcgc atggcaaact   1200

gccaccaacc cctcagtttt tgtcaagctg tcagaccctc cagcacaagt ttcagtacca   1260

ttcatgtcac ctgcgagtgc ttaccaatgg ttttatgacg gttatcccac attcggagaa   1320

cacaaacagg agaaggatct cgaatatggg gcatgtccta acaacatgat gggcacgttc   1380

tcagtgcgga ctgtagggac ctccaagtcc aagtaccctt tagtggttag gatttacatg   1440

agaatgaagc acgtcagggc gtggatacct cgcccgatgc gcaaccaaaa ctacctattc   1500

aaagccaacc caaattatgc tggcaactcc attaagccaa ctggtaccag tcgcacagcg   1560

atcactactc tcccgggaga gaatctatat tttcaagggc ccggcggagg tagtcaccat   1620

catcaccatc actaatgacc ggt                                           1643


<210> SEQ ID NO 49
<211> LENGTH: 523
<212> TYPE: PRT
<213> ORGANISM: artificial
<220> FEATURE:
<223> OTHER INFORMATION: Amino acid sequence of fusion protein
      [SNAPlike - proTEV - VP1 EV71 - proTEV- Histag]

<400> SEQUENCE: 49

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Gly Asp
        195                 200                 205

Arg Val Ala Asp Val Ile Glu Ser Ser Lys Gly Asn Ser Val Ser Arg
    210                 215                 220

Ala Leu Thr Gln Ala Leu Pro Ala Pro Thr Gly Gln Asn Thr Gln Val
225                 230                 235                 240

Ser Ser His Arg Leu Asp Thr Gly Lys Val Pro Ala Leu Gln Ala Ala
```

```
                245                 250                 255

Glu Ile Gly Ala Ser Ser Asn Ala Ser Asp Glu Ser Met Ile Glu Thr
            260                 265                 270

Arg Cys Val Leu Asn Ser His Ser Thr Ala Glu Thr Thr Leu Asp Ser
        275                 280                 285

Phe Phe Ser Arg Ala Gly Leu Val Gly Glu Ile Asp Leu Pro Leu Glu
    290                 295                 300

Gly Thr Thr Asn Pro Asn Gly Tyr Ala Asn Trp Asp Ile Asp Ile Thr
305                 310                 315                 320

Gly Tyr Ala Gln Met Arg Arg Lys Val Glu Leu Phe Thr Tyr Met Arg
                325                 330                 335

Phe Asp Ala Glu Phe Thr Phe Val Ala Cys Thr Pro Thr Gly Glu Val
            340                 345                 350

Val Pro Gln Leu Leu Gln Tyr Met Phe Val Pro Pro Gly Ala Pro Lys
        355                 360                 365

Pro Asp Ser Arg Glu Ser Leu Ala Trp Gln Thr Ala Thr Asn Pro Ser
    370                 375                 380

Val Phe Val Lys Leu Ser Asp Pro Pro Ala Gln Val Ser Val Pro Phe
385                 390                 395                 400

Met Ser Pro Ala Ser Ala Tyr Gln Trp Phe Tyr Asp Gly Tyr Pro Thr
                405                 410                 415

Phe Gly Glu His Lys Gln Glu Lys Asp Leu Glu Tyr Gly Ala Cys Pro
            420                 425                 430

Asn Asn Met Met Gly Thr Phe Ser Val Arg Thr Val Gly Thr Ser Lys
        435                 440                 445

Ser Lys Tyr Pro Leu Val Val Arg Ile Tyr Met Arg Met Lys His Val
    450                 455                 460

Arg Ala Trp Ile Pro Arg Pro Met Arg Asn Gln Asn Tyr Leu Phe Lys
465                 470                 475                 480

Ala Asn Pro Asn Tyr Ala Gly Asn Ser Ile Lys Pro Thr Gly Thr Ser
                485                 490                 495

Arg Thr Ala Ile Thr Thr Leu Pro Gly Glu Asn Leu Tyr Phe Gln Gly
            500                 505                 510

Pro Gly Gly Gly Ser His His His His His His
        515                 520


<210> SEQ ID NO 50
<211> LENGTH: 2386
<212> TYPE: DNA
<213> ORGANISM: artificial
<220> FEATURE:
<223> OTHER INFORMATION: DNA Sequence encoding chimeric DeSNAPuniv-JE.
      -sE (ssBiP- sE from JEV strain SA-14 -SNAPlike) for expression in
      S2 cells

<400> SEQUENCE: 50

atgaagttat gcatattact ggccgtcgtg gcctttgttg gcctctcgct cgggagatct      60

atgaagttgt cgaatttcca ggggaagctt ttgatgacca tcaacaacac ggacattgca     120

gacgttatcg tgattcccac ctcaaaagga gagaacagat gctgggtccg ggcaatcgac     180

gtcggctaca tgtgtgagga cactatcacg tacgaatgtc ctaagcttac catgggcaat     240

gatccagagg atgtggattg ctggtgtgac aaccaagaag tctacgtcca atatggacgg     300

tgcacgcgga ccaggcattc caagcgaagc aggagatccg tgtcggtcca aacacatggg     360

gagagttcac tagtgaataa aaaagaggct tggctggatt caacgaaagc cacacgatat     420
```

```
ctcatgaaaa ctgagaactg gatcataagg aatcctggct atgctttcct ggcggcggta    480

cttggctgga tgcttggcag taacaacggt caacgcgtgg tatttaccat cctcctgctg    540

ttggtcgctc cggcttacag ttttaattgt ctgggaatgg gcaatcgtga cttcatagaa    600

ggagccagtg gagccacttg ggtggacttg gtgctagaag gagatagctg cttgacaatc    660

atggcaaacg acaaaccaac attggacgtc cgcatgatta acatcgaagc tagccaactt    720

gctgaggtca gaagttactg ctatcatgct tcagtcactg acatctcgac ggtggctcgg    780

tgccccacga ctggagaagc tcacaacgag aagcgagctg atagtagcta tgtgtgcaaa    840

caaggcttca ctgaccgtgg gtggggcaac ggatgtggac ttttcgggaa gggaagcatt    900

gacacatgtg caaaattctc ctgcaccagt aaagcgattg ggagaacaat ccagccagaa    960

aacatcaaat acgaagttgg catttttgtg catggaacca ccacttcgga aaaccatggg   1020

aattattcag cgcaagttgg ggcgtcccag gcggcaaagt ttacagtaac acccaatgct   1080

ccttcgataa ccctcaaact tggtgactac ggagaagtca cactggactg tgagccaagg   1140

agtggactga acactgaagc gttttacgtc atgaccgtgg ggtcaaagtc atttctggtc   1200

catagggagt ggtttcatga cctcgctctc ccctggacgt ccccttcgag cacagcgtgg   1260

agaaacagag aactcctcat ggaatttgaa ggggcgcacg ccacaaaaca gtccgttgtt   1320

gctcttgggt cacaggaagg aggcctccat caggcgttgg caggagccat cgtggtggag   1380

tactcaagct cagtgaagtt aacatcaggc cacctgaaat gtaggctgaa aatggacaaa   1440

ctggctctga aaggcacaac ctatggcatg tgtacagaaa aattctcgtt cgcgaaaaat   1500

ccggcggaca ctggtcacgg aacagttgtc attgaactct cctactctgg gagtgatggc   1560

tcctgcaaaa ttccgattgt ttccgttgcg agcctcaatg acatgacccc cgttgggcgg   1620

ctggtgacag tgaacccctt cgtcgcgact tccagtgcca actcaaaggt gctggtcgag   1680

atggaacccc ccttcggaga ctcctacatc gtagttggaa ggggagacaa gcagatcaac   1740

caccattggc acaaagctgg gcggccgcac ggcggaggta gcaaagactg cgaaatgaag   1800

cgcaccaccc tggatagccc tctgggcaag ctggaactgt ctgggtgcga acagggcctg   1860

cacgagatca agctgctggg caaaggaaca tctgccgccg acgccgtgga agtgcctgcc   1920

ccagccgccg tgctgggcgg accagagcca ctgatgcagg ccaccgcctg gctcaacgcc   1980

tactttcacc agcctgaggc catcgaggag ttccctgtgc cagccctgca ccacccagtg   2040

ttccagcagg agagctttac ccgccaggtg ctgtggaaac tgctgaaagt ggtgaagttc   2100

ggagaggtca tcagctacca gcagctggcc gccctggccg gcaatcccgc cgccaccgcc   2160

gccgtgaaaa ccgccctgag cggaaatccc gtgcccattc tgatcccctg ccaccgggtg   2220

gtgtctagct ctggcgccgt gggggctac gagggcgggc tcgccgtgaa agagtggctg   2280

ctggcccacg agggccacag actgggcaag cctgggctgg gtcctgcagg tataggcgcg   2340

ccagggtccc tggagcatca tcatcatcat cattgatgac gggccc                 2386
```

<210> SEQ ID NO 51
<211> LENGTH: 773
<212> TYPE: PRT
<213> ORGANISM: artificial
<220> FEATURE:
<223> OTHER INFORMATION: Amino acid Sequence of fusion protein [sE from JEV strain SA-14 - SNAPlike - Histag]

<400> SEQUENCE: 51

```
Arg Ser Met Lys Leu Ser Asn Phe Gln Gly Lys Leu Leu Met Thr Ile
1               5                   10                  15
```

```
Asn Asn Thr Asp Ile Ala Asp Val Ile Val Ile Pro Thr Ser Lys Gly
            20                  25                  30

Glu Asn Arg Cys Trp Val Arg Ala Ile Asp Val Gly Tyr Met Cys Glu
        35                  40                  45

Asp Thr Ile Thr Tyr Glu Cys Pro Lys Leu Thr Met Gly Asn Asp Pro
    50                  55                  60

Glu Asp Val Asp Cys Trp Cys Asp Asn Gln Glu Val Tyr Val Gln Tyr
65                  70                  75                  80

Gly Arg Cys Thr Arg Thr Arg His Ser Lys Arg Ser Arg Arg Ser Val
                85                  90                  95

Ser Val Gln Thr His Gly Glu Ser Ser Leu Val Asn Lys Lys Glu Ala
            100                 105                 110

Trp Leu Asp Ser Thr Lys Ala Thr Arg Tyr Leu Met Lys Thr Glu Asn
        115                 120                 125

Trp Ile Ile Arg Asn Pro Gly Tyr Ala Phe Leu Ala Ala Val Leu Gly
    130                 135                 140

Trp Met Leu Gly Ser Asn Asn Gly Gln Arg Val Val Phe Thr Ile Leu
145                 150                 155                 160

Leu Leu Leu Val Ala Pro Ala Tyr Ser Phe Asn Cys Leu Gly Met Gly
                165                 170                 175

Asn Arg Asp Phe Ile Glu Gly Ala Ser Gly Ala Thr Trp Val Asp Leu
            180                 185                 190

Val Leu Glu Gly Asp Ser Cys Leu Thr Ile Met Ala Asn Asp Lys Pro
        195                 200                 205

Thr Leu Asp Val Arg Met Ile Asn Ile Glu Ala Ser Gln Leu Ala Glu
    210                 215                 220

Val Arg Ser Tyr Cys Tyr His Ala Ser Val Thr Asp Ile Ser Thr Val
225                 230                 235                 240

Ala Arg Cys Pro Thr Thr Gly Glu Ala His Asn Glu Lys Arg Ala Asp
                245                 250                 255

Ser Ser Tyr Val Cys Lys Gln Gly Phe Thr Asp Arg Gly Trp Gly Asn
            260                 265                 270

Gly Cys Gly Leu Phe Gly Lys Gly Ser Ile Asp Thr Cys Ala Lys Phe
        275                 280                 285

Ser Cys Thr Ser Lys Ala Ile Gly Arg Thr Ile Gln Pro Glu Asn Ile
    290                 295                 300

Lys Tyr Glu Val Gly Ile Phe Val His Gly Thr Thr Thr Ser Glu Asn
305                 310                 315                 320

His Gly Asn Tyr Ser Ala Gln Val Gly Ala Ser Gln Ala Ala Lys Phe
                325                 330                 335

Thr Val Thr Pro Asn Ala Pro Ser Ile Thr Leu Lys Leu Gly Asp Tyr
            340                 345                 350

Gly Glu Val Thr Leu Asp Cys Glu Pro Arg Ser Gly Leu Asn Thr Glu
        355                 360                 365

Ala Phe Tyr Val Met Thr Val Gly Ser Lys Ser Phe Leu Val His Arg
    370                 375                 380

Glu Trp Phe His Asp Leu Ala Leu Pro Trp Thr Ser Pro Ser Ser Thr
385                 390                 395                 400

Ala Trp Arg Asn Arg Glu Leu Leu Met Glu Phe Glu Gly Ala His Ala
                405                 410                 415

Thr Lys Gln Ser Val Val Ala Leu Gly Ser Gln Glu Gly Gly Leu His
            420                 425                 430
```

```
Gln Ala Leu Ala Gly Ala Ile Val Val Glu Tyr Ser Ser Ser Val Lys
        435                 440                 445

Leu Thr Ser Gly His Leu Lys Cys Arg Leu Lys Met Asp Lys Leu Ala
    450                 455                 460

Leu Lys Gly Thr Thr Tyr Gly Met Cys Thr Glu Lys Phe Ser Phe Ala
465                 470                 475                 480

Lys Asn Pro Ala Asp Thr Gly His Gly Thr Val Val Ile Glu Leu Ser
                485                 490                 495

Tyr Ser Gly Ser Asp Gly Ser Cys Lys Ile Pro Ile Val Ser Val Ala
            500                 505                 510

Ser Leu Asn Asp Met Thr Pro Val Gly Arg Leu Val Thr Val Asn Pro
        515                 520                 525

Phe Val Ala Thr Ser Ser Ala Asn Ser Lys Val Leu Val Glu Met Glu
    530                 535                 540

Pro Pro Phe Gly Asp Ser Tyr Ile Val Val Gly Arg Gly Asp Lys Gln
545                 550                 555                 560

Ile Asn His His Trp His Lys Ala Gly Arg Pro His Gly Gly Gly Ser
                565                 570                 575

Lys Asp Cys Glu Met Lys Arg Thr Thr Leu Asp Ser Pro Leu Gly Lys
            580                 585                 590

Leu Glu Leu Ser Gly Cys Glu Gln Gly Leu His Glu Ile Lys Leu Leu
        595                 600                 605

Gly Lys Gly Thr Ser Ala Ala Asp Ala Val Glu Val Pro Ala Pro Ala
    610                 615                 620

Ala Val Leu Gly Gly Pro Glu Pro Leu Met Gln Ala Thr Ala Trp Leu
625                 630                 635                 640

Asn Ala Tyr Phe His Gln Pro Glu Ala Ile Glu Glu Phe Pro Val Pro
                645                 650                 655

Ala Leu His His Pro Val Phe Gln Gln Glu Ser Phe Thr Arg Gln Val
            660                 665                 670

Leu Trp Lys Leu Leu Lys Val Val Lys Phe Gly Glu Val Ile Ser Tyr
        675                 680                 685

Gln Gln Leu Ala Ala Leu Ala Gly Asn Pro Ala Ala Thr Ala Ala Val
    690                 695                 700

Lys Thr Ala Leu Ser Gly Asn Pro Val Pro Ile Leu Ile Pro Cys His
705                 710                 715                 720

Arg Val Val Ser Ser Ser Gly Ala Val Gly Gly Tyr Glu Gly Gly Leu
                725                 730                 735

Ala Val Lys Glu Trp Leu Leu Ala His Glu Gly His Arg Leu Gly Lys
            740                 745                 750

Pro Gly Leu Gly Pro Ala Gly Ile Gly Ala Pro Gly Ser Leu Glu His
        755                 760                 765

His His His His His
    770
```

<210> SEQ ID NO 52
<211> LENGTH: 1020
<212> TYPE: DNA
<213> ORGANISM: artificial
<220> FEATURE:
<223> OTHER INFORMATION: DNA Sequence encoding the fusion protein BiPlike-SNAPlike-EDIII from Japanese encephalitis virus genotype I cloned into pMT/BiP/SNAP for expression in S2 cells

<400> SEQUENCE: 52
atgaaactat gtattctact tgcagttgtt gcgttcgtag gattgtcctt aagatctgac     60

```
aaagactgcg aaatgaaaag aactacattg gattcaccac ttgggaagtt ggaactgagt    120

ggatgcgagc aaggattgca tgaaattaag ctactgggaa aaggaacttc tgctgctgat    180

gcagttgaag ttccagcacc agcagctgtt cttggaggtc ctgagcccct catgcaagcc    240

acagcctggc ttaacgcata tttccaccag cctgaggcca ttgaggaatt tccagtcccc    300

gcccttcacc atcctgtgtt tcagcaggag agcttcaccc gccaggtcct gtggaaattg    360

ctgaaggtgg tcaagtttgg tgaagtgatt tcatatcagc aacttgctgc attggccggt    420

aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc agggtccctg gagggaggtg gcgggtctgc tctgaagggc    660

acgacttacg gcatgtgtac agaaaaattc tcgttcgcga aaaatccagc ggacacaggc    720

catggaacag ttgtcattga gctcacatac tctggaagcg atggtccctg taaaattccg    780

attgtctcag tcgcgagttt aaacgacatg acccctgtgg ggaggctggt aacagtaaac    840

cccttcgtcg cgacatctag ctccaactca aaggtgctgg ttgagatgga acctcccttc    900

ggagactctt acatcgtggt tggaagaggg gataagcaga ttaaccatca ctggcacaaa    960

gctggaagca cgctgggtaa aggaggtggc catcaccatc accatcactg atgaccggtt   1020
```

```
<210> SEQ ID NO 53
<211> LENGTH: 319
<212> TYPE: PRT
<213> ORGANISM: artificial
<220> FEATURE:
<223> OTHER INFORMATION: Amino acid Sequence of the fusion protein
      SNAPlike-EDIII from Japanese encephalitis virus genotype I -
      Histag

<400> SEQUENCE: 53

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
```

```
            180                 185                 190

Leu Glu Gly Gly Gly Gly Ser Ala Leu Lys Gly Thr Thr Tyr Gly Met
        195                 200                 205

Cys Thr Glu Lys Phe Ser Phe Ala Lys Asn Pro Ala Asp Thr Gly His
    210                 215                 220

Gly Thr Val Val Ile Glu Leu Thr Tyr Ser Gly Ser Asp Gly Pro Cys
225                 230                 235                 240

Lys Ile Pro Ile Val Ser Val Ala Ser Leu Asn Asp Met Thr Pro Val
                245                 250                 255

Gly Arg Leu Val Thr Val Asn Pro Phe Val Ala Thr Ser Ser Ser Asn
            260                 265                 270

Ser Lys Val Leu Val Glu Met Glu Pro Pro Phe Gly Asp Ser Tyr Ile
        275                 280                 285

Val Val Gly Arg Gly Asp Lys Gln Ile Asn His His Trp His Lys Ala
    290                 295                 300

Gly Ser Thr Leu Gly Lys Gly Gly Gly His His His His His His
305                 310                 315
```

<210> SEQ ID NO 54
<211> LENGTH: 406
<212> TYPE: DNA
<213> ORGANISM: artificial
<220> FEATURE:
<223> OTHER INFORMATION: DNA sequence encoding Domain III of envelope E protein from Japanese encephalitis virus of genotype 1 (JE-1.EDIII)

<400> SEQUENCE: 54

```
gcgcgccagg gtccctggag ggaggtggcg ggtctgctct gaagggcacg acttacggca     60

tgtgtacaga aaaattctcg ttcgcgaaaa atccagcgga cacaggccat ggaacagttg    120

tcattgagct cacatactct ggaagcgatg gtccctgtaa aattccgatt gtctcagtcg    180

cgagtttaaa cgacatgacc cctgtgggga ggctggtaac agtaaacccc ttcgtcgcga    240

catctagctc caactcaaag gtgctggttg agatggaacc tcccttcgga gactcttaca    300

tcgtggttgg aagaggggat aagcagatta accatcactg gcacaaagct ggaagcacgc    360

tgggtaaagg aggtggccat caccatcacc atcactgatg accggt                   406
```

<210> SEQ ID NO 55
<211> LENGTH: 406
<212> TYPE: DNA
<213> ORGANISM: artificial
<220> FEATURE:
<223> OTHER INFORMATION: DNA sequence encoding Domain III of envelope E protein from Japanese encephalitis virus of genotype 2 (JE-2.EDIII)

<400> SEQUENCE: 55

```
gcgcgccagg gtccctggag ggaggtggcg ggtctgctct gaaaggcaca acctatggta     60

tgtgcacaga aaactcctcg ttccgaaaaa atccagcgga cacaggccat ggaacagttg    120

tcattgagct cacatactct gggagtgatg gtccctgtaa gattccaaat gtctccgttg    180

cgagcctgaa tgacatgacc cctgtaggga ggctggtaac agtaaacccc tttgtcgcga    240

catccagcgc caactcaaaa gtgctggttg aaatggaacc cccttttgga gattcttaca    300

tcgtggtcgg aagaggtgac aagcagatca atcatcactg gcacaaagct ggaagcacgc    360

tgggcaaagg aggtggccat caccatcacc atcactgatg accggt                   406
```

<210> SEQ ID NO 56
<211> LENGTH: 406
<212> TYPE: DNA
<213> ORGANISM: artificial
<220> FEATURE:
<223> OTHER INFORMATION: DNA sequence encoding Domain III of envelope E protein from Japanese encephalitis virus of genotype 4 (JE-4.EDIII)

<400> SEQUENCE: 56
gcgcgccagg gtccctggag ggaggtggcg ggtctgctct gaaaggcaca acctatggaa 60
tgtgcacaga aaagttctcg tttgcaaaga atccagcaga cactggtcat ggaacagttg 120
tcattgaact cctgtattct ggaagtgacg gcccctgtaa catcccaatt gtctcagtgg 180
tcagtctaaa cgacatgact ccagttggaa ggttggtgac agtgaacccc ttcgttgcca 240
catccagttc caattcaaag gtcttagttg agatggaacc tccttttgga gactcctaca 300
ttgtggtcgg gagaggagaa aaacaaatca accaccactg gcacaaacct ggaagcacat 360
tgggcaaagg aggtggccat caccatcacc atcactgatg accggt 406

<210> SEQ ID NO 57
<211> LENGTH: 406
<212> TYPE: DNA
<213> ORGANISM: artificial
<220> FEATURE:
<223> OTHER INFORMATION: DNA sequence encoding Domain III of envelope E protein from Japanese encephalitis virus of genotype 5 (JE-5.EDIII)

<400> SEQUENCE: 57
gcgcgccagg gtccctggag ggaggtggcg ggtctgcgtt gaaagggacc acctatggta 60
tgtgcacaga gaagttctct ttttccaaga atccagctga cactggtcat ggtacggttg 120
tcatagaatt gcagtacacc ggcactgacg gaccttgcaa gatacccatc tcttcggtgg 180
ccagtctgaa tgatttaact ccagttggta gattggtgac agtcaatcct tttgttgcca 240
catccaccgc caattcgaag gttttggtag aattggaacc accatttgga gattcattca 300
ttgttgtcgg aagaggagat aagcagatca atcaccattg gcacaaggct ggcagttcac 360
tgggaaaggg aggtggccat caccatcacc atcactgatg accggt 406

<210> SEQ ID NO 58
<211> LENGTH: 394
<212> TYPE: DNA
<213> ORGANISM: artificial
<220> FEATURE:
<223> OTHER INFORMATION: DNA sequence of Domain III encoding envelope E protein from Rabensburg virus (RabV.EDIII)

<400> SEQUENCE: 58
gcgcgccagg aggtggcggg tctcagctca aaggaacgac ctatggagta tgcgcaaaag 60
ccttcaagtt ttctgggaat ccagctgaca cagggcatgg caccgtggtc ttagagttgc 120
aatacaccgg aaccgatggt ccttgtaagg tgcctgtctc ttccgtggct tcactcaacg 180
acctaactcc cgttgggaga ctggtgacag tgaatccctt tgttgctgca gctactgcta 240
attcaaaggt tctgatagaa ctggaacctc cattcggtga ctcatacatt gtggtaggta 300
gaggagaaca ccagataaac caccattggc acaagtctgg aagcagtatt ggaaagggag 360
gtggccatca ccatcaccat cactgatgac cggt 394

<210> SEQ ID NO 59
<211> LENGTH: 1020

<212> TYPE: DNA
<213> ORGANISM: artificial
<220> FEATURE:
<223> OTHER INFORMATION: DNA Sequence encoding the fusion protein BiPlike -SNAPlike-EDIII from Japanese encephalitis virus genotype 2 cloned into pMT/BiP/SNAP for expression in S2 cells

<400> SEQUENCE: 59
atgaaactat gtattctact tgcagttgtt gcgttcgtag gattgtcctt aagatctgac 60
aaagactgcg aaatgaaaag aactacattg gattcaccac ttgggaagtt ggaactgagt 120
ggatgcgagc aaggattgca tgaaattaag ctactgggaa aaggaacttc tgctgctgat 180
gcagttgaag ttccagcacc agcagctgtt cttggaggtc ctgagcccct catgcaagcc 240
acagcctggc ttaacgcata tttccaccag cctgaggcca ttgaggaatt tccagtcccc 300
gcccttcacc atcctgtgtt tcagcaggag agcttcaccc gccaggtcct gtggaaattg 360
ctgaaggtgg tcaagtttgg tgaagtgatt tcatatcagc aacttgctgc attggccggt 420
aaccccgcag ctacagctgc cgtgaaaact gctctcagcg gaaatcctgt gcccatcctg 480
atcccttgtc acagagtcgt ttcatcttcc ggagctgtag gtggctatga aggaggactg 540
gcagttaagg agtggctgct ggctcatgaa ggtcatagac ttggaaagcc tgggctgggt 600
cctgctggta taggcgcgcc agggtccctg gagggaggtg gcgggtctgc tctgaaaggc 660
acaacctatg gtatgtgcac agaaaactcc tcgttccgaa aaaatccagc ggacacaggc 720
catggaacag ttgtcattga gctcacatac tctgggagtg atggtccctg taagattcca 780
aatgtctccg ttgcgagcct gaatgacatg acccctgtag ggaggctggt aacagtaaac 840
ccctttgtcg cgacatccag cgccaactca aaagtgctgg ttgaaatgga accccctttt 900
ggagattctt acatcgtggt cggaagaggt gacaagcaga tcaatcatca ctggcacaaa 960
gctggaagca cgctgggcaa aggaggtggc catcaccatc accatcactg atgaccggtt 1020

<210> SEQ ID NO 60
<211> LENGTH: 319
<212> TYPE: PRT
<213> ORGANISM: artificial
<220> FEATURE:
<223> OTHER INFORMATION: Amino acid Sequence of the fusion protein SNAPlike-EDIII from Japanese encephalitis virus genotype 2 - Histag

<400> SEQUENCE: 60

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

Ile Ser Tyr Gln Gln Leu Ala Ala Leu Ala Gly Asn Pro Ala Ala Thr
115 120 125

-continued

```
Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Asn Ser Ser Phe Arg Lys Asn Pro Ala Asp Thr Gly His
    210                 215                 220

Gly Thr Val Val Ile Glu Leu Thr Tyr Ser Gly Ser Asp Gly Pro Cys
225                 230                 235                 240

Lys Ile Pro Asn Val Ser Val Ala Ser Leu Asn Asp Met Thr Pro Val
                245                 250                 255

Gly Arg Leu Val Thr Val Asn Pro Phe Val Ala Thr Ser Ser Ala Asn
            260                 265                 270

Ser Lys Val Leu Val Glu Met Glu Pro Pro Phe Gly Asp Ser Tyr Ile
        275                 280                 285

Val Val Gly Arg Gly Asp Lys Gln Ile Asn His His Trp His Lys Ala
    290                 295                 300

Gly Ser Thr Leu Gly Lys Gly Gly Gly His His His His His His
305                 310                 315
```

<210> SEQ ID NO 61
<211> LENGTH: 1020
<212> TYPE: DNA
<213> ORGANISM: artificial
<220> FEATURE:
<223> OTHER INFORMATION: DNA Sequence encoding the fusion protein BiPlike -SNAPlike-EDIII from Japanese encephalitis virus genotype 4 cloned into pMT/BiP/SNAP for expression in S2 cells

<400> SEQUENCE: 61

```
atgaaactat gtattctact tgcagttgtt gcgttcgtag gattgtcctt aagatctgac     60

aaagactgcg aaatgaaaag aactacattg gattcaccac ttgggaagtt ggaactgagt    120

ggatgcgagc aaggattgca tgaaattaag ctactgggaa aaggaacttc tgctgctgat    180

gcagttgaag ttccagcacc agcagctgtt cttggaggtc ctgagcccct catgcaagcc    240

acagcctggc ttaacgcata tttccaccag cctgaggcca ttgaggaatt tccagtcccc    300

gcccttcacc atcctgtgtt tcagcaggag agcttcaccc gccaggtcct gtggaaattg    360

ctgaaggtgg tcaagtttgg tgaagtgatt tcatatcagc aacttgctgc attggccggt    420

aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc agggtccctg gagggaggtg gcgggtctgc tctgaaaggc    660

acaacctatg gaatgtgcac agaaaagttc tcgtttgcaa agaatccagc agacactggt    720

catggaacag ttgtcattga actcctgtat tctggaagtg acggcccctg taacatccca    780

attgtctcag tggtcagtct aaacgacatg actccagttg gaaggttggt gacagtgaac    840

cccttcgttg ccacatccag ttccaattca aaggtcttag ttgagatgga acctcctttt    900

ggagactcct acattgtggt cgggagagga gaaaaacaaa tcaaccacca ctggcacaaa    960
```

cctggaagca cattgggcaa aggaggtggc catcaccatc accatcactg atgaccggtt 1020

<210> SEQ ID NO 62
<211> LENGTH: 319
<212> TYPE: PRT
<213> ORGANISM: artificial
<220> FEATURE:
<223> OTHER INFORMATION: Amino acid Sequence of the fusion protein SNAPlike-EDIII from Japanese encephalitis virus genotype 4 - Histag

<400> SEQUENCE: 62

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Lys Phe Ser Phe Ala Lys Asn Pro Ala Asp Thr Gly His
    210                 215                 220

Gly Thr Val Val Ile Glu Leu Leu Tyr Ser Gly Ser Asp Gly Pro Cys
225                 230                 235                 240

Asn Ile Pro Ile Val Ser Val Val Ser Leu Asn Asp Met Thr Pro Val
                245                 250                 255

Gly Arg Leu Val Thr Val Asn Pro Phe Val Ala Thr Ser Ser Ser Asn
            260                 265                 270

Ser Lys Val Leu Val Glu Met Glu Pro Pro Phe Gly Asp Ser Tyr Ile
        275                 280                 285

Val Val Gly Arg Gly Glu Lys Gln Ile Asn His His Trp His Lys Pro
    290                 295                 300

Gly Ser Thr Leu Gly Lys Gly Gly Gly His His His His His His
305                 310                 315
```

<210> SEQ ID NO 63
<211> LENGTH: 1020
<212> TYPE: DNA

<213> ORGANISM: artificial
<220> FEATURE:
<223> OTHER INFORMATION: DNA Sequence encoding the fusion protein BiPlike -SNAPlike-EDIII from Japanese encephalitis virus genotype 5 cloned into pMT/BiP/SNAP for expression in S2 cells

<400> SEQUENCE: 63

```
atgaaactat gtattctact tgcagttgtt gcgttcgtag gattgtcctt aagatctgac     60

aaagactgcg aaatgaaaag aactacattg gattcaccac ttgggaagtt ggaactgagt    120

ggatgcgagc aaggattgca tgaaattaag ctactgggaa aaggaacttc tgctgctgat    180

gcagttgaag ttccagcacc agcagctgtt cttggaggtc ctgagcccct catgcaagcc    240

acagcctggc ttaacgcata tttccaccag cctgaggcca ttgaggaatt tccagtcccc    300

gcccttcacc atcctgtgtt tcagcaggag agcttcaccc gccaggtcct gtggaaattg    360

ctgaaggtgg tcaagtttgg tgaagtgatt tcatatcagc aacttgctgc attggccggt    420

aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc agggtccctg gagggaggtg gcgggtctgc gttgaaaggg    660

accacctatg gtatgtgcac agagaagttc tctttttcca agaatccagc tgacactggt    720

catggtacgg ttgtcataga attgcagtac accggcactg acggaccttg caagataccc    780

atctcttcgg tggccagtct gaatgattta actccagttg gtagattggt gacagtcaat    840

ccttttgttg ccacatccac cgccaattcg aaggttttgg tagaattgga accaccattt    900

ggagattcat tcattgttgt cggaagagga gataagcaga tcaatcacca ttggcacaag    960

gctggcagtt cactgggaaa gggaggtggc catcaccatc accatcactg atgaccggtt   1020
```

<210> SEQ ID NO 64
<211> LENGTH: 319
<212> TYPE: PRT
<213> ORGANISM: artificial
<220> FEATURE:
<223> OTHER INFORMATION: Amino acid Sequence of the fusion protein SNAPlike-EDIII from Japanese encephalitis virus genotype 5 - Histag

<400> SEQUENCE: 64

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
```

```
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Ala Leu Lys Gly Thr Thr Tyr Gly Met
        195                 200                 205

Cys Thr Glu Lys Phe Ser Phe Ser Lys Asn Pro Ala Asp Thr Gly His
    210                 215                 220

Gly Thr Val Val Ile Glu Leu Gln Tyr Thr Gly Thr Asp Gly Pro Cys
225                 230                 235                 240

Lys Ile Pro Ile Ser Ser Val Ala Ser Leu Asn Asp Leu Thr Pro Val
                245                 250                 255

Gly Arg Leu Val Thr Val Asn Pro Phe Val Ala Thr Ser Thr Ala Asn
            260                 265                 270

Ser Lys Val Leu Val Glu Leu Glu Pro Pro Phe Gly Asp Ser Phe Ile
        275                 280                 285

Val Val Gly Arg Gly Asp Lys Gln Ile Asn His His Trp His Lys Ala
    290                 295                 300

Gly Ser Ser Leu Gly Lys Gly Gly Gly His His His His His His
305                 310                 315


<210> SEQ ID NO 65
<211> LENGTH: 1008
<212> TYPE: DNA
<213> ORGANISM: artificial
<220> FEATURE:
<223> OTHER INFORMATION: DNA Sequence encoding the fusion protein
      BiPlike -SNAPlike-EDIII from Rabensburg virus cloned into
      pMT/BiP/SNAP for expression in S2 cells

<400> SEQUENCE: 65

atgaaactat gtattctact tgcagttgtt gcgttcgtag gattgtcctt aagatctgac     60

aaagactgcg aaatgaaaag aactacattg gattcaccac ttgggaagtt ggaactgagt    120

ggatgcgagc aaggattgca tgaaattaag ctactgggaa aaggaacttc tgctgctgat    180

gcagttgaag ttccagcacc agcagctgtt cttggaggtc ctgagcccct catgcaagcc    240

acagcctggc ttaacgcata tttccaccag cctgaggcca ttgaggaatt tccagtcccc    300

gcccttcacc atcctgtgtt tcagcaggag agcttcaccc gccaggtcct gtggaaattg    360

ctgaaggtgg tcaagtttgg tgaagtgatt tcatatcagc aacttgctgc attggccggt    420

aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc aggaggtggc gggtctcagc tcaaaggaac gacctatgga    660

gtatgcgcaa aagccttcaa gttttctggg aatccagctg acacagggca tggcaccgtg    720

gtcttagagt tgcaatacac cggaaccgat ggtccttgta aggtgcctgt ctcttccgtg    780

gcttcactca acgacctaac tcccgttggg agactggtga cagtgaatcc ctttgttgct    840

gcagctactg ctaattcaaa ggttctgata gaactggaac ctccattcgg tgactcatac    900

attgtggtag gtagaggaga acaccagata aaccaccatt ggcacaagtc tggaagcagt    960
```

-continued attggaaagg gaggtggcca tcaccatcac catcactgat gaccggtt 1008

<210> SEQ ID NO 66
<211> LENGTH: 314
<212> TYPE: PRT
<213> ORGANISM: artificial
<220> FEATURE:
<223> OTHER INFORMATION: Amino acid Sequence of the fusion protein SNAPlike-EDIII from Rabensburg virus - Histag

<400> SEQUENCE: 66

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Ser Gln Leu Lys Gly Thr Thr Tyr Gly Val Cys Ala Lys Ala
        195                 200                 205

Phe Lys Phe Ser Gly Asn Pro Ala Asp Thr Gly His Gly Thr Val Val
    210                 215                 220

Leu Glu Leu Gln Tyr Thr Gly Thr Asp Gly Pro Cys Lys Val Pro Val
225                 230                 235                 240

Ser Ser Val Ala Ser Leu Asn Asp Leu Thr Pro Val Gly Arg Leu Val
                245                 250                 255

Thr Val Asn Pro Phe Val Ala Ala Ala Thr Ala Asn Ser Lys Val Leu
            260                 265                 270

Ile Glu Leu Glu Pro Pro Phe Gly Asp Ser Tyr Ile Val Val Gly Arg
        275                 280                 285

Gly Glu His Gln Ile Asn His His Trp His Lys Ser Gly Ser Ser Ile
    290                 295                 300

Gly Lys Gly Gly Gly His His His His His
305                 310
```

<210> SEQ ID NO 67
<211> LENGTH: 977
<212> TYPE: DNA
<213> ORGANISM: artificial
<220> FEATURE:

<223> OTHER INFORMATION: DNA Sequence encoding the fusion protein ssBiP-SNAPlike-EDIII from an insect flavivirus virus cloned into pMT/BiP/SNAP for expression in S2 cells

<400> SEQUENCE: 67

```
atgaaactat gtattctact tgcagttgtt gcgttcgtag gattgtcctt aagatctgac      60

aaagactgcg aaatgaaaag aactacattg gattcaccac ttgggaagtt ggaactgagt     120

ggatgcgagc aaggattgca tgaaattaag ctactgggaa aaggaacttc tgctgctgat     180

gcagttgaag ttccagcacc agcagctgtt cttggaggtc ctgagcccct catgcaagcc     240

acagcctggc ttaacgcata tttccaccag cctgaggcca ttgaggaatt tccagtcccc     300

gcccttcacc atcctgtgtt tcagcaggag agcttcaccc gccaggtcct gtggaaattg     360

ctgaaggtgg tcaagtttgg tgaagtgatt tcatatcagc aacttgctgc attggccggt     420

aaccccgcag ctacagctgc cgtgaaaact gctctcagcg gaaatcctgt gcccatcctg     480

atcccttgtc acagagtcgt ttcatcttcc ggagctgtag gtggctatga aggaggactg     540

gcagttaagg agtggctgct ggctcatgaa ggtcatagac ttggaaagcc tgggctgggt     600

cctgctggta taggcgcgcc aggaggtggc ggggaagcgc agacagtgtt ctctcaatcc     660

ccttgggggt tcgaaggaat agcggagata acactaaaag aggcccaaaa gagcatttgt     720

tcactacctt tgtcttgtgt gggctgtagc ttgttgtctt ccaaggtcgt tttccttgag     780

acaacaacga aagctgccgt ccacgttgga tgtgggaatg gaacttctgt tctaacagtt     840

ggaactactc ctgtgagtat cgactgtgta gtaacgcccc tgtcgcaggt gtggaggctc     900

gtgtcgcacg tcaccggaag atacaccaaa cttgggtttg gaggtggcca tcaccatcac     960

catcactgat gaccggt                                                    977
```

<210> SEQ ID NO 68
<211> LENGTH: 305
<212> TYPE: PRT
<213> ORGANISM: artificial
<220> FEATURE:
<223> OTHER INFORMATION: Amino acid Sequence of the fusion protein SNAPlike-EDIII from a insect flavivirus - Histag

<400> SEQUENCE: 68

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
```

-continued

```
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Glu Ala Gln Thr Val Phe Ser Gln Ser Pro Trp Gly Phe Glu
        195                 200                 205

Gly Ile Ala Glu Ile Thr Leu Lys Glu Ala Gln Lys Ser Ile Cys Ser
    210                 215                 220

Leu Pro Leu Ser Cys Val Gly Cys Ser Leu Leu Ser Ser Lys Val Val
225                 230                 235                 240

Phe Leu Glu Thr Thr Thr Lys Ala Ala Val His Val Gly Cys Gly Asn
                245                 250                 255

Gly Thr Ser Val Leu Thr Val Gly Thr Thr Pro Val Ser Ile Asp Cys
            260                 265                 270

Val Val Thr Pro Leu Ser Gln Val Trp Arg Leu Val Ser His Val Thr
        275                 280                 285

Gly Arg Tyr Thr Lys Leu Gly Phe Gly Gly Gly His His His His His
    290                 295                 300

His
305
```

<210> SEQ ID NO 69
<211> LENGTH: 1783
<212> TYPE: DNA
<213> ORGANISM: artificial
<220> FEATURE:
<223> OTHER INFORMATION: DNA sequence encoding ssBiP-sE2 from Ross River virus strain QML-1 -SNAPlike-Histag for expression in S2 cells

<400> SEQUENCE: 69

```
atgaagttat gcatattact ggccgtcgtg gcctttgttg gcctctcgct cgggagatct     60

agtgtaacag agcacttcaa tgtgtataag gctactagac catacctagc acattgcgct    120

gattgcgggg acgggtactt ctgctatagc ccagttgcca tcgagaagat ccgagatgag    180

gcgtctgatg gcatgctcaa gatccaagtc tccgcccaaa taggtctgga caaggcaggc    240

acccacgccc acacgaagct ccgatatatg gctggtcacg atgttcagga atctaagaga    300

gattccttga gggtgtacac gtccgcagcg tgctccatac atgggacgat gggacacttc    360

atcgtcgcac actgtccacc aggcgactac ctcaaggttt cgttcgagga cgcagattcg    420

cacgtgaagg catgtaaggt ccaatacaag cacaatccat tgccggtggg tagagagaag    480

ttcgtggtta gaccacactt tggcgtagag ctgccatgca cctcatacca gctgacaacg    540

gctcccaccg acgaggagat tgacatgcat acaccgccag atataccgga tcgcaccctg    600

ctatcacaga cggcgggcaa cgtcaaaata acagcaggcg gcaggactat caggtacaat    660

tgtacctgcg gccgtgacaa cgtaggcact accagtactg acaagaccat caacacatgc    720

aagattgacc aatgccatgc tgccgtcacc agccatgaca aatggcaatt tacctctcca    780

tttgttccca gggctgatca gacagctagg aaaggcaagg tacacgttcc gttccctctg    840

actaacgtca cctgccgagt gccgttggct cgagcgccgg atgtcaccta tggtaagaag    900

gaggtgaccc tgagattaca cccagatcat ccgacactct tctcctatag gagtttagga    960

gccgaaccgc acccgtacga ggaatgggtt gacaagttct ctgagcgcat catcccagtg   1020

acggaagaag ggattgaata ccagtggggc aacaacccgc cggtccgcct gtgggcgcaa   1080
```

```
ctgacgaccg agggcaaacc ccatggatgg ccacatgaaa tcattcagta ctattatgga   1140

ctataccccg ccgccacgcg gccgcacggc ggaggtagca aagactgcga aatgaagcgc   1200

accaccctgg atagccctct gggcaagctg gaactgtctg ggtgcgaaca gggcctgcac   1260

gagatcaagc tgctgggcaa aggaacatct gccgccgacg ccgtggaagt gcctgcccca   1320

gccgccgtgc tgggcggacc agagccactg atgcaggcca ccgcctggct caacgcctac   1380

tttcaccagc ctgaggccat cgaggagttc cctgtgccag ccctgcacca cccagtgttc   1440

cagcaggaga gctttacccg ccaggtgctg tggaaactgc tgaaagtggt gaagttcgga   1500

gaggtcatca gctaccagca gctggccgcc ctggccggca atcccgccgc caccgccgcc   1560

gtgaaaaccg ccctgagcgg aaatcccgtg cccattctga tcccctgcca ccgggtggtg   1620

tctagctctg gcgccgtggg gggctacgag ggcgggctcg ccgtgaaaga gtggctgctg   1680

gcccacgagg gccacagact gggcaagcct gggctgggtc ctgcaggtat aggcgcgcca   1740

gggtccctgg agcatcatca tcatcatcat tgatgacggg ccc                     1783


<210> SEQ ID NO 70
<211> LENGTH: 572
<212> TYPE: PRT
<213> ORGANISM: artificial
<220> FEATURE:
<223> OTHER INFORMATION: Amino acid sequence of the fusion protein [sE2
      from Ross River virus strain QML-1 -SNAPlike-Histag]

<400> SEQUENCE: 70

Arg Ser Ser Val Thr Glu His Phe Asn Val Tyr Lys Ala Thr Arg Pro
1               5                   10                  15

Tyr Leu Ala His Cys Ala Asp Cys Gly Asp Gly Tyr Phe Cys Tyr Ser
            20                  25                  30

Pro Val Ala Ile Glu Lys Ile Arg Asp Glu Ala Ser Asp Gly Met Leu
        35                  40                  45

Lys Ile Gln Val Ser Ala Gln Ile Gly Leu Asp Lys Ala Gly Thr His
    50                  55                  60

Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
            100                 105                 110

Leu Lys Val Ser Phe Glu Asp Ala Asp Ser His Val Lys Ala Cys Lys
        115                 120                 125

Val Gln Tyr Lys His Asn Pro Leu Pro Val Gly Arg Glu Lys Phe Val
    130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
            180                 185                 190

Thr Ala Gly Gly Arg Thr Ile Arg Tyr Asn Cys Thr Cys Gly Arg Asp
        195                 200                 205

Asn Val Gly Thr Thr Ser Thr Asp Lys Thr Ile Asn Thr Cys Lys Ile
    210                 215                 220

Asp Gln Cys His Ala Ala Val Thr Ser His Asp Lys Trp Gln Phe Thr
225                 230                 235                 240
```

```
Ser Pro Phe Val Pro Arg Ala Asp Gln Thr Ala Arg Lys Gly Lys Val
                245                 250                 255

His Val Pro Phe Pro Leu Thr Asn Val Thr Cys Arg Val Pro Leu Ala
            260                 265                 270

Arg Ala Pro Asp Val Thr Tyr Gly Lys Lys Glu Val Thr Leu Arg Leu
        275                 280                 285

His Pro Asp His Pro Thr Leu Phe Ser Tyr Arg Ser Leu Gly Ala Glu
    290                 295                 300

Pro His Pro Tyr Glu Glu Trp Val Asp Lys Phe Ser Glu Arg Ile Ile
305                 310                 315                 320

Pro Val Thr Glu Glu Gly Ile Glu Tyr Gln Trp Gly Asn Asn Pro Pro
                325                 330                 335

Val Arg Leu Trp Ala Gln Leu Thr Thr Glu Gly Lys Pro His Gly Trp
            340                 345                 350

Pro His Glu Ile Ile Gln Tyr Tyr Tyr Gly Leu Tyr Pro Ala Ala Thr
        355                 360                 365

Arg Pro His Gly Gly Gly Ser Lys Asp Cys Glu Met Lys Arg Thr Thr
    370                 375                 380

Leu Asp Ser Pro Leu Gly Lys Leu Glu Leu Ser Gly Cys Glu Gln Gly
385                 390                 395                 400

Leu His Glu Ile Lys Leu Leu Gly Lys Gly Thr Ser Ala Ala Asp Ala
                405                 410                 415

Val Glu Val Pro Ala Pro Ala Ala Val Leu Gly Gly Pro Glu Pro Leu
            420                 425                 430

Met Gln Ala Thr Ala Trp Leu Asn Ala Tyr Phe His Gln Pro Glu Ala
        435                 440                 445

Ile Glu Glu Phe Pro Val Pro Ala Leu His His Pro Val Phe Gln Gln
    450                 455                 460

Glu Ser Phe Thr Arg Gln Val Leu Trp Lys Leu Leu Lys Val Val Lys
465                 470                 475                 480

Phe Gly Glu Val Ile Ser Tyr Gln Gln Leu Ala Ala Leu Ala Gly Asn
                485                 490                 495

Pro Ala Ala Thr Ala Ala Val Lys Thr Ala Leu Ser Gly Asn Pro Val
            500                 505                 510

Pro Ile Leu Ile Pro Cys His Arg Val Val Ser Ser Ser Gly Ala Val
        515                 520                 525

Gly Gly Tyr Glu Gly Gly Leu Ala Val Lys Glu Trp Leu Leu Ala His
    530                 535                 540

Glu Gly His Arg Leu Gly Lys Pro Gly Leu Gly Pro Ala Gly Ile Gly
545                 550                 555                 560

Ala Pro Gly Ser Leu Glu His His His His His His
                565                 570
```

<210> SEQ ID NO 71
<211> LENGTH: 1783
<212> TYPE: DNA
<213> ORGANISM: artificial
<220> FEATURE:
<223> OTHER INFORMATION: DNA sequence encoding ssBiP-sE2 from Mayaro virus strain IQD2668 -SNAPlike-Histag for expression in S2 cells

<400> SEQUENCE: 71

```
atgaagttat gcatattact ggccgtcgtg gcctttgttg gcctctcgct cgggagatct     60

agtgtaacag agcacttcaa tgtgtataag gctactagac catacctagc acattgcgct    120
```

```
gattgcgggg acgggtactt ctgctatagc ccagttgcca tcgagaagat ccgagatgag    180

gcgtctgatg gcatgctcaa gatccaagtc tccgcccaaa taggtctgga caaggcaggc    240

acccacgccc acacgaagct ccgatatatg gctggtcacg atgttcagga atctaagaga    300

gattccttga gggtgtacac gtccgcagcg tgctccatac atgggacgat gggacacttc    360

atcgtcgcac actgtccacc aggcgactac ctcaaggttt cgttcgagga cgcagattcg    420

cacgtgaagg catgtaaggt ccaatacaag cacaatccat tgccggtggg tagagagaag    480

ttcgtggtta gaccacactt tggcgtagag ctgccatgca cctcatacca gctgacaacg    540

gctcccaccg acgaggagat tgacatgcat acaccgccag atataccgga tcgcaccctg    600

ctatcacaga cggcgggcaa cgtcaaaata acagcaggcg gcaggactat caggtacaat    660

tgtacctgcg gccgtgacaa cgtaggcact accagtactg acaagaccat caacacatgc    720

aagattgacc aatgccatgc tgccgtcacc agccatgaca aatggcaatt tacctctcca    780

tttgttccca gggctgatca gacagctagg aaaggcaagg tacacgttcc gttccctctg    840

actaacgtca cctgccgagt gccgttggct cgagcgccgg atgtcaccta tggtaagaag    900

gaggtgaccc tgagattaca cccagatcat ccgacactct tctcctatag gagtttagga    960

gccgaaccgc acccgtacga ggaatgggtt gacaagttct ctgagcgcat catcccagtg   1020

acggaagaag ggattgaata ccagtggggc aacaacccgc cggtccgcct gtgggcgcaa   1080

ctgacgaccg agggcaaacc ccatggatgg ccacatgaaa tcattcagta ctattatgga   1140

ctataccccg ccgccacgcg gccgcacggc ggaggtagca aagactgcga aatgaagcgc   1200

accaccctgg atagccctct gggcaagctg gaactgtctg ggtgcgaaca gggcctgcac   1260

gagatcaagc tgctgggcaa aggaacatct gccgccgacg ccgtggaagt gcctgcccca   1320

gccgccgtgc tgggcggacc agagccactg atgcaggcca ccgcctggct caacgcctac   1380

tttcaccagc ctgaggccat cgaggagttc cctgtgccag ccctgcacca cccagtgttc   1440

cagcaggaga gctttacccg ccaggtgctg tggaaactgc tgaaagtggt gaagttcgga   1500

gaggtcatca gctaccagca gctggccgcc ctggccggca atcccgccgc caccgccgcc   1560

gtgaaaaccg ccctgagcgg aaatcccgtg cccattctga tcccctgcca ccgggtggtg   1620

tctagctctg gcgccgtggg gggctacgag ggcgggctcg ccgtgaaaga gtggctgctg   1680

gcccacgagg gccacagact gggcaagcct gggctgggtc ctgcaggtat aggcgcgcca   1740

gggtccctgg agcatcatca tcatcatcat tgatgacggg ccc                     1783
```

```
<210> SEQ ID NO 72
<211> LENGTH: 572
<212> TYPE: PRT
<213> ORGANISM: artificial
<220> FEATURE:
<223> OTHER INFORMATION: Amino acid sequence of the fusion protein [sE2
      from Mayaro virus strain IQD2668 -SNAPlike-Histag]

<400> SEQUENCE: 72

Arg Ser Ser Val Thr Glu His Phe Asn Val Tyr Lys Ala Thr Arg Pro
1               5                   10                  15

Tyr Leu Ala His Cys Ala Asp Cys Gly Asp Gly Tyr Phe Cys Tyr Ser
            20                  25                  30

Pro Val Ala Ile Glu Lys Ile Arg Asp Glu Ala Ser Asp Gly Met Leu
        35                  40                  45

Lys Ile Gln Val Ser Ala Gln Ile Gly Leu Asp Lys Ala Gly Thr His
    50                  55                  60
```

-continued

```
Ala His Thr Lys Leu Arg Tyr Met Ala Gly His Asp Val Gln Glu Ser
65                  70                  75                  80

Lys Arg Asp Ser Leu Arg Val Tyr Thr Ser Ala Ala Cys Ser Ile His
                85                  90                  95

Gly Thr Met Gly His Phe Ile Val Ala His Cys Pro Pro Gly Asp Tyr
            100                 105                 110

Leu Lys Val Ser Phe Glu Asp Ala Asp Ser His Val Lys Ala Cys Lys
        115                 120                 125

Val Gln Tyr Lys His Asn Pro Leu Pro Val Gly Arg Glu Lys Phe Val
    130                 135                 140

Val Arg Pro His Phe Gly Val Glu Leu Pro Cys Thr Ser Tyr Gln Leu
145                 150                 155                 160

Thr Thr Ala Pro Thr Asp Glu Glu Ile Asp Met His Thr Pro Pro Asp
                165                 170                 175

Ile Pro Asp Arg Thr Leu Leu Ser Gln Thr Ala Gly Asn Val Lys Ile
            180                 185                 190

Thr Ala Gly Gly Arg Thr Ile Arg Tyr Asn Cys Thr Cys Gly Arg Asp
        195                 200                 205

Asn Val Gly Thr Thr Ser Thr Asp Lys Thr Ile Asn Thr Cys Lys Ile
    210                 215                 220

Asp Gln Cys His Ala Ala Val Thr Ser His Asp Lys Trp Gln Phe Thr
225                 230                 235                 240

Ser Pro Phe Val Pro Arg Ala Asp Gln Thr Ala Arg Lys Gly Lys Val
                245                 250                 255

His Val Pro Phe Pro Leu Thr Asn Val Thr Cys Arg Val Pro Leu Ala
            260                 265                 270

Arg Ala Pro Asp Val Thr Tyr Gly Lys Lys Glu Val Thr Leu Arg Leu
        275                 280                 285

His Pro Asp His Pro Thr Leu Phe Ser Tyr Arg Ser Leu Gly Ala Glu
    290                 295                 300

Pro His Pro Tyr Glu Glu Trp Val Asp Lys Phe Ser Glu Arg Ile Ile
305                 310                 315                 320

Pro Val Thr Glu Glu Gly Ile Glu Tyr Gln Trp Gly Asn Asn Pro Pro
                325                 330                 335

Val Arg Leu Trp Ala Gln Leu Thr Thr Glu Gly Lys Pro His Gly Trp
            340                 345                 350

Pro His Glu Ile Ile Gln Tyr Tyr Tyr Gly Leu Tyr Pro Ala Ala Thr
        355                 360                 365

Arg Pro His Gly Gly Gly Ser Lys Asp Cys Glu Met Lys Arg Thr Thr
    370                 375                 380

Leu Asp Ser Pro Leu Gly Lys Leu Glu Leu Ser Gly Cys Glu Gln Gly
385                 390                 395                 400

Leu His Glu Ile Lys Leu Leu Gly Lys Gly Thr Ser Ala Ala Asp Ala
                405                 410                 415

Val Glu Val Pro Ala Pro Ala Ala Val Leu Gly Gly Pro Glu Pro Leu
            420                 425                 430

Met Gln Ala Thr Ala Trp Leu Asn Ala Tyr Phe His Gln Pro Glu Ala
        435                 440                 445

Ile Glu Glu Phe Pro Val Pro Ala Leu His His Pro Val Phe Gln Gln
    450                 455                 460

Glu Ser Phe Thr Arg Gln Val Leu Trp Lys Leu Leu Lys Val Val Lys
465                 470                 475                 480

Phe Gly Glu Val Ile Ser Tyr Gln Gln Leu Ala Ala Leu Ala Gly Asn
```

```
                485                 490                 495

Pro Ala Ala Thr Ala Ala Val Lys Thr Ala Leu Ser Gly Asn Pro Val
            500                 505                 510

Pro Ile Leu Ile Pro Cys His Arg Val Val Ser Ser Ser Gly Ala Val
        515                 520                 525

Gly Gly Tyr Glu Gly Gly Leu Ala Val Lys Glu Trp Leu Leu Ala His
    530                 535                 540

Glu Gly His Arg Leu Gly Lys Pro Gly Leu Gly Pro Ala Gly Ile Gly
545                 550                 555                 560

Ala Pro Gly Ser Leu Glu His His His His His His
                565                 570


<210> SEQ ID NO 73
<211> LENGTH: 1786
<212> TYPE: DNA
<213> ORGANISM: artificial
<220> FEATURE:
<223> OTHER INFORMATION: DNA sequence encoding ssBiP-sE2 from Western
      Equine Encephalitis virus -SNAPlike-Histag for expression in S2
      cells

<400> SEQUENCE: 73

atgaagttat gcatattact ggccgtcgtg gcctttgttg gcctctcgct cgggagatct     60

agcattaccg atgacttcac actgaccagt ccctacctgg ggttctgccc gtattgcaga    120

cactcaacgc cgtgtttcag cccaataaaa attgagaacg tgtgggacga atctgatgat    180

ggatcgatta gaatccaggt ctcggcacaa ttcggctaca atcaggcagg cactgcggat    240

gtcaccaaat tccgttacat gtctttcgac cacgaccatg acatcaagga agacagtatg    300

gagaaaatag ctatcagcac atctggaccc tgccgtcgtc ttggccacaa agggtacttc    360

ctgttagctc aatgtcctcc aggtgacagt gtaaccgtca gtatcacgag cggagcatct    420

gagaattcat gcaccgtgga gaaaaagatc aggaggaagt ttgtcggtag agaggagtac    480

ttgttcccac ccgtccatgg aaagctggta aagtgccacg tttacgatca cttgaaggag    540

acgtctgccg ggtacataac catgcacagg ccaggcccac acgcgtataa gtcctatctg    600

gaggaagcgt caggcgaagt gtacattaaa ccaccttctg gcaagaacgt cacctacgaa    660

tgtaagtgtg gcgactacag cacaggtatc gtgagcacgc gaacgaagat gaacggctgc    720

actaaagcaa aacagtgcat tgcctacaag agcgaccaaa cgaaatgggt cttcaactcg    780

ccggatctta ttaggcacac agaccactca gtgcaaggta aattgcacat tccattccgc    840

ttgacaccga cagtctgccc ggttccgtta gctcacacgc ctacagtcac gaagtggttc    900

aaaggcatca ccctccacct gactgcaatg cgaccaacat tgctgacaac gagaaaattg    960

gggctgcgag cagacgcaac agcagaatgg attacagggt ctacatccag gaattttct    1020

gtggggcgag aagggctgga gtacgtatgg ggtaaccatg aaccagtcag agtctgggcc   1080

caggagtcgg caccaggcga cccacatgga tggccgcatg agatcatcat ccactattat   1140

catcggcatc cagtctacac gcggccgcac ggcggaggta gcaaagactg cgaaatgaag   1200

cgcaccaccc tggatagccc tctgggcaag ctggaactgt ctgggtgcga acagggcctg   1260

cacgagatca agctgctggg caaaggaaca tctgccgccg acgccgtgga agtgcctgcc   1320

ccagccgccg tgctgggcgg accagagcca ctgatgcagg ccaccgcctg gctcaacgcc   1380

tactttcacc agcctgaggc catcgaggag ttccctgtgc cagccctgca ccacccagtg   1440

ttccagcagg agagctttac ccgccaggtg ctgtggaaac tgctgaaagt ggtgaagttc   1500
```

-continued

```
ggagaggtca tcagctacca gcagctggcc gccctggccg gcaatcccgc cgccaccgcc   1560

gccgtgaaaa ccgccctgag cggaaatccc gtgcccattc tgatcccctg ccaccgggtg   1620

gtgtctagct ctggcgccgt ggggggctac gagggcgggc tcgccgtgaa agagtggctg   1680

ctggcccacg agggccacag actgggcaag cctgggctgg gtcctgcagg tataggcgcg   1740

ccagggtccc tggagcatca tcatcatcat cattgatgac gggccc                  1786
```

<210> SEQ ID NO 74
<211> LENGTH: 573
<212> TYPE: PRT
<213> ORGANISM: artificial
<220> FEATURE:
<223> OTHER INFORMATION: Amino acid sequence of the fusion protein [sE2 from Western Equine Encephalitis -SNAPlike-Histag]

<400> SEQUENCE: 74

```
Arg Ser Ser Ile Thr Asp Asp Phe Thr Leu Thr Ser Pro Tyr Leu Gly
1               5                   10                  15

Phe Cys Pro Tyr Cys Arg His Ser Thr Pro Cys Phe Ser Pro Ile Lys
            20                  25                  30

Ile Glu Asn Val Trp Asp Glu Ser Asp Asp Gly Ser Ile Arg Ile Gln
        35                  40                  45

Val Ser Ala Gln Phe Gly Tyr Asn Gln Ala Gly Thr Ala Asp Val Thr
    50                  55                  60

Lys Phe Arg Tyr Met Ser Phe Asp His Asp His Asp Ile Lys Glu Asp
65                  70                  75                  80

Ser Met Glu Lys Ile Ala Ile Ser Thr Ser Gly Pro Cys Arg Arg Leu
                85                  90                  95

Gly His Lys Gly Tyr Phe Leu Leu Ala Gln Cys Pro Pro Gly Asp Ser
            100                 105                 110

Val Thr Val Ser Ile Thr Ser Gly Ala Ser Glu Asn Ser Cys Thr Val
        115                 120                 125

Glu Lys Lys Ile Arg Arg Lys Phe Val Gly Arg Glu Glu Tyr Leu Phe
    130                 135                 140

Pro Pro Val His Gly Lys Leu Val Lys Cys His Val Tyr Asp His Leu
145                 150                 155                 160

Lys Glu Thr Ser Ala Gly Tyr Ile Thr Met His Arg Pro Gly Pro His
                165                 170                 175

Ala Tyr Lys Ser Tyr Leu Glu Glu Ala Ser Gly Glu Val Tyr Ile Lys
            180                 185                 190

Pro Pro Ser Gly Lys Asn Val Thr Tyr Glu Cys Lys Cys Gly Asp Tyr
        195                 200                 205

Ser Thr Gly Ile Val Ser Thr Arg Thr Lys Met Asn Gly Cys Thr Lys
    210                 215                 220

Ala Lys Gln Cys Ile Ala Tyr Lys Ser Asp Gln Thr Lys Trp Val Phe
225                 230                 235                 240

Asn Ser Pro Asp Leu Ile Arg His Thr Asp His Ser Val Gln Gly Lys
                245                 250                 255

Leu His Ile Pro Phe Arg Leu Thr Pro Thr Val Cys Pro Val Pro Leu
            260                 265                 270

Ala His Thr Pro Thr Val Thr Lys Trp Phe Lys Gly Ile Thr Leu His
        275                 280                 285

Leu Thr Ala Met Arg Pro Thr Leu Leu Thr Thr Arg Lys Leu Gly Leu
    290                 295                 300

Arg Ala Asp Ala Thr Ala Glu Trp Ile Thr Gly Ser Thr Ser Arg Asn
```

-continued 305 310 315 320

Phe Ser Val Gly Arg Glu Gly Leu Glu Tyr Val Trp Gly Asn His Glu
325 330 335

Pro Val Arg Val Trp Ala Gln Glu Ser Ala Pro Gly Asp Pro His Gly
340 345 350

Trp Pro His Glu Ile Ile Ile His Tyr Tyr His Arg His Pro Val Tyr
355 360 365

Thr Arg Pro His Gly Gly Gly Ser Lys Asp Cys Glu Met Lys Arg Thr
370 375 380

Thr Leu Asp Ser Pro Leu Gly Lys Leu Glu Leu Ser Gly Cys Glu Gln
385 390 395 400

Gly Leu His Glu Ile Lys Leu Leu Gly Lys Gly Thr Ser Ala Ala Asp
405 410 415

Ala Val Glu Val Pro Ala Pro Ala Ala Val Leu Gly Gly Pro Glu Pro
420 425 430

Leu Met Gln Ala Thr Ala Trp Leu Asn Ala Tyr Phe His Gln Pro Glu
435 440 445

Ala Ile Glu Glu Phe Pro Val Pro Ala Leu His His Pro Val Phe Gln
450 455 460

Gln Glu Ser Phe Thr Arg Gln Val Leu Trp Lys Leu Leu Lys Val Val
465 470 475 480

Lys Phe Gly Glu Val Ile Ser Tyr Gln Gln Leu Ala Ala Leu Ala Gly
485 490 495

Asn Pro Ala Ala Thr Ala Ala Val Lys Thr Ala Leu Ser Gly Asn Pro
500 505 510

Val Pro Ile Leu Ile Pro Cys His Arg Val Val Ser Ser Ser Gly Ala
515 520 525

Val Gly Gly Tyr Glu Gly Gly Leu Ala Val Lys Glu Trp Leu Leu Ala
530 535 540

His Glu Gly His Arg Leu Gly Lys Pro Gly Leu Gly Pro Ala Gly Ile
545 550 555 560

Gly Ala Pro Gly Ser Leu Glu His His His His His His
565 570

<210> SEQ ID NO 75
<211> LENGTH: 1786
<212> TYPE: DNA
<213> ORGANISM: artificial
<220> FEATURE:
<223> OTHER INFORMATION: DNA sequence encoding ssBiP-sE2 from Eastern Equine Encephalitis virus -SNAPlike-Histag for expression in S2 cells

<400> SEQUENCE: 75
atgaagttat gcatattact ggccgtcgtg gcctttgttg gcctctcgct cgggagatct 60
gatttggaca ctcatttcac ccagtataag ttggcacgcc cgtatattgc tgattgccct 120
aactgtgggc atagtcggtg cgacagccct atagctatag aagaagtcag aggggatgcg 180
cacgcaggag tcatccgcat ccagacatca gctatgttcg gtctgaagac ggatggagtc 240
gatttggcct acatgagttt catgaacggc aaaacgcaga aatcaataaa gatcgacaac 300
ctgcatgtgc gcacctcagc cccttgttcc ctcgtgtcgc accacggcta ttacatcctg 360
gctcaatgcc caccagggga cacggttaca gttgggtttc acgacgggcc taaccgccat 420
acgtgcacag ttgcccataa ggtagaattc aggccagtgg gtagagagaa ataccgtcac 480
ccacctgaac atggagttga attaccgtgt aaccgttaca ctcacaagcg tgcagaccaa 540

```
ggacactatg ttgagatgca tcaacccggg ctagttgccg accactctct ccttagcatc    600
cacagtgcca aggtgaaaat tacggtaccg agcggcgccc aagtgaaata ctactgcaag    660
tgcccagatg tacgagaggg aattaccagc agcgaccata caaccacctg cacggatgtc    720
aaacaatgca gggcttacct gattgacaac aaaaaatggg tgtacaactc tggaagactg    780
cctcgaggag agggcgacac ttttaaagga aaacttcatg tgccctttgt gcctgttaag    840
gccaagtgca tcgccacgct ggcaccggag cctctagttg agcacaaaca ccgcaccctg    900
attttacacc tgcacccgga ccatccgacc ttgctgacga ccaggtcact tggaagtgat    960
gcaaatccaa ctcgacaatg gattgagcga ccaacaactg tcaatttcac agtcaccgga   1020
gaagggttgg agtatacctg ggaaaccat ccaccaaaaa gagtatgggc tcaagagtca   1080
ggagaaggga atccacatgg atggccgcac gaagtggtag tctattacta caacaggtac   1140
ccgttaacca caattatcgg gcggccgcac ggcggaggta gcaaagactg cgaaatgaag   1200
cgcaccaccc tggatagccc tctgggcaag ctggaactgt ctgggtgcga acagggcctg   1260
cacgagatca agctgctggg caaaggaaca tctgccgccg acgccgtgga agtgcctgcc   1320
ccagccgccg tgctgggcgg accagagcca ctgatgcagg ccaccgcctg gctcaacgcc   1380
tactttcacc agcctgaggc catcgaggag ttccctgtgc cagccctgca ccacccagtg   1440
ttccagcagg agagctttac ccgccaggtg ctgtggaaac tgctgaaagt ggtgaagttc   1500
ggagaggtca tcagctacca gcagctggcc gccctggccg gcaatcccgc cgccaccgcc   1560
gccgtgaaaa ccgccctgag cggaaatccc gtgcccattc tgatcccctg ccaccgggtg   1620
gtgtctagct ctggcgccgt gggggctac gagggcgggc tcgccgtgaa agagtggctg   1680
ctggcccacg agggccacag actgggcaag cctgggctgg gtcctgcagg tataggcgcg   1740
ccagggtccc tggagcatca tcatcatcat cattgatgac gggccc                  1786
```

```
<210> SEQ ID NO 76
<211> LENGTH: 573
<212> TYPE: PRT
<213> ORGANISM: artificial
<220> FEATURE:
<223> OTHER INFORMATION: Amino acid sequence of the fusion protein [sE2
      from Eastern Equine Encephalitis -SNAPlike-Histag]

<400> SEQUENCE: 76

Arg Ser Asp Leu Asp Thr His Phe Thr Gln Tyr Lys Leu Ala Arg Pro
1               5                   10                  15

Tyr Ile Ala Asp Cys Pro Asn Cys Gly His Ser Arg Cys Asp Ser Pro
            20                  25                  30

Ile Ala Ile Glu Glu Val Arg Gly Asp Ala His Ala Gly Val Ile Arg
        35                  40                  45

Ile Gln Thr Ser Ala Met Phe Gly Leu Lys Thr Asp Gly Val Asp Leu
    50                  55                  60

Ala Tyr Met Ser Phe Met Asn Gly Lys Thr Gln Lys Ser Ile Lys Ile
65                  70                  75                  80

Asp Asn Leu His Val Arg Thr Ser Ala Pro Cys Ser Leu Val Ser His
                85                  90                  95

His Gly Tyr Tyr Ile Leu Ala Gln Cys Pro Pro Gly Asp Thr Val Thr
            100                 105                 110

Val Gly Phe His Asp Gly Pro Asn Arg His Thr Cys Thr Val Ala His
        115                 120                 125

Lys Val Glu Phe Arg Pro Val Gly Arg Glu Lys Tyr Arg His Pro Pro
```

-continued

```
    130                 135                 140

Glu His Gly Val Glu Leu Pro Cys Asn Arg Tyr Thr His Lys Arg Ala
145                 150                 155                 160

Asp Gln Gly His Tyr Val Glu Met His Gln Pro Gly Leu Val Ala Asp
                165                 170                 175

His Ser Leu Leu Ser Ile His Ser Ala Lys Val Lys Ile Thr Val Pro
            180                 185                 190

Ser Gly Ala Gln Val Lys Tyr Tyr Cys Lys Cys Pro Asp Val Arg Glu
        195                 200                 205

Gly Ile Thr Ser Ser Asp His Thr Thr Thr Cys Thr Asp Val Lys Gln
    210                 215                 220

Cys Arg Ala Tyr Leu Ile Asp Asn Lys Lys Trp Val Tyr Asn Ser Gly
225                 230                 235                 240

Arg Leu Pro Arg Gly Glu Gly Asp Thr Phe Lys Gly Lys Leu His Val
                245                 250                 255

Pro Phe Val Pro Val Lys Ala Lys Cys Ile Ala Thr Leu Ala Pro Glu
            260                 265                 270

Pro Leu Val Glu His Lys His Arg Thr Leu Ile Leu His Leu His Pro
        275                 280                 285

Asp His Pro Thr Leu Leu Thr Thr Arg Ser Leu Gly Ser Asp Ala Asn
    290                 295                 300

Pro Thr Arg Gln Trp Ile Glu Arg Pro Thr Thr Val Asn Phe Thr Val
305                 310                 315                 320

Thr Gly Glu Gly Leu Glu Tyr Thr Trp Gly Asn His Pro Pro Lys Arg
                325                 330                 335

Val Trp Ala Gln Glu Ser Gly Glu Gly Asn Pro His Gly Trp Pro His
            340                 345                 350

Glu Val Val Val Tyr Tyr Tyr Asn Arg Tyr Pro Leu Thr Thr Ile Ile
        355                 360                 365

Gly Arg Pro His Gly Gly Gly Ser Lys Asp Cys Glu Met Lys Arg Thr
    370                 375                 380

Thr Leu Asp Ser Pro Leu Gly Lys Leu Glu Leu Ser Gly Cys Glu Gln
385                 390                 395                 400

Gly Leu His Glu Ile Lys Leu Leu Gly Lys Gly Thr Ser Ala Ala Asp
                405                 410                 415

Ala Val Glu Val Pro Ala Pro Ala Ala Val Leu Gly Gly Pro Glu Pro
            420                 425                 430

Leu Met Gln Ala Thr Ala Trp Leu Asn Ala Tyr Phe His Gln Pro Glu
        435                 440                 445

Ala Ile Glu Glu Phe Pro Val Pro Ala Leu His His Pro Val Phe Gln
    450                 455                 460

Gln Glu Ser Phe Thr Arg Gln Val Leu Trp Lys Leu Leu Lys Val Val
465                 470                 475                 480

Lys Phe Gly Glu Val Ile Ser Tyr Gln Gln Leu Ala Ala Leu Ala Gly
                485                 490                 495

Asn Pro Ala Ala Thr Ala Ala Val Lys Thr Ala Leu Ser Gly Asn Pro
            500                 505                 510

Val Pro Ile Leu Ile Pro Cys His Arg Val Val Ser Ser Ser Gly Ala
        515                 520                 525

Val Gly Gly Tyr Glu Gly Gly Leu Ala Val Lys Glu Trp Leu Leu Ala
    530                 535                 540

His Glu Gly His Arg Leu Gly Lys Pro Gly Leu Gly Pro Ala Gly Ile
545                 550                 555                 560
```

```
Gly Ala Pro Gly Ser Leu Glu His His His His His His
                565                 570


<210> SEQ ID NO 77
<211> LENGTH: 1792
<212> TYPE: DNA
<213> ORGANISM: artificial
<220> FEATURE:
<223> OTHER INFORMATION: DNA sequence encoding ssBiP-sE2 from Venezuelan
      Equine Encephalitis virus -SNAPlike-Histag for expression in S2
      cells

<400> SEQUENCE: 77

atgaagttat gcatattact ggccgtcgtg gcctttgttg gcctctcgct cgggagatct     60

agatcttcta ccgaggagct gtttaaggag tataagctaa cgcgccctta catggccaga    120

tgcatcagat gtgccgttgg gagctgccat agtccaatag caattgaggc agtgaagagc    180

gacgggcacg acggctatgt tagacttcag acttcctcgc agtatggcct ggattcctct    240

ggcaacttaa agggaaggac tatgcggtat gatatgcacg ggaccattga agagatacca    300

ctacatcaag tgtcactcca cacatctcgc ccgtgtcaca ttgtggatgg gcatggttat    360

tttctgcttg ctaggtgccc ggcaggggac tccatcacca tggaatttaa gaaaggttca    420

gtcacacact cctgctcagt gccgtatgaa gtgaaattta atcctgtagg cagagaactc    480

tacactcatc caccagaaca cggagcagag caagcgtgcc aagtctacgc gcacgatgca    540

cagaacagag gagcttatgt cgagatgcac ctcccgggct cagaagtgga cagcagtttg    600

atttccttga gcggcagttc agtcaccgtg acacctcctg tcgggactag cgccttggtg    660

aaatgcaagt gcggcggcac aaagatctcc gaaaccatca acaaggcaaa acagttcagc    720

cagtgcacaa agaaggagca gtgcagagca tatcgactgc agaatgacaa gtgggtgtat    780

aattctgaca aactgcccaa agcagcggga gccaccctaa aaggaaaact acacgtcccg    840

ttcttgctgg cagacggcaa atgcaccgtg cctctagcac cggaacctat gataaccttc    900

ggtttccgat cagtgtcact gaaactgcac cctaagaatc ccacatatct gaccactcgc    960

caacttgctg atgagcctca ttacacgcac gagctcatat ctgaaccagc tgttaggaat   1020

tttaccgtca ctgaaaaggg gtgggagttt gtatggggaa accatccgcc gaaaaggttt   1080

tgggcacagg aaacagcacc cggaaatcca catgggctgc cacatgaggt gataactcat   1140

tattaccaca gataccctat gtccacgcgg ccgcacggcg gaggtagcaa agactgcgaa   1200

atgaagcgca ccaccctgga tagccctctg ggcaagctgg aactgtctgg gtgcgaacag   1260

ggcctgcacg agatcaagct gctgggcaaa ggaacatctg ccgccgacgc cgtggaagtg   1320

cctgccccag ccgccgtgct gggcggacca gagccactga tgcaggccac cgcctggctc   1380

aacgcctact ttcaccagcc tgaggccatc gaggagttcc ctgtgccagc cctgcaccac   1440

ccagtgttcc agcaggagag ctttacccgc caggtgctgt ggaaactgct gaaagtggtg   1500

aagttcggag aggtcatcag ctaccagcag ctggccgccc tggccggcaa tcccgccgcc   1560

accgccgccg tgaaaaccgc cctgagcgga aatcccgtgc ccattctgat cccctgccac   1620

cgggtggtgt ctagctctgg cgccgtgggg ggctacgagg gcgggctcgc cgtgaaagag   1680

tggctgctgg cccacgaggg ccacagactg ggcaagcctg ggctgggtcc tgcaggtata   1740

ggcgcgccag ggtccctgga gcatcatcat catcatcatt gatgacgggc cc           1792


<210> SEQ ID NO 78
<211> LENGTH: 575
```

<212> TYPE: PRT
<213> ORGANISM: artificial
<220> FEATURE:
<223> OTHER INFORMATION: Amino acid sequence of the fusion protein [sE2 from Venezuelan Equine Encephalitis -SNAPlike-Histag]

<400> SEQUENCE: 78

```
Arg Ser Arg Ser Ser Thr Glu Glu Leu Phe Lys Glu Tyr Lys Leu Thr
1               5                   10                  15

Arg Pro Tyr Met Ala Arg Cys Ile Arg Cys Ala Val Gly Ser Cys His
            20                  25                  30

Ser Pro Ile Ala Ile Glu Ala Val Lys Ser Asp Gly His Asp Gly Tyr
        35                  40                  45

Val Arg Leu Gln Thr Ser Ser Gln Tyr Gly Leu Asp Ser Ser Gly Asn
    50                  55                  60

Leu Lys Gly Arg Thr Met Arg Tyr Asp Met His Gly Thr Ile Glu Glu
65                  70                  75                  80

Ile Pro Leu His Gln Val Ser Leu His Thr Ser Arg Pro Cys His Ile
                85                  90                  95

Val Asp Gly His Gly Tyr Phe Leu Leu Ala Arg Cys Pro Ala Gly Asp
            100                 105                 110

Ser Ile Thr Met Glu Phe Lys Lys Gly Ser Val Thr His Ser Cys Ser
        115                 120                 125

Val Pro Tyr Glu Val Lys Phe Asn Pro Val Gly Arg Glu Leu Tyr Thr
    130                 135                 140

His Pro Pro Glu His Gly Ala Glu Gln Ala Cys Gln Val Tyr Ala His
145                 150                 155                 160

Asp Ala Gln Asn Arg Gly Ala Tyr Val Glu Met His Leu Pro Gly Ser
                165                 170                 175

Glu Val Asp Ser Ser Leu Ile Ser Leu Ser Gly Ser Ser Val Thr Val
            180                 185                 190

Thr Pro Pro Val Gly Thr Ser Ala Leu Val Lys Cys Lys Cys Gly Gly
        195                 200                 205

Thr Lys Ile Ser Glu Thr Ile Asn Lys Ala Lys Gln Phe Ser Gln Cys
    210                 215                 220

Thr Lys Lys Glu Gln Cys Arg Ala Tyr Arg Leu Gln Asn Asp Lys Trp
225                 230                 235                 240

Val Tyr Asn Ser Asp Lys Leu Pro Lys Ala Ala Gly Ala Thr Leu Lys
                245                 250                 255

Gly Lys Leu His Val Pro Phe Leu Leu Ala Asp Gly Lys Cys Thr Val
            260                 265                 270

Pro Leu Ala Pro Glu Pro Met Ile Thr Phe Gly Phe Arg Ser Val Ser
        275                 280                 285

Leu Lys Leu His Pro Lys Asn Pro Thr Tyr Leu Thr Thr Arg Gln Leu
    290                 295                 300

Ala Asp Glu Pro His Tyr Thr His Glu Leu Ile Ser Glu Pro Ala Val
305                 310                 315                 320

Arg Asn Phe Thr Val Thr Glu Lys Gly Trp Glu Phe Val Trp Gly Asn
                325                 330                 335

His Pro Pro Lys Arg Phe Trp Ala Gln Glu Thr Ala Pro Gly Asn Pro
            340                 345                 350

His Gly Leu Pro His Glu Val Ile Thr His Tyr Tyr His Arg Tyr Pro
        355                 360                 365

Met Ser Thr Arg Pro His Gly Gly Gly Ser Lys Asp Cys Glu Met Lys
    370                 375                 380
```

```
Arg Thr Thr Leu Asp Ser Pro Leu Gly Lys Leu Glu Leu Ser Gly Cys
385                 390                 395                 400

Glu Gln Gly Leu His Glu Ile Lys Leu Leu Gly Lys Gly Thr Ser Ala
                405                 410                 415

Ala Asp Ala Val Glu Val Pro Ala Pro Ala Ala Val Leu Gly Gly Pro
            420                 425                 430

Glu Pro Leu Met Gln Ala Thr Ala Trp Leu Asn Ala Tyr Phe His Gln
        435                 440                 445

Pro Glu Ala Ile Glu Glu Phe Pro Val Pro Ala Leu His His Pro Val
    450                 455                 460

Phe Gln Gln Glu Ser Phe Thr Arg Gln Val Leu Trp Lys Leu Leu Lys
465                 470                 475                 480

Val Val Lys Phe Gly Glu Val Ile Ser Tyr Gln Gln Leu Ala Ala Leu
                485                 490                 495

Ala Gly Asn Pro Ala Ala Thr Ala Ala Val Lys Thr Ala Leu Ser Gly
            500                 505                 510

Asn Pro Val Pro Ile Leu Ile Pro Cys His Arg Val Val Ser Ser Ser
        515                 520                 525

Gly Ala Val Gly Gly Tyr Glu Gly Gly Leu Ala Val Lys Glu Trp Leu
    530                 535                 540

Leu Ala His Glu Gly His Arg Leu Gly Lys Pro Gly Leu Gly Pro Ala
545                 550                 555                 560

Gly Ile Gly Ala Pro Gly Ser Leu Glu His His His His His His
                565                 570                 575
```

<210> SEQ ID NO 79
<211> LENGTH: 1442
<212> TYPE: DNA
<213> ORGANISM: artificial
<220> FEATURE:
<223> OTHER INFORMATION: DNA sequence encoding ssBiP- SNAPlike-Akabane N protein-proTEV cleavage site-Histag for expression in S2 cells

<400> SEQUENCE: 79

```
atgaagttat gcatattact ggccgtcgtg gtggcctttg ttggcctctc gctcgggaga     60

tctgacaaag actgcgaaat gaaaagaact acattggatt caccacttgg gaagttggaa    120

ctgagtggat gcgagcaagg attgcatgaa attaagctac tgggaaaagg aacttctgct    180

gctgatgcag ttgaagttcc agcaccagca gctgttcttg gaggtcctga gcccctcatg    240

caagccacag cctggcttaa cgcatatttc caccagcctg aggccattga ggaatttcca    300

gtccccgccc ttcaccatcc tgtgtttcag caggagagct tcacccgcca ggtcctgtgg    360

aaattgctga aggtggtcaa gtttggtgaa gtgatttcat atcagcaact tgctgcattg    420

gccggtaacc ccgcagctac agctgccgtg aaaactgctc tcagcggaaa tcctgtgccc    480

atcctgatcc cttgtcacag agtcgtttca tcttccggag ctgtaggtgg ctatgaagga    540

ggactggcag ttaaggagtg gctgctggct catgaaggtc atagacttgg aaagcctggg    600

ctgggtcctg ctggtatagg cgcgccaggg tccctaggtg gcggatccga aaacctgtac    660

ttccagagcg atatcgcaaa tcaatttatt ttcaacgatg ttccacaacg gaatgcagct    720

acatttaatc cggatgcagg gtatgtggca tttatcagta agtatgggca gcagctcaac    780

tttactgttg ctagagtctt cttcctcaac cagaagaagg ccaagatggt cttacataag    840

acgccacaac caagtgtcga tcttactttt gcaggggtca aatttacagt ggttaataac    900

cattttcccc agtatactgc aaatccggtg tcagacactg cctttacgct ccatcgcatc    960
```

tcgggctact tagctcgatg ggttgctgag cagtgcaagg ctaatcagat caaacttgca 1020
gaggcagctg ctacaatcgt aatgccgctg gctgaagtga agggctgcac ctggagtgat 1080
gggtacgcaa tgtacctagg ctttgcccct ggtgctgaga tgtttctgga aacctttgag 1140
ttttacccat tggttattga catgcaccgt gtgataaagg atgggatgga tgtcaacttc 1200
atgaggaagg tcttacgcca gagatatggg cagctgactg cagaagaatg gatgacatct 1260
aagttggacg cagtcaaggc tgcatttagc tcagttgccc aaatatcctg ggccaaatct 1320
ggcttctcac ctgcagctag agctttcctg gctcaatttg gtattcagat cccgggagag 1380
aatctatatt ttcaagggcc cggcggaggt agtcaccatc atcaccatca ctaatgaccg 1440
gt 1442

<210> SEQ ID NO 80
<211> LENGTH: 458
<212> TYPE: PRT
<213> ORGANISM: artificial
<220> FEATURE:
<223> OTHER INFORMATION: Amino acid sequence of fusion protein
[SNAPlike-Akabane N protein-Histag]

<400> SEQUENCE: 80

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

Ile Ser Tyr Gln Gln Leu Ala Ala Leu Ala Gly Asn Pro Ala Ala Thr
115 120 125

Ala Ala Val Lys Thr Ala Leu Ser Gly Asn Pro Val Pro Ile Leu Ile
130 135 140

Pro Cys His Arg Val Val Ser Ser Ser Gly Ala Val Gly Gly Tyr Glu
145 150 155 160

Gly Gly Leu Ala Val Lys Glu Trp Leu Leu Ala His Glu Gly His Arg
165 170 175

Leu Gly Lys Pro Gly Leu Gly Pro Ala Gly Ile Gly Ala Pro Gly Ser
180 185 190

Leu Gly Gly Gly Ser Glu Asn Leu Tyr Phe Gln Ser Asp Ile Ala Asn
195 200 205

Gln Phe Ile Phe Asn Asp Val Pro Gln Arg Asn Ala Ala Thr Phe Asn
210 215 220

Pro Asp Ala Gly Tyr Val Ala Phe Ile Ser Lys Tyr Gly Gln Gln Leu
225 230 235 240

Asn Phe Thr Val Ala Arg Val Phe Phe Leu Asn Gln Lys Lys Ala Lys
245 250 255

Met Val Leu His Lys Thr Pro Gln Pro Ser Val Asp Leu Thr Phe Ala

```
            260                 265                 270

Gly Val Lys Phe Thr Val Val Asn Asn His Phe Pro Gln Tyr Thr Ala
        275                 280                 285

Asn Pro Val Ser Asp Thr Ala Phe Thr Leu His Arg Ile Ser Gly Tyr
    290                 295                 300

Leu Ala Arg Trp Val Ala Glu Gln Cys Lys Ala Asn Gln Ile Lys Leu
305                 310                 315                 320

Ala Glu Ala Ala Ala Thr Ile Val Met Pro Leu Ala Glu Val Lys Gly
                325                 330                 335

Cys Thr Trp Ser Asp Gly Tyr Ala Met Tyr Leu Gly Phe Ala Pro Gly
            340                 345                 350

Ala Glu Met Phe Leu Glu Thr Phe Glu Phe Tyr Pro Leu Val Ile Asp
        355                 360                 365

Met His Arg Val Ile Lys Asp Gly Met Asp Val Asn Phe Met Arg Lys
    370                 375                 380

Val Leu Arg Gln Arg Tyr Gly Gln Leu Thr Ala Glu Glu Trp Met Thr
385                 390                 395                 400

Ser Lys Leu Asp Ala Val Lys Ala Ala Phe Ser Ser Val Ala Gln Ile
                405                 410                 415

Ser Trp Ala Lys Ser Gly Phe Ser Pro Ala Ala Arg Ala Phe Leu Ala
            420                 425                 430

Gln Phe Gly Ile Gln Ile Pro Gly Glu Asn Leu Tyr Phe Gln Gly Pro
        435                 440                 445

Gly Gly Gly Ser His His His His His His
    450                 455
```

<210> SEQ ID NO 81
<211> LENGTH: 1451
<212> TYPE: DNA
<213> ORGANISM: artificial
<220> FEATURE:
<223> OTHER INFORMATION: DNA sequence encoding ssBiP- SNAPlike-Amino N protein-proTEV cleavage site-Histag for expression in S2 cells

<400> SEQUENCE: 81

```
atgaagttat gcatattact ggccgtcgtg gtggcctttg ttggcctctc gctcgggaga     60

tctagatctg acaaagactg cgaaatgaaa agaactacat tggattcacc acttgggaag    120

ttggaactga gtggatgcga gcaaggattg catgaaatta agctactggg aaaaggaact    180

tctgctgctg atgcagttga agttccagca ccagcagctg ttcttggagg tcctgagccc    240

ctcatgcaag ccacagcctg gcttaacgca tatttccacc agcctgaggc cattgaggaa    300

tttccagtcc ccgcccttca ccatcctgtg tttcagcagg agagcttcac ccgccaggtc    360

ctgtggaaat tgctgaaggt ggtcaagttt ggtgaagtga tttcatatca gcaacttgct    420

gcattggccg gtaaccccgc agctacagct gccgtgaaaa ctgctctcag cggaaatcct    480

gtgcccatcc tgatcccttg tcacagagtc gtttcatctt ccggagctgt aggtggctat    540

gaaggaggac tggcagttaa ggagtggctg ctggctcatg aaggtcatag acttggaaag    600

cctgggctgg gtcctgctgg tataggcgcg ccagggtccc taggtggcgg atccgaaaac    660

ctgtacttcc agagcgatat cgcaaaccaa tttattttcc aagatgttcc tcaacggaat    720

ctcgctacat ttaacccgga ggtcgggtat gtggcattta ttgctaaaca tgggtcccaa    780

ctcaatttcg ataccgttag agtcttcttc ctcaatcaga agaaggccaa gatggtgctc    840

agtaagacgg cacaaccaag tgttgatctt acatttggtg gcatcaaatt tacactggtt    900
```

aataaccatt ttccccaata cacagcaaat cctgtgccag acactgccct cactctccac 960
cgtctctcag gttatctagc aaaatgggtt gcagaccaat gcaaaacaaa tcagattaaa 1020
ctggctgagg ccatggaaaa aattgtcatg ccacttgctg aagtgaaagg ttgcacctgg 1080
actgaaggac tgactatgta tctgggattt gcaccaggcg ctgaaatgtt tttagaaaca 1140
tttgagttct accctttggt tattgacatg cacagagtgc tgaaagatgg aatggatgtc 1200
aactttatga gaaaggtcct tcgccagcgc tatggcacat tgactgcaga acagtggatg 1260
actcaaaaaa tagatgctgt ccgtgcagcc ttcaatgctg ttgggcagct aagttgggct 1320
aaatcaggat tctcaccagc tgccagagcc ttccttgccc aattcggcat aaacatgatc 1380
ccgggagaga atctatattt tcaagggccc ggcggaggta gtcaccatca tcaccatcac 1440
taatgaccgg t 1451

<210> SEQ ID NO 82
<211> LENGTH: 459
<212> TYPE: PRT
<213> ORGANISM: artificial
<220> FEATURE:
<223> OTHER INFORMATION: Amino acid sequence of fusion protein [SNAPlike-Amino N protein-Histag]

<400> SEQUENCE: 82

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

Ile Ser Tyr Gln Gln Leu Ala Ala Leu Ala Gly Asn Pro Ala Ala Thr
115 120 125

Ala Ala Val Lys Thr Ala Leu Ser Gly Asn Pro Val Pro Ile Leu Ile
130 135 140

Pro Cys His Arg Val Val Ser Ser Ser Gly Ala Val Gly Gly Tyr Glu
145 150 155 160

Gly Gly Leu Ala Val Lys Glu Trp Leu Leu Ala His Glu Gly His Arg
165 170 175

Leu Gly Lys Pro Gly Leu Gly Pro Ala Gly Ile Gly Ala Pro Gly Ser
180 185 190

Leu Gly Gly Gly Ser Glu Asn Leu Tyr Phe Gln Ser Asp Ile Ala Asn
195 200 205

Gln Phe Ile Phe Gln Asp Val Pro Gln Arg Asn Leu Ala Thr Phe Asn
210 215 220

Pro Glu Val Gly Tyr Val Ala Phe Ile Ala Lys His Gly Ser Gln Leu
225 230 235 240

Asn Phe Asp Thr Val Arg Val Phe Phe Leu Asn Gln Lys Lys Ala Lys
245 250 255

-continued

```
Met Val Leu Ser Lys Thr Ala Gln Pro Ser Val Asp Leu Thr Phe Gly
            260                 265                 270

Gly Ile Lys Phe Thr Leu Val Asn Asn His Phe Pro Gln Tyr Thr Ala
        275                 280                 285

Asn Pro Val Pro Asp Thr Ala Leu Thr Leu His Arg Leu Ser Gly Tyr
    290                 295                 300

Leu Ala Lys Trp Val Ala Asp Gln Cys Lys Thr Asn Gln Ile Lys Leu
305                 310                 315                 320

Ala Glu Ala Met Glu Lys Ile Val Met Pro Leu Ala Glu Val Lys Gly
                325                 330                 335

Cys Thr Trp Thr Glu Gly Leu Thr Met Tyr Leu Gly Phe Ala Pro Gly
            340                 345                 350

Ala Glu Met Phe Leu Glu Thr Phe Glu Phe Tyr Pro Leu Val Ile Asp
        355                 360                 365

Met His Arg Val Leu Lys Asp Gly Met Asp Val Asn Phe Met Arg Lys
    370                 375                 380

Val Leu Arg Gln Arg Tyr Gly Thr Leu Thr Ala Glu Gln Trp Met Thr
385                 390                 395                 400

Gln Lys Ile Asp Ala Val Arg Ala Ala Phe Asn Ala Val Gly Gln Leu
                405                 410                 415

Ser Trp Ala Lys Ser Gly Phe Ser Pro Ala Ala Arg Ala Phe Leu Ala
            420                 425                 430

Gln Phe Gly Ile Asn Met Ile Pro Gly Glu Asn Leu Tyr Phe Gln Gly
        435                 440                 445

Pro Gly Gly Gly Ser His His His His His His
    450                 455
```

<210> SEQ ID NO 83
<211> LENGTH: 1448
<212> TYPE: DNA
<213> ORGANISM: artificial
<220> FEATURE:
<223> OTHER INFORMATION: DNA sequence encoding ssBiP - SNAPlike-Shamonda N protein-proTEV cleavage site-Histag for expression in S2 cells

<400> SEQUENCE: 83

```
atgaagttat gcatattact ggccgtcgtg gtggcctttg ttggcctctc gctcgggaga      60

tctagatctg acaaagactg cgaaatgaaa agaactacat tggattcacc acttgggaag     120

ttggaactga gtggatgcga gcaaggattg catgaaatta agctactggg aaaaggaact     180

tctgctgctg atgcagttga agttccagca ccagcagctg ttcttggagg tcctgagccc     240

ctcatgcaag ccacagcctg gcttaacgca tatttccacc agcctgaggc cattgaggaa     300

tttccagtcc ccgcccttca ccatcctgtg tttcagcagg agagcttcac ccgccaggtc     360

ctgtggaaat tgctgaaggt ggtcaagttt ggtgaagtga tttcatatca gcaacttgct     420

gcattggccg gtaaccccgc agctacagct gccgtgaaaa ctgctctcag cggaaatcct     480

gtgcccatcc tgatcccttg tcacagagtc gtttcatctt ccggagctgt aggtggctat     540

gaaggaggac tggcagttaa ggagtggctg ctggctcatg aaggtcatag acttggaaag     600

cctgggctgg gtcctgctgg tataggcgcg ccagggtccc taggtggcgg atccgaaaac     660

ctgtacttcc agagcgatat ctcaagccaa ttcatttttg aagatgtacc acaacggaat     720

gcagctacat ttaacccgga aggtgggtat gtggcattta ttggtaagta tgggcaacaa     780

ctcaatttcg gggttgctaa agtcttcttc ctcaaccaga agaaggccaa aatggtccta     840

cataagacgg gacaaccaag tgtcgatctt acttttggtg gggtcaaatt cacagtggtt     900
```

aataaccatt ttccccaata tgtctcaaat cctgtgccag acaatgccat tacacttcac 960
aggatgtcag gttatctagc acgctggatt gctgatacat gcaaggctag tgtcctcaaa 1020
ctagctgaag ctagtgctca aattgtcatg ccccttgctg aggttaaggg atgtacctgg 1080
gctgatggtt atacaatgta tcttggattt gcacctgggg ccgaaatgtt ccttgatgct 1140
tttgattttt atccgctagt tatcgaaatg catagggtcc ttaaggacaa tatggatgta 1200
aattttatga aaaaagtcct ccgccaacgc tatggaacaa tgactgctga agaatggatg 1260
actcagaaaa taccagaaat aaaggctgct ttcaattctg ttggacaact tgcctgggct 1320
aaatctggat tctctcctgc tgctagaact ttcttgcagc aatttggtat caacatcccg 1380
ggagagaatc tatattttca agggcccggc ggaggtagtc accatcatca ccatcactaa 1440
tgaccggt 1448

<210> SEQ ID NO 84
<211> LENGTH: 458
<212> TYPE: PRT
<213> ORGANISM: artificial
<220> FEATURE:
<223> OTHER INFORMATION: Amino acid sequence of fusion protein [SNAPlike-Shamonda N protein-Histag]

<400> SEQUENCE: 84

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ser
        195                 200                 205

Gln Phe Ile Phe Glu Asp Val Pro Gln Arg Asn Ala Ala Thr Phe Asn
    210                 215                 220

Pro Glu Gly Gly Tyr Val Ala Phe Ile Gly Lys Tyr Gly Gln Gln Leu
225                 230                 235                 240

Asn Phe Gly Val Ala Lys Val Phe Phe Leu Asn Gln Lys Lys Ala Lys
                245                 250                 255

```
Met Val Leu His Lys Thr Gly Gln Pro Ser Val Asp Leu Thr Phe Gly
            260                 265                 270

Gly Val Lys Phe Thr Val Val Asn Asn His Phe Pro Gln Tyr Val Ser
        275                 280                 285

Asn Pro Val Pro Asp Asn Ala Ile Thr Leu His Arg Met Ser Gly Tyr
    290                 295                 300

Leu Ala Arg Trp Ile Ala Asp Thr Cys Lys Ala Ser Val Leu Lys Leu
305                 310                 315                 320

Ala Glu Ala Ser Ala Gln Ile Val Met Pro Leu Ala Glu Val Lys Gly
                325                 330                 335

Cys Thr Trp Ala Asp Gly Tyr Thr Met Tyr Leu Gly Phe Ala Pro Gly
            340                 345                 350

Ala Glu Met Phe Leu Asp Ala Phe Asp Phe Tyr Pro Leu Val Ile Glu
        355                 360                 365

Met His Arg Val Leu Lys Asp Asn Met Asp Val Asn Phe Met Lys Lys
    370                 375                 380

Val Leu Arg Gln Arg Tyr Gly Thr Met Thr Ala Glu Glu Trp Met Thr
385                 390                 395                 400

Gln Lys Ile Pro Glu Ile Lys Ala Ala Phe Asn Ser Val Gly Gln Leu
                405                 410                 415

Ala Trp Ala Lys Ser Gly Phe Ser Pro Ala Ala Arg Thr Phe Leu Gln
            420                 425                 430

Gln Phe Gly Ile Asn Ile Pro Gly Glu Asn Leu Tyr Phe Gln Gly Pro
        435                 440                 445

Gly Gly Gly Ser His His His His His His
    450                 455
```

<210> SEQ ID NO 85
<211> LENGTH: 1991
<212> TYPE: DNA
<213> ORGANISM: artificial
<220> FEATURE:
<223> OTHER INFORMATION: DNA sequence encoding ssBiP -SNAPlike-proTEV cleavage site-N protein from human betacoronavirus strain 2cEMC/2012- Histag for expression in S2 cells

<400> SEQUENCE: 85

```
atgaagttat gcatattact ggccgtcgtg gtggcctttg ttggcctctc gctcgggaga     60

tctagatctg acaaagactg cgaaatgaaa agaactacat tggattcacc acttgggaag    120

ttggaactga gtggatgcga gcaaggattg catgaaatta agctactggg aaaaggaact    180

tctgctgctg atgcagttga agttccagca ccagcagctg ttcttggagg tcctgagccc    240

ctcatgcaag ccacagcctg gcttaacgca tatttccacc agcctgaggc cattgaggaa    300

tttccagtcc ccgcccttca ccatcctgtg tttcagcagg agagcttcac ccgccaggtc    360

ctgtggaaat tgctgaaggt ggtcaagttt ggtgaagtga tttcatatca gcaacttgct    420

gcattggccg gtaaccccgc agctacagct gccgtgaaaa ctgctctcag cggaaatcct    480

gtgcccatcc tgatcccttg tcacagagtc gtttcatctt ccggagctgt aggtggctat    540

gaaggaggac tggcagttaa ggagtggctg ctggctcatg aaggtcatag acttggaaag    600

cctgggctgg gtcctgctgg tataggcgcg ccagggtccc taggtggcgg atccgaaaac    660

ctgtacttcc agagcgatat cgcatcccct gctgcacctc gtgctgtttc ctttgccgat    720

aacaatgata taacaaatac aaacctatct cgaggtagag gacgtaatcc aaaaccacga    780

gctgcaccaa ataacactgt ctcttggtac actgggctta cccaacacgg gaaagtccct    840
```

```
cttacctttc cacctgggca gggtgtacct cttaatgcca attctacccc tgcgcaaaat    900

gctgggtatt ggcggagaca ggacagaaaa attaataccg ggaatggaat taagcaactg    960

gctcccaggt ggtacttcta ctacactgga actggacccg aagcagcact cccattccgg   1020

gctgttaagg atggcatcgt ttgggtccat gaagatggcg ccactgatgc tccttcaact   1080

tttgggacgc ggaaccctaa caatgattca gctattgtta cacaattcgc gcccggtact   1140

aaacttccta aaaacttcca cattgagggg actggaggca atagtcaatc atcttcaaga   1200

gcctctagct taagcagaaa ctcttccagg tctagttcac aaggttcaag atcaggaaac   1260

tctacccgcg gcacttctcc aggtccatct ggaatcggag cagtaggagg tgatctactt   1320

taccttgatc ttctgaacag actacaagcc cttgagtctg gcaaagtaaa gcaatcgcag   1380

ccaaaagtaa tcactaagaa agatgctgct gctgctaaaa ataagatgcg ccacaagcgc   1440

acttccacca aaagtttcaa catggtgcag gcttttggtc ttcgcggacc aggagacctc   1500

cagggaaact ttggtgatct tcaattgaat aaactcggca ctgaggaccc acgttggccc   1560

caaattgctg agcttgctcc tacagccagt gcttttatgg gtatgtcgca atttaaactt   1620

acccatcaga acaatgatga tcatggcaac cctgtgtact tccttcggta cagtggagcc   1680

attaaacttg acccaaagaa tcccaactac aataagtggt tggagcttct tgagcaaaat   1740

attgatgcct acaaaacctt ccctaagaag gaaaagaaac aaaaggcacc aaaagaagaa   1800

tcaacagacc aaatgtctga acctccaaag gagcagcgtg tgcaaggtag catcactcag   1860

cgcactcgca cccgtccaag tgttcagcct ggtccaatga ttgatgttaa cactgatggc   1920

ccgggagaga atctatattt tcaagggccc ggcggaggta gtcaccatca tcaccatcac   1980

taatgaccgg t                                                        1991
```

<210> SEQ ID NO 86
<211> LENGTH: 639
<212> TYPE: PRT
<213> ORGANISM: artificial
<220> FEATURE:
<223> OTHER INFORMATION: Amino acid sequence of fusion protein
      [SNAPlike-proTEV-COV N protein-Histag]

<400> SEQUENCE: 86

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140
```

-continued

```
Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala Ser
        195                 200                 205

Pro Ala Ala Pro Arg Ala Val Ser Phe Ala Asp Asn Asn Asp Ile Thr
    210                 215                 220

Asn Thr Asn Leu Ser Arg Gly Arg Gly Arg Asn Pro Lys Pro Arg Ala
225                 230                 235                 240

Ala Pro Asn Asn Thr Val Ser Trp Tyr Thr Gly Leu Thr Gln His Gly
                245                 250                 255

Lys Val Pro Leu Thr Phe Pro Pro Gly Gln Gly Val Pro Leu Asn Ala
            260                 265                 270

Asn Ser Thr Pro Ala Gln Asn Ala Gly Tyr Trp Arg Arg Gln Asp Arg
        275                 280                 285

Lys Ile Asn Thr Gly Asn Gly Ile Lys Gln Leu Ala Pro Arg Trp Tyr
    290                 295                 300

Phe Tyr Tyr Thr Gly Thr Gly Pro Glu Ala Ala Leu Pro Phe Arg Ala
305                 310                 315                 320

Val Lys Asp Gly Ile Val Trp Val His Glu Asp Gly Ala Thr Asp Ala
                325                 330                 335

Pro Ser Thr Phe Gly Thr Arg Asn Pro Asn Asn Asp Ser Ala Ile Val
            340                 345                 350

Thr Gln Phe Ala Pro Gly Thr Lys Leu Pro Lys Asn Phe His Ile Glu
        355                 360                 365

Gly Thr Gly Gly Asn Ser Gln Ser Ser Ser Arg Ala Ser Ser Leu Ser
    370                 375                 380

Arg Asn Ser Ser Arg Ser Ser Ser Gln Gly Ser Arg Ser Gly Asn Ser
385                 390                 395                 400

Thr Arg Gly Thr Ser Pro Gly Pro Ser Gly Ile Gly Ala Val Gly Gly
                405                 410                 415

Asp Leu Leu Tyr Leu Asp Leu Leu Asn Arg Leu Gln Ala Leu Glu Ser
            420                 425                 430

Gly Lys Val Lys Gln Ser Gln Pro Lys Val Ile Thr Lys Lys Asp Ala
        435                 440                 445

Ala Ala Ala Lys Asn Lys Met Arg His Lys Arg Thr Ser Thr Lys Ser
    450                 455                 460

Phe Asn Met Val Gln Ala Phe Gly Leu Arg Gly Pro Gly Asp Leu Gln
465                 470                 475                 480

Gly Asn Phe Gly Asp Leu Gln Leu Asn Lys Leu Gly Thr Glu Asp Pro
                485                 490                 495

Arg Trp Pro Gln Ile Ala Glu Leu Ala Pro Thr Ala Ser Ala Phe Met
            500                 505                 510

Gly Met Ser Gln Phe Lys Leu Thr His Gln Asn Asn Asp Asp His Gly
        515                 520                 525

Asn Pro Val Tyr Phe Leu Arg Tyr Ser Gly Ala Ile Lys Leu Asp Pro
    530                 535                 540

Lys Asn Pro Asn Tyr Asn Lys Trp Leu Glu Leu Leu Glu Gln Asn Ile
545                 550                 555                 560

Asp Ala Tyr Lys Thr Phe Pro Lys Lys Glu Lys Lys Gln Lys Ala Pro
```

```
                565                 570                 575

Lys Glu Glu Ser Thr Asp Gln Met Ser Glu Pro Pro Lys Glu Gln Arg
            580                 585                 590

Val Gln Gly Ser Ile Thr Gln Arg Thr Arg Thr Arg Pro Ser Val Gln
        595                 600                 605

Pro Gly Pro Met Ile Asp Val Asn Thr Asp Gly Pro Gly Glu Asn Leu
    610                 615                 620

Tyr Phe Gln Gly Pro Gly Gly Gly Ser His His His His His His
625                 630                 635


<210> SEQ ID NO 87
<211> LENGTH: 4465
<212> TYPE: DNA
<213> ORGANISM: artificial
<220> FEATURE:
<223> OTHER INFORMATION: DNA sequence encoding ssBiP- S protein from
      human betacoronavirus strain 2cEMC/2012- SNAPlike - Histag for
      expression in S2 cells

<400> SEQUENCE: 87

atgaagttat gcatattact ggccgtcgtg gtggcctttg ttggcctctc gctcgggaga     60

tctagatctg tagggccaga ttctgttaag tctgcttgta ttgaggttga tatacaacag    120

actttctttg ataaaacttg gcctaggcca attgatgttt ctaaggctga cggtattata    180

taccctcaag gccgtacata ttctaacata actatcactt atcaaggtct tttccctat     240

cagggagacc atggtgatat gtatgtttac tctgcaggac atgctacagg cacaactcca    300

caaaagttgt ttgtagctaa ctattctcag gacgtcaaac agtttgctaa tgggtttgtc    360

gtccgtatag gagcagctgc caattccact ggcactgtta ttattagccc atctaccagc    420

gctactatac gaaaaattta ccctgctttt atgctgggtt cttcagttgg taatttctca    480

gatggtaaaa tgggccgctt cttcaatcat actctagttc ttttgcccga tggatgtggc    540

actttactta gagcttttta ttgtattcta gagcctcgct ctggaaatca ttgtcctgct    600

ggcaattcct atacttcttt tgccacttat cacactcctg caacagattg ttctgatggc    660

aattacaatc gtaatgccag tctgaactct tttaaggagt attttaattt acgtaactgc    720

acctttatgt acacttataa cattaccgaa gatgagattt tagagtggtt tggcattaca    780

caaactgctc aaggtgttca cctcttctca tctcggtatg ttgatttgta cggcggcaat    840

atgtttcaat ttgccacctt gcctgtttat gatactatta agtattattc tatcattcct    900

cacagtattc gttctatcca aagtgataga aaggcttggg ctgccttcta cgtatataaa    960

cttcaaccgt taactttcct gttggatttt tctgttgatg gttatatacg cagagctata   1020

gactgtggtt ttaatgattt gtcacaactc cactgctcat atgaatcctt cgatgttgaa   1080

tctggagttt attcagtttc gtctttcgaa gcaaaacctt ctggctcagt tgtggaacag   1140

gctgaaggtg ttgaatgtga tttttcacct cttctgtctg gcacacctcc tcaggtttat   1200

aatttcaagc gtttggtttt taccaattgc aattataatc ttaccaaatt gctttcactt   1260

ttttctgtga atgattttac ttgtagtcaa atatctccag cagcaattgc aagcaactgt   1320

tattcttcac tgattttgga ttacttttca tacccactta gtatgaaatc cgatctcagt   1380

gttagttctg ctggtccaat atcccagttt aattataaac agtccttttc taatcccaca   1440

tgtttgattt tagcgactgt tcctcataac cttactacta ttactaagcc tcttaagtac   1500

agctatatta acaagtgctc tcgtcttctt tctgatgatc gtactgaagt acctcagtta   1560

gtgaacgcta atcaatactc accctgtgta tccattgtcc catccactgt gtgggaagac   1620
```

ggtgattatt ataggaaaca actatctcca cttgaaggtg gtggctggct tgttgctagt 1680
ggctcaactg ttgccatgac tgagcaatta cagatgggct ttggtattac agttcaatat 1740
ggtacagaca ccaatagtgt ttgccccaag ctggaatttg ctaatgacac aaaaattgcc 1800
tctcaattag gcaattgcgt ggaatattcc ctctatggtg tttcgggccg tggtgttttt 1860
cagaattgca cagctgtagg tgttcgacag cagcgctttg tttatgatgc gtaccagaat 1920
ttagttggct attattctga tgatggcaac tactactgtt tgcgtgcttg tgttagtgtt 1980
cctgtttctg tcatctatga taaagaaact aaaacccacg ctactctatt tggtagtgtt 2040
gcatgtgaac acatttcttc taccatgtct caatactccc gttctacgcg atcaatgctt 2100
aaacggcgag attctacata tggccccctt cagacacctg ttggttgtgt cctaggactt 2160
gttaattcct ctttgttcgt agaggactgc aagttgcctc ttggtcaatc tctctgtgct 2220
cttcctgaca cacctagtac tctcacacct cgcagtgtgc gctctgttcc aggtgaaatg 2280
cgcttggcat ccattgcttt taatcatcct attcaggttg atcaacttaa tagtagttat 2340
tttaaattaa gtatacccac taatttttcc tttggtgtga ctcaggagta cattcagaca 2400
accattcaga aagttactgt tgattgtaaa cagtacgttt gcaatggttt ccagaagtgt 2460
gagcaattac tgcgcgagta tggccagttt tgttccaaaa taaaccaggc tctccatggt 2520
gccaatttac gccaggatga ttctgtacgt aatttgtttg cgagcgtgaa aagctctcaa 2580
tcatctccta tcataccagg ttttggaggt gactttaatt tgacacttct agaacctgtt 2640
tctatatcta ctggcagtcg tagtgcacgt agtgctattg aggatttgct atttgacaaa 2700
gtcactatag ctgatcctgg ttatatgcaa ggttacgatg attgcatgca gcaaggtcca 2760
gcatcagctc gtgatcttat ttgtgctcaa tatgtggctg gttacaaagt attacctcct 2820
cttatggatg ttaatatgga agccgcgtat acttcatctt tgcttggcag catagcaggt 2880
gttggctgga ctgctggctt atcctccttt gctgctattc catttgcaca gagtatcttt 2940
tataggttaa acggtgttgg cattactcaa caggttcttt cagagaacca aaagctcatt 3000
gccaataagt ttaatcaggc tctgggagct atgcaaacag gcttcactac aactaatgaa 3060
gcctttcaga aggttcagga tgctgtgaac aacaatgcac aggctctatc caaattagcg 3120
agcgagctat ctaatacttt tggtgctatt tccgcctcta ttggagacat catacaacgt 3180
cttgatgttc tcgaacagga cgcccaaata gacagactta ttaatggccg tttgacaaca 3240
ctaaatgctt ttgttgcaca gcagcttgtt cgttccgaat cagctgctct ttccgctcaa 3300
ttggctaaag ataaagtcaa tgagtgtgtc aaggcacaat ccaagcgttc tggattttgc 3360
ggtcaaggca cacatatagt gtcctttgtt gtaaatgccc ctaatggcct ttacttcatg 3420
catgttggtt attaccctag caaccacatt gaggttgttt ctgcttatgg tctttgcgat 3480
gcagctaacc ctactaattg tatagcccct gttaatggct actttattaa aactaataac 3540
actaggattg ttgatgagtg gtcatatact ggctcgtcct tctatgcacc tgagcccatt 3600
acctccctta atactaagta tgttgcacca caggtgacat accaaaacat ttctactaac 3660
ctccctcctc ctcttctcgg caattccacc gggattgact tccaagatga gttggatgag 3720
tttttcaaaa atgttagcac cagtatacct aattttggtt ccctaacaca gattaatact 3780
acattactcg atcttaccta cgagatgttg tctcttcaac aagttgttaa agcccttaag 3840
cggccgcacg gcggaggtag caaagactgc gaaatgaagc gcaccaccct ggatagccct 3900
ctgggcaagc tggaactgtc tgggtgcgaa cagggcctgc acgagatcaa gctgctgggc 3960

```
aaaggaacat ctgccgccga cgccgtggaa gtgcctgccc cagccgccgt gctgggcgga   4020

ccagagccac tgatgcaggc caccgcctgg ctcaacgcct actttcacca gcctgaggcc   4080

atcgaggagt tccctgtgcc agccctgcac cacccagtgt tccagcagga gagctttacc   4140

cgccaggtgc tgtggaaact gctgaaagtg gtgaagttcg gagaggtcat cagctaccag   4200

cagctggccg ccctggccgg caatcccgcc gccaccgccg ccgtgaaaac cgccctgagc   4260

ggaaatcccg tgcccattct gatcccctgc caccgggtgg tgtctagctc tggcgccgtg   4320

gggggctacg agggcgggct cgccgtgaaa gagtggctgc tggcccacga gggccacaga   4380

ctgggcaagc ctgggctggg tcctgcaggt ataggcgcgc cagggtccct ggagcatcat   4440

catcatcatc attgatgacg ggccc                                         4465
```

<210> SEQ ID NO 88
<211> LENGTH: 1463
<212> TYPE: PRT
<213> ORGANISM: artificial
<220> FEATURE:
<223> OTHER INFORMATION: Amino acid sequence of fusion protein [huCOV.S protein -SNAPlike-Histag]

<400> SEQUENCE: 88

```
Arg Ser Val Gly Pro Asp Ser Val Lys Ser Ala Cys Ile Glu Val Asp
1               5                   10                  15

Ile Gln Gln Thr Phe Phe Asp Lys Thr Trp Pro Arg Pro Ile Asp Val
            20                  25                  30

Ser Lys Ala Asp Gly Ile Ile Tyr Pro Gln Gly Arg Thr Tyr Ser Asn
        35                  40                  45

Ile Thr Ile Thr Tyr Gln Gly Leu Phe Pro Tyr Gln Gly Asp His Gly
    50                  55                  60

Asp Met Tyr Val Tyr Ser Ala Gly His Ala Thr Gly Thr Thr Pro Gln
65                  70                  75                  80

Lys Leu Phe Val Ala Asn Tyr Ser Gln Asp Val Lys Gln Phe Ala Asn
                85                  90                  95

Gly Phe Val Val Arg Ile Gly Ala Ala Ala Asn Ser Thr Gly Thr Val
            100                 105                 110

Ile Ile Ser Pro Ser Thr Ser Ala Thr Ile Arg Lys Ile Tyr Pro Ala
        115                 120                 125

Phe Met Leu Gly Ser Ser Val Gly Asn Phe Ser Asp Gly Lys Met Gly
    130                 135                 140

Arg Phe Phe Asn His Thr Leu Val Leu Leu Pro Asp Gly Cys Gly Thr
145                 150                 155                 160

Leu Leu Arg Ala Phe Tyr Cys Ile Leu Glu Pro Arg Ser Gly Asn His
                165                 170                 175

Cys Pro Ala Gly Asn Ser Tyr Thr Ser Phe Ala Thr Tyr His Thr Pro
            180                 185                 190

Ala Thr Asp Cys Ser Asp Gly Asn Tyr Asn Arg Asn Ala Ser Leu Asn
        195                 200                 205

Ser Phe Lys Glu Tyr Phe Asn Leu Arg Asn Cys Thr Phe Met Tyr Thr
    210                 215                 220

Tyr Asn Ile Thr Glu Asp Glu Ile Leu Glu Trp Phe Gly Ile Thr Gln
225                 230                 235                 240

Thr Ala Gln Gly Val His Leu Phe Ser Ser Arg Tyr Val Asp Leu Tyr
                245                 250                 255

Gly Gly Asn Met Phe Gln Phe Ala Thr Leu Pro Val Tyr Asp Thr Ile
            260                 265                 270
```

```
Lys Tyr Tyr Ser Ile Ile Pro His Ser Ile Arg Ser Ile Gln Ser Asp
        275                 280                 285

Arg Lys Ala Trp Ala Ala Phe Tyr Val Tyr Lys Leu Gln Pro Leu Thr
    290                 295                 300

Phe Leu Leu Asp Phe Ser Val Asp Gly Tyr Ile Arg Arg Ala Ile Asp
305                 310                 315                 320

Cys Gly Phe Asn Asp Leu Ser Gln Leu His Cys Ser Tyr Glu Ser Phe
                325                 330                 335

Asp Val Glu Ser Gly Val Tyr Ser Val Ser Ser Phe Glu Ala Lys Pro
            340                 345                 350

Ser Gly Ser Val Val Glu Gln Ala Glu Gly Val Glu Cys Asp Phe Ser
        355                 360                 365

Pro Leu Leu Ser Gly Thr Pro Pro Gln Val Tyr Asn Phe Lys Arg Leu
    370                 375                 380

Val Phe Thr Asn Cys Asn Tyr Asn Leu Thr Lys Leu Leu Ser Leu Phe
385                 390                 395                 400

Ser Val Asn Asp Phe Thr Cys Ser Gln Ile Ser Pro Ala Ala Ile Ala
                405                 410                 415

Ser Asn Cys Tyr Ser Ser Leu Ile Leu Asp Tyr Phe Ser Tyr Pro Leu
            420                 425                 430

Ser Met Lys Ser Asp Leu Ser Val Ser Ser Ala Gly Pro Ile Ser Gln
        435                 440                 445

Phe Asn Tyr Lys Gln Ser Phe Ser Asn Pro Thr Cys Leu Ile Leu Ala
    450                 455                 460

Thr Val Pro His Asn Leu Thr Thr Ile Thr Lys Pro Leu Lys Tyr Ser
465                 470                 475                 480

Tyr Ile Asn Lys Cys Ser Arg Leu Leu Ser Asp Asp Arg Thr Glu Val
                485                 490                 495

Pro Gln Leu Val Asn Ala Asn Gln Tyr Ser Pro Cys Val Ser Ile Val
            500                 505                 510

Pro Ser Thr Val Trp Glu Asp Gly Asp Tyr Tyr Arg Lys Gln Leu Ser
        515                 520                 525

Pro Leu Glu Gly Gly Gly Trp Leu Val Ala Ser Gly Ser Thr Val Ala
    530                 535                 540

Met Thr Glu Gln Leu Gln Met Gly Phe Gly Ile Thr Val Gln Tyr Gly
545                 550                 555                 560

Thr Asp Thr Asn Ser Val Cys Pro Lys Leu Glu Phe Ala Asn Asp Thr
                565                 570                 575

Lys Ile Ala Ser Gln Leu Gly Asn Cys Val Glu Tyr Ser Leu Tyr Gly
            580                 585                 590

Val Ser Gly Arg Gly Val Phe Gln Asn Cys Thr Ala Val Gly Val Arg
        595                 600                 605

Gln Gln Arg Phe Val Tyr Asp Ala Tyr Gln Asn Leu Val Gly Tyr Tyr
    610                 615                 620

Ser Asp Asp Gly Asn Tyr Tyr Cys Leu Arg Ala Cys Val Ser Val Pro
625                 630                 635                 640

Val Ser Val Ile Tyr Asp Lys Glu Thr Lys Thr His Ala Thr Leu Phe
                645                 650                 655

Gly Ser Val Ala Cys Glu His Ile Ser Ser Thr Met Ser Gln Tyr Ser
            660                 665                 670

Arg Ser Thr Arg Ser Met Leu Lys Arg Arg Asp Ser Thr Tyr Gly Pro
        675                 680                 685
```

```
Leu Gln Thr Pro Val Gly Cys Val Leu Gly Leu Val Asn Ser Ser Leu
    690                 695                 700

Phe Val Glu Asp Cys Lys Leu Pro Leu Gly Gln Ser Leu Cys Ala Leu
705                 710                 715                 720

Pro Asp Thr Pro Ser Thr Leu Thr Pro Arg Ser Val Arg Ser Val Pro
                725                 730                 735

Gly Glu Met Arg Leu Ala Ser Ile Ala Phe Asn His Pro Ile Gln Val
            740                 745                 750

Asp Gln Leu Asn Ser Ser Tyr Phe Lys Leu Ser Ile Pro Thr Asn Phe
        755                 760                 765

Ser Phe Gly Val Thr Gln Glu Tyr Ile Gln Thr Thr Ile Gln Lys Val
    770                 775                 780

Thr Val Asp Cys Lys Gln Tyr Val Cys Asn Gly Phe Gln Lys Cys Glu
785                 790                 795                 800

Gln Leu Leu Arg Glu Tyr Gly Gln Phe Cys Ser Lys Ile Asn Gln Ala
                805                 810                 815

Leu His Gly Ala Asn Leu Arg Gln Asp Asp Ser Val Arg Asn Leu Phe
            820                 825                 830

Ala Ser Val Lys Ser Ser Gln Ser Ser Pro Ile Ile Pro Gly Phe Gly
        835                 840                 845

Gly Asp Phe Asn Leu Thr Leu Leu Glu Pro Val Ser Ile Ser Thr Gly
    850                 855                 860

Ser Arg Ser Ala Arg Ser Ala Ile Glu Asp Leu Leu Phe Asp Lys Val
865                 870                 875                 880

Thr Ile Ala Asp Pro Gly Tyr Met Gln Gly Tyr Asp Asp Cys Met Gln
                885                 890                 895

Gln Gly Pro Ala Ser Ala Arg Asp Leu Ile Cys Ala Gln Tyr Val Ala
            900                 905                 910

Gly Tyr Lys Val Leu Pro Pro Leu Met Asp Val Asn Met Glu Ala Ala
        915                 920                 925

Tyr Thr Ser Ser Leu Leu Gly Ser Ile Ala Gly Val Gly Trp Thr Ala
    930                 935                 940

Gly Leu Ser Ser Phe Ala Ala Ile Pro Phe Ala Gln Ser Ile Phe Tyr
945                 950                 955                 960

Arg Leu Asn Gly Val Gly Ile Thr Gln Gln Val Leu Ser Glu Asn Gln
                965                 970                 975

Lys Leu Ile Ala Asn Lys Phe Asn Gln Ala Leu Gly Ala Met Gln Thr
            980                 985                 990

Gly Phe Thr Thr Thr Asn Glu Ala  Phe Gln Lys Val Gln  Asp Ala Val
        995                 1000                1005

Asn Asn  Asn Ala Gln Ala Leu  Ser Lys Leu Ala Ser  Glu Leu Ser
    1010                1015                1020

Asn Thr  Phe Gly Ala Ile Ser  Ala Ser Ile Gly Asp  Ile Ile Gln
    1025                1030                1035

Arg Leu  Asp Val Leu Glu Gln  Asp Ala Gln Ile Asp  Arg Leu Ile
    1040                1045                1050

Asn Gly  Arg Leu Thr Thr Leu  Asn Ala Phe Val Ala  Gln Gln Leu
    1055                1060                1065

Val Arg  Ser Glu Ser Ala Ala  Leu Ser Ala Gln Leu  Ala Lys Asp
    1070                1075                1080

Lys Val  Asn Glu Cys Val Lys  Ala Gln Ser Lys Arg  Ser Gly Phe
    1085                1090                1095

Cys Gly  Gln Gly Thr His Ile  Val Ser Phe Val Val  Asn Ala Pro
```

```
    1100                1105                1110

Asn Gly  Leu Tyr Phe Met His  Val Gly Tyr Tyr Pro  Ser Asn His
    1115                1120                1125

Ile Glu  Val Val Ser Ala Tyr  Gly Leu Cys Asp Ala  Ala Asn Pro
    1130                1135                1140

Thr Asn  Cys Ile Ala Pro Val  Asn Gly Tyr Phe Ile  Lys Thr Asn
    1145                1150                1155

Asn Thr  Arg Ile Val Asp Glu  Trp Ser Tyr Thr Gly  Ser Ser Phe
    1160                1165                1170

Tyr Ala  Pro Glu Pro Ile Thr  Ser Leu Asn Thr Lys  Tyr Val Ala
    1175                1180                1185

Pro Gln  Val Thr Tyr Gln Asn  Ile Ser Thr Asn Leu  Pro Pro Pro
    1190                1195                1200

Leu Leu  Gly Asn Ser Thr Gly  Ile Asp Phe Gln Asp  Glu Leu Asp
    1205                1210                1215

Glu Phe  Phe Lys Asn Val Ser  Thr Ser Ile Pro Asn  Phe Gly Ser
    1220                1225                1230

Leu Thr  Gln Ile Asn Thr Thr  Leu Leu Asp Leu Thr  Tyr Glu Met
    1235                1240                1245

Leu Ser  Leu Gln Gln Val Val  Lys Ala Leu Lys Arg  Pro His Gly
    1250                1255                1260

Gly Gly  Ser Lys Asp Cys Glu  Met Lys Arg Thr Thr  Leu Asp Ser
    1265                1270                1275

Pro Leu  Gly Lys Leu Glu Leu  Ser Gly Cys Glu Gln  Gly Leu His
    1280                1285                1290

Glu Ile  Lys Leu Leu Gly Lys  Gly Thr Ser Ala Ala  Asp Ala Val
    1295                1300                1305

Glu Val  Pro Ala Pro Ala Ala  Val Leu Gly Gly Pro  Glu Pro Leu
    1310                1315                1320

Met Gln  Ala Thr Ala Trp Leu  Asn Ala Tyr Phe His  Gln Pro Glu
    1325                1330                1335

Ala Ile  Glu Glu Phe Pro Val  Pro Ala Leu His His  Pro Val Phe
    1340                1345                1350

Gln Gln  Glu Ser Phe Thr Arg  Gln Val Leu Trp Lys  Leu Leu Lys
    1355                1360                1365

Val Val  Lys Phe Gly Glu Val  Ile Ser Tyr Gln Gln  Leu Ala Ala
    1370                1375                1380

Leu Ala  Gly Asn Pro Ala Ala  Thr Ala Ala Val Lys  Thr Ala Leu
    1385                1390                1395

Ser Gly  Asn Pro Val Pro Ile  Leu Ile Pro Cys His  Arg Val Val
    1400                1405                1410

Ser Ser  Ser Gly Ala Val Gly  Gly Tyr Glu Gly Gly  Leu Ala Val
    1415                1420                1425

Lys Glu  Trp Leu Leu Ala His  Glu Gly His Arg Leu  Gly Lys Pro
    1430                1435                1440

Gly Leu  Gly Pro Ala Gly Ile  Gly Ala Pro Gly Ser  Leu Glu His
    1445                1450                1455

His His  His His His
    1460
```

<210> SEQ ID NO 89
<211> LENGTH: 1325
<212> TYPE: DNA
<213> ORGANISM: artificial
<220> FEATURE:
<223> OTHER INFORMATION: DNA sequence encoding ssBiP - SNAPlike -proTEV-
C protein from hepatitis C virus strain TCHM-R2/03 of genotype
1b - -proTEV - Histag for expression in S2 cells

<400> SEQUENCE: 89

```
atgaagttat gcatattact ggccgtcgtg gtggcctttg ttggcctctc gctcgggaga     60

tctagatctg acaaagactg cgaaatgaaa agaactacat tggattcacc acttgggaag    120

ttggaactga gtggatgcga gcaaggattg catgaaatta agctactggg aaaaggaact    180

tctgctgctg atgcagttga agttccagca ccagcagctg ttcttggagg tcctgagccc    240

ctcatgcaag ccacagcctg gcttaacgca tatttccacc agcctgaggc cattgaggaa    300

tttccagtcc ccgcccttca ccatcctgtg tttcagcagg agagcttcac ccgccaggtc    360

ctgtggaaat tgctgaaggt ggtcaagttt ggtgaagtga tttcatatca gcaacttgct    420

gcattggccg gtaaccccgc agctacagct gccgtgaaaa ctgctctcag cggaaatcct    480

gtgcccatcc tgatcccttg tcacagagtc gtttcatctt ccggagctgt aggtggctat    540

gaaggaggac tggcagttaa ggagtggctg ctggctcatg aaggtcatag acttggaaag    600

cctgggctgg gtcctgctgg tataggcgcg ccagggtccc taggtggcgg atccgaaaac    660

ctgtacttcc agagcgatat cagtacaaat cctaaacctc aaagaaaaac taaacgaaat    720

actaatcgtc gtccacaaga tgttaagttt ccgggaggag gacaaattgt tggtggagtt    780

tacctattgc cgcgaagagg tcctcgttta ggtgttcgag caactagaaa aacttctgaa    840

cgatcacaac ctcgtggaag acgacaacct attcctaagg ctcgtcagcc tgaaggtaga    900

gcttgggctc agcctggtta tccttggcct ctatatggta atgaaggaat gggttgggca    960

ggatggctac tatcacctcg tggttctcga cctagttggg gtgcaaatga ccctcgacga   1020

agatcacgta atttaggtaa ggtaattgat acacttacat gtggttttgc tgatcttatg   1080

ggatatattc cactagtagg tgctccacta ggtggagctg caagagttct tgcacatggt   1140

gtacgagttc ttgaagatgg agtgaactat gcaacaggta atcttcctgg atgttcattt   1200

tctatttttc tattagcttt gctatcatgt ctgactattc cagcttcagc tggcccggga   1260

gagaatctat attttcaagg gcccggcgga ggtagtcacc atcatcacca tcactaatga   1320

ccggt                                                               1325
```

<210> SEQ ID NO 90
<211> LENGTH: 417
<212> TYPE: PRT
<213> ORGANISM: artificial
<220> FEATURE:
<223> OTHER INFORMATION: Amino acid sequence of fusion protein
[SNAPlike-proTEV-C protein of HCV-proTEV-Histag]

<400> SEQUENCE: 90

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80
```

```
Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Thr
        195                 200                 205

Asn Pro Lys Pro Gln Arg Lys Thr Lys Arg Asn Thr Asn Arg Arg Pro
    210                 215                 220

Gln Asp Val Lys Phe Pro Gly Gly Gly Gln Ile Val Gly Gly Val Tyr
225                 230                 235                 240

Leu Leu Pro Arg Arg Gly Pro Arg Leu Gly Val Arg Ala Thr Arg Lys
                245                 250                 255

Thr Ser Glu Arg Ser Gln Pro Arg Gly Arg Arg Gln Pro Ile Pro Lys
            260                 265                 270

Ala Arg Gln Pro Glu Gly Arg Ala Trp Ala Gln Pro Gly Tyr Pro Trp
        275                 280                 285

Pro Leu Tyr Gly Asn Glu Gly Met Gly Trp Ala Gly Trp Leu Leu Ser
    290                 295                 300

Pro Arg Gly Ser Arg Pro Ser Trp Gly Ala Asn Asp Pro Arg Arg Arg
305                 310                 315                 320

Ser Arg Asn Leu Gly Lys Val Ile Asp Thr Leu Thr Cys Gly Phe Ala
                325                 330                 335

Asp Leu Met Gly Tyr Ile Pro Leu Val Gly Ala Pro Leu Gly Gly Ala
            340                 345                 350

Ala Arg Val Leu Ala His Gly Val Arg Val Leu Glu Asp Gly Val Asn
        355                 360                 365

Tyr Ala Thr Gly Asn Leu Pro Gly Cys Ser Phe Ser Ile Phe Leu Leu
    370                 375                 380

Ala Leu Leu Ser Cys Leu Thr Ile Pro Ala Ser Ala Gly Pro Gly Glu
385                 390                 395                 400

Asn Leu Tyr Phe Gln Gly Pro Gly Gly Gly Ser His His His His His
                405                 410                 415

His
```

```
<210> SEQ ID NO 91
<211> LENGTH: 1376
<212> TYPE: DNA
<213> ORGANISM: artificial
<220> FEATURE:
<223> OTHER INFORMATION: DNA sequence encoding ssBiP- SNAPlike -
      MSP1(19) antigen from Plasmodium falciparum - proTEV - AMA-1(III)
      antigen from Plasmodium falciparum - Histag for expression in S2
      cells

<400> SEQUENCE: 91

atgaagttat gcatattact ggccgtcgtg gtggcctttg ttggcctctc gctcgggaga     60
```

```
tctagatctg acaaagactg cgaaatgaaa agaactacat tggattcacc acttgggaag    120

ttggaactga gtggatgcga gcaaggattg catgaaatta agctactggg aaaaggaact    180

tctgctgctg atgcagttga agttccagca ccagcagctg ttcttggagg tcctgagccc    240

ctcatgcaag ccacagcctg gcttaacgca tatttccacc agcctgaggc cattgaggaa    300

tttccagtcc ccgcccttca ccatcctgtg tttcagcagg agagcttcac ccgccaggtc    360

ctgtggaaat tgctgaaggt ggtcaagttt ggtgaagtga tttcatatca gcaacttgct    420

gcattggccg gtaaccccgc agctacagct gccgtgaaaa ctgctctcag cggaaatcct    480

gtgcccatcc tgatcccttg tcacagagtc gtttcatctt ccggagctgt aggtggctat    540

gaaggaggac tggcagttaa ggagtggctg ctggctcatg aaggtcatag acttggaaag    600

cctgggctgg gtcctgctgg tataggcgcg ccagggtccc taggtggcgg atccgaaaac    660

ctgtacttcc agagcgatat caaacaatgt ccacaaaatt ctggatgttt cagacattta    720

gatgaaagag aagaatgtaa atgtttatta aattacaaac aagaaggtga taaatgtgtt    780

gaaaatccaa atcttacttg taacgaaaat aatggtggat gtgatgcaga tgccaaatgt    840

accgaagaag attcaggcag caacggaaag aaaatcacat gtgaatgtac taaacctgat    900

tcttatccac ttttcgatgg tattttcgga ggtggctctg agaatctata ttttcaaggg    960

cccggtggag gcgaagttga aaacaatttt ccatgttcat tatataaaga tgaaataatg   1020

aaagaaatcg aaagagaatc aaaacgaatt aaattaaatg ataatgatga tgaagggaat   1080

aaaaaaatta tagctccaag aatttttatt tcagatgata aagacagttt aaaatgccca   1140

tgtgaccctg aaatggtaag taatagtaca tgtcgtttct ttgtatgtaa atgtgtagaa   1200

agaagggcag aagtaacatc aaataatgaa gttgtagtta aagaagaata taaagatgaa   1260

tatgcagata ttcctgaaca taaaccaact tatgataaaa tgctcccggg agagaatcta   1320

tattttcaag ggcccggcgg aggtagtcac catcatcacc atcactaatg accggt        1376
```

<210> SEQ ID NO 92
<211> LENGTH: 434
<212> TYPE: PRT
<213> ORGANISM: artificial
<220> FEATURE:
<223> OTHER INFORMATION: Amino acid sequence of fusion protein [SNAPlike-MSP1-proTEV-AMA1-Histag]

<400> SEQUENCE: 92

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125
```

```
Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Lys Gln
        195                 200                 205

Cys Pro Gln Asn Ser Gly Cys Phe Arg His Leu Asp Glu Arg Glu Glu
    210                 215                 220

Cys Lys Cys Leu Leu Asn Tyr Lys Gln Glu Gly Asp Lys Cys Val Glu
225                 230                 235                 240

Asn Pro Asn Leu Thr Cys Asn Glu Asn Asn Gly Gly Cys Asp Ala Asp
                245                 250                 255

Ala Lys Cys Thr Glu Glu Asp Ser Gly Ser Asn Gly Lys Lys Ile Thr
            260                 265                 270

Cys Glu Cys Thr Lys Pro Asp Ser Tyr Pro Leu Phe Asp Gly Ile Phe
        275                 280                 285

Gly Gly Gly Ser Glu Asn Leu Tyr Phe Gln Gly Pro Gly Gly Gly Glu
    290                 295                 300

Val Glu Asn Asn Phe Pro Cys Ser Leu Tyr Lys Asp Glu Ile Met Lys
305                 310                 315                 320

Glu Ile Glu Arg Glu Ser Lys Arg Ile Lys Leu Asn Asp Asn Asp Asp
                325                 330                 335

Glu Gly Asn Lys Lys Ile Ile Ala Pro Arg Ile Phe Ile Ser Asp Asp
            340                 345                 350

Lys Asp Ser Leu Lys Cys Pro Cys Asp Pro Glu Met Val Ser Asn Ser
        355                 360                 365

Thr Cys Arg Phe Phe Val Cys Lys Cys Val Glu Arg Arg Ala Glu Val
    370                 375                 380

Thr Ser Asn Asn Glu Val Val Val Lys Glu Glu Tyr Lys Asp Glu Tyr
385                 390                 395                 400

Ala Asp Ile Pro Glu His Lys Pro Thr Tyr Asp Lys Met Leu Pro Gly
                405                 410                 415

Glu Asn Leu Tyr Phe Gln Gly Pro Gly Gly Gly Ser His His His His
            420                 425                 430

His His
```

<210> SEQ ID NO 93
<211> LENGTH: 2195
<212> TYPE: DNA
<213> ORGANISM: artificial
<220> FEATURE:
<223> OTHER INFORMATION: DNA sequence encoding ssBiP- SNAPlike -proTEV- modified short form of HbpA from Leptospira interrogans serovar Lai str.56601 - proTEV- Histag for expression in S2 cells

<400> SEQUENCE: 93

```
atgaagttat gcatattact ggccgtcgtg gtggcctttg ttggcctctc gctcgggaga      60

tctagatctg acaaagactg cgaaatgaaa agaactacat tggattcacc acttgggaag     120

ttggaactga gtggatgcga gcaaggattg catgaaatta agctactggg aaaaggaact     180

tctgctgctg atgcagttga agttccagca ccagcagctg ttcttggagg tcctgagccc     240
```

ctcatgcaag ccacagcctg gcttaacgca tatttccacc agcctgaggc cattgaggaa 300
tttccagtcc ccgcccttca ccatcctgtg tttcagcagg agagcttcac ccgccaggtc 360
ctgtggaaat tgctgaaggt ggtcaagttt ggtgaagtga tttcatatca gcaacttgct 420
gcattggccg gtaaccccgc agctacagct gccgtgaaaa ctgctctcag cggaaatcct 480
gtgcccatcc tgatcccttg tcacagagtc gtttcatctt ccggagctgt aggtggctat 540
gaaggaggac tggcagttaa ggagtggctg ctggctcatg aaggtcatag acttggaaag 600
cctgggctgg gtcctgctgg tataggcgcg ccagggtccc taggtggcgg atccgaaaac 660
ctgtacttcc agagcgatat cttcaacacc acggccaaca tgggcttcag gaacgagtac 720
gtgagcggcg cggtgtccgc aggttacaat aagaaccccg gctacaggtt ggtcccaaac 780
tctcaggcga ctactgggaa cgcctatcag gacttgaaca cgggcatcaa cctgaccttc 840
aacccggacg gcaagttcaa ggggaagacg aggattctct accagcacag ggaccagaac 900
ggggtggacg tgacccagtc caaggccgtc ttcgaccgga acaacaagac gcacgacttc 960
ttggcgacgg ggtcgttgga gtacgggtta gggaagagga acttgatctc cttcaggggg 1020
aacatctcca agtgggagaa caagtactac aacaaccaga gggggtcgga cgagttggac 1080
gtgaagcagt tgaactcgga gttgacgtcg caggggaccg tgcagttgga catggaggcc 1140
tctgagaagc acttcatcac tgtaggtgcg gagtccttcg cgaacgagtt ggagtcggac 1200
cgcttgcaga gcaggtacgt gtacaggacg aggaaggcgg tgttcttcca ggacgagtgg 1260
accgtgtccc ggtcgccgag gattcgggtg gtgccaggag tgaggtacga cgacgactcg 1320
cagttcggga accagacgac gccgaagctg gcggcccggt acgacatatt gcagaacttg 1380
gtgtggaggg cgagctacgg gaggggatta cggccgccga gcttgcagga gttgtacctg 1440
cggttcgaga acccggccgt gggttacgtg gtggagggta acccgaactt gaagccggag 1500
cggtcgatca cgatcaactc ggacttggag tacagcccgt tcagcttctt gacgttctcc 1560
ttgagcgtgt accggaacga catcatcaac ctgatccagt acaagttcga ctcgaacaag 1620
gggagggagt tcgcggagtt ccagctgcag aacatcgcga aggcgtacac gagaggagga 1680
gagttcggcg tgcagtacag gttcttgaag tacttcacgc tggagttggg gtacaaccac 1740
acggacacga gggacctgag ctcggacagg ccgttggagg gcagggcgct gcaccaggcg 1800
tcggcgaact tcatctacaa ctcgcccgga ggattccaat tcaacctgag gggcaagcac 1860
ttggacaaga ggccgttcta cagctcgacc aacaacctgt cggcggccgg acaggactac 1920
atccccagcg aggtgaagtt gaacgagaac ccgcccgtga tctacgggaa gccgttcacg 1980
atcttgaacg tgaggatcga gcagaagttc ttcaacaagc acttcgcgct gttcttgggc 2040
gtggacaact tgctcaacca gtacgagctg gcgtacaacc ccacgcggcc gaggttctac 2100
tacggcggct tctcggccca gttcccggga gagaatctat attttcaagg gcccggcgga 2160
ggtagtcacc atcatcacca tcactaatga ccggt 2195

<210> SEQ ID NO 94
<211> LENGTH: 707
<212> TYPE: PRT
<213> ORGANISM: artificial
<220> FEATURE:
<223> OTHER INFORMATION: Amino acid sequence of fusion protein
[SNAPlike-proTEV-HbPA1-proTEV-Histag]

<400> SEQUENCE: 94

Arg Ser Asp Lys Asp Cys Glu Met Lys Arg Thr Thr Leu Asp Ser Pro

-continued

```
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Phe Asn
        195                 200                 205

Thr Thr Ala Asn Met Gly Phe Arg Asn Glu Tyr Val Ser Gly Ala Val
    210                 215                 220

Ser Ala Gly Tyr Asn Lys Asn Pro Gly Tyr Arg Leu Val Pro Asn Ser
225                 230                 235                 240

Gln Ala Thr Thr Gly Asn Ala Tyr Gln Asp Leu Asn Thr Gly Ile Asn
                245                 250                 255

Leu Thr Phe Asn Pro Asp Gly Lys Phe Lys Gly Lys Thr Arg Ile Leu
            260                 265                 270

Tyr Gln His Arg Asp Gln Asn Gly Val Asp Val Thr Gln Ser Lys Ala
        275                 280                 285

Val Phe Asp Arg Asn Asn Lys Thr His Asp Phe Leu Ala Thr Gly Ser
    290                 295                 300

Leu Glu Tyr Gly Leu Gly Lys Arg Asn Leu Ile Ser Phe Arg Gly Asn
305                 310                 315                 320

Ile Ser Lys Trp Glu Asn Lys Tyr Tyr Asn Asn Gln Arg Gly Ser Asp
                325                 330                 335

Glu Leu Asp Val Lys Gln Leu Asn Ser Glu Leu Thr Ser Gln Gly Thr
            340                 345                 350

Val Gln Leu Asp Met Glu Ala Ser Glu Lys His Phe Ile Thr Val Gly
        355                 360                 365

Ala Glu Ser Phe Ala Asn Glu Leu Glu Ser Asp Arg Leu Gln Ser Arg
    370                 375                 380

Tyr Val Tyr Arg Thr Arg Lys Ala Val Phe Phe Gln Asp Glu Trp Thr
385                 390                 395                 400

Val Ser Arg Ser Pro Arg Ile Arg Val Val Pro Gly Val Arg Tyr Asp
                405                 410                 415

Asp Asp Ser Gln Phe Gly Asn Gln Thr Thr Pro Lys Leu Ala Ala Arg
            420                 425                 430
```

Tyr Asp Ile Leu Gln Asn Leu Val Trp Arg Ala Ser Tyr Gly Arg Gly
        435                 440                 445

Leu Arg Pro Pro Ser Leu Gln Glu Leu Tyr Leu Arg Phe Glu Asn Pro
    450                 455                 460

Ala Val Gly Tyr Val Val Glu Gly Asn Pro Asn Leu Lys Pro Glu Arg
465                 470                 475                 480

Ser Ile Thr Ile Asn Ser Asp Leu Glu Tyr Ser Pro Phe Ser Phe Leu
                485                 490                 495

Thr Phe Ser Leu Ser Val Tyr Arg Asn Asp Ile Ile Asn Leu Ile Gln
            500                 505                 510

Tyr Lys Phe Asp Ser Asn Lys Gly Arg Glu Phe Ala Glu Phe Gln Leu
        515                 520                 525

Gln Asn Ile Ala Lys Ala Tyr Thr Arg Gly Gly Glu Phe Gly Val Gln
    530                 535                 540

Tyr Arg Phe Leu Lys Tyr Phe Thr Leu Glu Leu Gly Tyr Asn His Thr
545                 550                 555                 560

Asp Thr Arg Asp Leu Ser Ser Asp Arg Pro Leu Glu Gly Arg Ala Leu
                565                 570                 575

His Gln Ala Ser Ala Asn Phe Ile Tyr Asn Ser Pro Gly Gly Phe Gln
            580                 585                 590

Phe Asn Leu Arg Gly Lys His Leu Asp Lys Arg Pro Phe Tyr Ser Ser
        595                 600                 605

Thr Asn Asn Leu Ser Ala Ala Gly Gln Asp Tyr Ile Pro Ser Glu Val
    610                 615                 620

Lys Leu Asn Glu Asn Pro Pro Val Ile Tyr Gly Lys Pro Phe Thr Ile
625                 630                 635                 640

Leu Asn Val Arg Ile Glu Gln Lys Phe Phe Asn Lys His Phe Ala Leu
                645                 650                 655

Phe Leu Gly Val Asp Asn Leu Leu Asn Gln Tyr Glu Leu Ala Tyr Asn
            660                 665                 670

Pro Thr Arg Pro Arg Phe Tyr Tyr Gly Gly Phe Ser Ala Gln Phe Pro
        675                 680                 685

Gly Glu Asn Leu Tyr Phe Gln Gly Pro Gly Gly Gly Ser His His His
    690                 695                 700

His His His
705

<210> SEQ ID NO 95
<211> LENGTH: 968
<212> TYPE: DNA
<213> ORGANISM: artificial
<220> FEATURE:
<223> OTHER INFORMATION: DNA sequence encoding ssBiP- SNAPlike -proTEV-
      MUB40 - proTEV- Histag for expression in S2 cells

<400> SEQUENCE: 95
atgaagttat gcatattact ggccgtcgtg gtggcctttg ttggcctctc gctcgggaga     60
tcttcgcgag ctagcaccat gaaactatgt attctacttg cagttgttgc gttcgtagga    120
ttgtccttac ctacagctct ggcaagatct gacaaagact gcgaaatgaa aagaactaca    180
ttggattcac cacttgggaa gttggaactg agtggatgcg agcaaggatt gcatgaaatt    240
aagctactgg gaaaaggaac ttctgctgct gatgcagttg aagttccagc accagcagct    300
gttcttggag gtcctgagcc cctcatgcaa gccacagcct ggcttaacgc atatttccac    360
cagcctgagg ccattgagga atttccagtc cccgcccttc accatcctgt gtttcagcag    420

```
gagagcttca cccgccaggt cctgtggaaa ttgctgaagg tggtcaagtt tggtgaagtg    480

atttcatatc agcaacttgc tgcattggcc ggtaaccccg cagctacagc tgccgtgaaa    540

actgctctca gcggaaatcc tgtgcccatc ctgatccctt gtcacagagt cgtttcatct    600

tccggagctg taggtggcta tgaaggagga ctggcagtta aggagtggct gctggctcat    660

gaaggtcata gacttggaaa gcctgggctg ggtcctgctg gtataggcgc gccagggtcc    720

ctaggtggcg gatccgaaaa cctgtacttc cagagcgata tcacggctga aggcatcaag    780

aagtttgaag gcgacggtta tgaactgttc aaggacaact tcccagctgg tgagaagttc    840

gataacgatg acaccaacga tcaattctac acggtaatct tcaagcacca tcgtggcccg    900

ggagagaatc tatattttca agggcccggc ggaggtagtc accatcatca ccatcactaa    960

tgaccggt                                                             968
```

```
<210> SEQ ID NO 96
<211> LENGTH: 298
<212> TYPE: PRT
<213> ORGANISM: artificial
<220> FEATURE:
<223> OTHER INFORMATION: Amino acid sequence of fusion protein
      [SNAPlike-proTEV-MUB40-proTEV-Histag]

<400> SEQUENCE: 96

Ser Arg Ala Ser Thr Met Lys Leu Cys Ile Leu Leu Ala Val Val Ala
1               5                   10                  15

Phe Val Gly Leu Ser Leu Pro Thr Ala Leu Ala Arg Ser Asp Lys Asp
            20                  25                  30

Cys Glu Met Lys Arg Thr Thr Leu Asp Ser Pro Leu Gly Lys Leu Glu
        35                  40                  45

Leu Ser Gly Cys Glu Gln Gly Leu His Glu Ile Lys Leu Leu Gly Lys
    50                  55                  60

Gly Thr Ser Ala Ala Asp Ala Val Glu Val Pro Ala Pro Ala Ala Val
65                  70                  75                  80

Leu Gly Gly Pro Glu Pro Leu Met Gln Ala Thr Ala Trp Leu Asn Ala
                85                  90                  95

Tyr Phe His Gln Pro Glu Ala Ile Glu Glu Phe Pro Val Pro Ala Leu
            100                 105                 110

His His Pro Val Phe Gln Gln Glu Ser Phe Thr Arg Gln Val Leu Trp
        115                 120                 125

Lys Leu Leu Lys Val Val Lys Phe Gly Glu Val Ile Ser Tyr Gln Gln
    130                 135                 140

Leu Ala Ala Leu Ala Gly Asn Pro Ala Ala Thr Ala Ala Val Lys Thr
145                 150                 155                 160

Ala Leu Ser Gly Asn Pro Val Pro Ile Leu Ile Pro Cys His Arg Val
                165                 170                 175

Val Ser Ser Ser Gly Ala Val Gly Gly Tyr Glu Gly Gly Leu Ala Val
            180                 185                 190

Lys Glu Trp Leu Leu Ala His Glu Gly His Arg Leu Gly Lys Pro Gly
        195                 200                 205

Leu Gly Pro Ala Gly Ile Gly Ala Pro Gly Ser Leu Gly Gly Gly Ser
    210                 215                 220

Glu Asn Leu Tyr Phe Gln Ser Asp Ile Thr Ala Glu Gly Ile Lys Lys
225                 230                 235                 240

Phe Glu Gly Asp Gly Tyr Glu Leu Phe Lys Asp Asn Phe Pro Ala Gly
                245                 250                 255
```

```
Glu Lys Phe Asp Asn Asp Asp Thr Asn Asp Gln Phe Tyr Thr Val Ile
            260                 265                 270

Phe Lys His His Arg Gly Pro Gly Glu Asn Leu Tyr Phe Gln Gly Pro
        275                 280                 285

Gly Gly Gly Ser His His His His His His
    290                 295
```

<210> SEQ ID NO 97
<211> LENGTH: 1238
<212> TYPE: DNA
<213> ORGANISM: artificial
<220> FEATURE:
<223> OTHER INFORMATION: DNA sequence encoding ssBiP- SNAPlike -proTEV- soluble form of mouse C-type like lectin (CLEC5A) - proTEV- Histag for expression in S2 cells

<400> SEQUENCE: 97

```
atgaagttat gcatattact ggccgtcgtg gtggcctttg ttggcctctc gctcgggaga     60

tctagatctg acaaagactg cgaaatgaaa agaactacat tggattcacc acttgggaag    120

ttggaactga gtggatgcga gcaaggattg catgaaatta agctactggg aaaaggaact    180

tctgctgctg atgcagttga agttccagca ccagcagctg ttcttggagg tcctgagccc    240

ctcatgcaag ccacagcctg gcttaacgca tatttccacc agcctgaggc cattgaggaa    300

tttccagtcc ccgcccttca ccatcctgtg tttcagcagg agagcttcac ccgccaggtc    360

ctgtggaaat tgctgaaggt ggtcaagttt ggtgaagtga tttcatatca gcaacttgct    420

gcattggccg gtaaccccgc agctacagct gccgtgaaaa ctgctctcag cggaaatcct    480

gtgcccatcc tgatcccttg tcacagagtc gtttcatctt ccggagctgt aggtggctat    540

gaaggaggac tggcagttaa ggagtggctg ctggctcatg aaggtcatag acttggaaag    600

cctgggctgg gtcctgctgg tataggcgcg ccagggtccc taggtggcgg atccgaaaac    660

ctgtacttcc agagcgatat cgtttttggc aaaagtaatg atggcttcgt ccccacggag    720

agctacggaa ccactagtgt gcagaatgtc tcacaaatct ttgggagaaa tgacgaaagt    780

accatgccta caaggagcta tggaacagtc tgtcccagaa actgggattt tcaccaagga    840

aaatgctttt tcttctcctt ctccgaatca ccttggaaag acagcatgga ttattgtgca    900

acacaagggt ccacactggc aattgtcaac actccagaga aactgaagta tcttcaggac    960

atagctggta ttgagaatta ctttattggt ttggtacgtc agcctggaga gaaaaagtgg   1020

cgctggatca acaactctgt gttcaatggc aatgttacca atcaggacca gaacttcgac   1080

tgtgtcacta taggtctgac gaagacatat gatgctgcat catgtgaagt cagctatcgc   1140

tggatctgcg aaatgaatgc caaaggcccg ggagagaatc tatattttca agggcccggc   1200

ggaggtagtc accatcatca ccatcactaa tgaccggt                           1238
```

<210> SEQ ID NO 98
<211> LENGTH: 388
<212> TYPE: PRT
<213> ORGANISM: artificial
<220> FEATURE:
<223> OTHER INFORMATION: Amino acid sequence of fusion protein [SNAPlike-proTEV-moCLEC5A-proTEV-Histag]

<400> SEQUENCE: 98

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
```

```
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Val Phe
        195                 200                 205

Gly Lys Ser Asn Asp Gly Phe Val Pro Thr Glu Ser Tyr Gly Thr Thr
    210                 215                 220

Ser Val Gln Asn Val Ser Gln Ile Phe Gly Arg Asn Asp Glu Ser Thr
225                 230                 235                 240

Met Pro Thr Arg Ser Tyr Gly Thr Val Cys Pro Arg Asn Trp Asp Phe
                245                 250                 255

His Gln Gly Lys Cys Phe Phe Phe Ser Phe Ser Glu Ser Pro Trp Lys
            260                 265                 270

Asp Ser Met Asp Tyr Cys Ala Thr Gln Gly Ser Thr Leu Ala Ile Val
        275                 280                 285

Asn Thr Pro Glu Lys Leu Lys Tyr Leu Gln Asp Ile Ala Gly Ile Glu
    290                 295                 300

Asn Tyr Phe Ile Gly Leu Val Arg Gln Pro Gly Glu Lys Lys Trp Arg
305                 310                 315                 320

Trp Ile Asn Asn Ser Val Phe Asn Gly Asn Val Thr Asn Gln Asp Gln
                325                 330                 335

Asn Phe Asp Cys Val Thr Ile Gly Leu Thr Lys Thr Tyr Asp Ala Ala
            340                 345                 350

Ser Cys Glu Val Ser Tyr Arg Trp Ile Cys Glu Met Asn Ala Lys Gly
        355                 360                 365

Pro Gly Glu Asn Leu Tyr Phe Gln Gly Pro Gly Gly Gly Ser His His
    370                 375                 380

His His His His
385
```

<210> SEQ ID NO 99
<211> LENGTH: 1229
<212> TYPE: DNA
<213> ORGANISM: artificial
<220> FEATURE:
<223> OTHER INFORMATION: DNA sequence encoding ssBiP- SNAPlike -proTEV- soluble form of human C-type like lectin (CLEC5A) - proTEV- Histag for expression in S2 cells

<400> SEQUENCE: 99

```
atgaagttat gcatattact ggccgtcgtg gtggcctttg ttggcctctc gctcgggaga     60
tctagatctg acaaagactg cgaaatgaaa agaactacat tggattcacc acttgggaag    120
ttggaactga gtggatgcga gcaaggattg catgaaatta agctactggg aaaaggaact    180
tctgctgctg atgcagttga agttccagca ccagcagctg ttcttggagg tcctgagccc    240
ctcatgcaag ccacagcctg gcttaacgca tatttccacc agcctgaggc cattgaggaa    300
tttccagtcc ccgcccttca ccatcctgtg tttcagcagg agagcttcac ccgccaggtc    360
ctgtggaaat tgctgaaggt ggtcaagttt ggtgaagtga tttcatatca gcaacttgct    420
gcattggccg gtaaccccgc agctacagct gccgtgaaaa ctgctctcag cggaaatcct    480
gtgcccatcc tgatcccttg tcacagagtc gtttcatctt ccggagctgt aggtggctat    540
gaaggaggac tggcagttaa ggagtggctg ctggctcatg aaggtcatag acttggaaag    600
cctgggctgg gtcctgctgg tataggcgcg ccagggtccc taggtggcgg atccgaaaac    660
ctgtacttcc agagcgatat ctttaacaaa agtaacgatg gtttcaccac caccaggagc    720
tatggaacag tctcacagat ttttgggagc agttccccaa gtcccaacgg cttcattacc    780
acaaggagct atggaacagt ctgccccaaa gactgggaat tttatcaagc aagatgtttt    840
ttcttatcca cttctgaatc atcttggaat gaaagcaggg acttttgcaa aggaaaaggc    900
tccacattgg caattgtcaa cacgccagag aaactgaagt ttcttcagga cataactgat    960
gctgagaagt attttattgg cttaatttac catcgtgaag agaaaaggtg gcgttggatc   1020
aacaactctg tgttcaatgg caatgttacc aatcagaatc agaatttcaa ctgtgcgacc   1080
attggcctaa caaagacatt tgatgctgca tcatgtgaca tcagctaccg caggatctgt   1140
gagaagaatg ccaaaggccc gggagagaat ctatattttc aagggcccgg cggaggtagt   1200
caccatcatc accatcacta atgaccggt                                     1229
```

<210> SEQ ID NO 100
<211> LENGTH: 385
<212> TYPE: PRT
<213> ORGANISM: artificial
<220> FEATURE:
<223> OTHER INFORMATION: Amino acid sequence of fusion protein
      [SNAPlike-proTEV-huCLEC5A-proTEV-Histag]

<400> SEQUENCE: 100

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
```

-continued

```
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Phe Asn
        195                 200                 205

Lys Ser Asn Asp Gly Phe Thr Thr Thr Arg Ser Tyr Gly Thr Val Ser
    210                 215                 220

Gln Ile Phe Gly Ser Ser Ser Pro Ser Pro Asn Gly Phe Ile Thr Thr
225                 230                 235                 240

Arg Ser Tyr Gly Thr Val Cys Pro Lys Asp Trp Glu Phe Tyr Gln Ala
                245                 250                 255

Arg Cys Phe Phe Leu Ser Thr Ser Glu Ser Ser Trp Asn Glu Ser Arg
            260                 265                 270

Asp Phe Cys Lys Gly Lys Gly Ser Thr Leu Ala Ile Val Asn Thr Pro
        275                 280                 285

Glu Lys Leu Lys Phe Leu Gln Asp Ile Thr Asp Ala Glu Lys Tyr Phe
    290                 295                 300

Ile Gly Leu Ile Tyr His Arg Glu Glu Lys Arg Trp Arg Trp Ile Asn
305                 310                 315                 320

Asn Ser Val Phe Asn Gly Asn Val Thr Asn Gln Asn Gln Asn Phe Asn
                325                 330                 335

Cys Ala Thr Ile Gly Leu Thr Lys Thr Phe Asp Ala Ala Ser Cys Asp
            340                 345                 350

Ile Ser Tyr Arg Arg Ile Cys Glu Lys Asn Ala Lys Gly Pro Gly Glu
        355                 360                 365

Asn Leu Tyr Phe Gln Gly Pro Gly Gly Gly Ser His His His His His
    370                 375                 380

His
385


<210> SEQ ID NO 101
<211> LENGTH: 962
<212> TYPE: DNA
<213> ORGANISM: artificial
<220> FEATURE:
<223> OTHER INFORMATION: DNA sequence encoding BiPlike- SNAPlike- cxVAGO
      protein from Culex quinquefasciatus - Histag for expression in S2
      cells

<400> SEQUENCE: 101

atgaaactat gtattctact tgcagttgtt gcgttcgtag gattgtcctt aagatctgac      60

aaagactgcg aaatgaaaag aactacattg gattcaccac ttgggaagtt ggaactgagt     120

ggatgcgagc aaggattgca tgaaattaag ctactgggaa aaggaacttc tgctgctgat     180

gcagttgaag ttccagcacc agcagctgtt cttggaggtc ctgagcccct catgcaagcc     240

acagcctggc ttaacgcata tttccaccag cctgaggcca ttgaggaatt tccagtcccc     300

gcccttcacc atcctgtgtt tcagcaggag agcttcaccc gccaggtcct gtggaaattg     360

ctgaaggtgg tcaagtttgg tgaagtgatt tcatatcagc aacttgctgc attggccggt     420
```

```
aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc agggtccctg gagggaggtg gcgggtctga agccgttcta    660

caaaatgccg agcatccaga ttaccctgga aagtgttacg acgaaggtac gcagaccgtt    720

gtagctcccc tagaaagtgc gaagctacca aaatcgtgta caaaggtatt ctgctcgact    780

aacctttcac tgacctatac tacgtgtggg tcagtacttg tcaatgaccc gcactgcgag    840

aagatcgaac aagacctgac taaagacttc ccagagtgct gtcacaagta taaatgtgaa    900

ctggagggag tagtcacgta ccacggaggt ggccatcacc atcaccatca ctgatgaccg    960

gt                                                                   962
```

```
<210> SEQ ID NO 102
<211> LENGTH: 300
<212> TYPE: PRT
<213> ORGANISM: artificial
<220> FEATURE:
<223> OTHER INFORMATION: Amino acid sequence of fusion protein
      [SNAPlike-cxVAGO-Histag]

<400> SEQUENCE: 102

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Glu Ala Val Leu Gln Asn Ala Glu His
        195                 200                 205

Pro Asp Tyr Pro Gly Lys Cys Tyr Asp Glu Gly Thr Gln Thr Val Val
    210                 215                 220

Ala Pro Leu Glu Ser Ala Lys Leu Pro Lys Ser Cys Thr Lys Val Phe
225                 230                 235                 240

Cys Ser Thr Asn Leu Ser Leu Thr Tyr Thr Thr Cys Gly Ser Val Leu
                245                 250                 255
```

-continued

```
Val Asn Asp Pro His Cys Glu Lys Ile Glu Gln Asp Leu Thr Lys Asp
            260                 265                 270

Phe Pro Glu Cys Cys His Lys Tyr Lys Cys Glu Leu Glu Gly Val Val
        275                 280                 285

Thr Tyr His Gly Gly Gly His His His His His His
    290                 295                 300


<210> SEQ ID NO 103
<211> LENGTH: 962
<212> TYPE: DNA
<213> ORGANISM: artificial
<220> FEATURE:
<223> OTHER INFORMATION: DNA sequence encoding BiPlike- SNAPlike- aaVAGO
      protein from Aedes albopictus - Histag for expression in S2 cells

<400> SEQUENCE: 103

atgaaactat gtattctact tgcagttgtt gcgttcgtag gattgtcctt aagatctgac      60

aaagactgcg aaatgaaaag aactacattg gattcaccac ttgggaagtt ggaactgagt     120

ggatgcgagc aaggattgca tgaaattaag ctactgggaa aaggaacttc tgctgctgat     180

gcagttgaag ttccagcacc agcagctgtt cttggaggtc ctgagcccct catgcaagcc     240

acagcctggc ttaacgcata tttccaccag cctgaggcca ttgaggaatt tccagtcccc     300

gcccttcacc atcctgtgtt tcagcaggag agcttcaccc gccaggtcct gtggaaattg     360

ctgaaggtgg tcaagtttgg tgaagtgatt tcatatcagc aacttgctgc attggccggt     420

aaccccgcag ctacagctgc cgtgaaaact gctctcagcg gaaatcctgt gcccatcctg     480

atcccttgtc acagagtcgt ttcatcttcc ggagctgtag gtggctatga aggaggactg     540

gcagttaagg agtggctgct ggctcatgaa ggtcatagac ttggaaagcc tgggctgggt     600

cctgctggta taggcgcgcc agggtccctg gagggaggtg gcgggtctac ggctatcttc     660

ccaaattcgg agaacaaaga tttcccaggc gaatgctatg acacggagac taagattcat     720

ttcaagccag gggaaaatcg tcaacgacct ggcaactgtg aagagatgtc atgcggaact     780

gacttctcga ttcacttttt cggatgcgga ctagctatac tagacgatga cccggattgc     840

gagatcccag ttcaggattt cacaaaggac acgcagtgtt gccataagta caagtgtgtg     900

cgtaacggtg aagtcaatta cattggaggt ggccatcacc atcaccatca ctgatgaccg     960

gt                                                                    962


<210> SEQ ID NO 104
<211> LENGTH: 300
<212> TYPE: PRT
<213> ORGANISM: artificial
<220> FEATURE:
<223> OTHER INFORMATION: Amino acid sequence of fusion protein
      [SNAPlike-aaVAGO-Histag]

<400> SEQUENCE: 104

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80
```

```
Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Glu Gly Gly Gly Gly Ser Thr Ala Ile Phe Pro Asn Ser Glu Asn
        195                 200                 205

Lys Asp Phe Pro Gly Glu Cys Tyr Asp Thr Glu Thr Lys Ile His Phe
    210                 215                 220

Lys Pro Gly Glu Asn Arg Gln Arg Pro Gly Asn Cys Glu Glu Met Ser
225                 230                 235                 240

Cys Gly Thr Asp Phe Ser Ile His Phe Phe Gly Cys Gly Leu Ala Ile
                245                 250                 255

Leu Asp Asp Asp Pro Asp Cys Glu Ile Pro Val Gln Asp Phe Thr Lys
            260                 265                 270

Asp Thr Gln Cys Cys His Lys Tyr Lys Cys Val Arg Asn Gly Glu Val
        275                 280                 285

Asn Tyr Ile Gly Gly Gly His His His His His His
    290                 295                 300
```

<210> SEQ ID NO 105
<211> LENGTH: 4108
<212> TYPE: DNA
<213> ORGANISM: artificial
<220> FEATURE:
<223> OTHER INFORMATION: DNA sequence of OpIE2SP-SNAP cloned into pUC57 for constitutive expression of secreted chimeric SNAP-target protein in invertebrate cells

<400> SEQUENCE: 105

```
tcgcgcgttt cggtgatgac ggtgaaaacc tctgacacat gcagctcccg gagacggtca     60

cagcttgtct gtaagcggat gccgggagca gacaagcccg tcagggcgcg tcagcgggtg    120

ttggcgggtg tcggggctgg cttaactatg cggcatcaga gcagattgta ctgagagtgc    180

accatatgcg gtgtgaaata ccgcacagat gcgtaaggag aaaataccgc atcaggcgcc    240

attcgccatt caggctgcgc aactgttggg aagggcgatc ggtgcgggcc tcttcgctat    300

tacgccagct ggcgaaaggg ggatgtgctg caaggcgatt aagttgggta acgccagggt    360

tttcccagtc acgacgttgt aaaacgacgg ccagtggaat tctcatgatg ataaacaatg    420

tatggtgcta atgttgcttc aacaacaatt ctgttgaact gtgttttcat gtttgccaac    480

aagcaccttt atactcggtg gcctccccac caccaacttt tttgcactgc aaaaaaacac    540

gcttttgcac gcgggcccat acatagtaca aactctacgt ttcgtagact attttacata    600

aatagtctac accgttgtat acgctccaaa tacactacca cacattgaac ctttttgcag    660

tgcaaaaaag tacgtgtcgg cagtcacgta ggccggcctt atcgggtcgc gtcctgtcac    720
```

-continued

```
gtacgaatca cattatcgga ccggacgagt gttgtcttat cgtgacagga cgccagcttc    780
ctgtgttgct aaccgcagcc ggacgcaact ccttatcgga acaggacgcg cctccatatc    840
agccgcgcgt tatctcatgc gcgtgaccgg acacgaggcg cccgtcccgc ttatcgcgcc    900
tataaataca gcccgcaacg atctggtaaa cacagttgaa cagcatctgt tcgaaggatc    960
cttgatcgag ctagcatgaa actatgtatt ctacttgcag ttgttgcgtt cgtaggattg   1020
tccttaagat ctgacaaaga ctgcgaaatg aaaagaacta cattggattc accacttggg   1080
aagttggaac tgagtggatg cgagcaagga ttgcatgaaa ttaagctact gggaaaagga   1140
acttctgctg ctgatgcagt tgaagttcca gcaccagcag ctgttcttgg aggtcctgag   1200
cccctcatgc aagccacagc ctggcttaac gcatatttcc accagcctga ggccattgag   1260
gaatttccag tccccgccct tcaccatcct gtgtttcagc aggagagctt cacccgccag   1320
gtcctgtgga aattgctgaa ggtggtcaag tttggtgaag tgatttcata tcagcaactt   1380
gctgcattgg ccggtaaccc cgcagctaca gctgccgtga aaactgctct cagcggaaat   1440
cctgtgccca tcctgatccc ttgtcacaga gtcgtttcat cttccggagc tgtaggtggc   1500
tatgaaggag gactggcagt taaggagtgg ctgctggctc atgaaggtca tagacttgga   1560
aagcctgggc tgggtcctgc tggtataggc gcgccagggt ccctaggtgg cggatccgaa   1620
aacctgtact tccagagcga tatcggaggt ggaggcccgg gaggtggcgg aagtgactat   1680
aaagatgacg acgataagtg ataagcggcc gcaaaaccgg ttgagtttat ctgactaaat   1740
cttagtttgt attgtcatgt tttaatacaa tatgttatgt ttaaatatgt ttttaataaa   1800
ttttataaaa taatttcaac ttttattgta acaacattgt ccatttacac actcctttca   1860
agcgcgtgaa gcttggcgta atcatggtca tagctgtttc ctgtgtgaaa ttgttatccg   1920
ctcacaattc cacacaacat acgagccgga agcataaagt gtaaagcctg gggtgcctaa   1980
tgagtgagct aactcacatt aattgcgttg cgctcactgc ccgctttcca gtcgggaaac   2040
ctgtcgtgcc agctgcatta atgaatcggc caacgcgcgg ggagaggcgg tttgcgtatt   2100
gggcgctctt ccgcttcctc gctcactgac tcgctgcgct cggtcgttcg gctgcggcga   2160
gcggtatcag ctcactcaaa ggcggtaata cggttatcca cagaatcagg ggataacgca   2220
ggaaagaaca tgtgagcaaa aggccagcaa aaggccagga accgtaaaaa ggccgcgttg   2280
ctggcgtttt tccataggct ccgcccccct gacgagcatc acaaaaatcg acgctcaagt   2340
cagaggtggc gaaacccgac aggactataa agataccagg cgtttccccc tggaagctcc   2400
ctcgtgcgct ctcctgttcc gaccctgccg cttaccggat acctgtccgc ctttctccct   2460
tcgggaagcg tggcgctttc tcatagctca cgctgtaggt atctcagttc ggtgtaggtc   2520
gttcgctcca agctgggctg tgtgcacgaa ccccccgttc agcccgaccg ctgcgcctta   2580
tccggtaact atcgtcttga gtccaacccg gtaagacacg acttatcgcc actggcagca   2640
gccactggta acaggattag cagagcgagg tatgtaggcg gtgctacaga gttcttgaag   2700
tggtggccta actacggcta cactagaaga acagtatttg gtatctgcgc tctgctgaag   2760
ccagttacct tcggaaaaag agttggtagc tcttgatccg gcaaacaaac caccgctggt   2820
agcggtggtt tttttgtttg caagcagcag attacgcgca gaaaaaaagg atctcaagaa   2880
gatcctttga tcttttctac ggggtctgac gctcagtgga acgaaaactc acgttaaggg   2940
attttggtca tgagattatc aaaaaggatc ttcacctaga tccttttaaa ttaaaaatga   3000
agttttaaat caatctaaag tatatatgag taaacttggt ctgacagtta ccaatgctta   3060
atcagtgagg cacctatctc agcgatctgt ctatttcgtt catccatagt tgcctgactc   3120
```

cccgtcgtgt agataactac gatacgggag ggcttaccat ctggccccag tgctgcaatg 3180
ataccgcgag acccacgctc accggctcca gatttatcag caataaacca gccagccgga 3240
agggccgagc gcagaagtgg tcctgcaact ttatccgcct ccatccagtc tattaattgt 3300
tgccgggaag ctagagtaag tagttcgcca gttaatagtt tgcgcaacgt tgttgccatt 3360
gctacaggca tcgtggtgtc acgctcgtcg tttggtatgg cttcattcag ctccggttcc 3420
caacgatcaa ggcgagttac atgatccccc atgttgtgca aaaaagcggt tagctccttc 3480
ggtcctccga tcgttgtcag aagtaagttg gccgcagtgt tatcactcat ggttatggca 3540
gcactgcata attctcttac tgtcatgcca tccgtaagat gcttttctgt gactggtgag 3600
tactcaacca agtcattctg agaatagtgt atgcggcgac cgagttgctc ttgcccggcg 3660
tcaatacggg ataataccgc gccacatagc agaactttaa aagtgctcat cattggaaaa 3720
cgttcttcgg ggcgaaaact ctcaaggatc ttaccgctgt tgagatccag ttcgatgtaa 3780
cccactcgtg cacccaactg atcttcagca tcttttactt tcaccagcgt ttctgggtga 3840
gcaaaaacag gaaggcaaaa tgccgcaaaa aagggaataa gggcgacacg gaaatgttga 3900
atactcatac tcttcctttt tcaatattat tgaagcattt atcagggtta ttgtctcatg 3960
agcggataca tatttgaatg tatttagaaa aataaacaaa taggggttcc gcgcacattt 4020
ccccgaaaag tgccacctga cgtctaagaa accattatta tcatgacatt aacctataaa 4080
aataggcgta tcacgaggcc ctttcgtc 4108

<210> SEQ ID NO 106
<211> LENGTH: 24
<212> TYPE: DNA
<213> ORGANISM: artificial
<220> FEATURE:
<223> OTHER INFORMATION: DNA sequence of C-term peptide tag of OpIE2SP-SNAP

<400> SEQUENCE: 106
gactataaag atgacgacga taag 24

<210> SEQ ID NO 107
<211> LENGTH: 8
<212> TYPE: PRT
<213> ORGANISM: artificial
<220> FEATURE:
<223> OTHER INFORMATION: Amino acid sequence of C-term peptide tag of OpIE2SP-SNAP

<400> SEQUENCE: 107

Asp Tyr Lys Asp Asp Asp Asp Lys
1 5

<210> SEQ ID NO 108
<211> LENGTH: 2200
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Crimean-Congo hemorragic fever virus-proTEV2-Histag for expression in S2 cells

<400> SEQUENCE: 108
atgaagttat gcatattact ggccgtcgtg gcctttgttg gcctctcgct cgggagatct 60
gacaaagact gcgaaatgaa aagaactaca ttggattcac cacttgggaa gttggaactg 120
agtggatgcg agcaaggatt gcatgaaatt aagctactgg gaaaaggaac ttctgctgct 180

-continued

```
gatgcagttg aagttccagc accagcagct gttcttggag gtcctgagcc cctcatgcaa    240
gccacagcct ggcttaacgc atatttccac cagcctgagg ccattgagga atttccagtc    300
cccgcccttc accatcctgt gtttcagcag gagagcttca cccgccaggt cctgtggaaa    360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata gacttggaaa gcctgggctg    600
ggtcctgctg gtataggcgc gccagggtcc ctaggtggcg gatccgaaaa cctgtacttc    660
cagagcgata tcgaaaacaa gatcgaggtg aataacaaag atgagatgaa caggtggttt    720
gaagagttca aaaaaggaaa tggacttgtg gacaccttca caaactccta ttccttttgc    780
gagagtgttc ccaatttgga caggtttgtg tttcagatgg ccagtgccac cgatgatgca    840
cagaaggact ccatctacgc atctgctctg gtggaggcaa caaagttttg tgcacctata    900
tatgagtgcg catgggttag ctccactggc attgtaaaaa agggacttga atggttcgag    960
aaaaatgcag gaaccattaa gtcctgggat gaaagttata ctgagctaaa ggtcgacgtc   1020
ccgaaaatag agcagcttac gggttaccaa caagctgcct tgaagtggag aaaagacata   1080
ggtttccgtg tcaatgccaa cacagcagct ctgagcaaca aagtcctcgc agaatacaaa   1140
gtccctggtg agattgtgat gtctgtcaaa gagatgctgt cagacatgat taggagaagg   1200
aacctgattc taaacagggg tggtgatgag aacccacgtg gcccagtgag ccatgagcat   1260
gtagactggt gcagggagtt tgtcaaaggc aaatacatca tggccttcaa cccaccatgg   1320
ggggacatca acaagtcagg ccgttcagga atagcacttg ttgcaacagg ccttgctaag   1380
cttgcagaga ctgaaggaaa gggaatattt gatgaagcca aaaagactgt ggaggccctc   1440
aacgggtatc tggacaagca taaggacgaa gttgatagag caagcgccga cagcatgata   1500
acaaaccttc ttaagcatat tgccaaggca caggagctct ataaaaattc atctgcactt   1560
cgtgcacaaa gcgcacagat tgacactgct ttcagctcat actattggct ttacaaggct   1620
ggcgtgactc ctgaaacctt cccgacggtg tcacagttcc tctttgagct agggaaacag   1680
ccaagaggta ccaagaaaat gaagaaggct cttctgagca ccccaatgaa gtgggggaag   1740
aagctttatg agctctttgc cgatgattct ttccagcaga acaggattta catgcatcct   1800
gccgtgctta cagctggtag aatcagtgaa atgggagtct gctttgggac aatccctgtg   1860
gccaatcctg atgatgctgc ccaaggatct ggacacacta agtctattct caacctccgt   1920
accaacactg agaccaataa tccgtgtgcc aaaaccatcg tcaagctatt tgaagttcaa   1980
aaaacagggt tcaacattca ggacatggac atagtggcct ctgagcactt gctacaccaa   2040
tcccttgttg gcaagcaatc cccattccag aacgcctaca acgtcaaggg caatgccacc   2100
agtgctaaca tcatcccggg agagaatcta tattttcaag ggcccggcgg aggtagtcac   2160
catcatcacc atcactaatg accggtgcgg ccgcaagctt                         2200
```

<210> SEQ ID NO 109
<211> LENGTH: 707
<212> TYPE: PRT
<213> ORGANISM: artificial
<220> FEATURE:
<223> OTHER INFORMATION: Amino acid sequence of fusion protein
      [SNAPlike-proTEV1-CCHF.N-proTEV2-Histag]

<400> SEQUENCE: 109

-continued

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Glu Asn
        195                 200                 205

Lys Ile Glu Val Asn Asn Lys Asp Glu Met Asn Arg Trp Phe Glu Glu
    210                 215                 220

Phe Lys Lys Gly Asn Gly Leu Val Asp Thr Phe Thr Asn Ser Tyr Ser
225                 230                 235                 240

Phe Cys Glu Ser Val Pro Asn Leu Asp Arg Phe Val Phe Gln Met Ala
                245                 250                 255

Ser Ala Thr Asp Asp Ala Gln Lys Asp Ser Ile Tyr Ala Ser Ala Leu
            260                 265                 270

Val Glu Ala Thr Lys Phe Cys Ala Pro Ile Tyr Glu Cys Ala Trp Val
        275                 280                 285

Ser Ser Thr Gly Ile Val Lys Lys Gly Leu Glu Trp Phe Glu Lys Asn
    290                 295                 300

Ala Gly Thr Ile Lys Ser Trp Asp Glu Ser Tyr Thr Glu Leu Lys Val
305                 310                 315                 320

Asp Val Pro Lys Ile Glu Gln Leu Thr Gly Tyr Gln Gln Ala Ala Leu
                325                 330                 335

Lys Trp Arg Lys Asp Ile Gly Phe Arg Val Asn Ala Asn Thr Ala Ala
            340                 345                 350

Leu Ser Asn Lys Val Leu Ala Glu Tyr Lys Val Pro Gly Glu Ile Val
        355                 360                 365

Met Ser Val Lys Glu Met Leu Ser Asp Met Ile Arg Arg Arg Asn Leu
    370                 375                 380

Ile Leu Asn Arg Gly Gly Asp Glu Asn Pro Arg Gly Pro Val Ser His
385                 390                 395                 400

Glu His Val Asp Trp Cys Arg Glu Phe Val Lys Gly Lys Tyr Ile Met
                405                 410                 415
```

-continued

```
Ala Phe Asn Pro Pro Trp Gly Asp Ile Asn Lys Ser Gly Arg Ser Gly
            420                 425                 430

Ile Ala Leu Val Ala Thr Gly Leu Ala Lys Leu Ala Glu Thr Glu Gly
        435                 440                 445

Lys Gly Ile Phe Asp Glu Ala Lys Lys Thr Val Glu Ala Leu Asn Gly
    450                 455                 460

Tyr Leu Asp Lys His Lys Asp Glu Val Asp Arg Ala Ser Ala Asp Ser
465                 470                 475                 480

Met Ile Thr Asn Leu Leu Lys His Ile Ala Lys Ala Gln Glu Leu Tyr
                485                 490                 495

Lys Asn Ser Ser Ala Leu Arg Ala Gln Ser Ala Gln Ile Asp Thr Ala
            500                 505                 510

Phe Ser Ser Tyr Tyr Trp Leu Tyr Lys Ala Gly Val Thr Pro Glu Thr
        515                 520                 525

Phe Pro Thr Val Ser Gln Phe Leu Phe Glu Leu Gly Lys Gln Pro Arg
    530                 535                 540

Gly Thr Lys Lys Met Lys Lys Ala Leu Leu Ser Thr Pro Met Lys Trp
545                 550                 555                 560

Gly Lys Lys Leu Tyr Glu Leu Phe Ala Asp Asp Ser Phe Gln Gln Asn
                565                 570                 575

Arg Ile Tyr Met His Pro Ala Val Leu Thr Ala Gly Arg Ile Ser Glu
            580                 585                 590

Met Gly Val Cys Phe Gly Thr Ile Pro Val Ala Asn Pro Asp Asp Ala
        595                 600                 605

Ala Gln Gly Ser Gly His Thr Lys Ser Ile Leu Asn Leu Arg Thr Asn
    610                 615                 620

Thr Glu Thr Asn Asn Pro Cys Ala Lys Thr Ile Val Lys Leu Phe Glu
625                 630                 635                 640

Val Gln Lys Thr Gly Phe Asn Ile Gln Asp Met Asp Ile Val Ala Ser
                645                 650                 655

Glu His Leu Leu His Gln Ser Leu Val Gly Lys Gln Ser Pro Phe Gln
            660                 665                 670

Asn Ala Tyr Asn Val Lys Gly Asn Ala Thr Ser Ala Asn Ile Ile Pro
        675                 680                 685

Gly Glu Asn Leu Tyr Phe Gln Gly Pro Gly Gly Gly Ser His His His
    690                 695                 700

His His His
705
```

<210> SEQ ID NO 110
<211> LENGTH: 2974
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Ebola virus-proTEV2-Histag for expression in S2 cells

<400> SEQUENCE: 110

```
atgaagttat gcatattact ggccgtcgtg gcctttgttg gcctctcgct cgggagatct      60

gacaaagact gcgaaatgaa aagaactaca ttggattcac cacttgggaa gttggaactg     120

agtggatgcg agcaaggatt gcatgaaatt aagctactgg gaaaaggaac ttctgctgct     180

gatgcagttg aagttccagc accagcagct gttcttggag gtcctgagcc cctcatgcaa     240

gccacagcct ggcttaacgc atatttccac cagcctgagg ccattgagga atttccagtc     300
```

-continued

```
cccgcccttc accatcctgt gtttcagcag gagagcttca cccgccaggt cctgtggaaa    360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata gacttggaaa gcctgggctg    600
ggtcctgctg gtataggcgc gccagggtcc ctaggtggcg gatccgaaaa cctgtacttc    660
cagagcgata tcgattctcg tcctcagaaa atctggatgg cgccgagtct cactgaatct    720
gacatggatt accacaaaat cttgacagca ggtctgtccg ttcaacaggg gattgttcgg    780
caaagagtca tcccagtgta tcaagtaaac aatcttgaag aaatttgcca acttatcata    840
caggcctttg aagcaggtgt tgattttcaa gagagtgcgg acagtttcct tctcatgctt    900
tgtcttcatc atgcgtacca gggagattac aaactttttct tggaaagtgg cgcagtcaag    960
tatttggaag ggcacgggtt ccgttttgaa gtcaagaagc gtgatggagt gaagcgcctt   1020
gaggaattgc tgccagcagt atctagtgga aaaaacatta agagaacact tgctgccatg   1080
ccggaagagg agacaactga agctaatgcc ggtcagtttc tctcctttgc aagtctattc   1140
cttccgaaat tggtagtagg agaaaaggct tgccttgaga aggttcaaag gcaaattcaa   1200
gtacatgcag agcaaggact gatacaatat ccaacagctt ggcaatcagt aggacacatg   1260
atggtgattt tccgtttgat gcgaacaaat tttctgatca aatttctcct aatacaccaa   1320
gggatgcaca tggttgccgg gcatgatgcc aacgatgctg tgatttcaaa ttcagtggct   1380
caagctcgtt tttcaggctt attgattgtc aaaacagtac ttgatcatat cctacaaaag   1440
acagaacgag gagttcgtct ccatcctctt gcaaggaccg ccaaggtaaa aaatgaggtg   1500
aactccttta aggctgcact cagctccctg gccaagcatg gagagtatgc tcctttcgcc   1560
cgacttttga acctttctgg agtaaataat cttgagcatg gtcttttccc tcaactatcg   1620
gcaattgcac tcggagtcgc cacagcacac gggagtaccc tcgcaggagt aaatgttgga   1680
gaacagtatc aacaactcag agaggctgcc actgaggctg agaagcaact ccaacaatat   1740
gcagagtctc gcgaacttga ccatcttgga cttgatgatc aggaaaagaa aattcttatg   1800
aacttccatc agaaaaagaa cgaaatcagc ttccagcaaa caaacgctat ggtaactcta   1860
agaaaagagc gcctggccaa gctgacagaa gctatcactg ctgcgtcact gcccaaaaca   1920
agtggacatt acgatgatga tgacgacatt ccctttccag gacccatcaa tgatgacgac   1980
aatcctggcc atcaagatga tgatccgact gactcacagg atacgaccat tcccgatgtg   2040
gtggttgatc ccgatgatgg aagctacggc gaataccaga gttactcgga aaacggcatg   2100
aatgcaccag atgacttggt cctattcgat ctggacgagg acgacgagga cactaagcca   2160
gtgcctaata gatcgaccaa gggtggacaa cagaagaaca gtcaaaaggg ccagcatata   2220
gagggcagac agacacaatc caggccaatt caaaatgtcc caggccctca cagaacaatc   2280
caccacgcca gtgcgccact cacggacaat gacagaagaa atgaaccctc cggctcaacc   2340
agccctcgca tgctgacacc aattaacgaa gaggcagacc cactggacga tgccgacgac   2400
gagacgtcta gccttccgcc cttggagtca gatgatgaag agcaggacag ggacggaact   2460
tccaaccgca cacccactgt cgccccaccg gctcccgtat acagagatca ctctgaaaag   2520
aaagaactcc cgcaagacga gcaacaagat caggaccaca ctcaagaggc caggaaccag   2580
gacagtgaca acacccagtc agaacactct tttgaggaga tgtatcgcca cattctaaga   2640
tcacaggggc catttgatgc tgttttgtat tatcatatga tgaaggatga gcctgtagtt   2700
```

```
ttcagtacca gtgatggcaa agagtacacg tatccagact cccttgaaga ggaatatcca   2760

ccatggctca ctgaaaaaga ggctatgaat gaagagaata gatttgttac attggatggt   2820

caacaatttt attggccggt gatgaatcac aagaataaat tcatggcaat cctgcaacat   2880

catcagggcc cgggagagaa tctatatttt caagggcccg gcggaggtag tcaccatcat   2940

caccatcact aatgaccggt gcggccgcaa gctt                               2974


<210> SEQ ID NO 111
<211> LENGTH: 965
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 111

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Asp Ser
        195                 200                 205

Arg Pro Gln Lys Ile Trp Met Ala Pro Ser Leu Thr Glu Ser Asp Met
    210                 215                 220

Asp Tyr His Lys Ile Leu Thr Ala Gly Leu Ser Val Gln Gln Gly Ile
225                 230                 235                 240

Val Arg Gln Arg Val Ile Pro Val Tyr Gln Val Asn Asn Leu Glu Glu
                245                 250                 255

Ile Cys Gln Leu Ile Ile Gln Ala Phe Glu Ala Gly Val Asp Phe Gln
            260                 265                 270

Glu Ser Ala Asp Ser Phe Leu Leu Met Leu Cys Leu His His Ala Tyr
        275                 280                 285

Gln Gly Asp Tyr Lys Leu Phe Leu Glu Ser Gly Ala Val Lys Tyr Leu
    290                 295                 300
```

-continued

```
Glu Gly His Gly Phe Arg Phe Glu Val Lys Lys Arg Asp Gly Val Lys
305                 310                 315                 320

Arg Leu Glu Glu Leu Leu Pro Ala Val Ser Ser Gly Lys Asn Ile Lys
                325                 330                 335

Arg Thr Leu Ala Ala Met Pro Glu Glu Glu Thr Thr Glu Ala Asn Ala
            340                 345                 350

Gly Gln Phe Leu Ser Phe Ala Ser Leu Phe Leu Pro Lys Leu Val Val
        355                 360                 365

Gly Glu Lys Ala Cys Leu Glu Lys Val Gln Arg Gln Ile Gln Val His
    370                 375                 380

Ala Glu Gln Gly Leu Ile Gln Tyr Pro Thr Ala Trp Gln Ser Val Gly
385                 390                 395                 400

His Met Met Val Ile Phe Arg Leu Met Arg Thr Asn Phe Leu Ile Lys
                405                 410                 415

Phe Leu Leu Ile His Gln Gly Met His Met Val Ala Gly His Asp Ala
            420                 425                 430

Asn Asp Ala Val Ile Ser Asn Ser Val Ala Gln Ala Arg Phe Ser Gly
        435                 440                 445

Leu Leu Ile Val Lys Thr Val Leu Asp His Ile Leu Gln Lys Thr Glu
    450                 455                 460

Arg Gly Val Arg Leu His Pro Leu Ala Arg Thr Ala Lys Val Lys Asn
465                 470                 475                 480

Glu Val Asn Ser Phe Lys Ala Ala Leu Ser Ser Leu Ala Lys His Gly
                485                 490                 495

Glu Tyr Ala Pro Phe Ala Arg Leu Leu Asn Leu Ser Gly Val Asn Asn
            500                 505                 510

Leu Glu His Gly Leu Phe Pro Gln Leu Ser Ala Ile Ala Leu Gly Val
        515                 520                 525

Ala Thr Ala His Gly Ser Thr Leu Ala Gly Val Asn Val Gly Glu Gln
    530                 535                 540

Tyr Gln Gln Leu Arg Glu Ala Ala Thr Glu Ala Glu Lys Gln Leu Gln
545                 550                 555                 560

Gln Tyr Ala Glu Ser Arg Glu Leu Asp His Leu Gly Leu Asp Asp Gln
                565                 570                 575

Glu Lys Lys Ile Leu Met Asn Phe His Gln Lys Lys Asn Glu Ile Ser
            580                 585                 590

Phe Gln Gln Thr Asn Ala Met Val Thr Leu Arg Lys Glu Arg Leu Ala
        595                 600                 605

Lys Leu Thr Glu Ala Ile Thr Ala Ala Ser Leu Pro Lys Thr Ser Gly
    610                 615                 620

His Tyr Asp Asp Asp Asp Asp Ile Pro Phe Pro Gly Pro Ile Asn Asp
625                 630                 635                 640

Asp Asp Asn Pro Gly His Gln Asp Asp Asp Pro Thr Asp Ser Gln Asp
                645                 650                 655

Thr Thr Ile Pro Asp Val Val Val Asp Pro Asp Asp Gly Ser Tyr Gly
            660                 665                 670

Glu Tyr Gln Ser Tyr Ser Glu Asn Gly Met Asn Ala Pro Asp Asp Leu
        675                 680                 685

Val Leu Phe Asp Leu Asp Glu Asp Asp Glu Asp Thr Lys Pro Val Pro
    690                 695                 700

Asn Arg Ser Thr Lys Gly Gly Gln Gln Lys Asn Ser Gln Lys Gly Gln
705                 710                 715                 720

His Ile Glu Gly Arg Gln Thr Gln Ser Arg Pro Ile Gln Asn Val Pro
```

```
                725                 730                 735

Gly Pro His Arg Thr Ile His His Ala Ser Ala Pro Leu Thr Asp Asn
            740                 745                 750

Asp Arg Arg Asn Glu Pro Ser Gly Ser Thr Ser Pro Arg Met Leu Thr
        755                 760                 765

Pro Ile Asn Glu Glu Ala Asp Pro Leu Asp Asp Ala Asp Asp Glu Thr
    770                 775                 780

Ser Ser Leu Pro Pro Leu Glu Ser Asp Asp Glu Glu Gln Asp Arg Asp
785                 790                 795                 800

Gly Thr Ser Asn Arg Thr Pro Thr Val Ala Pro Pro Ala Pro Val Tyr
                805                 810                 815

Arg Asp His Ser Glu Lys Lys Glu Leu Pro Gln Asp Glu Gln Gln Asp
            820                 825                 830

Gln Asp His Thr Gln Glu Ala Arg Asn Gln Asp Ser Asp Asn Thr Gln
        835                 840                 845

Ser Glu His Ser Phe Glu Glu Met Tyr Arg His Ile Leu Arg Ser Gln
    850                 855                 860

Gly Pro Phe Asp Ala Val Leu Tyr Tyr His Met Met Lys Asp Glu Pro
865                 870                 875                 880

Val Val Phe Ser Thr Ser Asp Gly Lys Glu Tyr Thr Tyr Pro Asp Ser
                885                 890                 895

Leu Glu Glu Glu Tyr Pro Pro Trp Leu Thr Glu Lys Glu Ala Met Asn
            900                 905                 910

Glu Glu Asn Arg Phe Val Thr Leu Asp Gly Gln Gln Phe Tyr Trp Pro
        915                 920                 925

Val Met Asn His Lys Asn Lys Phe Met Ala Ile Leu Gln His His Gln
    930                 935                 940

Gly Pro Gly Glu Asn Leu Tyr Phe Gln Gly Pro Gly Gly Gly Ser His
945                 950                 955                 960

His His His His His
                965


<210> SEQ ID NO 112
<211> LENGTH: 2842
<212> TYPE: DNA
<213> ORGANISM: artificial
<220> FEATURE:
<223> OTHER INFORMATION: DNA sequence encoding ssBiP-SNAPlike-proTEV1-N
      nucleoprotein of the Marburg virus-proTEV2-Histag for expression
      in S2 cells

<400> SEQUENCE: 112

atgaagttat gcatattact ggccgtcgtg gcctttgttg gcctctcgct cgggagatct     60

gacaaagact gcgaaatgaa aagaactaca ttggattcac cacttgggaa gttggaactg    120

agtggatgcg agcaaggatt gcatgaaatt aagctactgg gaaaaggaac ttctgctgct    180

gatgcagttg aagttccagc accagcagct gttcttggag gtcctgagcc cctcatgcaa    240

gccacagcct ggcttaacgc atatttccac cagcctgagg ccattgagga atttccagtc    300

cccgcccttc accatcctgt gtttcagcag gagagcttca cccgccaggt cctgtggaaa    360

ttgctgaagg tggtcaagtt tggtgaagtg atttcatatc agcaacttgc tgcattggcc    420

ggtaaccccg cagctacagc tgccgtgaaa actgctctca gcggaaatcc tgtgcccatc    480

ctgatccctt gtcacagagt cgtttcatct tccggagctg taggtggcta tgaaggagga    540

ctggcagtta aggagtggct gctggctcat gaaggtcata gacttggaaa gcctgggctg    600
```

```
ggtcctgctg gtataggcgc gccagggtcc ctaggtggcg gatccgaaaa cctgtacttc    660
cagagcgata tcgatttaca cagtttgttg gagttgggta caaaacccac tgcccctcat    720
gttcgtaata agaaagtgat attatttgac acaaatcatc aggttagtat ctgtaatcag    780
ataatagatg caataaactc agggattgat cttggtgatc tcctagaagg gggtttgctg    840
acgttgtgtg ttgagcatta ctataattct gataaggata aattcaacac aagtcctatc    900
gcgaagtact tacgtgatgc gggctatgaa tttgatgtca tcaagaatgc agatgcaacc    960
cgctttctgg atgtgattcc taatgaacct cattacagcc ctttaattct agcccttaag   1020
acattggaaa gtactgaatc tcagaggggg agaattgggc tctttttatc attttgcagt   1080
cttttcctcc caaaacttgt cgtcggagac cgagctagta tcgaaaaggc tttaagacaa   1140
gtaacagtgc atcaagaaca ggggatcgtc acatacccta atcattggct taccacaggc   1200
cacatgaaag taattttcgg gattttgagg tccagcttca ttttaaagtt tgtgttgatt   1260
catcaaggag taaatttggt gacaggtcat gatgcctatg acagtatcat tagtaattca   1320
gtaggtcaaa ctagattctc aggacttctt atcgtgaaaa cagttctgga gttcatcttg   1380
caaaaaactg attcaggggt gacactacat cctttggtgc ggacctccaa agtaaaaaat   1440
gaagttgcta gtttcaagca ggcgttgagc aacctagccc gacatgggga atacgcacca   1500
tttgcacggg ttctgaattt atcagggatt aacaacctcg aacatggact ctatcctcag   1560
ctttcagcaa ttgcgctggg tgtggcaaca gcacacggca gtacattggc tggtgtcaat   1620
gttggcgaac aatatcaaca actacgagag gcggcacatg atgcggaagt aaaactacaa   1680
aggcgacatg aacatcagga aattcaagct attgccgagg atgacgagga aaggaagata   1740
ttagaacaat tccaccttca gaaaactgaa atcacacaca gtcagacact agccgtcctc   1800
agccagaaac gagaaaaatt agctcgtctc gctgcagaaa ttgaaaacaa tattgtggaa   1860
gatcagggat ttaagcaatc acagaatcgg gtgtcacagt cgtttttgaa tgaccctaca   1920
cctgtggaag taacggttca agccaggccc atgaatcgac caactgctct gcctccccca   1980
gttgacgaca agattgagca tgaatctaca gaagatagct cttcttcaag tagctttgtt   2040
gacttgaatg atccatttgc actgctgaat gaggacgagg atactcttga tgacagtgtc   2100
atgatccccg gcacaacatc gagagaattt caagggattc ctgaaccgcc aagacaatcc   2160
caagacctca ataacagcca aggaaagcag gaagatgaat ccacaaatcc gattaagaaa   2220
cagtttctga gataccaaga attgcctcct gttcaagagg atgatgaatc ggaatacaca   2280
actgactctc aagaaagcat cgaccaacca ggttccgaca atgaacaagg agttgatctt   2340
ccacctcctc cgttgtacgc tcaggaaaaa agacaggacc caatacagca cccagcagca   2400
aaccctcaag atcccttcgg cagtattggt gatgtaaatg gtgacatctt agaacctata   2460
agatcacctt cttcaccatc tgctcctcag gaagacacaa ggatgaggga agcctatgaa   2520
ttgtcgcctg atttcacaaa tgatgaggat aatcagcaga attggccaca aagagtggtg   2580
acaaagaagg gtagaacttt cctttatcct aatgatcttc tgcaaacaaa tcctccagag   2640
tcacttataa cagccctcgt tgaggaatac caaaatcctg tctcagctaa ggagcttcaa   2700
gcagattggc ccgacatgtc atttgatgaa aggagacatg ttgcgatgaa cttgggcccg   2760
ggagagaatc tatattttca agggcccggc ggaggtagtc accatcatca ccatcactaa   2820
tgaccggtgc ggccgcaagc tt                                            2842
```

<210> SEQ ID NO 113
<211> LENGTH: 921

```
<212> TYPE: PRT
<213> ORGANISM: artificial
<220> FEATURE:
<223> OTHER INFORMATION: Amino acid sequence of fusion protein
      [SNAPlike-proTEV1-EBO.N-proTEV2-Histag]

<400> SEQUENCE: 113

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Asp Leu
        195                 200                 205

His Ser Leu Leu Glu Leu Gly Thr Lys Pro Thr Ala Pro His Val Arg
    210                 215                 220

Asn Lys Lys Val Ile Leu Phe Asp Thr Asn His Gln Val Ser Ile Cys
225                 230                 235                 240

Asn Gln Ile Ile Asp Ala Ile Asn Ser Gly Ile Asp Leu Gly Asp Leu
                245                 250                 255

Leu Glu Gly Gly Leu Leu Thr Leu Cys Val Glu His Tyr Tyr Asn Ser
            260                 265                 270

Asp Lys Asp Lys Phe Asn Thr Ser Pro Ile Ala Lys Tyr Leu Arg Asp
        275                 280                 285

Ala Gly Tyr Glu Phe Asp Val Ile Lys Asn Ala Asp Ala Thr Arg Phe
    290                 295                 300

Leu Asp Val Ile Pro Asn Glu Pro His Tyr Ser Pro Leu Ile Leu Ala
305                 310                 315                 320

Leu Lys Thr Leu Glu Ser Thr Glu Ser Gln Arg Gly Arg Ile Gly Leu
                325                 330                 335

Phe Leu Ser Phe Cys Ser Leu Phe Leu Pro Lys Leu Val Val Gly Asp
            340                 345                 350

Arg Ala Ser Ile Glu Lys Ala Leu Arg Gln Val Thr Val His Gln Glu
        355                 360                 365

Gln Gly Ile Val Thr Tyr Pro Asn His Trp Leu Thr Thr Gly His Met
    370                 375                 380
```

-continued

```
Lys Val Ile Phe Gly Ile Leu Arg Ser Ser Phe Ile Leu Lys Phe Val
385                 390                 395                 400

Leu Ile His Gln Gly Val Asn Leu Val Thr Gly His Asp Ala Tyr Asp
                405                 410                 415

Ser Ile Ile Ser Asn Ser Val Gly Gln Thr Arg Phe Ser Gly Leu Leu
            420                 425                 430

Ile Val Lys Thr Val Leu Glu Phe Ile Leu Gln Lys Thr Asp Ser Gly
        435                 440                 445

Val Thr Leu His Pro Leu Val Arg Thr Ser Lys Val Lys Asn Glu Val
    450                 455                 460

Ala Ser Phe Lys Gln Ala Leu Ser Asn Leu Ala Arg His Gly Glu Tyr
465                 470                 475                 480

Ala Pro Phe Ala Arg Val Leu Asn Leu Ser Gly Ile Asn Asn Leu Glu
                485                 490                 495

His Gly Leu Tyr Pro Gln Leu Ser Ala Ile Ala Leu Gly Val Ala Thr
            500                 505                 510

Ala His Gly Ser Thr Leu Ala Gly Val Asn Val Gly Glu Gln Tyr Gln
        515                 520                 525

Gln Leu Arg Glu Ala Ala His Asp Ala Glu Val Lys Leu Gln Arg Arg
    530                 535                 540

His Glu His Gln Glu Ile Gln Ala Ile Ala Glu Asp Asp Glu Glu Arg
545                 550                 555                 560

Lys Ile Leu Glu Gln Phe His Leu Gln Lys Thr Glu Ile Thr His Ser
                565                 570                 575

Gln Thr Leu Ala Val Leu Ser Gln Lys Arg Glu Lys Leu Ala Arg Leu
            580                 585                 590

Ala Ala Glu Ile Glu Asn Asn Ile Val Glu Asp Gln Gly Phe Lys Gln
        595                 600                 605

Ser Gln Asn Arg Val Ser Gln Ser Phe Leu Asn Asp Pro Thr Pro Val
    610                 615                 620

Glu Val Thr Val Gln Ala Arg Pro Met Asn Arg Pro Thr Ala Leu Pro
625                 630                 635                 640

Pro Pro Val Asp Asp Lys Ile Glu His Glu Ser Thr Glu Asp Ser Ser
                645                 650                 655

Ser Ser Ser Ser Phe Val Asp Leu Asn Asp Pro Phe Ala Leu Leu Asn
            660                 665                 670

Glu Asp Glu Asp Thr Leu Asp Asp Ser Val Met Ile Pro Gly Thr Thr
        675                 680                 685

Ser Arg Glu Phe Gln Gly Ile Pro Glu Pro Pro Arg Gln Ser Gln Asp
    690                 695                 700

Leu Asn Asn Ser Gln Gly Lys Gln Glu Asp Glu Ser Thr Asn Pro Ile
705                 710                 715                 720

Lys Lys Gln Phe Leu Arg Tyr Gln Glu Leu Pro Pro Val Gln Glu Asp
                725                 730                 735

Asp Glu Ser Glu Tyr Thr Thr Asp Ser Gln Glu Ser Ile Asp Gln Pro
            740                 745                 750

Gly Ser Asp Asn Glu Gln Gly Val Asp Leu Pro Pro Pro Pro Leu Tyr
        755                 760                 765

Ala Gln Glu Lys Arg Gln Asp Pro Ile Gln His Pro Ala Ala Asn Pro
    770                 775                 780

Gln Asp Pro Phe Gly Ser Ile Gly Asp Val Asn Gly Asp Ile Leu Glu
785                 790                 795                 800
```

```
Pro Ile Arg Ser Pro Ser Ser Pro Ser Ala Pro Gln Glu Asp Thr Arg
                805                 810                 815

Met Arg Glu Ala Tyr Glu Leu Ser Pro Asp Phe Thr Asn Asp Glu Asp
            820                 825                 830

Asn Gln Gln Asn Trp Pro Gln Arg Val Val Thr Lys Lys Gly Arg Thr
        835                 840                 845

Phe Leu Tyr Pro Asn Asp Leu Leu Gln Thr Asn Pro Pro Glu Ser Leu
    850                 855                 860

Ile Thr Ala Leu Val Glu Glu Tyr Gln Asn Pro Val Ser Ala Lys Glu
865                 870                 875                 880

Leu Gln Ala Asp Trp Pro Asp Met Ser Phe Asp Glu Arg Arg His Val
                885                 890                 895

Ala Met Asn Leu Gly Pro Gly Glu Asn Leu Tyr Phe Gln Gly Pro Gly
            900                 905                 910

Gly Gly Ser His His His His His His
        915                 920
```

<210> SEQ ID NO 114
<211> LENGTH: 2461
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Lassa virus-proTEV2-Histag for expression in S2 cells

<400> SEQUENCE: 114

```
atgaagttat gcatattact ggccgtcgtg gcctttgttg gcctctcgct cgggagatct     60

gacaaagact gcgaaatgaa aagaactaca ttggattcac cacttgggaa gttggaactg    120

agtggatgcg agcaaggatt gcatgaaatt aagctactgg gaaaaggaac ttctgctgct    180

gatgcagttg aagttccagc accagcagct gttcttggag gtcctgagcc cctcatgcaa    240

gccacagcct ggcttaacgc atatttccac cagcctgagg ccattgagga atttccagtc    300

cccgcccttc accatcctgt gtttcagcag gagagcttca cccgccaggt cctgtggaaa    360

ttgctgaagg tggtcaagtt tggtgaagtg atttcatatc agcaacttgc tgcattggcc    420

ggtaaccccg cagctacagc tgccgtgaaa actgctctca gcggaaatcc tgtgcccatc    480

ctgatccctt gtcacagagt cgtttcatct tccggagctg taggtggcta tgaaggagga    540

ctggcagtta aggagtggct gctggctcat gaaggtcata gacttggaaa gcctgggctg    600

ggtcctgctg gtataggcgc gccagggtcc ctaggtggcg gatccgaaaa cctgtacttc    660

cagagcgata tcagtgcctc aaaggaaata aaatcctttt tgtggacaca atctttgagg    720

agggaattat ctggttactg ctccaacatc aaactacagg tggtgaaaga tgcccaggct    780

cttttacatg gacttgactt ctccgaagtc agtaatgttc aacggttgat gcgcaaggag    840

agaagggatg acaatgattt gaaacggttg agggacctaa atcaagcggt caacaatctt    900

gttgaattaa aatcaactca acaaaagagt atactgagag ttgggactct aacctcagat    960

gacttattaa tcttagccgc tgacctagag aagttaaagt caaaggtgat cagaacagaa   1020

aggccattaa gtgcaggtgt ctatatgggc aacctaagct cacagcaact tgaccaaaga   1080

agagctctcc tgaatatgat aggaatgagt ggtggtaatc aaggggctcg ggctgggaga   1140

gatggagtgg tgagagtttg ggatgtgaaa aatgcagagt tgctcaataa tcagttcggg   1200

accatgccaa gtctgacact ggcatgtctg acaaaacagg ggcaggttga cttgaatgat   1260

gcagtacaag cattgacaga tttgggtttg atctacacag caaagtatcc caacacttca   1320
```

gacttagaca ggctgactca aagtcatccc atcctaaata tgattgacac caagaaaagc 1380
tctttgaata tctcaggtta taattttagc ttgggtgcag ctgtgaaggc aggagcttgc 1440
atgctggatg gtggcaatat gttggagaca atcaaggtgt cacctcagac aatggatggt 1500
atcctcaaat ccattttaaa ggtcaagaag gctcttggaa tgttcatttc agacacccct 1560
ggtgaaagga atccttatga aaacatactc tacaagattt gtttgtcagg agatggatgg 1620
ccatatattg catcaagaac ctcaataaca ggaagggcct gggaaaacac tgtcgttgat 1680
ctggaatcag atgggaagcc acagaaagct gacagcaaca attccagtaa atccctgcag 1740
tcggcagggt ttaccgctgg gcttacctat tctcagctga tgaccctcaa ggatgcaatg 1800
ctgcaacttg acccaaatgc taagacctgg atggacattg aaggaagacc tgaagatcca 1860
gtggaaattg ccctctatca accaagttca ggctgctaca tacacttctt ccgtgaacct 1920
actgatttaa agcagttcaa gcaggatgct aagtactcac atgggattga tgtcacagac 1980
ctcttcgcta cacaaccggg cttgaccagt gctgtcattg atgcactccc ccggaatatg 2040
gtcattacct gtcaggggtc cgatgacata aggaaactcc ttgaatcaca aggaagaaaa 2100
gacattaaac taattgatat tgccctcagc aaaactgatt ccaggaagta tgaaaatgca 2160
gtctgggacc agtataaaga cttatgccac atgcacacag gtgtcgttgt tgaaaagaag 2220
aaaagaggcg gtaaagagga aataacccct cactgtgcac taatggactg catcatgttt 2280
gatgcagcag tgtcaggagg actgaacaca tcggttttga gagcagtgct gcccagagat 2340
atggtgttca gaacatcgac acctagagtc gttctcccgg gagagaatct atattttcaa 2400
gggcccggcg gaggtagtca ccatcatcac catcactaat gaccggtgcg gccgcaagct 2460
t 2461

<210> SEQ ID NO 115
<211> LENGTH: 794
<212> TYPE: PRT
<213> ORGANISM: artificial
<220> FEATURE:
<223> OTHER INFORMATION: Amino acid sequence of fusion protein
[SNAPlike-proTEV1-LAS.N-proTEV2-Histag]

<400> SEQUENCE: 115

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

Ile Ser Tyr Gln Gln Leu Ala Ala Leu Ala Gly Asn Pro Ala Ala Thr
115 120 125

Ala Ala Val Lys Thr Ala Leu Ser Gly Asn Pro Val Pro Ile Leu Ile
130 135 140

-continued

```
Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ser Ala
        195                 200                 205

Ser Lys Glu Ile Lys Ser Phe Leu Trp Thr Gln Ser Leu Arg Arg Glu
    210                 215                 220

Leu Ser Gly Tyr Cys Ser Asn Ile Lys Leu Gln Val Val Lys Asp Ala
225                 230                 235                 240

Gln Ala Leu Leu His Gly Leu Asp Phe Ser Glu Val Ser Asn Val Gln
                245                 250                 255

Arg Leu Met Arg Lys Glu Arg Arg Asp Asp Asn Asp Leu Lys Arg Leu
            260                 265                 270

Arg Asp Leu Asn Gln Ala Val Asn Asn Leu Val Glu Leu Lys Ser Thr
        275                 280                 285

Gln Gln Lys Ser Ile Leu Arg Val Gly Thr Leu Thr Ser Asp Asp Leu
    290                 295                 300

Leu Ile Leu Ala Ala Asp Leu Glu Lys Leu Lys Ser Lys Val Ile Arg
305                 310                 315                 320

Thr Glu Arg Pro Leu Ser Ala Gly Val Tyr Met Gly Asn Leu Ser Ser
                325                 330                 335

Gln Gln Leu Asp Gln Arg Arg Ala Leu Leu Asn Met Ile Gly Met Ser
            340                 345                 350

Gly Gly Asn Gln Gly Ala Arg Ala Gly Arg Asp Gly Val Val Arg Val
        355                 360                 365

Trp Asp Val Lys Asn Ala Glu Leu Leu Asn Asn Gln Phe Gly Thr Met
    370                 375                 380

Pro Ser Leu Thr Leu Ala Cys Leu Thr Lys Gln Gly Gln Val Asp Leu
385                 390                 395                 400

Asn Asp Ala Val Gln Ala Leu Thr Asp Leu Gly Leu Ile Tyr Thr Ala
                405                 410                 415

Lys Tyr Pro Asn Thr Ser Asp Leu Asp Arg Leu Thr Gln Ser His Pro
            420                 425                 430

Ile Leu Asn Met Ile Asp Thr Lys Lys Ser Ser Leu Asn Ile Ser Gly
        435                 440                 445

Tyr Asn Phe Ser Leu Gly Ala Ala Val Lys Ala Gly Ala Cys Met Leu
    450                 455                 460

Asp Gly Gly Asn Met Leu Glu Thr Ile Lys Val Ser Pro Gln Thr Met
465                 470                 475                 480

Asp Gly Ile Leu Lys Ser Ile Leu Lys Val Lys Lys Ala Leu Gly Met
                485                 490                 495

Phe Ile Ser Asp Thr Pro Gly Glu Arg Asn Pro Tyr Glu Asn Ile Leu
            500                 505                 510

Tyr Lys Ile Cys Leu Ser Gly Asp Gly Trp Pro Tyr Ile Ala Ser Arg
        515                 520                 525

Thr Ser Ile Thr Gly Arg Ala Trp Glu Asn Thr Val Val Asp Leu Glu
    530                 535                 540

Ser Asp Gly Lys Pro Gln Lys Ala Asp Ser Asn Asn Ser Ser Lys Ser
545                 550                 555                 560

Leu Gln Ser Ala Gly Phe Thr Ala Gly Leu Thr Tyr Ser Gln Leu Met
```

-continued

```
                565                 570                 575

Thr Leu Lys Asp Ala Met Leu Gln Leu Asp Pro Asn Ala Lys Thr Trp
            580                 585                 590

Met Asp Ile Glu Gly Arg Pro Glu Asp Pro Val Glu Ile Ala Leu Tyr
        595                 600                 605

Gln Pro Ser Ser Gly Cys Tyr Ile His Phe Phe Arg Glu Pro Thr Asp
    610                 615                 620

Leu Lys Gln Phe Lys Gln Asp Ala Lys Tyr Ser His Gly Ile Asp Val
625                 630                 635                 640

Thr Asp Leu Phe Ala Thr Gln Pro Gly Leu Thr Ser Ala Val Ile Asp
                645                 650                 655

Ala Leu Pro Arg Asn Met Val Ile Thr Cys Gln Gly Ser Asp Asp Ile
            660                 665                 670

Arg Lys Leu Leu Glu Ser Gln Gly Arg Lys Asp Ile Lys Leu Ile Asp
        675                 680                 685

Ile Ala Leu Ser Lys Thr Asp Ser Arg Lys Tyr Glu Asn Ala Val Trp
    690                 695                 700

Asp Gln Tyr Lys Asp Leu Cys His Met His Thr Gly Val Val Val Glu
705                 710                 715                 720

Lys Lys Lys Arg Gly Gly Lys Glu Glu Ile Thr Pro His Cys Ala Leu
                725                 730                 735

Met Asp Cys Ile Met Phe Asp Ala Ala Val Ser Gly Gly Leu Asn Thr
            740                 745                 750

Ser Val Leu Arg Ala Val Leu Pro Arg Asp Met Val Phe Arg Thr Ser
        755                 760                 765

Thr Pro Arg Val Val Leu Pro Gly Glu Asn Leu Tyr Phe Gln Gly Pro
    770                 775                 780

Gly Gly Gly Ser His His His His His His
785                 790
```

<210> SEQ ID NO 116
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Junin virus-proTEV2-Histag for expression in S2 cells

<400> SEQUENCE: 116

```
atgaagttat gcatattact ggccgtcgtg gcctttgttg gcctctcgct cgggagatct     60

gacaaagact gcgaaatgaa aagaactaca ttggattcac cacttgggaa gttggaactg    120

agtggatgcg agcaaggatt gcatgaaatt aagctactgg gaaaaggaac ttctgctgct    180

gatgcagttg aagttccagc accagcagct gttcttggag gtcctgagcc cctcatgcaa    240

gccacagcct ggcttaacgc atatttccac cagcctgagg ccattgagga atttccagtc    300

cccgcccttc accatcctgt gtttcagcag gagagcttca cccgccaggt cctgtggaaa    360

ttgctgaagg tggtcaagtt tggtgaagtg atttcatatc agcaacttgc tgcattggcc    420

ggtaaccccg cagctacagc tgccgtgaaa actgctctca gcggaaatcc tgtgcccatc    480

ctgatccctt gtcacagagt cgtttcatct tccggagctg taggtggcta tgaaggagga    540

ctggcagtta aggagtggct gctggctcat gaaggtcata gacttggaaa gcctgggctg    600

ggtcctgctg gtataggcgc gccagggtcc ctaggtggcg gatccgaaaa cctgtacttc    660

cagagcgata tcgcacactc caaggaggtt cctagcttta gatggactca gtccttaagg    720
```

-continued

```
agaggtttga gccaattcac tcagactgtc aagtcagatg ttttgaagga cgccaagcta    780

attgctgaca gcatcgactt caaccaagtg gcacaggtgc agcgggcact cagaaagact    840

aaaaaggggg aagaagacct caataagttg agggacctga ataaagaggt tgacagactc    900

atgtccatga ggagtgttca acgaaacaca gttttcaagg tgggtgatct ggggagggat    960

gaactgatgg agttggcgtc tgaccttgag aaattaaaaa acaagataag aagagcagag   1020

acaggctctc aggggtttta catgggtaac ttgtcccagt cacaacttgc taaaagatca   1080

gagatattga gaacactggg atttcaacag caagggactg ggggaaatgg tgtggtgagg   1140

atatgggatg ttaaagaccc ttcaaagcta aacaatcagt ttggctctgt tcctgcattg   1200

acaattgcat gcatgactgt tcaaggaggt gagacaatga acagtgtcat acaggcttta   1260

acctcacttg ggcttctata cactgtgaag tatccaaact taagtgacct tgacagactg   1320

actcaggaac atgactgcct tcagattgtg actaaagatg aaagctccat caatatttct   1380

ggttacaact tcagtctttc agctgcagta aaggctggag catctattct tgatggtgga   1440

aacatgttgg aaacaatcag agtcacccca gaaaacttct cttccctcat aaaatcaacc   1500

attcaggtta aacgaagaga aggcatgttt attgatgaga aaccaggcaa tagaaatcct   1560

tatgaaaacc ttttgtacaa actttgtctt tctggcgatg gttggcctta tattggttca   1620

agatcacaaa tcacaggcag gtcatgggac aacacaagta ttgatctgac aaggaaacca   1680

gttgctggtc ctagacagcc ggaaaaaaac ggtcagaatt tgagattggc taacttgaca   1740

gagatacaag aagctgtcat cagagaggca gtggggaaac tcgaccccac caacaccctt   1800

tggctcgaca ttgaaggacc agccactgac cctgttgaga tggcattatt ccaacctgca   1860

ggtaagcagt acattcactg cttcagaaaa ccacatgatg agaaagggtt taaaaatggt   1920

agcagacact ctcacggcat cttaatgaag gacatagaag atgcaatgcc aggagttctt   1980

agttacgtga tcggcttgct gcctccagac atggttgtga ctactcaagg ttccgatgac   2040

atcaggaagt tgtttgacct ccatggaaga agggatctta aactggttga tgttaagctc   2100

acatctgaac aagccaggca gtttgatcaa caggtctggg agaaatatgg tcacttatgc   2160

aaatatcaca atggagtggt tgtcaataag aaaaagaggg aaaaggatac tcccttcaag   2220

ttggcctcca gtgaaccaca ctgtgctctg ctagactgca taatgtttca gtcagtgcta   2280

gatgggaagc tctatgagga ggaacctaca cctctattac caccgagctt gctgttcctc   2340

ccgaaggcag cctatgcact cccgggagag aatctatatt ttcaagggcc cggcggaggt   2400

agtcaccatc atcaccatca ctaatgaccg gtgcggccgc aagctt                  2446
```

<210> SEQ ID NO 117
<211> LENGTH: 789
<212> TYPE: PRT
<213> ORGANISM: artificial
<220> FEATURE:
<223> OTHER INFORMATION: Aa sequence of fusion protein
      [SNAPlike-proTEV1-JUN.N-proTEV2-Histag]

<400> SEQUENCE: 117

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45
```

```
Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Val Pro Ser Phe Arg Trp Thr Gln Ser Leu Arg Arg Gly
    210                 215                 220

Leu Ser Gln Phe Thr Gln Thr Val Lys Ser Asp Val Leu Lys Asp Ala
225                 230                 235                 240

Lys Leu Ile Ala Asp Ser Ile Asp Phe Asn Gln Val Ala Gln Val Gln
                245                 250                 255

Arg Ala Leu Arg Lys Thr Lys Lys Gly Glu Glu Asp Leu Asn Lys Leu
            260                 265                 270

Arg Asp Leu Asn Lys Glu Val Asp Arg Leu Met Ser Met Arg Ser Val
        275                 280                 285

Gln Arg Asn Thr Val Phe Lys Val Gly Asp Leu Gly Arg Asp Glu Leu
    290                 295                 300

Met Glu Leu Ala Ser Asp Leu Glu Lys Leu Lys Asn Lys Ile Arg Arg
305                 310                 315                 320

Ala Glu Thr Gly Ser Gln Gly Val Tyr Met Gly Asn Leu Ser Gln Ser
                325                 330                 335

Gln Leu Ala Lys Arg Ser Glu Ile Leu Arg Thr Leu Gly Phe Gln Gln
            340                 345                 350

Gln Gly Thr Gly Gly Asn Gly Val Val Arg Ile Trp Asp Val Lys Asp
        355                 360                 365

Pro Ser Lys Leu Asn Asn Gln Phe Gly Ser Val Pro Ala Leu Thr Ile
    370                 375                 380

Ala Cys Met Thr Val Gln Gly Gly Glu Thr Met Asn Ser Val Ile Gln
385                 390                 395                 400

Ala Leu Thr Ser Leu Gly Leu Leu Tyr Thr Val Lys Tyr Pro Asn Leu
                405                 410                 415

Ser Asp Leu Asp Arg Leu Thr Gln Glu His Asp Cys Leu Gln Ile Val
            420                 425                 430

Thr Lys Asp Glu Ser Ser Ile Asn Ile Ser Gly Tyr Asn Phe Ser Leu
        435                 440                 445

Ser Ala Ala Val Lys Ala Gly Ala Ser Ile Leu Asp Gly Gly Asn Met
    450                 455                 460

Leu Glu Thr Ile Arg Val Thr Pro Glu Asn Phe Ser Ser Leu Ile Lys
```

```
465                 470                 475                 480

Ser Thr Ile Gln Val Lys Arg Arg Glu Gly Met Phe Ile Asp Glu Lys
                485                 490                 495

Pro Gly Asn Arg Asn Pro Tyr Glu Asn Leu Leu Tyr Lys Leu Cys Leu
            500                 505                 510

Ser Gly Asp Gly Trp Pro Tyr Ile Gly Ser Arg Ser Gln Ile Thr Gly
        515                 520                 525

Arg Ser Trp Asp Asn Thr Ser Ile Asp Leu Thr Arg Lys Pro Val Ala
    530                 535                 540

Gly Pro Arg Gln Pro Glu Lys Asn Gly Gln Asn Leu Arg Leu Ala Asn
545                 550                 555                 560

Leu Thr Glu Ile Gln Glu Ala Val Ile Arg Glu Ala Val Gly Lys Leu
                565                 570                 575

Asp Pro Thr Asn Thr Leu Trp Leu Asp Ile Glu Gly Pro Ala Thr Asp
            580                 585                 590

Pro Val Glu Met Ala Leu Phe Gln Pro Ala Gly Lys Gln Tyr Ile His
        595                 600                 605

Cys Phe Arg Lys Pro His Asp Glu Lys Gly Phe Lys Asn Gly Ser Arg
    610                 615                 620

His Ser His Gly Ile Leu Met Lys Asp Ile Glu Asp Ala Met Pro Gly
625                 630                 635                 640

Val Leu Ser Tyr Val Ile Gly Leu Leu Pro Pro Asp Met Val Val Thr
                645                 650                 655

Thr Gln Gly Ser Asp Asp Ile Arg Lys Leu Phe Asp Leu His Gly Arg
            660                 665                 670

Arg Asp Leu Lys Leu Val Asp Val Lys Leu Thr Ser Glu Gln Ala Arg
        675                 680                 685

Gln Phe Asp Gln Gln Val Trp Glu Lys Tyr Gly His Leu Cys Lys Tyr
    690                 695                 700

His Asn Gly Val Val Val Asn Lys Lys Lys Arg Glu Lys Asp Thr Pro
705                 710                 715                 720

Phe Lys Leu Ala Ser Ser Glu Pro His Cys Ala Leu Leu Asp Cys Ile
                725                 730                 735

Met Phe Gln Ser Val Leu Asp Gly Lys Leu Tyr Glu Glu Glu Pro Thr
            740                 745                 750

Pro Leu Leu Pro Pro Ser Leu Leu Phe Leu Pro Lys Ala Ala Tyr Ala
        755                 760                 765

Leu Pro Gly Glu Asn Leu Tyr Phe Gln Gly Pro Gly Gly Gly Ser His
    770                 775                 780

His His His His His
785
```

<210> SEQ ID NO 118
<211> LENGTH: 2446
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Machupo virus-proTEV2-Histag for expression in S2 cells

<400> SEQUENCE: 118

```
atgaagttat gcatattact ggccgtcgtg gcctttgttg gcctctcgct cgggagatct     60

gacaaagact gcgaaatgaa aagaactaca ttggattcac cacttgggaa gttggaactg    120

agtggatgcg agcaaggatt gcatgaaatt aagctactgg gaaaaggaac ttctgctgct    180
```

```
gatgcagttg aagttccagc accagcagct gttcttggag gtcctgagcc cctcatgcaa    240
gccacagcct ggcttaacgc atatttccac cagcctgagg ccattgagga atttccagtc    300
cccgcccttc accatcctgt gtttcagcag gagagcttca cccgccaggt cctgtggaaa    360
ttgctgaagg tggtcaagtt tggtgaagtg atttcatatc agcaacttgc tgcattggcc    420
ggtaaccccg cagctacagc tgccgtgaaa actgctctca gcggaaatcc tgtgcccatc    480
ctgatccctt gtcacagagt cgtttcatct tccggagctg taggtggcta tgaaggagga    540
ctggcagtta aggagtggct gctggctcat gaaggtcata gacttggaaa gcctgggctg    600
ggtcctgctg gtataggcgc gccagggtcc ctaggtggcg gatccgaaaa cctgtacttc    660
cagagcgata tcgctcactc caaggaaatt cccagctttc ggtggactca gtcactgaga    720
agaggcctga gtcagttcac ccacactgtg aaaacagatg tgttgaaaga tgccaagctc    780
atagctgaca gcatcgactt caaccaggtt tcacaagtgc agagggctct cagaaagaac    840
aaaaggggtg aagaggatct gaacaagctg agggatttaa acaaagaagt ggataggctc    900
atgtctatga aaagcatcca gaaaaacacc atattcaaga ttggtgatct ggggagagat    960
gaattgatgg agcttgcatc agacttggaa aaactgaaga acaagataaa gaggactgag   1020
tcaggtcccc aagggctgta catgggtaat ttgtcacagc tgcaactgac aaagaggtca   1080
gaaatcttga agaccctggg attccaacag cagagaggtg ctggaaatgg tgtggttaga   1140
atctgggatg tctcagatcc atcaaaactg aataatcagt ttggttccat gccagctctc   1200
acaatcgctt gtatgactgt ccagggtgga gaaacgatga atagtgtggt ccaagcgttg   1260
acatctctgg gcctgttata cactgttaaa tatccgaatt taaatgacct tgacaagcta   1320
acactagagc acgaatgctt gcagatcgta actaaggacg agagctccat caacatctct   1380
ggctataact tcagtctgtc agctgctgtg aaagctggcg cctcaatact tgacggtggg   1440
aacatgctgg aaacaattag ggtcactcct gataatttct ccagcttgat taaatcaact   1500
ctgcaagtca agcgaaaaga ggggatgttt atagacgaga aacctgggaa tcgaaatcct   1560
tatgagaacc ttctgtataa attgtgtctc tcaggtgacg ggtggcctta cattggttcc   1620
agatcacaaa ttcttgggag gtcttgggac aacacaagtg ttgatctaac aaagaaacct   1680
caagttggac cgagacaacc cgagaaaaac ggtcagaatc taagactagc aaacctgact   1740
gaaatgcaag aagcagtgat taaagaggct gtaaagaagt tagaccccac taatacactg   1800
tggcttgaca ttgaagggcc tccaacagac cctgtggaat tggcactata tcagccagcc   1860
aacaagcatt atattcattg ttttagaaag ccacatgatg agaagggctt caaaaatggc   1920
agcagacatt cacatggcat cttgatgcaa gacatcgagg atgcaatgcc aggagtatta   1980
agttatgtaa taggtttact accacaagat atggtgatta caactcaagg ttctgacgac   2040
ataaggaaac ttttagacat tcatggacgg aaggatttaa agctggtaga tgtgaaactc   2100
acatctgatc aagcaagact ctatgatcag caaatttggg agaagtttgg acatctttgc   2160
aaacatcata atggagttgt tgtcaacaag aaaaagagag aaaaagactc tccattcaaa   2220
ttgagttctg gtgaacctca ctgtgctctg ttggattgta tcatgtatca atcagtgatg   2280
gatggcaaaa tggtagatga agaaccagtg gcacttttac ctctcagcct tctatttcta   2340
cccaaggcag cctttgcact cccgggagag aatctatatt ttcaagggcc cggcggaggt   2400
agtcaccatc atcaccatca ctaatgaccg gtgcggccgc aagctt                  2446
```

<210> SEQ ID NO 119

<211> LENGTH: 789
<212> TYPE: PRT
<213> ORGANISM: artificial
<220> FEATURE:
<223> OTHER INFORMATION: Amino acid sequence of fusion protein
[SNAPlike-proTEV1-MAC.N-proTEV2-Histag]

<400> SEQUENCE: 119

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Ile Pro Ser Phe Arg Trp Thr Gln Ser Leu Arg Arg Gly
    210                 215                 220

Leu Ser Gln Phe Thr His Thr Val Lys Thr Asp Val Leu Lys Asp Ala
225                 230                 235                 240

Lys Leu Ile Ala Asp Ser Ile Asp Phe Asn Gln Val Ser Gln Val Gln
                245                 250                 255

Arg Ala Leu Arg Lys Asn Lys Arg Gly Glu Glu Asp Leu Asn Lys Leu
            260                 265                 270

Arg Asp Leu Asn Lys Glu Val Asp Arg Leu Met Ser Met Lys Ser Ile
        275                 280                 285

Gln Lys Asn Thr Ile Phe Lys Ile Gly Asp Leu Gly Arg Asp Glu Leu
    290                 295                 300

Met Glu Leu Ala Ser Asp Leu Glu Lys Leu Lys Asn Lys Ile Lys Arg
305                 310                 315                 320

Thr Glu Ser Gly Pro Gln Gly Leu Tyr Met Gly Asn Leu Ser Gln Leu
                325                 330                 335

Gln Leu Thr Lys Arg Ser Glu Ile Leu Lys Thr Leu Gly Phe Gln Gln
            340                 345                 350

Gln Arg Gly Ala Gly Asn Gly Val Val Arg Ile Trp Asp Val Ser Asp
        355                 360                 365

Pro Ser Lys Leu Asn Asn Gln Phe Gly Ser Met Pro Ala Leu Thr Ile
```

```
    370                 375                 380

Ala Cys Met Thr Val Gln Gly Gly Glu Thr Met Asn Ser Val Val Gln
385                 390                 395                 400

Ala Leu Thr Ser Leu Gly Leu Leu Tyr Thr Val Lys Tyr Pro Asn Leu
                405                 410                 415

Asn Asp Leu Asp Lys Leu Thr Leu Glu His Glu Cys Leu Gln Ile Val
            420                 425                 430

Thr Lys Asp Glu Ser Ser Ile Asn Ile Ser Gly Tyr Asn Phe Ser Leu
        435                 440                 445

Ser Ala Ala Val Lys Ala Gly Ala Ser Ile Leu Asp Gly Gly Asn Met
    450                 455                 460

Leu Glu Thr Ile Arg Val Thr Pro Asp Asn Phe Ser Ser Leu Ile Lys
465                 470                 475                 480

Ser Thr Leu Gln Val Lys Arg Lys Glu Gly Met Phe Ile Asp Glu Lys
                485                 490                 495

Pro Gly Asn Arg Asn Pro Tyr Glu Asn Leu Leu Tyr Lys Leu Cys Leu
            500                 505                 510

Ser Gly Asp Gly Trp Pro Tyr Ile Gly Ser Arg Ser Gln Ile Leu Gly
        515                 520                 525

Arg Ser Trp Asp Asn Thr Ser Val Asp Leu Thr Lys Lys Pro Gln Val
    530                 535                 540

Gly Pro Arg Gln Pro Glu Lys Asn Gly Gln Asn Leu Arg Leu Ala Asn
545                 550                 555                 560

Leu Thr Glu Met Gln Glu Ala Val Ile Lys Glu Ala Val Lys Lys Leu
                565                 570                 575

Asp Pro Thr Asn Thr Leu Trp Leu Asp Ile Glu Gly Pro Pro Thr Asp
            580                 585                 590

Pro Val Glu Leu Ala Leu Tyr Gln Pro Ala Asn Lys His Tyr Ile His
        595                 600                 605

Cys Phe Arg Lys Pro His Asp Glu Lys Gly Phe Lys Asn Gly Ser Arg
    610                 615                 620

His Ser His Gly Ile Leu Met Gln Asp Ile Glu Asp Ala Met Pro Gly
625                 630                 635                 640

Val Leu Ser Tyr Val Ile Gly Leu Leu Pro Gln Asp Met Val Ile Thr
                645                 650                 655

Thr Gln Gly Ser Asp Asp Ile Arg Lys Leu Leu Asp Ile His Gly Arg
            660                 665                 670

Lys Asp Leu Lys Leu Val Asp Val Lys Leu Thr Ser Asp Gln Ala Arg
        675                 680                 685

Leu Tyr Asp Gln Gln Ile Trp Glu Lys Phe Gly His Leu Cys Lys His
    690                 695                 700

His Asn Gly Val Val Val Asn Lys Lys Lys Arg Glu Lys Asp Ser Pro
705                 710                 715                 720

Phe Lys Leu Ser Ser Gly Glu Pro His Cys Ala Leu Leu Asp Cys Ile
                725                 730                 735

Met Tyr Gln Ser Val Met Asp Gly Lys Met Val Asp Glu Glu Pro Val
            740                 745                 750

Ala Leu Leu Pro Leu Ser Leu Leu Phe Leu Pro Lys Ala Ala Phe Ala
        755                 760                 765

Leu Pro Gly Glu Asn Leu Tyr Phe Gln Gly Pro Gly Gly Gly Ser His
    770                 775                 780

His His His His His
785
```

<210> SEQ ID NO 120
<211> LENGTH: 2434
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Guanarito virus-proTEV2-Histag for expression in S2 cells

<400> SEQUENCE: 120
atgaagttat gcatattact ggccgtcgtg gcctttgttg gcctctcgct cgggagatct 60
gacaaagact gcgaaatgaa aagaactaca ttggattcac cacttgggaa gttggaactg 120
agtggatgcg agcaaggatt gcatgaaatt aagctactgg gaaaaggaac ttctgctgct 180
gatgcagttg aagttccagc accagcagct gttcttggag gtcctgagcc cctcatgcaa 240
gccacagcct ggcttaacgc atatttccac cagcctgagg ccattgagga atttccagtc 300
cccgcccttc accatcctgt gtttcagcag gagagcttca cccgccaggt cctgtggaaa 360
ttgctgaagg tggtcaagtt tggtgaagtg atttcatatc agcaacttgc tgcattggcc 420
ggtaaccccg cagctacagc tgccgtgaaa actgctctca gcggaaatcc tgtgcccatc 480
ctgatccctt gtcacagagt cgtttcatct tccggagctg taggtggcta tgaaggagga 540
ctggcagtta aggagtggct gctggctcat gaaggtcata gacttggaaa gcctgggctg 600
ggtcctgctg gtataggcgc gccagggtcc ctaggtggcg gatccgaaaa cctgtacttc 660
cagagcgata tcgctcactc caaagaaatc cccagcttcc gctggactca atctctaagg 720
agagaactag ggatgttcac agaaccaacc aaatcaagtg ttcttaatga tgcaaagctc 780
attgcagact ccccttgattt cacacaagtt tctcaagttc aaagactcct acgtaagtcc 840
aaacgaggag acactgatct tgataaactt agggacttaa ataaagaagt tgatagactg 900
atgagcatga aaagtgttca gaacaacaca gttctgaaag ttggtgattt gggcaaagat 960
gaattaatgg acttggcctc tgacctagaa aaactaaaga agaagattgg agatagggaa 1020
agcaatagtc caaggatgta catgggaaac ttgacgcagt cacaattgga aaaaagagca 1080
gggattctta gaaccctggg attccaacaa caaagggggg ctgcaggtgg ggttgtcagg 1140
ttgtgggatg tatctgatcc ctccaaactg aataaccaat ttggttcaat gccagctctt 1200
accattgcct gcatgacagt tcagggagga gaaacaatga acaatgttgt gcaggcacta 1260
acatcacttg gtcttctcta cactgtcaaa tatcccaatc ttgatgacct ggaaaaacta 1320
actttagaac acgactgcct acagattata acaaaggatg agagtgcact caacatatct 1380
ggttataact tcagtctttc agctgctgta aaagctggtg catcacttat agatggtggc 1440
aacatgctgg agacaataaa agtcacaccc aacaacttct cttctattgt caaggccgca 1500
ttgaacgtca aaagaagaga aggcatgttc atagatgaga gaccgggcaa tagaaaccct 1560
tatgagaacc ttctctacaa gctgtgtttg tctggggagg gttggccata tattggatca 1620
aggtcacaaa tactcgggag gtcttgggac aacacaagtg tcgatttaaa tgcaagacct 1680
gtaacaggtc cccgagctcc tgaaaagaat ggacaaaata tcagactatc aaatctttct 1740
gaaatgcaag aagcgatcgt aaaggaagca atgaggaaat tagattcatc agacacaatc 1800
tggatggaca ttgaaggccc gccaactgat cctgtggagt tggcagtttt ccaaccttct 1860
tcaggaaact atgtacactg tttcagaaaa cctcatgatg agaaaggttt taaaaatgga 1920
agtaggcact cacacggcat actattaaag gaccttgaag atgctcaacc tggtctattg 1980

```
agttacgtca ttggcttatt gccacagggt tcagttatca ctgttcaagg ggcagatgac   2040

atcaaaaagc tattcgacat acatggaagg aaagatttaa aacttgttga tgtcagactg   2100

actggggaac agtccagaat ttttgaacag gaagtttggg aaaaatttgg ccacctctgc   2160

agagcacaca atggtgtcat tgttcctaag aagaaaaaca aggaggctaa ctccacgaag   2220

gagccacact gtgctcttct cgattgcatc atgtttcagt ctgttcttga tggtcatctt   2280

cccgacacca ttcccattca actgctacca aacacattag tgttccaagc caagagcgca   2340

tttgtgatcc cgggagagaa tctatatttt caagggcccg gcggaggtag tcaccatcat   2400

caccatcact aatgaccggt gcggccgcaa gctt                               2434


<210> SEQ ID NO 121
<211> LENGTH: 785
<212> TYPE: PRT
<213> ORGANISM: artificial
<220> FEATURE:
<223> OTHER INFORMATION: Amino acid sequence of fusion protein
      [SNAPlike-proTEV1-GUA.N-proTEV2-Histag]

<400> SEQUENCE: 121

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Ala His
        195                 200                 205

Ser Lys Glu Ile Pro Ser Phe Arg Trp Thr Gln Ser Leu Arg Arg Glu
    210                 215                 220

Leu Gly Met Phe Thr Glu Pro Thr Lys Ser Ser Val Leu Asn Asp Ala
225                 230                 235                 240

Lys Leu Ile Ala Asp Ser Leu Asp Phe Thr Gln Val Ser Gln Val Gln
                245                 250                 255

Arg Leu Leu Arg Lys Ser Lys Arg Gly Asp Thr Asp Leu Asp Lys Leu
            260                 265                 270

Arg Asp Leu Asn Lys Glu Val Asp Arg Leu Met Ser Met Lys Ser Val
```

-continued

```
        275                 280                 285

Gln Asn Asn Thr Val Leu Lys Val Gly Asp Leu Gly Lys Asp Glu Leu
    290                 295                 300

Met Asp Leu Ala Ser Asp Leu Glu Lys Leu Lys Lys Lys Ile Gly Asp
305                 310                 315                 320

Arg Glu Ser Asn Ser Pro Arg Met Tyr Met Gly Asn Leu Thr Gln Ser
                325                 330                 335

Gln Leu Glu Lys Arg Ala Gly Ile Leu Arg Thr Leu Gly Phe Gln Gln
            340                 345                 350

Gln Arg Gly Ala Ala Gly Gly Val Val Arg Leu Trp Asp Val Ser Asp
        355                 360                 365

Pro Ser Lys Leu Asn Asn Gln Phe Gly Ser Met Pro Ala Leu Thr Ile
    370                 375                 380

Ala Cys Met Thr Val Gln Gly Gly Glu Thr Met Asn Asn Val Val Gln
385                 390                 395                 400

Ala Leu Thr Ser Leu Gly Leu Leu Tyr Thr Val Lys Tyr Pro Asn Leu
                405                 410                 415

Asp Asp Leu Glu Lys Leu Thr Leu Glu His Asp Cys Leu Gln Ile Ile
            420                 425                 430

Thr Lys Asp Glu Ser Ala Leu Asn Ile Ser Gly Tyr Asn Phe Ser Leu
        435                 440                 445

Ser Ala Ala Val Lys Ala Gly Ala Ser Leu Ile Asp Gly Gly Asn Met
    450                 455                 460

Leu Glu Thr Ile Lys Val Thr Pro Asn Asn Phe Ser Ser Ile Val Lys
465                 470                 475                 480

Ala Ala Leu Asn Val Lys Arg Arg Glu Gly Met Phe Ile Asp Glu Arg
                485                 490                 495

Pro Gly Asn Arg Asn Pro Tyr Glu Asn Leu Leu Tyr Lys Leu Cys Leu
            500                 505                 510

Ser Gly Glu Gly Trp Pro Tyr Ile Gly Ser Arg Ser Gln Ile Leu Gly
        515                 520                 525

Arg Ser Trp Asp Asn Thr Ser Val Asp Leu Asn Ala Arg Pro Val Thr
    530                 535                 540

Gly Pro Arg Ala Pro Glu Lys Asn Gly Gln Asn Ile Arg Leu Ser Asn
545                 550                 555                 560

Leu Ser Glu Met Gln Glu Ala Ile Val Lys Glu Ala Met Arg Lys Leu
                565                 570                 575

Asp Ser Ser Asp Thr Ile Trp Met Asp Ile Glu Gly Pro Pro Thr Asp
            580                 585                 590

Pro Val Glu Leu Ala Val Phe Gln Pro Ser Ser Gly Asn Tyr Val His
        595                 600                 605

Cys Phe Arg Lys Pro His Asp Glu Lys Gly Phe Lys Asn Gly Ser Arg
    610                 615                 620

His Ser His Gly Ile Leu Leu Lys Asp Leu Glu Asp Ala Gln Pro Gly
625                 630                 635                 640

Leu Leu Ser Tyr Val Ile Gly Leu Leu Pro Gln Gly Ser Val Ile Thr
                645                 650                 655

Val Gln Gly Ala Asp Asp Ile Lys Lys Leu Phe Asp Ile His Gly Arg
            660                 665                 670

Lys Asp Leu Lys Leu Val Asp Val Arg Leu Thr Gly Glu Gln Ser Arg
        675                 680                 685

Ile Phe Glu Gln Glu Val Trp Glu Lys Phe Gly His Leu Cys Arg Ala
    690                 695                 700
```

His Asn Gly Val Ile Val Pro Lys Lys Lys Asn Lys Glu Ala Asn Ser
705 710 715 720

Thr Lys Glu Pro His Cys Ala Leu Leu Asp Cys Ile Met Phe Gln Ser
725 730 735

Val Leu Asp Gly His Leu Pro Asp Thr Ile Pro Ile Gln Leu Leu Pro
740 745 750

Asn Thr Leu Val Phe Gln Ala Lys Ser Ala Phe Val Ile Pro Gly Glu
755 760 765

Asn Leu Tyr Phe Gln Gly Pro Gly Gly Gly Ser His His His His His
770 775 780

His
785

<210> SEQ ID NO 122
<211> LENGTH: 2440
<212> TYPE: DNA
<213> ORGANISM: artificial
<220> FEATURE:
<223> OTHER INFORMATION: DNA sequence encoding ssBiP-SNAPlike-proTEV1-N nucleoprotein of the Sabia virus-proTEV2-Histag for expression in S2 cells

<400> SEQUENCE: 122
atgaagttat gcatattact ggccgtcgtg gcctttgttg gcctctcgct cgggagatct 60
gacaaagact gcgaaatgaa aagaactaca ttggattcac cacttgggaa gttggaactg 120
agtggatgcg agcaaggatt gcatgaaatt aagctactgg gaaaaggaac ttctgctgct 180
gatgcagttg aagttccagc accagcagct gttcttggag gtcctgagcc cctcatgcaa 240
gccacagcct ggcttaacgc atatttccac cagcctgagg ccattgagga atttccagtc 300
cccgcccttc accatcctgt gtttcagcag gagagcttca cccgccaggt cctgtggaaa 360
ttgctgaagg tggtcaagtt tggtgaagtg atttcatatc agcaacttgc tgcattggcc 420
ggtaaccccg cagctacagc tgccgtgaaa actgctctca gcggaaatcc tgtgcccatc 480
ctgatccctt gtcacagagt cgtttcatct tccggagctg taggtggcta tgaaggagga 540
ctggcagtta aggagtggct gctggctcat gaaggtcata gacttggaaa gcctgggctg 600
ggtcctgctg gtataggcgc gccagggtcc ctaggtggcg gatccgaaaa cctgtacttc 660
cagagcgata tcagcaactc aaaggaaatc cccagcttca gatggactca atccctgaga 720
agagggctca gtgagttcac aacacccgtg aagaccgatg ttctgaggga tgccaaaatg 780
atacttgatg gtcttgattt caatcaagtc tctcttgttc aaagaatcct tagaaagtct 840
aaaaggaatg atggtgatct tgataaactg agagacctaa ataaagaagt ggacaacctg 900
atgagcatga agagttccca aagagacaca atcttaaaac ttggtgatct caacaaatct 960
gaactgatgg atcttgcatc agacctggag aaactgaaaa gaaaagttgg acaaacagaa 1020
agatcagcct caggaggtgt gtacctggga aacctttccc aatcacagct caccaaaagg 1080
tctgatcttt taaggaaact tggttttcaa cagcagcaag tgaggtctcc aggggttgta 1140
aggatttggg acgtagctga tccgaacagg ctgaataatc aatttggatc tgtccctgca 1200
ctgacaatcg cttgtatgac taaacaaagt gacaatacca tgggggatgt tgttcaggca 1260
ctaacatctt tgggacttct ttatacagtt aagttcccca acctgattga cctagaaaaa 1320
cttacagcag aacatgactg tcttcaaata gtgactaaag atgagagcgg cttgaacatc 1380
tcaggatata actatagtct ttctgcagct gttaaagctg gtgcaacgct tctggatggt 1440

```
ggtaacatgc tggaaaccat aaggatcact cctgacaact tttctcagat cataaagaca   1500

accctatcca taaagaaaaa ggaaggcatg tttgtagatg agaaacctgg aaatagaaac   1560

ccttatgaaa accttctgta caaaatctgc ctttcaggag aaggttggcc ttacattggc   1620

tccagatccc agatcaaggg taggtcatgg gaaaacacca ctgttgattt aagcacaaag   1680

ccccaacaag ggccgagaac accagaaaag gcaggtcaga acattagact ctcccacttg   1740

actgagttgc aagagtcagt tgtgagagag gcaatgggta agattgaccc aactctgaca   1800

acatggattg acattgaggg taccagtaat gatccggttg aattagcatt gtaccaacca   1860

gacacaggta attatatcct ctgttatagg aaaccacatg atgagaaggg gttcaaaaat   1920

ggtagcaggc attcacatgg gatgttgcta aaggacctag aatctgcaca gccaggcttg   1980

ctcagctatg ttatagggct ccttcctcaa aacatggtcc tcaccaccca aggttcagat   2040

gatataaggc gcttagtaga tacacacggt cgcaaagact taaagattgt cgacattaaa   2100

ttggcatctg aacaggcgag aaagtttgag gagccaatct ggtcagattt tggtcacctc   2160

tgtaagaaac acaatggagt tattgtgcca aagaaaaaga aagacaaaga catcccacag   2220

tcctcagagc cacactgtgc cctacttgat tgtctaatgt ttcagtcagc catagcaggc   2280

caaccacctc aaaccaaact ggaaggttta ttgcctgatg cattgctctt cacactggag   2340

gcagcattca ccatcccggg agagaatcta tattttcaag ggcccggcgg aggtagtcac   2400

catcatcacc atcactaatg accggtgcgg ccgcaagctt                         2440
```

```
<210> SEQ ID NO 123
<211> LENGTH: 787
<212> TYPE: PRT
<213> ORGANISM: artificial
<220> FEATURE:
<223> OTHER INFORMATION: Amino acid sequence of fusion protein
      [SNAPlike-proTEV1-SAB.N-proTEV2-Histag]

<400> SEQUENCE: 123

Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
```

```
            180                 185                 190

Leu Gly Gly Gly Ser Glu Asn Leu Tyr Phe Gln Ser Asp Ile Ser Asn
        195                 200                 205

Ser Lys Glu Ile Pro Ser Phe Arg Trp Thr Gln Ser Leu Arg Arg Gly
    210                 215                 220

Leu Ser Glu Phe Thr Thr Pro Val Lys Thr Asp Val Leu Arg Asp Ala
225                 230                 235                 240

Lys Met Ile Leu Asp Gly Leu Asp Phe Asn Gln Val Ser Leu Val Gln
                245                 250                 255

Arg Ile Leu Arg Lys Ser Lys Arg Asn Asp Gly Asp Leu Asp Lys Leu
            260                 265                 270

Arg Asp Leu Asn Lys Glu Val Asp Asn Leu Met Ser Met Lys Ser Ser
        275                 280                 285

Gln Arg Asp Thr Ile Leu Lys Leu Gly Asp Leu Asn Lys Ser Glu Leu
    290                 295                 300

Met Asp Leu Ala Ser Asp Leu Glu Lys Leu Lys Arg Lys Val Gly Gln
305                 310                 315                 320

Thr Glu Arg Ser Ala Ser Gly Gly Val Tyr Leu Gly Asn Leu Ser Gln
                325                 330                 335

Ser Gln Leu Thr Lys Arg Ser Asp Leu Leu Arg Lys Leu Gly Phe Gln
            340                 345                 350

Gln Gln Gln Val Arg Ser Pro Gly Val Val Arg Ile Trp Asp Val Ala
        355                 360                 365

Asp Pro Asn Arg Leu Asn Asn Gln Phe Gly Ser Val Pro Ala Leu Thr
    370                 375                 380

Ile Ala Cys Met Thr Lys Gln Ser Asp Asn Thr Met Gly Asp Val Val
385                 390                 395                 400

Gln Ala Leu Thr Ser Leu Gly Leu Leu Tyr Thr Val Lys Phe Pro Asn
                405                 410                 415

Leu Ile Asp Leu Glu Lys Leu Thr Ala Glu His Asp Cys Leu Gln Ile
            420                 425                 430

Val Thr Lys Asp Glu Ser Gly Leu Asn Ile Ser Gly Tyr Asn Tyr Ser
        435                 440                 445

Leu Ser Ala Ala Val Lys Ala Gly Ala Thr Leu Leu Asp Gly Gly Asn
    450                 455                 460

Met Leu Glu Thr Ile Arg Ile Thr Pro Asp Asn Phe Ser Gln Ile Ile
465                 470                 475                 480

Lys Thr Thr Leu Ser Ile Lys Lys Lys Glu Gly Met Phe Val Asp Glu
                485                 490                 495

Lys Pro Gly Asn Arg Asn Pro Tyr Glu Asn Leu Leu Tyr Lys Ile Cys
            500                 505                 510

Leu Ser Gly Glu Gly Trp Pro Tyr Ile Gly Ser Arg Ser Gln Ile Lys
        515                 520                 525

Gly Arg Ser Trp Glu Asn Thr Thr Val Asp Leu Ser Thr Lys Pro Gln
    530                 535                 540

Gln Gly Pro Arg Thr Pro Glu Lys Ala Gly Gln Asn Ile Arg Leu Ser
545                 550                 555                 560

His Leu Thr Glu Leu Gln Glu Ser Val Val Arg Glu Ala Met Gly Lys
                565                 570                 575

Ile Asp Pro Thr Leu Thr Thr Trp Ile Asp Ile Glu Gly Thr Ser Asn
            580                 585                 590

Asp Pro Val Glu Leu Ala Leu Tyr Gln Pro Asp Thr Gly Asn Tyr Ile
        595                 600                 605
```

```
Leu Cys Tyr Arg Lys Pro His Asp Glu Lys Gly Phe Lys Asn Gly Ser
    610                 615                 620

Arg His Ser His Gly Met Leu Leu Lys Asp Leu Glu Ser Ala Gln Pro
625                 630                 635                 640

Gly Leu Leu Ser Tyr Val Ile Gly Leu Leu Pro Gln Asn Met Val Leu
                645                 650                 655

Thr Thr Gln Gly Ser Asp Asp Ile Arg Arg Leu Val Asp Thr His Gly
            660                 665                 670

Arg Lys Asp Leu Lys Ile Val Asp Ile Lys Leu Ala Ser Glu Gln Ala
        675                 680                 685

Arg Lys Phe Glu Glu Pro Ile Trp Ser Asp Phe Gly His Leu Cys Lys
    690                 695                 700

Lys His Asn Gly Val Ile Val Pro Lys Lys Lys Lys Asp Lys Asp Ile
705                 710                 715                 720

Pro Gln Ser Ser Glu Pro His Cys Ala Leu Leu Asp Cys Leu Met Phe
                725                 730                 735

Gln Ser Ala Ile Ala Gly Gln Pro Pro Gln Thr Lys Leu Glu Gly Leu
            740                 745                 750

Leu Pro Asp Ala Leu Leu Phe Thr Leu Glu Ala Ala Phe Thr Ile Pro
        755                 760                 765

Gly Glu Asn Leu Tyr Phe Gln Gly Pro Gly Gly Gly Ser His His His
    770                 775                 780

His His His
785


<210> SEQ ID NO 124
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Omsk virus-Histag for expression in S2 cells

<400> SEQUENCE: 124

atgaaactat gtattctact tgcagttgtt gcgttcgtag gattgtcctt aagatctgac      60

aaagactgcg aaatgaaaag aactacattg gattcaccac ttgggaagtt ggaactgagt     120

ggatgcgagc aaggattgca tgaaattaag ctactgggaa aaggaacttc tgctgctgat     180

gcagttgaag ttccagcacc agcagctgtt cttggaggtc ctgagcccct catgcaagcc     240

acagcctggc ttaacgcata tttccaccag cctgaggcca ttgaggaatt tccagtcccc     300

gcccttcacc atcctgtgtt tcagcaggag agcttcaccc gccaggtcct gtggaaattg     360

ctgaaggtgg tcaagtttgg tgaagtgatt tcatatcagc aacttgctgc attggccggt     420

aaccccgcag ctacagctgc cgtgaaaact gctctcagcg gaaatcctgt gcccatcctg     480

atcccttgtc acagagtcgt ttcatcttcc ggagctgtag gtggctatga aggaggactg     540

gcagttaagg agtggctgct ggctcatgaa ggtcatagac ttggaaagcc tgggctgggt     600

cctgctggta taggcgcgcc aggaggtggc gggctggaaa aactcaagat gaagggtctt     660

acctatacaa tgtgcgacaa ggcaaagttc acgtggaaaa gagctcccac agacagtggg     720

cacgacacag ttgtcatgga agtcgctttc tctggaacaa agccttgcag aatacccgtc     780

agggctgtgg cacatggttc cccagatgtg gatgtggcca tgctcataac gccaaatcca     840

acaatcgaaa acaatggagg tggctttata gagatgcagc tcccccccagg agacaacatc     900

atctatgttg ggaactaaa acaccagtgg ttccagaagg ggagtagcat tggcggaggt      960
```

ggccatcacc atcaccatca ctgatgaccg gt 992

<210> SEQ ID NO 125
<211> LENGTH: 310
<212> TYPE: PRT
<213> ORGANISM: artificial
<220> FEATURE:
<223> OTHER INFORMATION: Amino acid sequence of fusion protein [SNAPlike-OMSK.EDIII-Histag]

<400> SEQUENCE: 125

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

Pro Val Pro Ala Leu His His Pro Val Phe Gln Gln Glu Ser Phe Thr
85 90 95

Arg Gln Val Leu Trp Lys Leu Leu Lys Val Val Lys Phe Gly Glu Val
100 105 110

Ile Ser Tyr Gln Gln Leu Ala Ala Leu Ala Gly Asn Pro Ala Ala Thr
115 120 125

Ala Ala Val Lys Thr Ala Leu Ser Gly Asn Pro Val Pro Ile Leu Ile
130 135 140

Pro Cys His Arg Val Val Ser Ser Ser Gly Ala Val Gly Gly Tyr Glu
145 150 155 160

Gly Gly Leu Ala Val Lys Glu Trp Leu Leu Ala His Glu Gly His Arg
165 170 175

Leu Gly Lys Pro Gly Leu Gly Pro Ala Gly Ile Gly Ala Pro Gly Gly
180 185 190

Gly Gly Leu Glu Lys Leu Lys Met Lys Gly Leu Thr Tyr Thr Met Cys
195 200 205

Asp Lys Ala Lys Phe Thr Trp Lys Arg Ala Pro Thr Asp Ser Gly His
210 215 220

Asp Thr Val Val Met Glu Val Ala Phe Ser Gly Thr Lys Pro Cys Arg
225 230 235 240

Ile Pro Val Arg Ala Val Ala His Gly Ser Pro Asp Val Asp Val Ala
245 250 255

Met Leu Ile Thr Pro Asn Pro Thr Ile Glu Asn Asn Gly Gly Gly Phe
260 265 270

Ile Glu Met Gln Leu Pro Pro Gly Asp Asn Ile Ile Tyr Val Gly Glu
275 280 285

Leu Lys His Gln Trp Phe Gln Lys Gly Ser Ser Ile Gly Gly Gly Gly
290 295 300

His His His His His His
305 310

<210> SEQ ID NO 126
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
protein of the Kyasanur Forest Disease virus-Histag for expression
in S2 cells

<400> SEQUENCE: 126

```
atgaaactat gtattctact tgcagttgtt gcgttcgtag gattgtcctt aagatctgac     60

aaagactgcg aaatgaaaag aactacattg gattcaccac ttgggaagtt ggaactgagt    120

ggatgcgagc aaggattgca tgaaattaag ctactgggaa aaggaacttc tgctgctgat    180

gcagttgaag ttccagcacc agcagctgtt cttggaggtc ctgagcccct catgcaagcc    240

acagcctggc ttaacgcata tttccaccag cctgaggcca ttgaggaatt tccagtcccc    300

gcccttcacc atcctgtgtt tcagcaggag agcttcaccc gccaggtcct gtggaaattg    360

ctgaaggtgg tcaagtttgg tgaagtgatt tcatatcagc aacttgctgc attggccggt    420

aaccccgcag ctacagctgc cgtgaaaact gctctcagcg gaaatcctgt gcccatcctg    480

atcccttgtc acagagtcgt ttcatcttcc ggagctgtag gtggctatga aggaggactg    540

gcagttaagg agtggctgct ggctcatgaa ggtcatagac ttggaaagcc tgggctgggt    600

cctgctggta taggcgcgcc aggaggtggc gggcttgaaa aacttaagat gaaagggatg    660

acatacacgg tttgtgaggg atcaaaattt gcttggaaaa ggccgccaac cgacagtgga    720

catgataccg tagtcatgga ggtgacttac accgggagca agccatgcag aataccagtg    780

agagccgtgg cccatggaga acccaatgtt aacgtggcaa gtctaataac cccaaaccca    840

tccatggaaa caactggagg agggttcgtt gagctacagc taccaccagg agacaacatc    900

atctatgttg gtgagctgag ccaccagtgg tttcagaagg gcagcacaat tggcggaggt    960

ggccatcacc atcaccatca ctgatgaccg gt                                  992
```

<210> SEQ ID NO 127
<211> LENGTH: 310
<212> TYPE: PRT
<213> ORGANISM: artificial
<220> FEATURE:
<223> OTHER INFORMATION: Amino acid sequence of fusion protein
[SNAPlike-KYA.EDIII-Histag]

<400> SEQUENCE: 127

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140
```

-continued

```
Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Leu Glu Lys Leu Lys Met Lys Gly Met Thr Tyr Thr Val Cys
        195                 200                 205

Glu Gly Ser Lys Phe Ala Trp Lys Arg Pro Pro Thr Asp Ser Gly His
    210                 215                 220

Asp Thr Val Val Met Glu Val Thr Tyr Thr Gly Ser Lys Pro Cys Arg
225                 230                 235                 240

Ile Pro Val Arg Ala Val Ala His Gly Glu Pro Asn Val Asn Val Ala
                245                 250                 255

Ser Leu Ile Thr Pro Asn Pro Ser Met Glu Thr Thr Gly Gly Gly Phe
            260                 265                 270

Val Glu Leu Gln Leu Pro Pro Gly Asp Asn Ile Ile Tyr Val Gly Glu
        275                 280                 285

Leu Ser His Gln Trp Phe Gln Lys Gly Ser Thr Ile Gly Gly Gly Gly
    290                 295                 300

His His His His His His
305                 310


<210> SEQ ID NO 128
<211> LENGTH: 992
<212> TYPE: DNA
<213> ORGANISM: artificial
<220> FEATURE:
<223> OTHER INFORMATION: DNA sequence encoding BiPlike-SNAPlike- EDIII
      protein of the Alkhumra virus-Histag for expression in S2 cells

<400> SEQUENCE: 128

atgaaactat gtattctact tgcagttgtt gcgttcgtag gattgtcctt aagatctgac      60

aaagactgcg aaatgaaaag aactacattg gattcaccac ttgggaagtt ggaactgagt     120

ggatgcgagc aaggattgca tgaaattaag ctactgggaa aaggaacttc tgctgctgat     180

gcagttgaag ttccagcacc agcagctgtt cttggaggtc ctgagcccct catgcaagcc     240

acagcctggc ttaacgcata tttccaccag cctgaggcca ttgaggaatt tccagtcccc     300

gcccttcacc atcctgtgtt tcagcaggag agcttcaccc gccaggtcct gtggaaattg     360

ctgaaggtgg tcaagtttgg tgaagtgatt tcatatcagc aacttgctgc attggccggt     420

aaccccgcag ctacagctgc cgtgaaaact gctctcagcg gaaatcctgt gcccatcctg     480

atcccttgtc acagagtcgt ttcatcttcc ggagctgtag gtggctatga aggaggactg     540

gcagttaagg agtggctgct ggctcatgaa ggtcatagac ttggaaagcc tgggctgggt     600

cctgctggta taggcgcgcc aggaggtggc gggcttgaaa aactcaagat gaaaggaatg     660

acatacacgg tctgtgaggg atcaaagttt gcttggaaga ggccgccaac cgacagtggg     720

catgacactg tggtcatgga agtgacttac actgggagca agccatgcag aataccagtg     780

agagccgtgg cccatggaga acctaatgtc aatgtagcta gcctgataac tccaaatcca     840

tccatggaga caactggagg aggtttcgtt gaactgcagc tgccaccagg agacaacatc     900

atctatgttg gtgagctgag tcaccagtgg tttcagaagg gtagtacaat aggcggaggt     960

ggccatcacc atcaccatca ctgatgaccg gt                                   992
```

<210> SEQ ID NO 129
<211> LENGTH: 310
<212> TYPE: PRT
<213> ORGANISM: artificial
<220> FEATURE:
<223> OTHER INFORMATION: Amino acid sequence of fusion protein [SNAPlike-ALK.EDIII-Histag]

<400> SEQUENCE: 129

```
Arg Ser Asp Lys Asp Cys Glu Met Lys Arg Thr Thr Leu Asp Ser Pro
1               5                   10                  15

Leu Gly Lys Leu Glu Leu Ser Gly Cys Glu Gln Gly Leu His Glu Ile
            20                  25                  30

Lys Leu Leu Gly Lys Gly Thr Ser Ala Ala Asp Ala Val Glu Val Pro
        35                  40                  45

Ala Pro Ala Ala Val Leu Gly Gly Pro Glu Pro Leu Met Gln Ala Thr
    50                  55                  60

Ala Trp Leu Asn Ala Tyr Phe His Gln Pro Glu Ala Ile Glu Glu Phe
65                  70                  75                  80

Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Gly
            180                 185                 190

Gly Gly Leu Glu Lys Leu Lys Met Lys Gly Met Thr Tyr Thr Val Cys
        195                 200                 205

Glu Gly Ser Lys Phe Ala Trp Lys Arg Pro Pro Thr Asp Ser Gly His
    210                 215                 220

Asp Thr Val Val Met Glu Val Thr Tyr Thr Gly Ser Lys Pro Cys Arg
225                 230                 235                 240

Ile Pro Val Arg Ala Val Ala His Gly Glu Pro Asn Val Asn Val Ala
                245                 250                 255

Ser Leu Ile Thr Pro Asn Pro Ser Met Glu Thr Thr Gly Gly Gly Phe
            260                 265                 270

Val Glu Leu Gln Leu Pro Pro Gly Asp Asn Ile Ile Tyr Val Gly Glu
        275                 280                 285

Leu Ser His Gln Trp Phe Gln Lys Gly Ser Thr Ile Gly Gly Gly Gly
    290                 295                 300

His His His His His His
305                 310
```

<210> SEQ ID NO 130
<211> LENGTH: 1288
<212> TYPE: DNA
<213> ORGANISM: artificial
<220> FEATURE:
<223> OTHER INFORMATION: DNA sequence encoding ssBiP- Glycoprotein GP1 from Lassa virus- SNAPlike-Histag for expression in S2 cells

<400> SEQUENCE: 130

```
atgaagttat gcatattact ggccgtcgtg gcctttgttg gcctctcgct cgggagatct     60
accagtctgt acaagggggt gtacgagctt cagactctgg aactgaacat ggagacactc    120
aacatgacca tgcctctctc ctgcacaaag aacaacagtc atcattacat aatggtgggc    180
aatgagacag gactggaact gaccttgacc aacacgagca tcatcaatca caagttctgc    240
aacctgtctg atgcccacaa gaagaacctc tacgaccacg ctctgatgag cataatctca    300
actttccact tgtccatccc caacttcaac cagtacgagg caatgagctg cgatttcaat    360
gggggcaaga tcagtgtgca gtacaacctg agtcacagct acgctgggga tgcagccaac    420
cattgtggca ctgtggcaaa cggtgtgttg cagactttca tgaggatggc ttggggcggg    480
agctacatcg ctcttgactc aggccgtggc aactgggact gtatcatgac tagttaccaa    540
tacctgataa tccagaacac aacctgggaa gatcactgcc aattctccag accatctccc    600
atcggctacc tcgggctcct ctcacaaagg actagagata tttacatcag tagaagattg    660
ctgcggccgc acggcggagg tagcaaagac tgcgaaatga agcgcaccac cctggatagc    720
cctctgggca agctggaact gtctgggtgc gaacagggcc tgcacgagat caagctgctg    780
ggcaaaggaa catctgccgc cgacgccgtg gaagtgcctg ccccagccgc cgtgctgggc    840
ggaccagagc cactgatgca ggccaccgcc tggctcaacg cctactttca ccagcctgag    900
gccatcgagg agttccctgt gccagccctg caccacccag tgttccagca ggagagcttt    960
acccgccagg tgctgtggaa actgctgaaa gtggtgaagt tcggagaggt catcagctac   1020
cagcagctgg ccgccctggc cggcaatccc gccgccaccg ccgccgtgaa aaccgccctg   1080
agcggaaatc ccgtgcccat tctgatcccc tgccaccggg tggtgtctag ctctggcgcc   1140
gtggggggct acgagggcgg gctcgccgtg aaagagtggc tgctggccca cgagggccac   1200
agactgggca agcctgggct gggtcctgca ggtataggcg cgccagggtc cctggagcat   1260
catcatcatc atcattgatg acgggccc                                      1288
```

<210> SEQ ID NO 131
<211> LENGTH: 407
<212> TYPE: PRT
<213> ORGANISM: artificial
<220> FEATURE:
<223> OTHER INFORMATION: Amino acid sequence of fusion protein
      [LAS.ectoGP1- SNAPlike-Histag]

<400> SEQUENCE: 131

```
Arg Ser Thr Ser Leu Tyr Lys Gly Val Tyr Glu Leu Gln Thr Leu Glu
1               5                   10                  15

Leu Asn Met Glu Thr Leu Asn Met Thr Met Pro Leu Ser Cys Thr Lys
            20                  25                  30

Asn Asn Ser His His Tyr Ile Met Val Gly Asn Glu Thr Gly Leu Glu
        35                  40                  45

Leu Thr Leu Thr Asn Thr Ser Ile Ile Asn His Lys Phe Cys Asn Leu
    50                  55                  60

Ser Asp Ala His Lys Lys Asn Leu Tyr Asp His Ala Leu Met Ser Ile
65                  70                  75                  80

Ile Ser Thr Phe His Leu Ser Ile Pro Asn Phe Asn Gln Tyr Glu Ala
                85                  90                  95

Met Ser Cys Asp Phe Asn Gly Gly Lys Ile Ser Val Gln Tyr Asn Leu
            100                 105                 110

Ser His Ser Tyr Ala Gly Asp Ala Ala Asn His Cys Gly Thr Val Ala
```

```
        115                 120                 125

Asn Gly Val Leu Gln Thr Phe Met Arg Met Ala Trp Gly Gly Ser Tyr
    130                 135                 140

Ile Ala Leu Asp Ser Gly Arg Gly Asn Trp Asp Cys Ile Met Thr Ser
145                 150                 155                 160

Tyr Gln Tyr Leu Ile Ile Gln Asn Thr Thr Trp Glu Asp His Cys Gln
                165                 170                 175

Phe Ser Arg Pro Ser Pro Ile Gly Tyr Leu Gly Leu Leu Ser Gln Arg
            180                 185                 190

Thr Arg Asp Ile Tyr Ile Ser Arg Arg Leu Leu Arg Pro His Gly Gly
        195                 200                 205

Gly Ser Lys Asp Cys Glu Met Lys Arg Thr Thr Leu Asp Ser Pro Leu
    210                 215                 220

Gly Lys Leu Glu Leu Ser Gly Cys Glu Gln Gly Leu His Glu Ile Lys
225                 230                 235                 240

Leu Leu Gly Lys Gly Thr Ser Ala Ala Asp Ala Val Glu Val Pro Ala
                245                 250                 255

Pro Ala Ala Val Leu Gly Gly Pro Glu Pro Leu Met Gln Ala Thr Ala
            260                 265                 270

Trp Leu Asn Ala Tyr Phe His Gln Pro Glu Ala Ile Glu Glu Phe Pro
        275                 280                 285

Val Pro Ala Leu His His Pro Val Phe Gln Gln Glu Ser Phe Thr Arg
    290                 295                 300

Gln Val Leu Trp Lys Leu Leu Lys Val Val Lys Phe Gly Glu Val Ile
305                 310                 315                 320

Ser Tyr Gln Gln Leu Ala Ala Leu Ala Gly Asn Pro Ala Ala Thr Ala
                325                 330                 335

Ala Val Lys Thr Ala Leu Ser Gly Asn Pro Val Pro Ile Leu Ile Pro
            340                 345                 350

Cys His Arg Val Val Ser Ser Ser Gly Ala Val Gly Gly Tyr Glu Gly
        355                 360                 365

Gly Leu Ala Val Lys Glu Trp Leu Leu Ala His Glu Gly His Arg Leu
    370                 375                 380

Gly Lys Pro Gly Leu Gly Pro Ala Gly Ile Gly Ala Pro Gly Ser Leu
385                 390                 395                 400

Glu His His His His His His
                405


<210> SEQ ID NO 132
<211> LENGTH: 1264
<212> TYPE: DNA
<213> ORGANISM: artificial
<220> FEATURE:
<223> OTHER INFORMATION: DNA sequence encoding ssBiP- Glycoprotein GP1
      from Junin virus- SNAPlike-Histag for expression in S2 cells

<400> SEQUENCE: 132

atgaagttat gcatattact ggccgtcgtg gcctttgttg gcctctcgct cgggagatct      60

gaggaggctt tcaagatcgg cctgcacacc gagttccaga cggtgtcctt ctcgatggtg     120

ggcctcttct ccaacaaccc acacgacctg cctttgttgt gtaccttgaa caagagccat     180

ctgtacatta agggggggcaa cgcttcattc cagatcagct tcgacgacat cgcggtgttg     240

ttgccacagt acgacgttat catccagcac ccagcagaca tgagctggtg ctccaagagt     300

gatgatcaga tttggttgtc tcagtggttc atgaatgctg tgggacatga ttggcaccta     360
```

-continued

```
gacccaccat tcctgtgtag gaaccgtaca aagacagaag gcttcatctt ccaagtcaac    420

acctccaaga ctggtgttaa tgaaaattat gctaagaagt tcaagactgg catgcaccac    480

ttgtatagag agtaccctga ctcttgcccg aacggcaagc tgtgcttaat gaaggcacaa    540

cctaccagtt ggcctctcca atgtccactc gaccacgtca acacattaca cttccttaca    600

agaggcaaga acattcagct tccaaggagg tccttgaagc ggccgcacgg cggaggtagc    660

aaagactgcg aaatgaagcg caccaccctg gatagccctc tgggcaagct ggaactgtct    720

gggtgcgaac agggcctgca cgagatcaag ctgctgggca aaggaacatc tgccgccgac    780

gccgtggaag tgcctgcccc agccgccgtg ctgggcggac cagagccact gatgcaggcc    840

accgcctggc tcaacgccta ctttcaccag cctgaggcca tcgaggagtt ccctgtgcca    900

gccctgcacc acccagtgtt ccagcaggag agctttaccc gccaggtgct gtggaaactg    960

ctgaaagtgg tgaagttcgg agaggtcatc agctaccagc agctggccgc cctggccggc   1020

aatcccgccg ccaccgccgc cgtgaaaacc gccctgagcg gaaatcccgt gcccattctg   1080

atcccctgcc accgggtggt gtctagctct ggcgccgtgg ggggctacga gggcgggctc   1140

gccgtgaaag agtggctgct ggcccacgag ggccacagac tgggcaagcc tgggctgggt   1200

cctgcaggta taggcgcgcc agggtccctg gagcatcatc atcatcatca ttgatgacgg   1260

gccc                                                                1264
```

<210> SEQ ID NO 133
<211> LENGTH: 399
<212> TYPE: PRT
<213> ORGANISM: artificial
<220> FEATURE:
<223> OTHER INFORMATION: Amino acid sequence of fusion protein [JUN.ectoGP1- SNAPlike-Histag]

<400> SEQUENCE: 133

```
Arg Ser Glu Glu Ala Phe Lys Ile Gly Leu His Thr Glu Phe Gln Thr
1               5                   10                  15

Val Ser Phe Ser Met Val Gly Leu Phe Ser Asn Asn Pro His Asp Leu
            20                  25                  30

Pro Leu Leu Cys Thr Leu Asn Lys Ser His Leu Tyr Ile Lys Gly Gly
        35                  40                  45

Asn Ala Ser Phe Gln Ile Ser Phe Asp Asp Ile Ala Val Leu Leu Pro
    50                  55                  60

Gln Tyr Asp Val Ile Ile Gln His Pro Ala Asp Met Ser Trp Cys Ser
65                  70                  75                  80

Lys Ser Asp Asp Gln Ile Trp Leu Ser Gln Trp Phe Met Asn Ala Val
                85                  90                  95

Gly His Asp Trp His Leu Asp Pro Pro Phe Leu Cys Arg Asn Arg Thr
            100                 105                 110

Lys Thr Glu Gly Phe Ile Phe Gln Val Asn Thr Ser Lys Thr Gly Val
        115                 120                 125

Asn Glu Asn Tyr Ala Lys Lys Phe Lys Thr Gly Met His His Leu Tyr
    130                 135                 140

Arg Glu Tyr Pro Asp Ser Cys Pro Asn Gly Lys Leu Cys Leu Met Lys
145                 150                 155                 160

Ala Gln Pro Thr Ser Trp Pro Leu Gln Cys Pro Leu Asp His Val Asn
                165                 170                 175

Thr Leu His Phe Leu Thr Arg Gly Lys Asn Ile Gln Leu Pro Arg Arg
            180                 185                 190
```

-continued

```
Ser Leu Lys Arg Pro His Gly Gly Gly Ser Lys Asp Cys Glu Met Lys
        195                 200                 205

Arg Thr Thr Leu Asp Ser Pro Leu Gly Lys Leu Glu Leu Ser Gly Cys
    210                 215                 220

Glu Gln Gly Leu His Glu Ile Lys Leu Leu Gly Lys Gly Thr Ser Ala
225                 230                 235                 240

Ala Asp Ala Val Glu Val Pro Ala Pro Ala Ala Val Leu Gly Gly Pro
                245                 250                 255

Glu Pro Leu Met Gln Ala Thr Ala Trp Leu Asn Ala Tyr Phe His Gln
            260                 265                 270

Pro Glu Ala Ile Glu Glu Phe Pro Val Pro Ala Leu His His Pro Val
        275                 280                 285

Phe Gln Gln Glu Ser Phe Thr Arg Gln Val Leu Trp Lys Leu Leu Lys
    290                 295                 300

Val Val Lys Phe Gly Glu Val Ile Ser Tyr Gln Gln Leu Ala Ala Leu
305                 310                 315                 320

Ala Gly Asn Pro Ala Ala Thr Ala Ala Val Lys Thr Ala Leu Ser Gly
                325                 330                 335

Asn Pro Val Pro Ile Leu Ile Pro Cys His Arg Val Val Ser Ser Ser
            340                 345                 350

Gly Ala Val Gly Gly Tyr Glu Gly Gly Leu Ala Val Lys Glu Trp Leu
        355                 360                 365

Leu Ala His Glu Gly His Arg Leu Gly Lys Pro Gly Leu Gly Pro Ala
    370                 375                 380

Gly Ile Gly Ala Pro Gly Ser Leu Glu His His His His His His
385                 390                 395
```

<210> SEQ ID NO 134
<211> LENGTH: 1297
<212> TYPE: DNA
<213> ORGANISM: artificial
<220> FEATURE:
<223> OTHER INFORMATION: DNA sequence encoding ssBiP- Glycoprotein GP1 from Machupo virus- SNAPlike-Histag for expression in S2 cells

<400> SEQUENCE: 134

```
atgaagttat gcatattact ggccgtcgtg gcctttgttg gcctctcgct cgggagatct      60

gacggcacat tcaagatcgg cctgcacacg gagttccagt cagtcaccct caccatgcag     120

agacttttgg ctaaccattc aaacgagctc ccgtctctct gcatgctgaa caacagtttc     180

tattatatga ggggaggtgt gaacaccttc ctgatccgtg tttctgatat ttcagtcctc     240

atgaaggagt acgatgtatc aatctacgag ccagaggacc tcggaaactg tctgaacaag     300

tctgactcaa gctgggctat ccattggttc tcaaacgctt tgggacatga ctggctgatg     360

gaccctccaa tgctctgtag aaacaagaca aagaaggagg gatctaacat ccaattcaac     420

atcagcaagg ctgatgatgc cagagtgtat ggaaagaaga tcagaaacgg tatgaggcat     480

ctcttcaggg gcttccatga cccgtgtgag gaagggaagg tgtgctacct gaccatcaac     540

cagtgtggtg accccagttc cttcgactac tgtggcgtga accatctgtc caagtgtcag     600

ttcgaccatg tgaacaccct gcatttcctg gtgagaagta agacacatct caacttcgag     660

aggtctttga agcggccgca cggcggaggt agcaaagact gcgaaatgaa gcgcaccacc     720

ctggatagcc ctctgggcaa gctggaactg tctgggtgcg aacagggcct gcacgagatc     780

aagctgctgg gcaaaggaac atctgccgcc gacgccgtgg aagtgcctgc cccagccgcc     840

gtgctgggcg gaccagagcc actgatgcag gccaccgcct ggctcaacgc ctactttcac     900
```

```
cagcctgagg ccatcgagga gttccctgtg ccagccctgc accacccagt gttccagcag    960

gagagcttta cccgccaggt gctgtggaaa ctgctgaaag tggtgaagtt cggagaggtc   1020

atcagctacc agcagctggc cgccctggcc ggcaatcccg ccgccaccgc cgccgtgaaa   1080

accgccctga gcggaaatcc cgtgcccatt ctgatcccct gccaccgggt ggtgtctagc   1140

tctggcgccg tgggggcta cgagggcggg ctcgccgtga aagagtggct gctggcccac   1200

gagggccaca gactgggcaa gcctgggctg ggtcctgcag gtataggcgc gccagggtcc   1260

ctggagcatc atcatcatca tcattgatga cgggccc                            1297
```

<210> SEQ ID NO 135
<211> LENGTH: 410
<212> TYPE: PRT
<213> ORGANISM: artificial
<220> FEATURE:
<223> OTHER INFORMATION: Amino acid sequence of fusion protein
[MAC.ectoGP1- SNAPlike-Histag]

<400> SEQUENCE: 135

```
Arg Ser Asp Gly Thr Phe Lys Ile Gly Leu His Thr Glu Phe Gln Ser
1               5                   10                  15

Val Thr Leu Thr Met Gln Arg Leu Leu Ala Asn His Ser Asn Glu Leu
            20                  25                  30

Pro Ser Leu Cys Met Leu Asn Asn Ser Phe Tyr Tyr Met Arg Gly Gly
        35                  40                  45

Val Asn Thr Phe Leu Ile Arg Val Ser Asp Ile Ser Val Leu Met Lys
    50                  55                  60

Glu Tyr Asp Val Ser Ile Tyr Glu Pro Glu Asp Leu Gly Asn Cys Leu
65                  70                  75                  80

Asn Lys Ser Asp Ser Ser Trp Ala Ile His Trp Phe Ser Asn Ala Leu
                85                  90                  95

Gly His Asp Trp Leu Met Asp Pro Pro Met Leu Cys Arg Asn Lys Thr
            100                 105                 110

Lys Lys Glu Gly Ser Asn Ile Gln Phe Asn Ile Ser Lys Ala Asp Asp
        115                 120                 125

Ala Arg Val Tyr Gly Lys Lys Ile Arg Asn Gly Met Arg His Leu Phe
    130                 135                 140

Arg Gly Phe His Asp Pro Cys Glu Glu Gly Lys Val Cys Tyr Leu Thr
145                 150                 155                 160

Ile Asn Gln Cys Gly Asp Pro Ser Ser Phe Asp Tyr Cys Gly Val Asn
                165                 170                 175

His Leu Ser Lys Cys Gln Phe Asp His Val Asn Thr Leu His Phe Leu
            180                 185                 190

Val Arg Ser Lys Thr His Leu Asn Phe Glu Arg Ser Leu Lys Arg Pro
        195                 200                 205

His Gly Gly Gly Ser Lys Asp Cys Glu Met Lys Arg Thr Thr Leu Asp
    210                 215                 220

Ser Pro Leu Gly Lys Leu Glu Leu Ser Gly Cys Glu Gln Gly Leu His
225                 230                 235                 240

Glu Ile Lys Leu Leu Gly Lys Gly Thr Ser Ala Ala Asp Ala Val Glu
                245                 250                 255

Val Pro Ala Pro Ala Ala Val Leu Gly Gly Pro Glu Pro Leu Met Gln
            260                 265                 270

Ala Thr Ala Trp Leu Asn Ala Tyr Phe His Gln Pro Glu Ala Ile Glu
        275                 280                 285
```

```
Glu Phe Pro Val Pro Ala Leu His His Pro Val Phe Gln Gln Glu Ser
    290                 295                 300

Phe Thr Arg Gln Val Leu Trp Lys Leu Leu Lys Val Val Lys Phe Gly
305                 310                 315                 320

Glu Val Ile Ser Tyr Gln Gln Leu Ala Ala Leu Ala Gly Asn Pro Ala
                325                 330                 335

Ala Thr Ala Ala Val Lys Thr Ala Leu Ser Gly Asn Pro Val Pro Ile
            340                 345                 350

Leu Ile Pro Cys His Arg Val Val Ser Ser Ser Gly Ala Val Gly Gly
        355                 360                 365

Tyr Glu Gly Gly Leu Ala Val Lys Glu Trp Leu Leu Ala His Glu Gly
    370                 375                 380

His Arg Leu Gly Lys Pro Gly Leu Gly Pro Ala Gly Ile Gly Ala Pro
385                 390                 395                 400

Gly Ser Leu Glu His His His His His His
                405                 410
```

<210> SEQ ID NO 136
<211> LENGTH: 1246
<212> TYPE: DNA
<213> ORGANISM: artificial
<220> FEATURE:
<223> OTHER INFORMATION: DNA sequence encoding ssBiP- Glycoprotein GP1 from Guanarito virus- SNAPlike-Histag for expression in S2 cells

<400> SEQUENCE: 136

```
atgaagttat gcatattact ggccgtcgtg gcctttgttg gcctctcgct cgggagatct      60
ttcaaggttg gtcatcatac gaacttcgag tcgttcacgg ttaagctggg aggtgtcttc     120
catgaattgc cttcgctgtg tagggtcaac aactcctaca gtctgatcag gctctcccat     180
aacagtaacc aggcattgtc ggttgagtac gtggatgtgc accctgtcct ctgttcgtcc     240
agtccaacca tcctcgacaa ctacacgcaa tgtatcaagg gctcgccaga gttcgattgg     300
attctcgggt ggacgatcaa gggattggga catgacttct tgagagatcc aagaatctgc     360
tgtgagccta agaagacgac taacgctgag ttcacgttcc aattgaactt gacggatagt     420
cctgagaccc atcactacag gagcaagatt gaggtaggca tccgacactt gttcgggaac     480
tacatcacca acgatagcta ctcgaagatg tccgtggtta tgaggaacac cacctgggaa     540
ggtcaatgct cgaacagtca tgtgaacacg ctgagattcc tcgttaagaa cgcaggttac     600
ctcgttggaa ggaagccact gcggccgcac ggcggaggta gcaaagactg cgaaatgaag     660
cgcaccaccc tggatagccc tctgggcaag ctggaactgt ctgggtgcga acagggcctg     720
cacgagatca agctgctggg caaaggaaca tctgccgccg acgccgtgga agtgcctgcc     780
ccagccgccg tgctgggcgg accagagcca ctgatgcagg ccaccgcctg gctcaacgcc     840
tactttcacc agcctgaggc catcgaggag ttccctgtgc cagccctgca ccacccagtg     900
ttccagcagg agagctttac ccgccaggtg ctgtggaaac tgctgaaagt ggtgaagttc     960
ggagaggtca tcagctacca gcagctggcc gccctggccg gcaatcccgc cgccaccgcc    1020
gccgtgaaaa ccgccctgag cggaaatccc gtgcccattc tgatcccctg ccaccgggtg    1080
gtgtctagct ctggcgccgt ggggggctac gagggcgggc tcgccgtgaa agagtggctg    1140
ctggcccacg agggccacag actgggcaag cctgggctgg gtcctgcagg tataggcgcg    1200
ccagggtccc tggagcatca tcatcatcat cattgatgac gggccc                   1246
```

<210> SEQ ID NO 137
<211> LENGTH: 393
<212> TYPE: PRT
<213> ORGANISM: artificial
<220> FEATURE:
<223> OTHER INFORMATION: Amino acid sequence of fusion protein
[GUA.ectoGP1- SNAPlike-Histag]

<400> SEQUENCE: 137

```
Arg Ser Phe Lys Val Gly His His Thr Asn Phe Glu Ser Phe Thr Val
1               5                   10                  15

Lys Leu Gly Gly Val Phe His Glu Leu Pro Ser Leu Cys Arg Val Asn
            20                  25                  30

Asn Ser Tyr Ser Leu Ile Arg Leu Ser His Asn Ser Asn Gln Ala Leu
        35                  40                  45

Ser Val Glu Tyr Val Asp Val His Pro Val Leu Cys Ser Ser Ser Pro
    50                  55                  60

Thr Ile Leu Asp Asn Tyr Thr Gln Cys Ile Lys Gly Ser Pro Glu Phe
65                  70                  75                  80

Asp Trp Ile Leu Gly Trp Thr Ile Lys Gly Leu Gly His Asp Phe Leu
                85                  90                  95

Arg Asp Pro Arg Ile Cys Cys Glu Pro Lys Lys Thr Thr Asn Ala Glu
            100                 105                 110

Phe Thr Phe Gln Leu Asn Leu Thr Asp Ser Pro Glu Thr His His Tyr
        115                 120                 125

Arg Ser Lys Ile Glu Val Gly Ile Arg His Leu Phe Gly Asn Tyr Ile
    130                 135                 140

Thr Asn Asp Ser Tyr Ser Lys Met Ser Val Val Met Arg Asn Thr Thr
145                 150                 155                 160

Trp Glu Gly Gln Cys Ser Asn Ser His Val Asn Thr Leu Arg Phe Leu
                165                 170                 175

Val Lys Asn Ala Gly Tyr Leu Val Gly Arg Lys Pro Leu Arg Pro His
            180                 185                 190

Gly Gly Gly Ser Lys Asp Cys Glu Met Lys Arg Thr Thr Leu Asp Ser
        195                 200                 205

Pro Leu Gly Lys Leu Glu Leu Ser Gly Cys Glu Gln Gly Leu His Glu
    210                 215                 220

Ile Lys Leu Leu Gly Lys Gly Thr Ser Ala Ala Asp Ala Val Glu Val
225                 230                 235                 240

Pro Ala Pro Ala Ala Val Leu Gly Gly Pro Glu Pro Leu Met Gln Ala
                245                 250                 255

Thr Ala Trp Leu Asn Ala Tyr Phe His Gln Pro Glu Ala Ile Glu Glu
            260                 265                 270

Phe Pro Val Pro Ala Leu His His Pro Val Phe Gln Gln Glu Ser Phe
        275                 280                 285

Thr Arg Gln Val Leu Trp Lys Leu Leu Lys Val Val Lys Phe Gly Glu
    290                 295                 300

Val Ile Ser Tyr Gln Gln Leu Ala Ala Leu Ala Gly Asn Pro Ala Ala
305                 310                 315                 320

Thr Ala Ala Val Lys Thr Ala Leu Ser Gly Asn Pro Val Pro Ile Leu
                325                 330                 335

Ile Pro Cys His Arg Val Val Ser Ser Ser Gly Ala Val Gly Gly Tyr
            340                 345                 350

Glu Gly Gly Leu Ala Val Lys Glu Trp Leu Leu Ala His Glu Gly His
        355                 360                 365
```

-continued

```
Arg Leu Gly Lys Pro Gly Leu Gly Pro Ala Gly Ile Gly Ala Pro Gly
    370                 375                 380

Ser Leu Glu His His His His His His
385                 390


<210> SEQ ID NO 138
<211> LENGTH: 1273
<212> TYPE: DNA
<213> ORGANISM: artificial
<220> FEATURE:
<223> OTHER INFORMATION: DNA sequence encoding ssBiP- Glycoprotein GP1
      from Sabia virus- SNAPlike-Histag for expression in S2 cells

<400> SEQUENCE: 138

atgaagttat gcatattact ggccgtcgtg gcctttgttg gcctctcgct cgggagatct      60

ttcagaatcg gaaggagcac agaattgcag aacatcacgt tcgatatgtt gaaggtgttc     120

gaggaccacc ccacatcctg catggtgaac cattccacct actacgtcca tgagaacaag     180

aacgccactt ggtgtctgga ggtgtccgtg actgatgtta ccctgctcat ggctgaacat     240

gatcgtcaag tcctcaacaa cctgtcgaac tgtgtgcacc ctgcagtcga gcacagaagc     300

aggatggttg gcttgctgga gtggatcttc agagccctga agtacgactt caaccatgat     360

ccaacaccgt tgtgtcagaa gcagacttcg acagtgaacg agacacgtgt gcagatcaac     420

atcactgagg ggttcgggtc ccacgggttc gaagatacca tcctccagag actcggggtt     480

ctgttcggtt cgagaattgc attctcgaac atccaggact tgggtaagaa gaggttcttg     540

ttgatcagga actcgacttg gaagaaccaa tgcgagatga accatgtgaa ctccatgcac     600

ttgatgttgg cgaacgctgg tcgctcgtcc ggttcgagaa gaccactgcg gccgcacggc     660

ggaggtagca aagactgcga aatgaagcgc accaccctgg atagccctct gggcaagctg     720

gaactgtctg ggtgcgaaca gggcctgcac gagatcaagc tgctgggcaa aggaacatct     780

gccgccgacg ccgtggaagt gcctgcccca gccgccgtgc tgggcggacc agagccactg     840

atgcaggcca ccgcctggct caacgcctac tttcaccagc ctgaggccat cgaggagttc     900

cctgtgccag ccctgcacca cccagtgttc cagcaggaga gctttacccg ccaggtgctg     960

tggaaactgc tgaaagtggt gaagttcgga gaggtcatca gctaccagca gctggccgcc    1020

ctggccggca atcccgccgc caccgccgcc gtgaaaaccg ccctgagcgg aaatcccgtg    1080

cccattctga tcccctgcca ccgggtggtg tctagctctg gcgccgtggg gggctacgag    1140

ggcgggctcg ccgtgaaaga gtggctgctg gcccacgagg gccacagact gggcaagcct    1200

gggctgggtc ctgcaggtat aggcgcgcca gggtccctgg agcatcatca tcatcatcat    1260

tgatgacggg ccc                                                       1273


<210> SEQ ID NO 139
<211> LENGTH: 396
<212> TYPE: PRT
<213> ORGANISM: artificial
<220> FEATURE:
<223> OTHER INFORMATION: Amino acid sequence of fusion protein
      [SAB.ectoGP1- SNAPlike-Histag]

<400> SEQUENCE: 139

Arg Ser Thr Glu Leu Gln Asn Ile Thr Phe Asp Met Leu Lys Val Phe
1               5                   10                  15

Glu Asp His Pro Thr Ser Cys Met Val Asn His Ser Thr Tyr Tyr Val
            20                  25                  30

His Glu Asn Lys Asn Ala Thr Trp Cys Leu Glu Val Ser Val Thr Asp
```

```
        35                  40                  45

Val Thr Leu Leu Met Ala Glu His Asp Arg Gln Val Leu Asn Asn Leu
    50                  55                  60

Ser Asn Cys Val His Pro Ala Val Glu His Arg Ser Arg Met Val Gly
65                  70                  75                  80

Leu Leu Glu Trp Ile Phe Arg Ala Leu Lys Tyr Asp Phe Asn His Asp
                85                  90                  95

Pro Thr Pro Leu Cys Gln Lys Gln Thr Ser Thr Val Asn Glu Thr Arg
            100                 105                 110

Val Gln Ile Asn Ile Thr Glu Gly Phe Gly Ser His Gly Phe Glu Asp
        115                 120                 125

Thr Ile Leu Gln Arg Leu Gly Val Leu Phe Gly Ser Arg Ile Ala Phe
    130                 135                 140

Ser Asn Ile Gln Asp Leu Gly Lys Lys Arg Phe Leu Leu Ile Arg Asn
145                 150                 155                 160

Ser Thr Trp Lys Asn Gln Cys Glu Met Asn His Val Asn Ser Met His
                165                 170                 175

Leu Met Leu Ala Asn Ala Gly Arg Ser Ser Gly Ser Arg Arg Pro Leu
            180                 185                 190

Arg Pro His Gly Gly Gly Ser Lys Asp Cys Glu Met Lys Arg Thr Thr
        195                 200                 205

Leu Asp Ser Pro Leu Gly Lys Leu Glu Leu Ser Gly Cys Glu Gln Gly
    210                 215                 220

Leu His Glu Ile Lys Leu Leu Gly Lys Gly Thr Ser Ala Ala Asp Ala
225                 230                 235                 240

Val Glu Val Pro Ala Pro Ala Ala Val Leu Gly Gly Pro Glu Pro Leu
                245                 250                 255

Met Gln Ala Thr Ala Trp Leu Asn Ala Tyr Phe His Gln Pro Glu Ala
            260                 265                 270

Ile Glu Glu Phe Pro Val Pro Ala Leu His His Pro Val Phe Gln Gln
        275                 280                 285

Glu Ser Phe Thr Arg Gln Val Leu Trp Lys Leu Leu Lys Val Val Lys
    290                 295                 300

Phe Gly Glu Val Ile Ser Tyr Gln Gln Leu Ala Ala Leu Ala Gly Asn
305                 310                 315                 320

Pro Ala Ala Thr Ala Ala Val Lys Thr Ala Leu Ser Gly Asn Pro Val
                325                 330                 335

Pro Ile Leu Ile Pro Cys His Arg Val Val Ser Ser Ser Gly Ala Val
            340                 345                 350

Gly Gly Tyr Glu Gly Gly Leu Ala Val Lys Glu Trp Leu Leu Ala His
        355                 360                 365

Glu Gly His Arg Leu Gly Lys Pro Gly Leu Gly Pro Ala Gly Ile Gly
    370                 375                 380

Ala Pro Gly Ser Leu Glu His His His His His His
385                 390                 395


<210> SEQ ID NO 140
<211> LENGTH: 1189
<212> TYPE: DNA
<213> ORGANISM: artificial
<220> FEATURE:
<223> OTHER INFORMATION: DNA sequence encoding ssBiP- Glycoprotein GP2
      from Lassa virus- SNAPlike-Histag for expression in S2 cells

<400> SEQUENCE: 140
```

```
atgaagttat gcatattact ggccgtcgtg gcctttgttg gcctctcgct cgggagatct      60

ggcacattca catggacact gtcggattct gaaggtaagg acacaccagg gggatactgt     120

ctgaccaggt ggatgctgat cgaggctgaa ctgaagtgct tcgggaacac agctgtggcg     180

aagtgtaacg agaagcatga tgaggagttc tgtgacatgc tgaggctgtt cgacttcaac     240

aagcaagcca tccagaggtt gaaggctgaa gcacagatga gcatccagtt gatcaacaag     300

gcagtgaatg ccttgatcaa cgaccaactg atcatgaaga accatctgcg ggacatcatg     360

ggtatcccat actgtaacta cagcaagtac tggtacctca accacacaac tactgggaga     420

acatcgctgc ccaagtgttg gctggtgtcg aacggttcgt acttgaacga gacccacttc     480

tccgatgaca tcgaacaaca agctgacaac atgatcactg agatgttgca gaaggagtac     540

atggagaggc aggggaagac accgcggccg cacggcggag gtagcaaaga ctgcgaaatg     600

aagcgcacca ccctggatag ccctctgggc aagctggaac tgtctgggtg cgaacagggc     660

ctgcacgaga tcaagctgct gggcaaagga acatctgccg ccgacgccgt ggaagtgcct     720

gccccagccg ccgtgctggg cggaccagag ccactgatgc aggccaccgc ctggctcaac     780

gcctactttc accagcctga ggccatcgag gagttccctg tgccagccct gcaccaccca     840

gtgttccagc aggagagctt tacccgccag gtgctgtgga aactgctgaa agtggtgaag     900

ttcggagagg tcatcagcta ccagcagctg gccgccctgg ccggcaatcc cgccgccacc     960

gccgccgtga aaaccgccct gagcggaaat cccgtgccca ttctgatccc ctgccaccgg    1020

gtggtgtcta gctctggcgc cgtggggggc tacgagggcg ggctcgccgt gaaagagtgg    1080

ctgctggccc acgagggcca cagactgggc aagcctgggc tgggtcctgc aggtataggc    1140

gcgccagggt ccctggagca tcatcatcat catcattgat gacgggccc                1189
```

<210> SEQ ID NO 141
<211> LENGTH: 374
<212> TYPE: PRT
<213> ORGANISM: artificial
<220> FEATURE:
<223> OTHER INFORMATION: Amino acid sequence of fusion protein
      [LAS.ectoGP2- SNAPlike-Histag]

<400> SEQUENCE: 141

```
Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45

Asp Glu Glu Phe Cys Asp Met Leu Arg Leu Phe Asp Phe Asn Lys Gln
    50                  55                  60

Ala Ile Gln Arg Leu Lys Ala Glu Ala Gln Met Ser Ile Gln Leu Ile
65                  70                  75                  80

Asn Lys Ala Val Asn Ala Leu Ile Asn Asp Gln Leu Ile Met Lys Asn
                85                  90                  95

His Leu Arg Asp Ile Met Gly Ile Pro Tyr Cys Asn Tyr Ser Lys Tyr
            100                 105                 110

Trp Tyr Leu Asn His Thr Thr Thr Gly Arg Thr Ser Leu Pro Lys Cys
        115                 120                 125

Trp Leu Val Ser Asn Gly Ser Tyr Leu Asn Glu Thr His Phe Ser Asp
    130                 135                 140

Asp Ile Glu Gln Gln Ala Asp Asn Met Ile Thr Glu Met Leu Gln Lys
```

```
145                 150                 155                 160

Glu Tyr Met Glu Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 142
<211> LENGTH: 1189
<212> TYPE: DNA
<213> ORGANISM: artificial
<220> FEATURE:
<223> OTHER INFORMATION: DNA sequence encoding ssBiP- Glycoprotein GP2 from Junin virus- SNAPlike-Histag for expression in S2 cells

<400> SEQUENCE: 142

```
atgaagttat gcatattact ggccgtcgtg gcctttgttg gcctctcgct cgggagatct      60

gcattcttct cctggtcgtt gacagactca tccggcaagg atacccctgg aggctactgc     120

ctggaagagt ggatgctcgt ggcagccaag atgaagtgct tcggcaacac tgctgtggcc     180

aagtgcaact tgaaccatga ctcggagttc tgtgacatgt tgaggctgtt cgattacaac     240

aagaacgcta tcaagaccct gaacgatgag actaagaagc aagtgaacct gatggggcag     300

acaatcaacg ccctgatctc ggacaacttg ttgatgaaga acaagatcag ggaactgatg     360

agtgtccctt actgcaacta cacgaagttc tggtacgtca accacacact ctccggacaa     420

cactcgttgc caaggtgctg gttgatcaag aacaacagct acttgaacat ctccgacttc     480

cgtaacgact ggatcttgga gagtgacttc ttgatctccg agatgctgag caaggagtac     540

tcggacaggc agggtaagac tccgcggccg cacggcggag gtagcaaaga ctgcgaaatg     600

aagcgcacca ccctggatag ccctctgggc aagctggaac tgtctgggtg cgaacagggc     660

ctgcacgaga tcaagctgct gggcaaagga acatctgccg ccgacgccgt ggaagtgcct     720
```

```
gccccagccg ccgtgctggg cggaccagag ccactgatgc aggccaccgc ctggctcaac    780

gcctactttc accagcctga ggccatcgag gagttccctg tgccagccct gcaccaccca    840

gtgttccagc aggagagctt tacccgccag gtgctgtgga aactgctgaa agtggtgaag    900

ttcggagagg tcatcagcta ccagcagctg gccgccctgg ccggcaatcc cgccgccacc    960

gccgccgtga aaaccgccct gagcggaaat cccgtgccca ttctgatccc ctgccaccgg   1020

gtggtgtcta gctctggcgc cgtggggggc tacgagggcg ggctcgccgt gaaagagtgg   1080

ctgctggccc acgagggcca cagactgggc aagcctgggc tgggtcctgc aggtataggc   1140

gcgccagggt ccctggagca tcatcatcat catcattgat gacgggccc               1189
```

<210> SEQ ID NO 143
<211> LENGTH: 374
<212> TYPE: PRT
<213> ORGANISM: artificial
<220> FEATURE:
<223> OTHER INFORMATION: Amino acid sequence of fusion protein
[JUN.ectoGP2- SNAPlike-Histag]

<400> SEQUENCE: 143

```
Arg Ser Gly Thr Phe Thr Trp Thr Leu Ser Asp Ser Glu Gly Lys Asp
1               5                   10                  15

Thr Pro Gly Gly Tyr Cys Leu Thr Arg Trp Met Leu Ile Glu Ala Glu
            20                  25                  30

Leu Lys Cys Phe Gly Asn Thr Ala Val Ala Lys Cys Asn Glu Lys His
        35                  40                  45

Asp Glu Glu Phe Cys Asp Met Leu Arg Leu Phe Asp Phe Asn Lys Gln
    50                  55                  60

Ala Ile Gln Arg Leu Lys Ala Glu Ala Gln Met Ser Ile Gln Leu Ile
65                  70                  75                  80

Asn Lys Ala Val Asn Ala Leu Ile Asn Asp Gln Leu Ile Met Lys Asn
                85                  90                  95

His Leu Arg Asp Ile Met Gly Ile Pro Tyr Cys Asn Tyr Ser Lys Tyr
            100                 105                 110

Trp Tyr Leu Asn His Thr Thr Thr Gly Arg Thr Ser Leu Pro Lys Cys
        115                 120                 125

Trp Leu Val Ser Asn Gly Ser Tyr Leu Asn Glu Thr His Phe Ser Asp
    130                 135                 140

Asp Ile Glu Gln Gln Ala Asp Asn Met Ile Thr Glu Met Leu Gln Lys
145                 150                 155                 160

Glu Tyr Met Glu Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
```

-continued

```
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 144
<211> LENGTH: 1189
<212> TYPE: DNA
<213> ORGANISM: artificial
<220> FEATURE:
<223> OTHER INFORMATION: DNA sequence encoding ssBiP-Glycoprotein GP2 from Machupo virus- SNAPlike-Histag for expression in S2 cells

<400> SEQUENCE: 144

```
atgaagttat gcatattact ggccgtcgtg gcctttgttg gcctctcgct cgggagatct     60

gcattcttct catggtcgct gaccgactcc tccggcaagg acatgccagg aggttactgt    120

ctggaggaat ggatgttgat cgcagccaag atgaagtgct tcggcaacac cgctgtcgct    180

aagtgtaacc agaaccatga ctcagagttc tgtgatatgc tgaggctatt cgactacaac    240

aagaacgcaa tcaagaccct caacgatgaa tcgaagaagg agatcaacct gctaagccag    300

accgtgaacg ccttgatctc ggataacttg ttaatgaaga acaagatcaa ggagctaatg    360

agcatccctt actgtaatta cacgaagttc tggtacgtca accataccct gacagggcag    420

cacacgctgc caaggtgttg gttgatcagg aacggaagtt acctcaacac ctcggagttc    480

aggaacgact ggatcttgga gagtgatcac ctcatctcgg agatgttgag taaggaatac    540

gctgagaggc aaggcaagac cccgcggccg cacggcggag gtagcaaaga ctgcgaaatg    600

aagcgcacca ccctggatag ccctctgggc aagctggaac tgtctgggtg cgaacagggc    660

ctgcacgaga tcaagctgct gggcaaagga acatctgccg ccgacgccgt ggaagtgcct    720

gccccagccg ccgtgctggg cggaccagag ccactgatgc aggccaccgc ctggctcaac    780

gcctactttc accagcctga ggccatcgag gagttccctg tgccagccct gcaccaccca    840

gtgttccagc aggagagctt tacccgccag gtgctgtgga aactgctgaa agtggtgaag    900

ttcggagagg tcatcagcta ccagcagctg gccgccctgg ccggcaatcc cgccgccacc    960

gccgccgtga aaaccgccct gagcggaaat cccgtgccca ttctgatccc ctgccaccgg   1020

gtggtgtcta gctctggcgc cgtggggggc tacgagggcg ggctcgccgt gaaagagtgg   1080

ctgctggccc acgagggcca cagactgggc aagcctgggc tgggtcctgc aggtataggc   1140

gcgccagggt ccctggagca tcatcatcat catcattgat gacgggccc             1189
```

<210> SEQ ID NO 145
<211> LENGTH: 374
<212> TYPE: PRT
<213> ORGANISM: artificial
<220> FEATURE:
<223> OTHER INFORMATION: Amino acid sequence of fusion protein [MAC.ectoGP2- SNAPlike-Histag]

<400> SEQUENCE: 145

```
Arg Ser Ala Phe Phe Ser Trp Ser Leu Thr Asp Ser Ser Gly Lys Asp
1               5                   10                  15

Met Pro Gly Gly Tyr Cys Leu Glu Glu Trp Met Leu Ile Ala Ala Lys
            20                  25                  30

Met Lys Cys Phe Gly Asn Thr Ala Val Ala Lys Cys Asn Gln Asn His
        35                  40                  45

Asp Ser Glu Phe Cys Asp Met Leu Arg Leu Phe Asp Tyr Asn Lys Asn
    50                  55                  60

Ala Ile Lys Thr Leu Asn Asp Glu Ser Lys Lys Glu Ile Asn Leu Leu
65                  70                  75                  80

Ser Gln Thr Val Asn Ala Leu Ile Ser Asp Asn Leu Leu Met Lys Asn
                85                  90                  95

Lys Ile Lys Glu Leu Met Ser Ile Pro Tyr Cys Asn Tyr Thr Lys Phe
            100                 105                 110

Trp Tyr Val Asn His Thr Leu Thr Gly Gln His Thr Leu Pro Arg Cys
        115                 120                 125

Trp Leu Ile Arg Asn Gly Ser Tyr Leu Asn Thr Ser Glu Phe Arg Asn
    130                 135                 140

Asp Trp Ile Leu Glu Ser Asp His Leu Ile Ser Glu Met Leu Ser Lys
145                 150                 155                 160

Glu Tyr Ala Glu Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 146
<211> LENGTH: 1189
<212> TYPE: DNA

<213> ORGANISM: artificial
<220> FEATURE:
<223> OTHER INFORMATION: DNA sequence encoding ssBiP-Glycoprotein GP2 from Guanarito virus- SNAPlike-Histag for expression in S2 cells

<400> SEQUENCE: 146

```
atgaagttat gcatattact ggccgtcgtg gcctttgttg gcctctcgct cgggagatct     60

gcattcttca gttggtcgct gtctgacccg aagggtaatg acatgccagg tggttactgt    120

ctggagaggt ggatgttggt cgctggggac ttgaagtgct tcggcaacac agctgtcgcc    180

aagtgtaact tgaaccatga ttccgagttc tgtgacatgt tgaggctgtt cgacttcaac    240

aagaacgcca tcgagaagct gaacaaccag actaagactg ctgtcaacat gttgactcac    300

tcgatcaaca gtctgatctc cgataacttg ttgatgagga acaagctgaa ggagattttg    360

aaggtcccat actgcaacta cacaagattc tggtacatca accacacgaa gtccggcgag    420

cactcgctgc ctcggtgttg gctggtcagt aacggttcct acttgaacga gagtgacttc    480

aggaacgagt ggatcttgga gagtgatcac ctgatcgcag agatgttgag caaggaatac    540

caagataggc aggggaagac tccgcggccg cacggcggag gtagcaaaga ctgcgaaatg    600

aagcgcacca ccctggatag ccctctgggc aagctggaac tgtctgggtg cgaacagggc    660

ctgcacgaga tcaagctgct gggcaaagga acatctgccg ccgacgccgt ggaagtgcct    720

gccccagccg ccgtgctggg cggaccagag ccactgatgc aggccaccgc ctggctcaac    780

gcctactttc accagcctga ggccatcgag gagttccctg tgccagccct gcaccaccca    840

gtgttccagc aggagagctt tacccgccag gtgctgtgga aactgctgaa agtggtgaag    900

ttcggagagg tcatcagcta ccagcagctg gccgccctgg ccggcaatcc cgccgccacc    960

gccgccgtga aaaccgccct gagcggaaat cccgtgccca ttctgatccc ctgccaccgg   1020

gtggtgtcta gctctggcgc cgtgggggc tacgagggcg ggctcgccgt gaaagagtgg   1080

ctgctggccc acgagggcca cagactgggc aagcctgggc tgggtcctgc aggtataggc   1140

gcgccagggt ccctggagca tcatcatcat catcattgat gacgggccc              1189
```

<210> SEQ ID NO 147
<211> LENGTH: 374
<212> TYPE: PRT
<213> ORGANISM: artificial
<220> FEATURE:
<223> OTHER INFORMATION: Amino acid sequence of fusion protein [GUA.ectoGP2- SNAPlike-Histag]

<400> SEQUENCE: 147

```
Arg Ser Ala Phe Phe Ser Trp Ser Leu Ser Asp Pro Lys Gly Asn Asp
1               5                   10                  15

Met Pro Gly Gly Tyr Cys Leu Glu Arg Trp Met Leu Val Ala Gly Asp
            20                  25                  30

Leu Lys Cys Phe Gly Asn Thr Ala Val Ala Lys Cys Asn Leu Asn His
        35                  40                  45

Asp Ser Glu Phe Cys Asp Met Leu Arg Leu Phe Asp Phe Asn Lys Asn
    50                  55                  60

Ala Ile Glu Lys Leu Asn Asn Gln Thr Lys Thr Ala Val Asn Met Leu
65                  70                  75                  80

Thr His Ser Ile Asn Ser Leu Ile Ser Asp Asn Leu Leu Met Arg Asn
                85                  90                  95

Lys Leu Lys Glu Ile Leu Lys Val Pro Tyr Cys Asn Tyr Thr Arg Phe
            100                 105                 110
```

```
Trp Tyr Ile Asn His Thr Lys Ser Gly Glu His Ser Leu Pro Arg Cys
        115                 120                 125

Trp Leu Val Ser Asn Gly Ser Tyr Leu Asn Glu Ser Asp Phe Arg Asn
    130                 135                 140

Glu Trp Ile Leu Glu Ser Asp His Leu Ile Ala Glu Met Leu Ser Lys
145                 150                 155                 160

Glu Tyr Gln Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240

Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370
```

<210> SEQ ID NO 148
<211> LENGTH: 1189
<212> TYPE: DNA
<213> ORGANISM: artificial
<220> FEATURE:
<223> OTHER INFORMATION: DNA sequence encoding ssBiP-Glycoprotein GP2 from Sabia virus- SNAPlike-Histag for expression in S2 cells

<400> SEQUENCE: 148

```
atgaagttat gcatattact ggccgtcgtg gcctttgttg gcctctcgct cgggagatct      60

ggcatcttct cctggacgat cacggatgca gtgggcaacg acatgcctgg tggttactgt     120

ctggagagat ggatgctggt gacgtcggat cttaagtgct tcggcaacac ggcactggcg     180

aagtgtaacc tcgaccacga ttcggagttc tgtgacatgt tgaagttgtt cgagttcaac     240

aagaaggcga tcgagacatt gaacgacaac acgaagaaca aggtgaactt gctgacccac     300

tcgatcaacg cattgatctc cgacaacttg ctgatgaaga accgactcaa ggaattgttg     360

aacacgcctt actgtaacta caccaagttc tggtatgtca accacacggc atccggggag     420

cactcattgc cacggtgctg gctggttagg aacaatagct acttgaacga gagtgagttc     480

aggaatgatt ggatcatcga gagtgatcac ttgttgtccg agatgctcaa caaggaatac     540
```

```
atcgatagac agggcaagac gccgcggccg cacggcggag gtagcaaaga ctgcgaaatg    600

aagcgcacca ccctggatag ccctctgggc aagctggaac tgtctgggtg cgaacagggc    660

ctgcacgaga tcaagctgct gggcaaagga acatctgccg ccgacgccgt ggaagtgcct    720

gccccagccg ccgtgctggg cggaccagag ccactgatgc aggccaccgc ctggctcaac    780

gcctactttc accagcctga ggccatcgag gagttccctg tgccagccct gcaccaccca    840

gtgttccagc aggagagctt tacccgccag gtgctgtgga aactgctgaa agtggtgaag    900

ttcggagagg tcatcagcta ccagcagctg gccgccctgg ccggcaatcc cgccgccacc    960

gccgccgtga aaaccgccct gagcggaaat cccgtgccca ttctgatccc ctgccaccgg   1020

gtggtgtcta gctctggcgc cgtgggggc tacgagggcg ggctcgccgt gaaagagtgg   1080

ctgctggccc acgagggcca cagactgggc aagcctgggc tgggtcctgc aggtataggc   1140

gcgccagggt ccctggagca tcatcatcat catcattgat gacgggccc               1189
```

```
<210> SEQ ID NO 149
<211> LENGTH: 374
<212> TYPE: PRT
<213> ORGANISM: artificial
<220> FEATURE:
<223> OTHER INFORMATION: Amino acid sequence of fusion protein
      [SAB.ectoGP2- SNAPlike-Histag]

<400> SEQUENCE: 149

Arg Ser Gly Ile Phe Ser Trp Thr Ile Thr Asp Ala Val Gly Asn Asp
1               5                   10                  15

Met Pro Gly Gly Tyr Cys Leu Glu Arg Trp Met Leu Val Thr Ser Asp
            20                  25                  30

Leu Lys Cys Phe Gly Asn Thr Ala Leu Ala Lys Cys Asn Leu Asp His
        35                  40                  45

Asp Ser Glu Phe Cys Asp Met Leu Lys Leu Phe Glu Phe Asn Lys Lys
    50                  55                  60

Ala Ile Glu Thr Leu Asn Asp Asn Thr Lys Asn Lys Val Asn Leu Leu
65                  70                  75                  80

Thr His Ser Ile Asn Ala Leu Ile Ser Asp Asn Leu Leu Met Lys Asn
                85                  90                  95

Arg Leu Lys Glu Leu Leu Asn Thr Pro Tyr Cys Asn Tyr Thr Lys Phe
            100                 105                 110

Trp Tyr Val Asn His Thr Ala Ser Gly Glu His Ser Leu Pro Arg Cys
        115                 120                 125

Trp Leu Val Arg Asn Asn Ser Tyr Leu Asn Glu Ser Glu Phe Arg Asn
    130                 135                 140

Asp Trp Ile Ile Glu Ser Asp His Leu Leu Ser Glu Met Leu Asn Lys
145                 150                 155                 160

Glu Tyr Ile Asp Arg Gln Gly Lys Thr Pro Arg Pro His Gly Gly Gly
                165                 170                 175

Ser Lys Asp Cys Glu Met Lys Arg Thr Thr Leu Asp Ser Pro Leu Gly
            180                 185                 190

Lys Leu Glu Leu Ser Gly Cys Glu Gln Gly Leu His Glu Ile Lys Leu
        195                 200                 205

Leu Gly Lys Gly Thr Ser Ala Ala Asp Ala Val Glu Val Pro Ala Pro
    210                 215                 220

Ala Ala Val Leu Gly Gly Pro Glu Pro Leu Met Gln Ala Thr Ala Trp
225                 230                 235                 240
```

```
Leu Asn Ala Tyr Phe His Gln Pro Glu Ala Ile Glu Glu Phe Pro Val
                245                 250                 255

Pro Ala Leu His His Pro Val Phe Gln Gln Glu Ser Phe Thr Arg Gln
            260                 265                 270

Val Leu Trp Lys Leu Leu Lys Val Val Lys Phe Gly Glu Val Ile Ser
        275                 280                 285

Tyr Gln Gln Leu Ala Ala Leu Ala Gly Asn Pro Ala Ala Thr Ala Ala
    290                 295                 300

Val Lys Thr Ala Leu Ser Gly Asn Pro Val Pro Ile Leu Ile Pro Cys
305                 310                 315                 320

His Arg Val Val Ser Ser Ser Gly Ala Val Gly Gly Tyr Glu Gly Gly
                325                 330                 335

Leu Ala Val Lys Glu Trp Leu Leu Ala His Glu Gly His Arg Leu Gly
            340                 345                 350

Lys Pro Gly Leu Gly Pro Ala Gly Ile Gly Ala Pro Gly Ser Leu Glu
        355                 360                 365

His His His His His His
    370


<210> SEQ ID NO 150
<211> LENGTH: 2774
<212> TYPE: DNA
<213> ORGANISM: artificial
<220> FEATURE:
<223> OTHER INFORMATION: DNA sequence encoding BiPlike-
      SNAPlike-proTEV1-C protein of Hepatitis E virus- proTEV2-Histag
      for expression in S2 cells

<400> SEQUENCE: 150

atgaaactat gtattctact tgcagttgtt gcgttcgtag gattgtcctt acctacagct     60

ctggcaagat ctgacaaaga ctgcgaaatg aaaagaacta cattggattc accacttggg    120

aagttggaac tgagtggatg cgagcaagga ttgcatgaaa ttaagctact gggaaaagga    180

acttctgctg ctgatgcagt tgaagttcca gcaccagcag ctgttcttgg aggtcctgag    240

cccctcatgc aagccacagc ctggcttaac gcatatttcc accagcctga ggccattgag    300

gaatttccag tccccgccct tcaccatcct gtgtttcagc aggagagctt cacccgccag    360

gtcctgtgga aattgctgaa ggtggtcaag tttggtgaag tgatttcata tcagcaactt    420

gctgcattgg ccggtaaccc cgcagctaca gctgccgtga aaactgctct cagcggaaat    480

cctgtgccca tcctgatccc ttgtcacaga gtcgtttcat cttccggagc tgtaggtggc    540

tatgaaggag gactggcagt taaggagtgg ctgctggctc atgaaggtca tagacttgga    600

aagcctgggc tgggtcctgc tggtataggc gcgccagggt ccctaggtgg cggatccgaa    660

aacctgtact tccagagcga tatcaataac atgttctttt gctctgtgca tggagatgcc    720

accatgcgct ctcgggcttt tctgtttttg ttcctcgtgt ttctgcctat gctgcccgcg    780

ccaccggccg gtcagccgtc tggccgccgc cgcgggcggc gcagcggcgg tgccggcggt    840

ggtttctggg gtgaccggat tgattctcag cccttcgccc tcccctatat tcatccaacc    900

aacccctcg cacctgacat tccagccgca gccggggctg gagctcgccc tcggcagcca     960

gcccgcccac tcggctccgc ttggcgtgac caatcccagc gccccgccac ttccgcccgt   1020

cgtcgatctg ccccagctgg ggcttcgccg ctgactgctg tggccccggc cccgatact    1080

gttcctgttc ccgatgtcga ttctcgcggc gctatattac gccgccagta taatttatca   1140

acatccccgc taacatctac tattgccact ggtactaacc ttgttctata tgctgctccg   1200
```

ctgagccctt tgcttccgct ccaagatgga actaacactc acattatggc cactgaagca 1260
tcaaattatg cccagtaccg tgttgtccgc gctaccatcc ggtaccgtcc gcttgtgccg 1320
aacgctgtcg gcggatacgc tatatctatc tctttctggc ctcagacaac tactaccccg 1380
acatctgtgg acatgaactc tatcacctcc acggatgtcc gaatccttgt ccagcctggt 1440
attgcttcag aacttgtgat ccccagtgag cgcctgcatt atcgtaacca aggctggcgc 1500
tctgttgaga cctctggtgt tgcggaggag gaggcgacct ccggccttgt catgctttgc 1560
atccacggat cacctgtaaa ttcttacacc aatacgcctt atactggtgc ccttggcttg 1620
cttgatttcg cactcgagct cgagttccgc aatttgacac ctggtaacac gaacacacgt 1680
gtttcccgct actcgagtag tgcgcgccac aagctacgcc gagggcctga tggcactgct 1740
gagttaacta cgactgctgc tacacgcttt atgaaggacc ttcattttac agggactaat 1800
ggagttggtg aagtcggtcg tggtatagcg ctaactctgt tcaaccttgc tgatacgctt 1860
ctcggcgggc tcccgacaga attgatttcg tcggctggtg gtcagctatt ttattctcgc 1920
cccgtcgtct cagccaatgg cgagccgacg gtgaagctct acacttcagt cgagaacgct 1980
cagcaggata agggtatagc tatcccacat gatattgatc ttggtgagtc ccgtgttgtc 2040
attcaggatt atgataacca acatgagcag gatcgtccca ccccttctcc tgctccctct 2100
cggccttttt ctgtccttcg tgctaatgat gtgctatggc tttcacttac agcagctgag 2160
tatgatcaga ctacctatgg ctcctctact aatcccatgt atgtctctga taccgtgaca 2220
tttgtcaatg ttgctactgg tgcccagggg gtatctcgct ctctggactg gtctaaagtc 2280
acccttgatg ggcgcccact tatgactatc cagcagtatt ctaagacttt ctttgttctg 2340
cccctccgtg gcaagctctc cttctgggag gccggtacca ctaaggccgg ctacccttat 2400
aattataata ctactgccag tgaccagatt ttaattgaga atgcagctgg tcaccgtgta 2460
tgcatctcaa cctacactac taatcttgga tctggccctg tttctatttc tgctgtcggt 2520
gtcctcgcac ctcactctgc gttggccgct ttagaggaca ctgttgacta tcctgctcgt 2580
gctcacactt ttgatgattt ctgccctgag tgccgtacac tcggccttca gggttgtgct 2640
ttccaatcaa ctgttgctga gctacagcgt cttaaaatga aggtgggtaa aactcgggag 2700
tacccgggag agaatctata ttttcaaggg cccggcggag gtagtcacca tcatcaccat 2760
cactaatgac cggt 2774

<210> SEQ ID NO 151
<211> LENGTH: 899
<212> TYPE: PRT
<213> ORGANISM: artificial
<220> FEATURE:
<223> OTHER INFORMATION: Aa sequence of fusion protein
[SNAPlike-proTEV1-HEV.C-proTEV2-Histag]

<400> SEQUENCE: 151

Arg Ser Asp Lys Asp Cys Glu Met Lys Arg Thr Thr Leu Asp Ser Pro
1 5 10 15

Leu Gly Lys Leu Glu Leu Ser Gly Cys Glu Gln Gly Leu His Glu Ile
20 25 30

Lys Leu Leu Gly Lys Gly Thr Ser Ala Ala Asp Ala Val Glu Val Pro
35 40 45

Ala Pro Ala Ala Val Leu Gly Gly Pro Glu Pro Leu Met Gln Ala Thr
50 55 60

Ala Trp Leu Asn Ala Tyr Phe His Gln Pro Glu Ala Ile Glu Glu Phe
65 70 75 80

```
Pro Val Pro Ala Leu His His Pro Val Phe Gln Gln Glu Ser Phe Thr
                85                  90                  95

Arg Gln Val Leu Trp Lys Leu Leu Lys Val Val Lys Phe Gly Glu Val
            100                 105                 110

Ile Ser Tyr Gln Gln Leu Ala Ala Leu Ala Gly Asn Pro Ala Ala Thr
        115                 120                 125

Ala Ala Val Lys Thr Ala Leu Ser Gly Asn Pro Val Pro Ile Leu Ile
    130                 135                 140

Pro Cys His Arg Val Val Ser Ser Ser Gly Ala Val Gly Gly Tyr Glu
145                 150                 155                 160

Gly Gly Leu Ala Val Lys Glu Trp Leu Leu Ala His Glu Gly His Arg
                165                 170                 175

Leu Gly Lys Pro Gly Leu Gly Pro Ala Gly Ile Gly Ala Pro Gly Ser
            180                 185                 190

Leu Gly Gly Gly Ser Glu Asn Leu Tyr Phe Gln Ser Asp Ile Asn Asn
        195                 200                 205

Met Phe Phe Cys Ser Val His Gly Asp Ala Thr Met Arg Ser Arg Ala
    210                 215                 220

Phe Leu Phe Leu Phe Leu Val Phe Leu Pro Met Leu Pro Ala Pro Pro
225                 230                 235                 240

Ala Gly Gln Pro Ser Gly Arg Arg Arg Gly Arg Arg Ser Gly Gly Ala
                245                 250                 255

Gly Gly Gly Phe Trp Gly Asp Arg Ile Asp Ser Gln Pro Phe Ala Leu
            260                 265                 270

Pro Tyr Ile His Pro Thr Asn Pro Phe Ala Pro Asp Ile Pro Ala Ala
        275                 280                 285

Ala Gly Ala Gly Ala Arg Pro Arg Gln Pro Ala Arg Pro Leu Gly Ser
    290                 295                 300

Ala Trp Arg Asp Gln Ser Gln Arg Pro Ala Thr Ser Ala Arg Arg Arg
305                 310                 315                 320

Ser Ala Pro Ala Gly Ala Ser Pro Leu Thr Ala Val Ala Pro Ala Pro
                325                 330                 335

Asp Thr Val Pro Val Pro Asp Val Asp Ser Arg Gly Ala Ile Leu Arg
            340                 345                 350

Arg Gln Tyr Asn Leu Ser Thr Ser Pro Leu Thr Ser Thr Ile Ala Thr
        355                 360                 365

Gly Thr Asn Leu Val Leu Tyr Ala Ala Pro Leu Ser Pro Leu Leu Pro
    370                 375                 380

Leu Gln Asp Gly Thr Asn Thr His Ile Met Ala Thr Glu Ala Ser Asn
385                 390                 395                 400

Tyr Ala Gln Tyr Arg Val Val Arg Ala Thr Ile Arg Tyr Arg Pro Leu
                405                 410                 415

Val Pro Asn Ala Val Gly Gly Tyr Ala Ile Ser Ile Ser Phe Trp Pro
            420                 425                 430

Gln Thr Thr Thr Thr Pro Thr Ser Val Asp Met Asn Ser Ile Thr Ser
        435                 440                 445

Thr Asp Val Arg Ile Leu Val Gln Pro Gly Ile Ala Ser Glu Leu Val
    450                 455                 460

Ile Pro Ser Glu Arg Leu His Tyr Arg Asn Gln Gly Trp Arg Ser Val
465                 470                 475                 480

Glu Thr Ser Gly Val Ala Glu Glu Glu Ala Thr Ser Gly Leu Val Met
                485                 490                 495
```

```
Leu Cys Ile His Gly Ser Pro Val Asn Ser Tyr Thr Asn Thr Pro Tyr
            500                 505                 510

Thr Gly Ala Leu Gly Leu Leu Asp Phe Ala Leu Glu Leu Glu Phe Arg
        515                 520                 525

Asn Leu Thr Pro Gly Asn Thr Asn Thr Arg Val Ser Arg Tyr Ser Ser
    530                 535                 540

Ser Ala Arg His Lys Leu Arg Arg Gly Pro Asp Gly Thr Ala Glu Leu
545                 550                 555                 560

Thr Thr Thr Ala Ala Thr Arg Phe Met Lys Asp Leu His Phe Thr Gly
                565                 570                 575

Thr Asn Gly Val Gly Glu Val Gly Arg Gly Ile Ala Leu Thr Leu Phe
            580                 585                 590

Asn Leu Ala Asp Thr Leu Leu Gly Gly Leu Pro Thr Glu Leu Ile Ser
        595                 600                 605

Ser Ala Gly Gly Gln Leu Phe Tyr Ser Arg Pro Val Val Ser Ala Asn
    610                 615                 620

Gly Glu Pro Thr Val Lys Leu Tyr Thr Ser Val Glu Asn Ala Gln Gln
625                 630                 635                 640

Asp Lys Gly Ile Ala Ile Pro His Asp Ile Asp Leu Gly Glu Ser Arg
                645                 650                 655

Val Val Ile Gln Asp Tyr Asp Asn Gln His Glu Gln Asp Arg Pro Thr
            660                 665                 670

Pro Ser Pro Ala Pro Ser Arg Pro Phe Ser Val Leu Arg Ala Asn Asp
        675                 680                 685

Val Leu Trp Leu Ser Leu Thr Ala Ala Glu Tyr Asp Gln Thr Thr Tyr
    690                 695                 700

Gly Ser Ser Thr Asn Pro Met Tyr Val Ser Asp Thr Val Thr Phe Val
705                 710                 715                 720

Asn Val Ala Thr Gly Ala Gln Gly Val Ser Arg Ser Leu Asp Trp Ser
                725                 730                 735

Lys Val Thr Leu Asp Gly Arg Pro Leu Met Thr Ile Gln Gln Tyr Ser
            740                 745                 750

Lys Thr Phe Phe Val Leu Pro Leu Arg Gly Lys Leu Ser Phe Trp Glu
        755                 760                 765

Ala Gly Thr Thr Lys Ala Gly Tyr Pro Tyr Asn Tyr Asn Thr Thr Ala
    770                 775                 780

Ser Asp Gln Ile Leu Ile Glu Asn Ala Ala Gly His Arg Val Cys Ile
785                 790                 795                 800

Ser Thr Tyr Thr Thr Asn Leu Gly Ser Gly Pro Val Ser Ile Ser Ala
                805                 810                 815

Val Gly Val Leu Ala Pro His Ser Ala Leu Ala Ala Leu Glu Asp Thr
            820                 825                 830

Val Asp Tyr Pro Ala Arg Ala His Thr Phe Asp Asp Phe Cys Pro Glu
        835                 840                 845

Cys Arg Thr Leu Gly Leu Gln Gly Cys Ala Phe Gln Ser Thr Val Ala
    850                 855                 860

Glu Leu Gln Arg Leu Lys Met Lys Val Gly Lys Thr Arg Glu Tyr Pro
865                 870                 875                 880

Gly Glu Asn Leu Tyr Phe Gln Gly Pro Gly Gly Gly Ser His His His
                885                 890                 895

His His His
```

<210> SEQ ID NO 152

-continued

```
<211> LENGTH: 51
<212> TYPE: DNA
<213> ORGANISM: artificial
<220> FEATURE:
<223> OTHER INFORMATION: DNA encoding biPlike sequence

<400> SEQUENCE: 152

atgaaactat gtattctact tgcagttgtt gcgttcgtag gattgtcctt a            51


<210> SEQ ID NO 153
<211> LENGTH: 17
<212> TYPE: PRT
<213> ORGANISM: artificial
<220> FEATURE:
<223> OTHER INFORMATION: Amino acid of BIPlike sequence

<400> SEQUENCE: 153

Met Lys Leu Cys Ile Leu Leu Ala Val Val Ala Phe Val Gly Leu Ser
1               5                   10                  15

Leu
```

MULTIPLEX IMMUNO SCREENING ASSAY

This application is the U.S. Natl. Stage of International Application PCT EP/2012/074986, filed Dec. 10, 2012, which claims the benefit of PCT/EP2011/072387, filed Dec. 9, 2011, and U.S. Provisional Appln. 61/642,924, filed May 4, 2012, all of which are hereby incorporated by reference.

BACKGROUND OF THE INVENTION

Infectious diseases and viral hemorrhagic fevers (VHFs) pose a significant public health problem, due to the severity of the diseases, high lethality, inter-human contagiousness of certain agents, and lack of effective treatment for most of them.

Some of them are caused by highly infectious RNA viruses from several families including the Flaviviridae (dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses) the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg). Transmission usually occurs by contact with infected animal reservoirs or arthropod vectors. Although the majority of those viruses have a higher occurrence in the tropics and subtropics, the geographic expansion of their natural reservoirs and vectors, and the increase in international travel have made the emergence of these agents in non-endemic areas highly probable. Control of epidemics crucially depends on the rapid detection and accurate identification of the agent, in order to define and implement timely and appropriate action. In this context, it is essential to produce and validate tools for early detection of outbreaks, precise identification of the etiologic agent, and improved disease surveillance.

In this respect, detection of antibodies in body fluids constitutes a major part of the diagnosis of virally induced diseases, autoimmune diseases and the detection of cancer. As a matter of fact, certain antibodies can serve as markers in diagnosis and can lead to prognosis and treatment, as their presence are known to correlate with the outbreak of a pathogen. This is particularly the case for the antibodies targeting viral antigens exclusively.

Current methods for detecting the presence of antibodies include diverse techniques such as immunofluorescence microscopy, chemiluminescence assay, Western blotting, Radio Immuno-Precipitation assay (RIP) and ELISA. For example, the team of Kim H-J. et al. recently developed a competitive ELISA for the detection of antibodies to Rift Valley Fever virus in goat and cattle (*The Journal of Veterinary Medical Science,* 2011). However, such techniques require measurement of each antibody separately, and thus are not useful for parallel, rapid, and high throughput analysis of multiple antibodies in a single sample of biological fluid. The parallel detection of several antibodies simultaneously may be particularly useful by minimizing the matrix effects that exist between individual assays, such as in ELISAs, because the calibrators and the antibodies are analyzed under the same conditions; it therefore will generate comparable results for the measurement of multiple antibodies present within the same sample.

Complicating the straightforward identification of pathogenically relevant antibodies, however, is that normal sera contain large amounts of natural antibodies which manifest themselves in complex staining patterns (Avrameas S. *Immunol. Today* 1991). The presence of these natural antibodies can complicate the differentiation of disease-associated antibodies from the complex background of "autoimmune noise", i.e. naturally occurring autoantibodies. That's why most of previous studies evaluated one or a few specific disease-related antibodies and have screened only a limited number of purified homologous or heterologous proteins as antigens by means of ELISA or RIA. A diagnosis based on these antibodies was impossible to establish. On the other hand, Western blotting has evolved as the most important tool to detect antibodies because it permits simultaneous screening for a wide spectrum of different antigens. A recent new technique, capable of analyzing these complex staining patterns of Western blots simultaneously, is based on digital image analysis. This technique has been successfully used in studies of myasthenia gravis, Graves' disease and experimental uveitis (Zimmerman C W, *Electrophoresis* 1995). The antibodies may also be detected and measured on a protein chip array using surface-enhanced laser desorption/ionization (SELDI) or matrix assisted laser desorption/ionization mass spectrometry techniques, preferably SELDI mass spectrometry technique (US 2006/166268). Yet, these techniques use large cumbersome equipment that is complex and expensive to maintain, and requires high amount of the biological samples to achieve the detection of antibodies being in a low amount.

In view of the foregoing, there exists a need for addressable systems and methods, which can provide additional improvements in high throughput, cost-effectiveness, and accuracy for molecular diagnosis of antibody-generating diseases. The present invention satisfies these and other needs.

FIGURE LEGENDS

FIG. 1 represents the oriented coupling of chimeric AGT-antigen proteins to substrate-coated microspheres. First step of coupling consists of coupling the AGT substrate BG-PEG-NH2 to the activated microspheres by amine coupling. The second step consists of contacting the substrate-coated microspheres with fusion proteins containing AGT (for example the SNAP mutant), said enzyme being intended to covalently attach to its BG-PEG-NH2 substrate, that is, to the microspheres.

Figure 2:
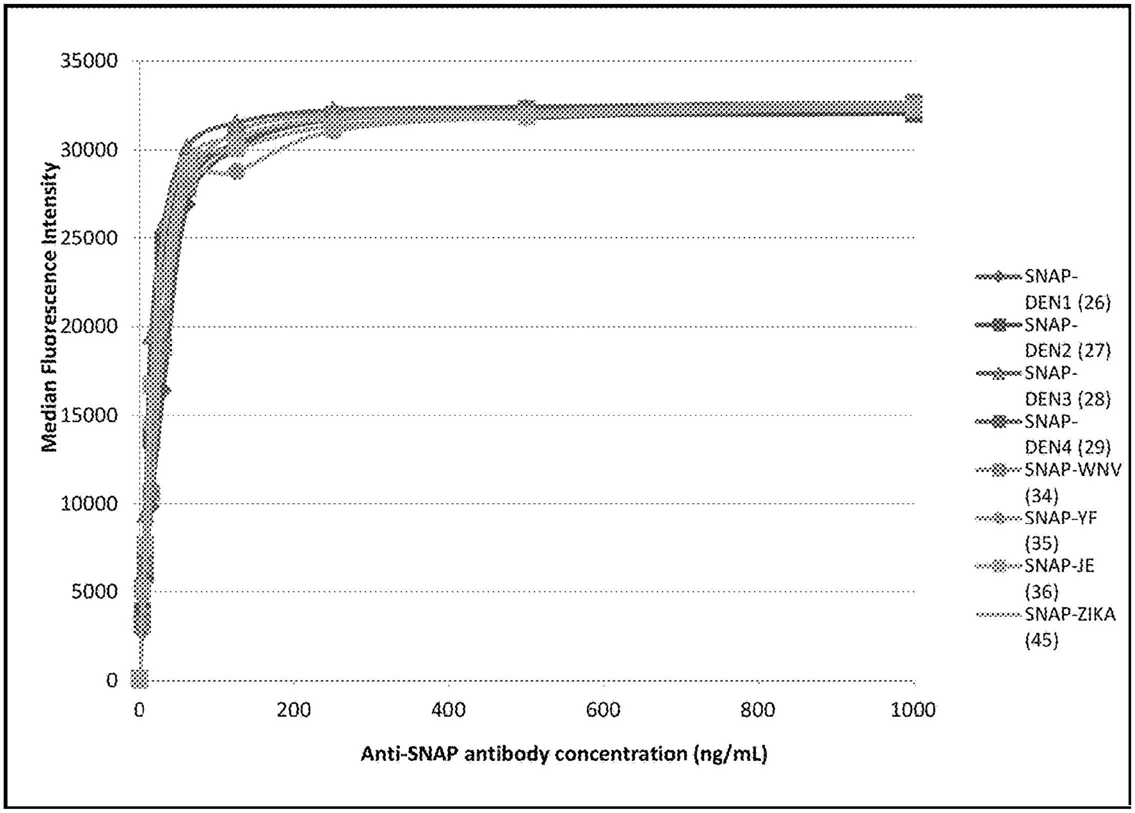

FIG. 2 shows the coupling efficiency of chimeric SNAP-viral antigens proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-ZIKA), as followed by anti-SNAP antibody.

Figure 3:
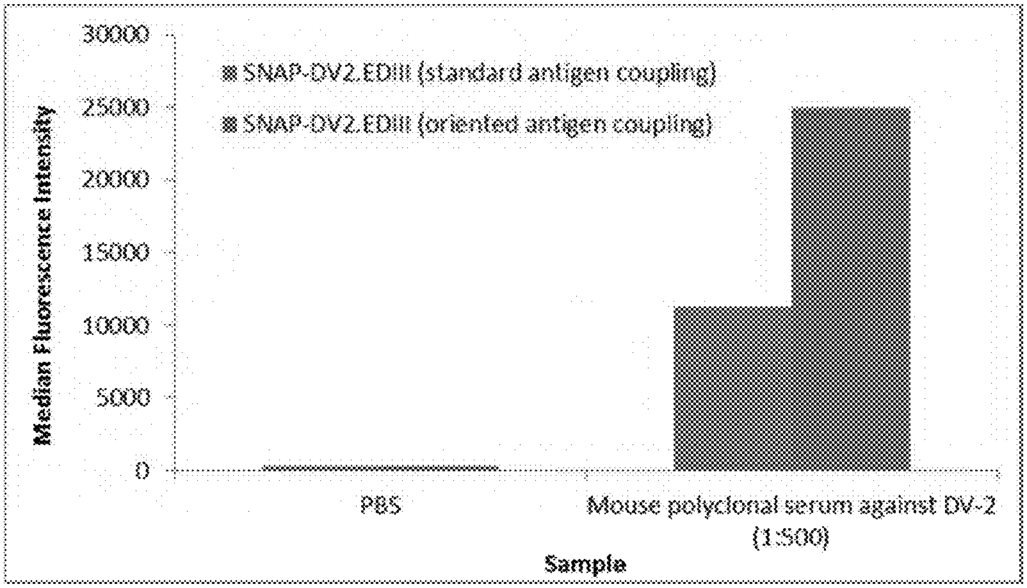

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through a standard amine coupling procedure, e.g. Bio-Plex Amine Coupling Kit, BIORAD.

Figure 4:
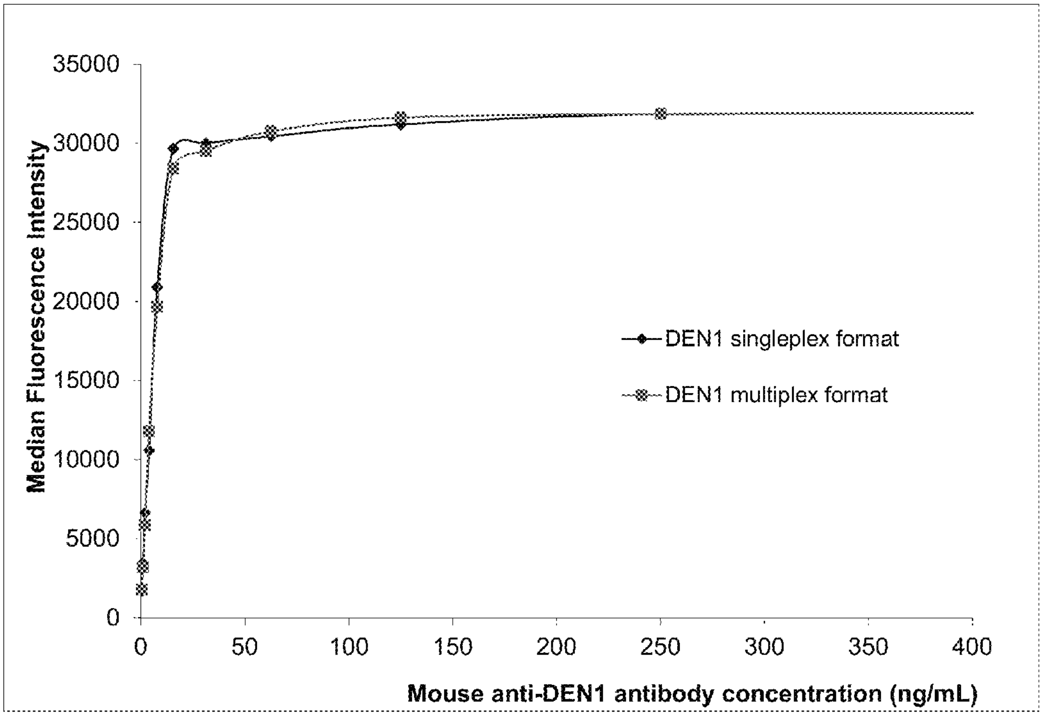

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex format with other chimeric SNAP-viral Ags proteins (SNAP-DV2.EDIII, SNAP.DV3.EDIII, SNAP.DV4.EDIII, SNAP-WNV, SNAP-YF, SNAP-JE, SNAP-TBE) coupled to microspheres.

Figure 5:
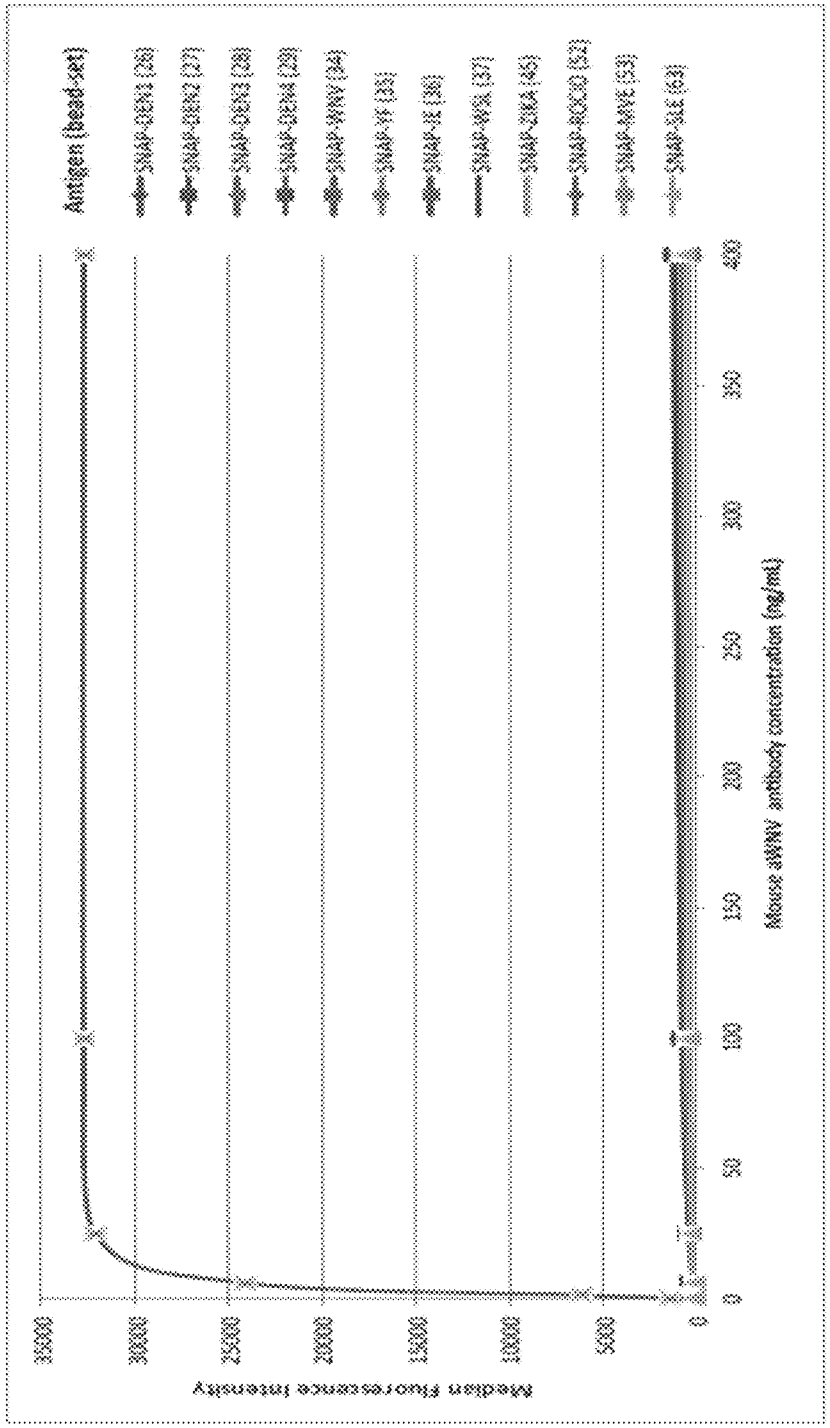

FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE) coupled to microspheres.

Figure 6:
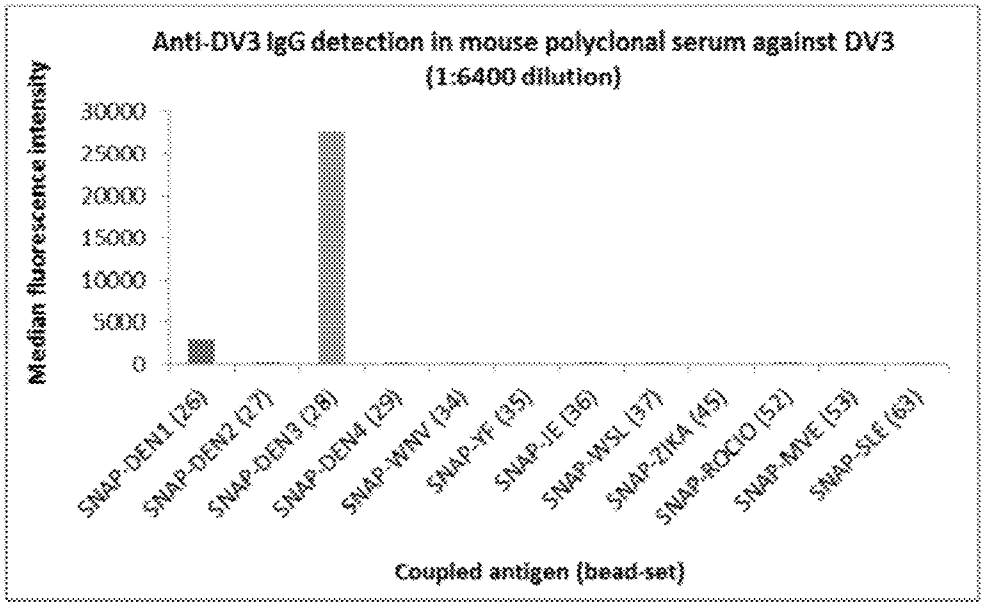
Figure 6:
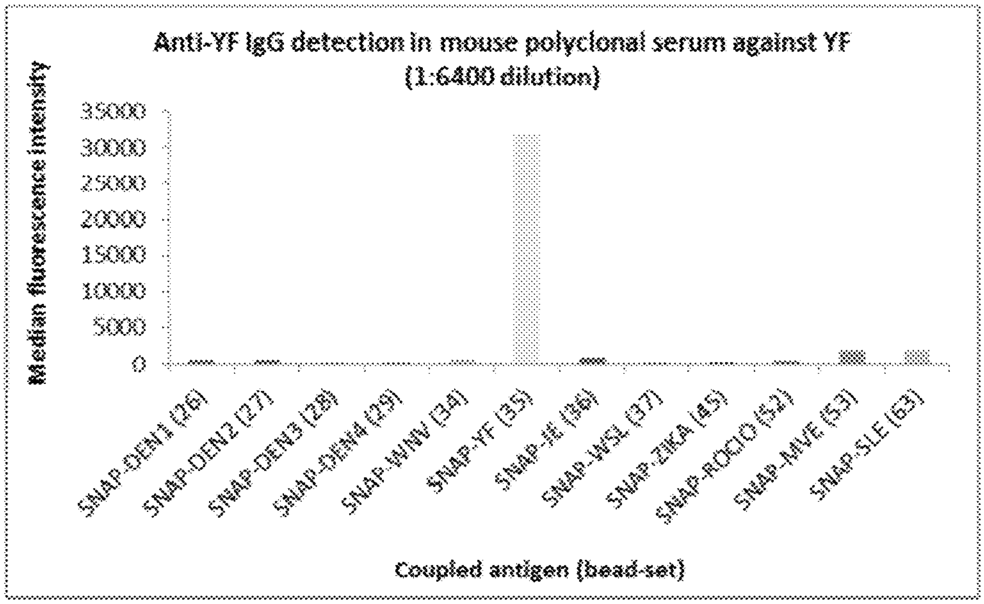
Figure 7:
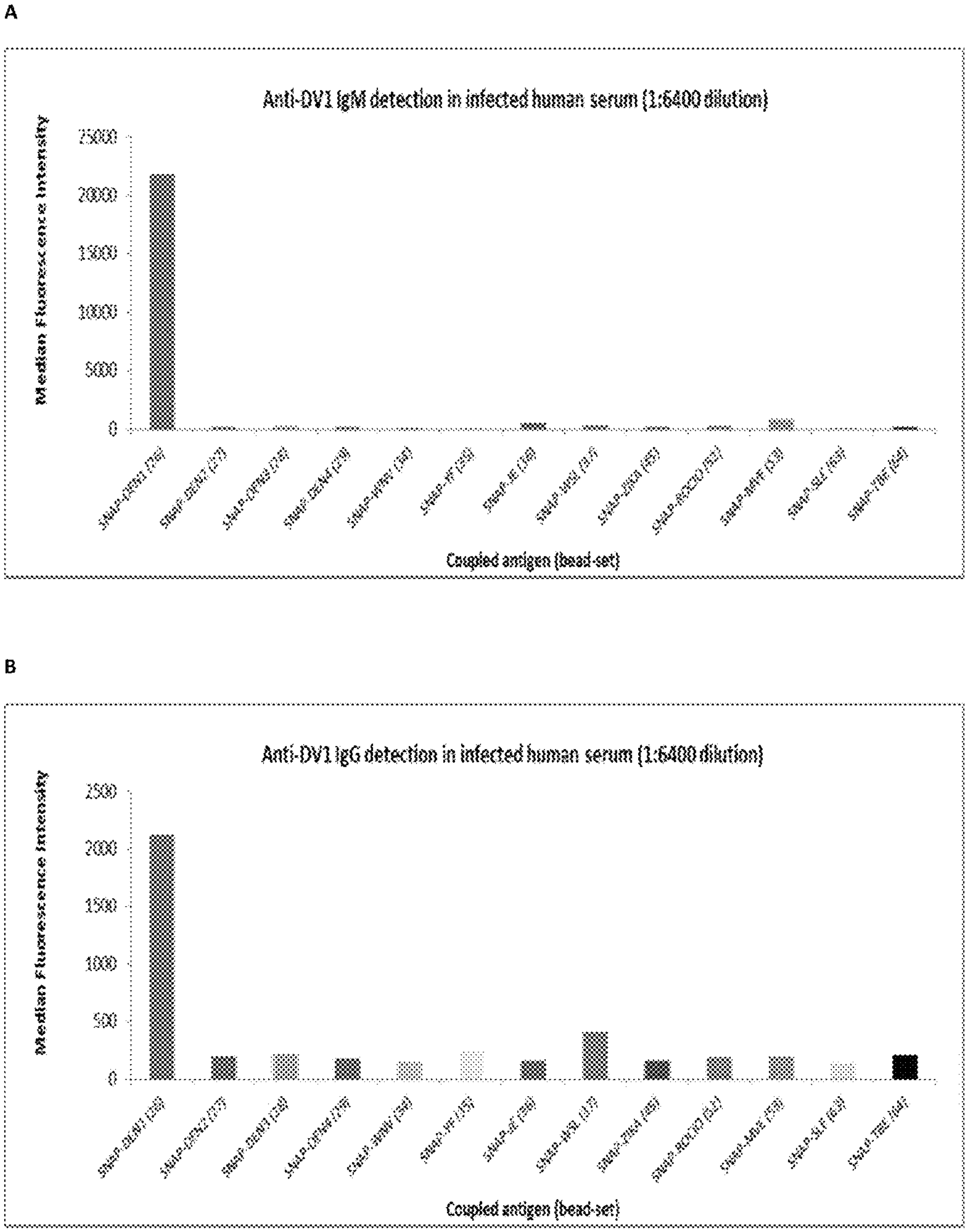

FIG. 6 shows the reactivity and specificity of anti-DV3 IgG detection in mouse polyclonal serum against DV3 (A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA) coupled to microspheres FIG. 7 shows the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA, SNAP-TBE) coupled to microspheres.

Figure 8:
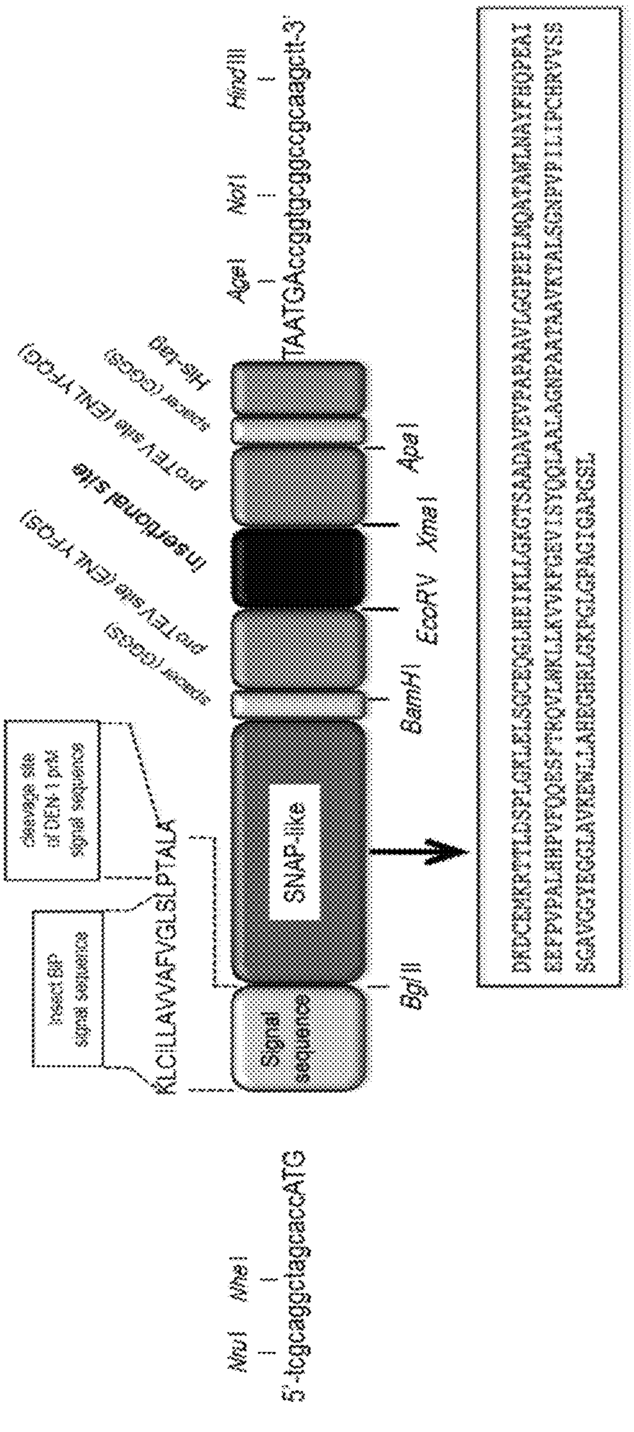

FIG. 8 discloses the structure of the pDeSNAPuniv cassette.

Figure 9:
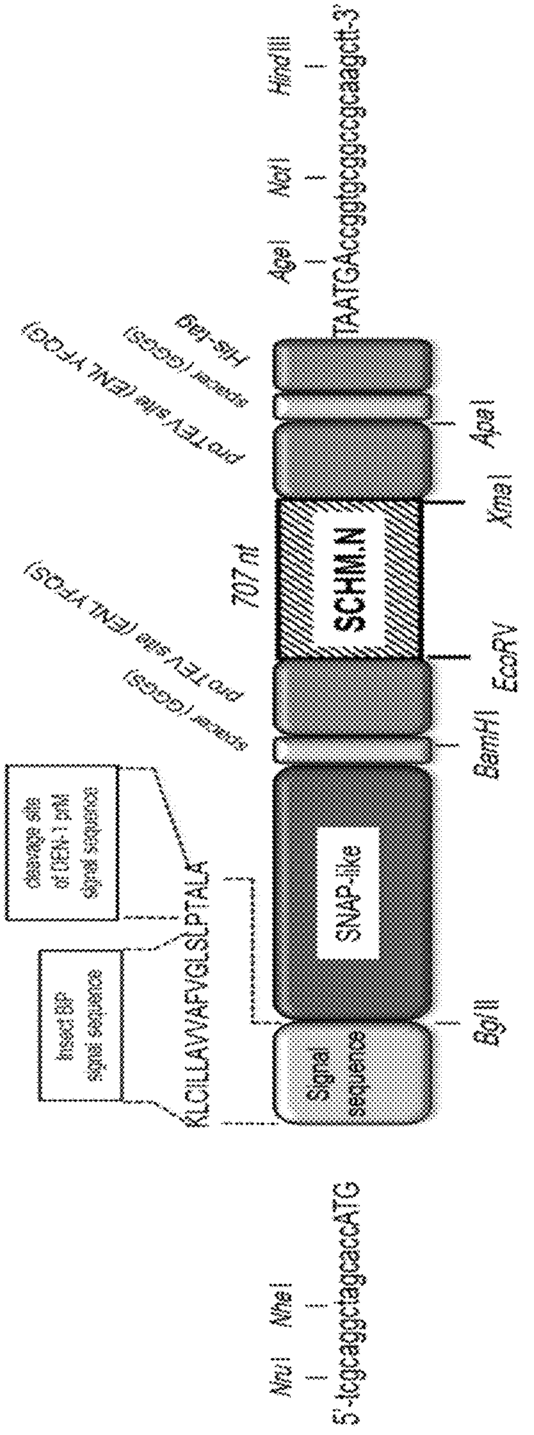

FIG. 9 discloses the structure of the pDeSNAPuniv/SBV.N cassette.

Figure 10:
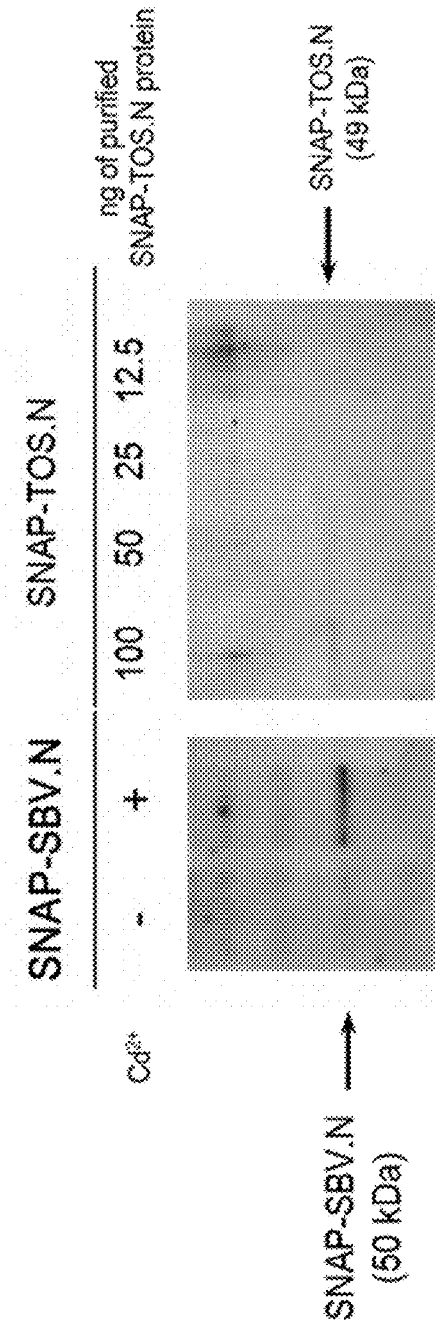
Figure 10:
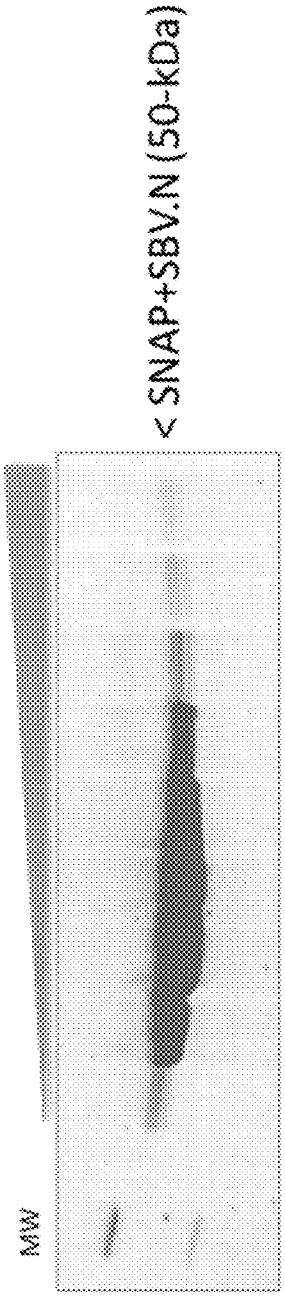

FIG. 10 shows (A) an immunoblot assay performed on the supernatants of S2/SNAP-SBV.N cells induced for 10 days with $Cd^{2+}$ (+) or non induced (−). The secreted chimeric protein SNAP-SBV.N (theorical MW 50 kDa) was detected using an anti-$His_{tag}$ antibody, in comparison to define amounts of highly purified chimeric protein SNAP-TOS.N (theorical MW 49 kDa). (B) Immunoblot performed on fractions of size-exclusion chromatography column (Coomassie blue staining of PAGE-SDS) corresponding to the final purification step of secreted SNAP+SBV.N protein from induced S2/SNAP+SBV.N cells for 10 days.

Figure 11:
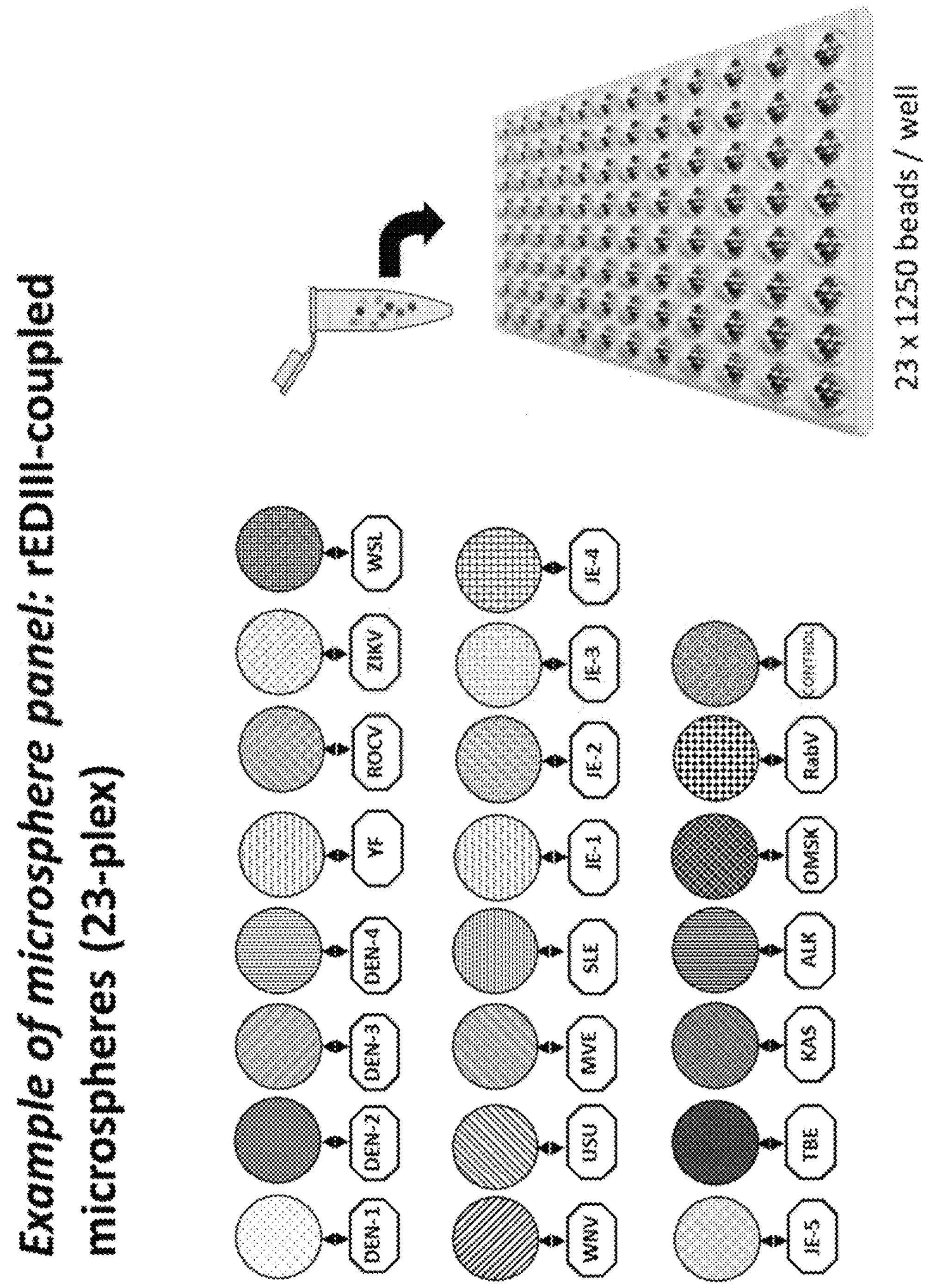

FIG. 11 shows an example of a device containing the antigen-coated microspheres of the invention.

DETAILED DESCRIPTION OF THE INVENTION

The 6-alkylguanine-DNA-alkyltransferase enzyme (AGT, also known as ATase or MGMT, and hereafter referred to as "AGT") is numbered EC 2.1.1.63 in the IUBMB enzyme nomenclature. It is a 6-alkylguanine-DNA-alkyltransferase DNA repair enzyme of 207 amino acid residues whose function in the cells is to repair alkylated DNA. More precisely, AGT acts on $O^6$-methylated guanine in DNA by irreversibly transferring the methyl group in an $S_N2$ reaction to a reactive cysteine residue (Cys 145). Recently, a number of O6-benzylguanine derivatives have been shown to irreversibly react with said enzyme by transferring their benzyl group to the active site cysteine of the AGT enzyme (cf. Damoiseaux et al., *ChemBiochem.*, 2001, WO 2004/031404 and WO 2005/085470).

The present inventors have developed and validated immunoassays leading to rapid and simultaneous detection of several antibodies generated by a wide range of diseases, in particular arboviral diseases and VHFs, in biological fluids.

To achieve both optimal sensitivity and specificity for the detection of low amount of antibodies, an oriented antigen coupling procedure has been developed. This oriented antigen coupling procedure is based on the covalent interaction between the AGT enzymes and their substrates, the O6-benzylguanine derivatives, which irreversibly react with AGT enzymes by transferring their benzyl group to the active site cysteine of the enzyme. Accordingly, a number of target antigens can be fused to an AGT enzyme moiety, resulting in different chimeric fusion proteins (hereafter referred to as [AGT-Antigen] fusion proteins), that can be used as capture reagents for the antibodies present in a biological sample. The present inventors have shown that this antibody capture is enhanced when these fusion proteins are bound to solid supports thanks to the specific AGT-substrate interaction. Coating the said solid supports with AGT-substrate is thus an essential step of the immunoassay of the invention.

More precisely, in the context of the invention, the method for coupling antigens to solid supports comprises the two following steps: i) the coating of solid surfaces with an AGT substrate (e.g. BG-PEG-amino), and ii) the covalent immobilization of chimeric [AGT-Antigen] fusion proteins using the AGT substrate as an anchor (see FIG. 1). Before being coated with said AGT substrate, the solid surfaces are advantageously functionalized, preferably by using an optimized two-step carbodiimide process (Kufer S K, *Eur. Biophys. J.* 2005), so that the AGT substrate is covalently attached to the solid surfaces. Once these steps have been performed, the solid surfaces carry AGT substrates that are irreversibly linked to the chimeric [AGT-antigen] fusion proteins. Due to the high specificity of this reaction, the fusion protein is exclusively coupled via the cysteine-containing domain of the AGT enzyme, thus leaving the antigen accessible for its interactions with antibodies.

This coupling procedure is very advantageous as it allows the binding of the antigen in an oriented manner on the solid supports. Also, this antigen coupling procedure advantageously enables to obtain a multimeric antigen organization on a solid surface, so as to enhance immunoglobulin G, and potentially immunoglobulin M, capture efficiency. Consequently, the antigen-coupled microspheres developed in the experimental part of the application have shown enhanced capture of specific antibodies as compared to antigen-coupled microspheres produced by standard non-oriented amine coupling procedures (see the experimental part below and FIG. 3). Finally, this antigen coupling procedure enables to obtain a high coupling efficiency and a long-term stability of the antigen-conjugated microspheres (>6 months at 4° C.).

Importantly, the solid supports used in the immunoassays of the invention should be intrinsically identifiable, so that it is possible to determine precisely which antigen is carried by which solid support. The antigen-coupled and identifiable solid supports are then used as capture reagents for specific human immunoglobulins and are therefore contacted with the biological sample of the patient.

The final step of the method of the invention involves the detection of the solid supports which are effectively bound to immunoglobulins. The identification of immunoglobulin-coated solid support(s) enables to diagnose which pathogen was infecting the patient (as each solid support matches with a defined pathogenic antigen). This final detection step is performed by any usual means, for example by using labeled detection antibodies and by identifying the nature of the solid support.

Advantageously, the method of the invention involves only the detection of the presence of antibodies in diseased patients, but knowledge about the identity of those antibodies is not required.

As shown in the experimental part of the application, the inventors have used the antigen-coupling procedure of the invention to generate a number of different antigen-coated fluorescent microspheres. Presently, 16 distinct sets of microspheres have been coupled with 16 purified chimeric [AGT-Antigen] fusion proteins, allowing titration of 16 serum antibodies specific to different proteins of the dengue serotypes 1 to 4, West Nile, yellow fever, Japanese encephalitis, tick-borne encephalitis, Saint-Louis encephalitis, Murray Valley encephalitis, Wesselsbron, Zika, Rocio, Usutu, Rift Valley fever, and chikungunya virus. These 16 distinct sets of microspheres have been mixed in a single sample without affecting the sensitivity and specificity of the detection (see FIG. 5). The production of this system is highly time- and cost-effective, as only a very small amount of recombinant antigen (<50 μg) is required to produce one set of antigen-coupled microspheres (~$1.25\times10^6$ microspheres), such set being sufficient to perform 500 individual assays.

In a first aspect, the present invention relates to a method for detecting at least two target antibodies in a biological sample comprising:

(a) contacting a first solid support comprising an AGT substrate covalently coupled to a first fusion protein comprising an AGT polypeptide having a O6-alkylguanine-DNA alkyltransferase activity and a first epitope that is recognized by a first target antibody with the biological sample;

(b) contacting a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody with the biological sample; and (c) detecting the presence or absence of the two target antibodies.

More precisely, the present invention relates to an in vitro assay method for detecting at least two different target antibodies present in a biological sample from a subject, said method comprising the steps of:

- (a) providing a first fusion protein comprising:
  - a polypeptide comprising a first epitope that is recognized by a first target antibody and
  - a AGT polypeptide having a O6-alkylguanine-DNA alkyltransferase activity,
- (b) contacting said first fusion protein with a first solid support, said support being covalently coupled with a substrate of said AGT polypeptide,
- (c) obtaining a first solid support covalently coupled with a first epitope that is recognized by the first target antibody,
- (d) providing a second fusion protein comprising:
  - a polypeptide comprising a second epitope, said second epitope being recognized by a second target antibody but not by said first target antibody, and
  - a AGT polypeptide having a O6-alkylguanine-DNA alkyltransferase activity,
- (e) contacting said second fusion protein with a second solid support, said support being covalently coupled with a substrate of said AGT polypeptide,
- (f) obtaining a second solid support covalently coupled with a second epitope that is recognized by the second target antibody, but not by said first target antibody, wherein said first and second solid supports can be specifically identified from each other,
- (g) contacting said biological sample with the first and second solid supports obtained in steps (c) and (f),
- (h) detecting the presence of said at least two target antibodies.

As used hereafter, the terms "an antibody", "a fusion protein", "an epitope", "an antigen", "an AGT polypeptide", "a solid support" and the like have obviously to be understood as usual in the art, that is, in a broad manner. In particular, they encompass not only particular single molecules but a number of said molecules. For example, the term "solid support" encompasses a subset of numerous identical solid supports, the term "microparticle" encompasses a subset of numerous identical microparticles, and the term "fusion protein" encompasses a number of identical single protein molecules. In the context of the present invention, it is noteworthy that a solid support carries a number of identical fusion proteins, said fusion proteins containing, apart from the AGT polypeptide, identical antigen, and therefore identical epitopes, so that the antibodies which will be detected on the solid support can be unambiguously identified.

As used herein, the term "fusion protein" means a polypeptide containing a protein or a polypeptide created through the artificial joining of two or more polypeptides. In the immunoassays of the invention, said fusion proteins contain a AGT polypeptide and an antigen, containing at least one epitope. Fusion proteins can be obtained through genetic engineering of a fusion gene. This typically involves removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either. If the two entities are proteins, a linker (or "spacer") peptides can be added, which makes it more likely that the proteins fold independently and behave as expected. In particular, the fusion proteins of the invention can be obtained by providing vectors comprising AGT encoding sequences in frame with an epitope or antigen encoding sequences, either attached to the N-terminal or to the C-terminal side of the AGT DNA sequence. These vectors may be introduced in prokaryotic hosts, including eubacteria such as *E. coli* bacteria, or eukaryotic hosts, e.g., yeast, insect cells or mammalian cells and the recombinant fusion proteins may be produced under appropriate conditions. Typical constructions are presented in the experimental part of this application.

The term "antibody" as used herein is intended to include monoclonal antibodies, polyclonal antibodies, and chimeric antibodies. Preferably, the antibodies which are to be detected by the immunoassays of the invention are polyclonal antibodies, which are present in biological samples of diseased patients, and have therefore been generated from different B cell sources. As such, they recognize different epitopes exhibited by a pathogenic antigen (on the other hand, monoclonal antibodies are derived from a single cell line and recognize the same epitope).

An antibody (or "immunoglobulin") consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

Antibody can be of different isotypes (namely IgA, IgD, IgE, IgG or IgM). Both IgG and IgM type antibodies can be detected by the present method. Of note, these isotypes are composed of two identical heavy chains and two identical light chains that are joined by disulfide bonds. Importantly, IgM antibodies form polymers where multiple immunoglobulins are covalently linked together with disulfide bonds, mostly as a pentamer but also as a hexamer, so that they have a molecular mass of approximately 900 kDa (in their pentamer form). Because each monomer has two antigen binding sites, a pentameric IgM has 10 binding sites. Typically, however, IgM antibodies cannot bind 10 antigens at the same time because the large size of most antigens hinders binding to nearby sites. Due to its polymeric nature, IgM possesses high avidity.

Antibody fragments can also be detected thanks to the present method. This term is intended to include Fab, Fab', F(ab')2, scFv, dsFv, ds-scFv, dimers, minibodies, diabodies, and multimers thereof and bispecific antibody fragments.

Monoclonal antibodies can be used in the present immunoassays; for example for detecting the immunoglobulins that are bound to the solid supports. As used herein, “monoclonal antibody” defines an antibody arising from a homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

The term “antigen” herein means any substance that causes the immune system to produce antibodies against the said substance. An “immunogenic” antigen is a specific type of antigen which is able to stimulate an adaptive immune response if injected on its own. At the molecular level, an antigen is thus characterized by its ability to be “bound” to the antigen-binding site of an antibody.

In the context of the present invention, an antibody is said to “bind” a define antigen (or epitope) or to “recognize” said antigen (or epitope) if said antibody has an affinity constant $K_a$ (which is the inverted dissociation constant, i.e. $1/K_d$) higher than $10^5$ $M^{-1}$, preferably higher than $10^6$ $M^{-1}$, more preferably higher than $10^7$ $M^{-1}$ for said antigen (or epitope). This affinity can be measured for example by equilibrium dialysis or by fluorescence quenching, both technologies being routinely used in the art.

In the context of the invention, antigens or epitopes include: proteins, lipoproteins, polysaccharides, and glycoproteins. Said proteins include viral, bacterial, parasitic, animal, and fungal proteins such as albumins, tetanus toxoid, diphtheria toxoid, pertussis toxoid, bacterial outer membrane proteins (including meningococcal outer membrane protein), RSV-F protein, malarial derived peptide, B-lactoglobulin B, aprotinin, ovalbumin, lysozyme, linear peptides, oligopeptides etc. Said antigens can also be tumor associated antigens such as carcinoembryonic antigen (CEA), CA 15-3, CA 125, CA 19-9, prostate specific antigen (PSA), TAA complexes, SSX2 or NERCMSL. Said antigens can also be haptens, and other moieties comprising low molecular weight molecules, such as saccharides, oligosaccharides, polysaccharides, peptides, mucins, toxins, and allergens (pollen, egg white). Infectious toxins are well known in the art. One can cite, as examples, the botulinum neurotoxins, the *Clostridium perfringens* epsilon toxin, ricin, saxitoxin, shigatoxin, tetrodotoxin, staphylococcal enterotoxins, etc. Mucins are also well known in the art. MUC5AC, MUC5B and MUC2 are examples thereof. In particular, they can be naturally-occurring polysaccharides such as Group B steptococcal and pneumococcal capsular polysaccharides (including type III), *Pseudomonas aeruginosa* mucoexopolysaccharide, and capsular polysaccharides (including fisher type I), and *Haemophilus influenzae* polysaccharides.

In another preferred embodiment, said antigen or epitope is expressed by a virus which is selected in the group consisting of: the influenza virus, the hepatitis A virus, the Hepatitis B virus, the Hepatitis C virus, the Hepatitis E virus, the Hepatitis G virus, the HIV virus, the yellow fever virus, the dengue virus, the Japanese encephalitis virus, the tick-borne encephalitis virus, the Usutu or West Nile viruses, the Rift Valley fever or Toscana viruses, the chikungunya virus, the respiratory synticial virus, the Rocio virus, the morbillivirus, the Murray encephalitis virus, the Wesselbron virus, the Zika virus, the lymphocytic choreomeningitis virus, the Ebola virus, the Marburg virus, the Crimean-Congo hemorrhagic fever virus, the Lassa virus, the Junin virus, the Machupo virus, the Sabia virus, the Guanarito virus, the mumps virus, the rabies virus, the rubella virus, the varicella zoster virus, the herpes simplex types 1 and 2, more generally an alphavirus, an adenovirus, an echovirus, a rotavirus, a flavivirus, a rhinovirus, an orthobunyavirus, a poliovirus, a human parvovirus, an enterovirus, a coronavirus, a human papillomavirus, the human cytomegalovirus, the Epstein-Barr virus, the parainfluenzae viruses from types 1, 2 and 3, or any identified virus.

In another preferred embodiment, said antigen or epitope is expressed by a virus belonging to a family which is selected from the group consisting of: the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg).

In another preferred embodiment, said antigen or epitope is expressed by a parasitic protozoa (such as those from the *Leishmania* genus, or *Toxoplasma Gondii, Entamoeba histolytica, Plasmodium falciparum, Pneumocystis carinii*, or *Giardia lamblia*), worms (such as nematodes, cestodes, or trematodes), or arthropods (such as crustaceans, insects, arachnids).

In another preferred embodiment, said antigen or epitope is expressed by an infectious bacterium, for example of the genera *Salmonella, Shigella, Streptococcus, Staphylococ-*

*cus, Mycoplasma, Diphteriae, Leptospirosa, Rickettsia* or *Escherichia*. In a further preferred embodiment, the said bacterium belongs to one of the species selected from *H. influenzae, S. pneumoniae, Klebsiella pneumoniae, S. aureus, Bacillus anthracis, Listeria monocytogenes, Bordetella pertussis, Clostridium tetani, S. epidermidis, N. meningiditis, Pseudomonas aeruginosa, Chlamydia trachomatis, Mycobacterium tuberculosis, Coxiella burnetii, Leptospirosa interrogans* and *E. coli*.

In another preferred embodiment, said antigen or epitope is expressed by a fungus or yeast (e.g. from the species *Candida, Aspergillus, Cryptococcus, Histoplasma, Pneumocystis*, or *Stachybotrys*).

Antigens usually present several surface features that can act as points of interaction for specific antibodies. Any such distinct molecular feature constitutes an epitope. As used herein, the term "epitope" therefore designates a particular molecular surface feature of an antigen, for example a fragment of an antigen, which is capable of being bound by at least one antibody. On a molecular level, an epitope therefore corresponds to a particular molecular surface feature of an antigen (for example a fragment of an antigen) which is recognized and bound by a specific antibody. In the context of the present invention, the "fusion proteins" contain at least one epitope that is recognized by a target antibody. Preferably, said fusion proteins contain whole antigens, comprising several epitopes. These epitopes can be linear or conformational epitopes. As used herein, a linear (or sequential) epitope is an epitope that is recognized by antibodies by its linear sequence of amino acids, or primary structure. In contrast, a conformational epitope is recognized by its specific three-dimensional shape. Preferably, the fusion proteins of the invention contain conformational epitopes, as most polyclonal antibodies recognize same.

It is important however that such antigens do not present cross-reactive epitopes, i.e. epitopes that are recognized by non-specific antibodies that will bind thereto. If it was the case, the specificity of the method of the invention would be decreased.

In a more preferred embodiment, said epitope is present on a viral protein which is selected in the group consisting of: the EDIII protein of the dengue virus 1 encoded by SEQ ID NO:3, the EDIII protein of the dengue virus 2 encoded by SEQ ID NO:4, the EDIII protein of the dengue virus 3 encoded by SEQ ID NO:5, the EDIII protein of the dengue virus 4 encoded by SEQ ID NO:6, the EDIII protein of the West Nile virus encoded by SEQ ID NO:7, the EDIII protein of the yellow fever virus encoded by SEQ ID NO:8, the EDIII protein of the Japanese encephalitis virus encoded by SEQ ID NO:9, the EDIII protein of the Zika virus encoded by SEQ ID NO:10, the EDIII protein of the Wesselbron virus encoded by SEQ ID NO:11, the EDIII protein of the Rocio virus encoded by SEQ ID NO:12, the EDIII protein of the Murray encephalitis virus encoded by SEQ ID NO:13, the EDIII protein of the Saint-Louis encephalitis virus encoded by SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, and the EDIII protein of the Rabensburg virus encoded by SEQ ID NO:58 and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

In a preferred embodiment, the first and second epitopes (or antigens) that are fused with the hAGT enzyme in the fusion proteins used in the method of the invention belong to the same taxonomic level, i.e. they belong to the same family (e.g. the Flaviviridae family, the Bunyaviridae family, the Arenaviridae family or the Filoviridae family) or genus or species, but which have different serotypes. In other words, the said first and second epitopes can be expressed by closely related viruses, e.g. belong to the same family, genus or species but having different serotypes such as the dengue virus 1, 2, 3, or 4.

Alternatively, in another preferred embodiment, said first and second epitopes (or antigens) belong to unrelated biological families or genus or specie.

Importantly, the immunoassays of the invention rely on the detection of a large number of antibodies, which are known or unknown. By "large number", it is herein understood at least 5, more preferably at least 15, more preferably at least 50 and even more preferably at least 100 antibodies. Therefore, in a preferred embodiment, the assay method of the invention is used to detect at least 5, more preferably at least 15, and preferably at least 50 and even more preferably at least 100 target antibodies in a biological sample from a subject. It is of no relevance for the method of the invention whether the particular antibodies are properly characterized, since the procedure relies only on the detection of the presence of said antibodies, and not on their nature.

In a preferred embodiment of the invention, the said first and second fusion proteins that are coupled with the said first and second solid supports are selected in the group consisting of:

SEQ ID NO:21 (corresponding to the fusion protein [SNAP-DEN1.EDIII])

SEQ ID NO:42 (corresponding to the fusion protein [SNAP-SBV.N])

SEQ ID NO:49 (corresponding to the fusion protein [SNAP-EV71.VP1])

SEQ ID NO:51 (corresponding to the fusion protein [SNAP-JE.sE])

SEQ ID NO:53 (corresponding to the fusion protein [SNAP-JE-1.EDIII])

SEQ ID NO:60 (corresponding to the fusion protein [SNAP-JE-2.EDIII])

SEQ ID NO:62 (corresponding to the fusion protein [SNAP-JE-4.EDIII])

SEQ ID NO:64 (corresponding to the fusion protein [SNAP-JE-5.EDIII])

SEQ ID NO:66 (corresponding to the fusion protein [SNAP-RabV.EDIII])

SEQ ID NO:68 (corresponding to the fusion protein [SNAP-flavivirus.EDIII])

SEQ ID NO:70 (corresponding to the fusion protein [SNAP-RR.sE2])

SEQ ID NO:72 (corresponding to the fusion protein [SNAP-MAY.sE2])

SEQ ID NO:74 (corresponding to the fusion protein [SNAP-WEE.sE2])

SEQ ID NO:76 (corresponding to the fusion protein [SNAP-EEE.sE2])

SEQ ID NO:78 (corresponding to the fusion protein [SNAP-VEE.sE2])

SEQ ID NO:80 (corresponding to the fusion protein [SNAP-AKA.N])

SEQ ID NO:82 (corresponding to the fusion protein [SNAP-AIN.N])
SEQ ID NO:84 (corresponding to the fusion protein [SNAP-SHA.N])
SEQ ID NO:86 (corresponding to the fusion protein [SNAP-huCOV.N])
SEQ ID NO:88 (corresponding to the fusion protein [SNAP-huCOV.S])
SEQ ID NO:90 (corresponding to the fusion protein [SNAP-HCV.C])
SEQ ID NO:92 (corresponding to the fusion protein [SNAP-MSP+AMA])
SEQ ID NO:94 (corresponding to the fusion protein [SNAP-HbpA1])
SEQ ID NO:96 (corresponding to the fusion protein [SNAP-MUB40])
SEQ ID NO:98 (corresponding to the fusion protein [SNAP-moCLEC5A])
SEQ ID NO:100 (corresponding to the fusion protein [SNAP-huCLEC5A])
SEQ ID NO:102 (corresponding to the fusion protein [SNAP-cxVAGO])
SEQ ID NO:104 (corresponding to the fusion protein [SNAP-aaVAGO])
SEQ ID NO:109 (corresponding to the fusion protein [SNAP-CCHF.N])
SEQ ID NO:111 (corresponding to the fusion protein [SNAP-EBO.N])
SEQ ID NO:113 (corresponding to the fusion protein [SNAP-MAR.N])
SEQ ID NO:115 (corresponding to the fusion protein [SNAP-LAS.N])
SEQ ID NO:117 (corresponding to the fusion protein [SNAP-JUN.N])
SEQ ID NO:119 (corresponding to the fusion protein [SNAP-MAC.N])
SEQ ID NO:121 (corresponding to the fusion protein [SNAP-GUA.N])
SEQ ID NO:123 (corresponding to the fusion protein [SNAP-SAB.N])
SEQ ID NO:125 (corresponding to the fusion protein [SNAP-OMSK.EDIII])
SEQ ID NO:127 (corresponding to the fusion protein [SNAP-KYA.EDIII])
SEQ ID NO:129 (corresponding to the fusion protein [SNAP-ALK.EDIII])
SEQ ID NO:131 (corresponding to the fusion protein [SNAP-LAS.ectoGP1])
SEQ ID NO:133 (corresponding to the fusion protein [SNAP-JUN.ectoGP1])
SEQ ID NO:135 (corresponding to the fusion protein [SNAP-MAC.ectoGP1])
SEQ ID NO:137 (corresponding to the fusion protein [SNAP-GUA.ectoGP1])
SEQ ID NO:139 (corresponding to the fusion protein [SNAP-SAB.ectoGP1])
SEQ ID NO:141 (corresponding to the fusion protein [SNAP-LAS.ectoGP2])
SEQ ID NO:143 (corresponding to the fusion protein [SNAP-JUN.ectoGP2])
SEQ ID NO:145 (corresponding to the fusion protein [SNAP-MAC.ectoGP2])
SEQ ID NO:147 (corresponding to the fusion protein [SNAP-GUA.ectoGP2])
SEQ ID NO:149 (corresponding to the fusion protein [SNAP-SAB.ectoGP2]), and
SEQ ID NO:151 (corresponding to the fusion protein [SNAP-HEV.C]).

Consequently, the in vitro method of the invention enables to detect target disease(s) that is (are) viral, bacterial, yeast or fungi-mediated infection. Preferably said viral infection is caused by a Papillomavirus or RNA viruses from the families of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) and the Filoviridae (Ebola, Marburg). Preferably, said bacterial infection is caused by *Leptospirosa Interrogans*. Preferably, said infection is caused by *Plasmodium falciparum*.

As used herein, the term "biological sample" refers to any samples which have been obtained from a patient and which might contain antibodies. Preferably, said biological sample is a biological fluid, for example an unfiltered biological fluid such as urine, cerebrospinal fluid, pleural fluid, synovial fluid, peritoneal fluid, amniotic fluid, gastric fluid, blood, serum, plasma, lymph fluid, interstitial fluid, saliva, physiological secretions, tears, mucus, sweat, milk, semen, seminal fluid, vaginal secretions, fluid from ulcers and other surface eruptions, blisters, and abscesses. It also refers to an extract of tissues including biopsies of normal, malignant, and suspect tissues or any other constituents of the body which may contain antibodies. The said biological sample can be pre-treated prior to use, such as preparing plasma from blood, diluting viscous fluids, or the like; methods of treatment can involve filtration, distillation, concentration, inactivation of interfering compounds, and the addition of reagents. In a preferred embodiment, said biological sample is chosen from whole blood, serum, plasma, urine, seminal fluid, cerebrospinal fluid and saliva.

Any polypeptide having $O^6$-alkylguanine-DNA alkyltransferase activity can be used in the method of the present invention. For the purpose of the invention, these polypeptides will be referred to as "AGT polypeptides".

AGT irreversibly transfers the alkyl group from its substrate, $O^6$-alkylguanine-DNA, to one of its cysteine residues. A substrate analogue that rapidly reacts with AGT is $O^6$-benzyl-guanine, the second order rate constant being approximately $10^3$ $sec^{-1}$ $M^{-1}$.

In the context of the invention, a polypeptide is said to have "$O^6$-alkylguanine-DNA alkyltransferase activity" (or "AGT activity") if it is capable of irreversibly transferring an alkyl group from a $O^6$-alkylguanine-containing molecule to one of its own cysteine residues. The "O6-alkylguanine-DNA alkyltransferase activity" of the said polypeptide can be demonstrated by, for example, contacting known labeled $O^6$-benzyl-guanine derivatives and monitoring the transfer of said label on to the tested polypeptide. If the assay is performed in cellulo or in cell extracts, the reaction of the endogenous AGT of the host cells should be controlled, so that endogenous AGT does not interfere with the said polypeptide. Therefore, known AGT-deficient cell lines are preferably used. Assays for identifying AGT activity are now well described. Several $O^6$-benzyl-guanine derivatives are commercially available ($O^6$-benzyl-guanine is distributed for example by Santa Cruz biotechnology, and fluorescently-labeled $O^6$-benzyl-guanine derivatives can be obtained from New England Biolabs NEB). Some of these assays are disclosed in WO 2005/085470 and in WO 2004/031405.

In the context of the invention, the "catalytic domain" of the AGT polypeptide corresponds to the active site of said enzyme, or, in other words, to the part of the enzyme at which the transfer of the alkyl group from its substrate, $O^6$-alkylguanine-DNA, to a reactive cysteine residue, occurs. In the structure of hAGT bound with $O^6$-benzylguanine in its active site, four amino acids are in proximity of either the benzyl ring (Pro140, Ser159, Gly160), or could make contact with the N9 of the nucleobase (Asn157). Mutations at position Pro140 and Gly160 have previously been shown to affect the reaction of hAGT with $O^6$-benzylguanine (Xu-Welliver et al., Biochemical Pharmacology 1999): a proline at position 140 is believed to be essential for its interaction with the benzyl ring, and the mutation Gly160Trp has been shown to increase the reactivity of hAGT towards $O^6$-benzylguanine.

In a preferred embodiment, the AGT polypeptide having $O^6$-alkylguanine-DNA alkyltransferase activity is the human AGT polypeptide (referenced as NP_002403.2) of sequence SEQ ID NO: 1, the mouse AGT identified as NP_032624.1 (SEQ ID NO: 18), the rat MGMT identified as NP_036993.1 (SEQ ID NO: 19) or a homologous sequence thereof, said homologous sequence having $O^6$-alkylguanine-DNA alkyltransferase activity.

As used herein, the term "homologous" refers to sequences that have sequence similarity. The term "sequence similarity", in all its grammatical forms, refers to the degree of identity or correspondence between nucleic acid or amino acid sequences. In the context of the invention, two amino acid sequences are "homologous" when at least about 80%, alternatively at least about 81%, alternatively at least about 82%, alternatively at least about 83%, alternatively at least about 84%, alternatively at least about 85%, alternatively at least about 86%, alternatively at least about 87%, alternatively at least about 88%, alternatively at least about 89%, alternatively at least about 90%, alternatively at least about 91%, alternatively at least about 92%, alternatively at least about 93%, alternatively at least about 94%, alternatively at least about 95%, alternatively at least about 96%, alternatively at least about 97%, alternatively at least about 98%, alternatively at least about 99% of the amino acids are similar. Preferably the similar or homologous polypeptide sequences are identified by using the algorithm of Needleman and Wunsch.

Preferably, the homologous sequence to the AGT enzyme shares at least 64% amino acid sequence identity, preferably at least about 65% amino acid sequence identity, alternatively at least about 66% amino acid sequence identity, alternatively at least about 67% amino acid sequence identity, alternatively at least about 68% amino acid sequence identity, alternatively at least about 69% amino acid sequence identity, alternatively at least about 70% amino acid sequence identity, alternatively at least about 71% amino acid sequence identity, alternatively at least about 72% amino acid sequence identity, alternatively at least about 73% amino acid sequence identity, alternatively at least about 74% amino acid sequence identity, alternatively at least about 75% amino acid sequence identity, alternatively at least about 76% amino acid sequence identity, alternatively at least about 77% amino acid sequence identity, alternatively at least about 78% amino acid sequence identity, alternatively at least about 79% amino acid sequence identity, alternatively at least 80% amino acid identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity with SEQ ID NO: 1. In a preferred embodiment, an homologous sequence of SEQ ID NO: 1 is at least 64%, preferably 70%, and more preferably 80% identical to SEQ ID NO: 1.

In a preferred embodiment, the said homologous polypeptide is a fragment or a mutant of the hAGT polypeptide of SEQ ID NO: 1, said fragment or mutant having a $O^6$-alkylguanine-DNA alkyltransferase activity.

Said fragments can have a size of at least 50, preferably 100, and more preferably 150 amino acids, and contain at least the "catalytic domain" of the AGT polypeptide as defined above, which is responsible of the $O^6$-alkylguanine-DNA alkyltransferase activity of the AGT enzyme. These fragments can be obtained using common techniques which are known by the skilled person.

Different mutant enzymes derived from native AGT have been described so far (Lim A. et al, 1996; Daniels D. S. et al, 2000; Juillerat A. et al, 2003, WO 2005/085470, WO 2004/031405). In particular, a mutant protein of 20 kDa containing the mutations Cys62Ala, Lys125Ala, Ala127Thr, Arg128Ala, Gly131Lys, Gly132Thr, Met134Leu, Arg135Ser, Cys150Ser, Asn157Gly, Ser159Glu truncated at amino acid 182 has been obtained (the so-called "AGT26" mutant in WO 2005/085470, also called "SNAP 26" in WO 2006/114409). This particular mutant "SNAP26" has been shown to have enhanced labelling activity.

In the context of the present invention, the sequence of a more preferred AGT polypeptide contains the mutations described in WO 2005/085470, which positions can be easily transposed in view of SEQ ID NO: 1, the starting methionine residue of SNAP26 corresponding to the methionine residue in position 32 of SEQ ID NO: 1 (31 amino acids should therefore be added to the positions disclosed in WO 2005/085470 so as to obtain the corresponding ones in SEQ ID NO: 1).

In a preferred embodiment, the AGT homologous sequence useful in the invention corresponds to the native AGT sequence of SEQ ID NO: 1, in which between 1 and 30, preferably between 6 and 25, and in particular 14, 15, 16, 17, 18, 19, 20, 21, 22, or 23 amino acids are substituted by other amino acids, and/or 1 to 40, preferably 1 to 20, in particular 10 to 20 amino acids, more preferably 15 amino acids at the C-terminus are deleted.

In a more preferred embodiment, the AGT homologous sequence contains the following mutations as compared with SEQ ID NO: 1:

(A) Lys31 replaced by Arg, or Met32 replaced by Ser, or Cys93 replaced by Ala, or Lys156 replaced by Ala, or Ala158 replaced by Thr, or Arg159 replaced by Ala, or Gly162 replaced by Lys, or Gly163 replaced by Thr, or Met165 replaced by Leu, or Arg166 replaced by Ser, or Cys181 replaced by Ser, or Asn188 replaced by Gly, or Ser190 replaced by Glu, or Gly214 replaced by Pro, or Ser215 replaced by Ala, or Ser216 replaced by Gly, or Gly217 replaced by Ile, or Leu218 replaced by Gly, or Gly220 replaced by Pro, or Ala221 replaced by Gly, or Trp222 replaced by Ser, or (B) Lys31-Met32 replaced by Arg-Ser, or Ala158-Arg159 replaced by Thr-Ala, or Gly162-Gly163 replaced by Lys-Thr, or Met165-Arg166 replaced by Leu-Ser, or Gly162-Gly163/Met165-Arg166 replaced by Lys-Thr/Leu-Ser, or Asn188/Ser190 replaced by Gly/Glu, or Gly214-Ser215-Ser216-Gly217-Leu218 replaced by Pro-Ala-Gly-Ile-Gly, or Gly220-Ala221-Trp222 replaced by Pro-Gly-Ser, preferably in combination with any other amino acid replacements cited in (A), or (C) Truncation after Leu223 (amino acids 224-238 are deleted), preferably in combination with any other amino acid replacement cited in (A) or (B).

Preferred AGT homologous sequences are those being truncated after Leu223.

Preferred AGT homologous sequences are those wherein two out of the modifications (B) are present, and optionally truncation after Leu223.

Preferred AGT homologous sequences are those wherein three out of the modifications (B) are present, and optionally truncation after Leu223.

Preferred AGT homologous sequences are those wherein four out of the modifications (B) are present, and optionally truncation after Leu223.

Preferred AGT homologous sequences are those wherein five out of the modifications (B) are present, and optionally truncation after Leu223.

Preferred AGT homologous sequences are those wherein six out of the modifications (B) are present, and optionally truncation after Leu223.

Other preferred AGT homologous sequences are those containing a combination of 2, 3, 4, 5, 6, 7, 8, 9, 10, 11, 12, 13, 14, 15, 16, 17, 18, 19, or 20 mutations chosen among the modifications disclosed in (A), and optionally truncated after Leu223.

In a far more preferred embodiment, the AGT polypeptide of the invention is the SNAP mutant of SEQ ID NO: 2, which is homologous to the hAGT enzyme and contains the mutations Lys31Arg, Met32Ser, Cys93Ala, Lys156Ala, Ala158Thr, Arg159Ala, Gly162Lys, Gly163Thr, Met165Leu, Arg166Ser, Cys181Ser, Asn188Gly, Ser190Glu, Gly214Pro, Ser215Ala, Ser216Gly, Gly217Ile, Leu218Gly, Gly220Pro, Ala221Gly, Trp222Ser and truncation after Leu223 as compared with SEQ ID NO: 1. The SNAP mutant of SEQ ID NO: 2 shares 77% homology with the amino acid sequence of the human 6-methylguanine-DNA-methyltransferase (NP_002403.2, SEQ ID NO: 1), and 70% homology with the amino acid sequence of the mouse 6-methylguanine-DNA-methyltransferase (NP_032624.1, SEQ ID NO: 18).

In an even more preferred embodiment, the AGT enzyme is the SNAP mutant protein of SEQ ID NO: 2 or a homologous thereof, having $O^6$-alkylguanine-DNA alkyltransferase activity. Preferably, said homologous sequence to the SNAP mutant protein is at least identical at more than 80%, preferably 81%, more preferably 82%, more preferably 83%, more preferably 84%, more preferably 85%, preferably 86%, more preferably 87%, more preferably 88%, more preferably 89%, more preferably 90%, more preferably 91%, more preferably 92%, more preferably 93%, more preferably 94%, more preferably 95%, more preferably 96% to the and even more preferably 97% to the SNAP mutant protein of sequence SEQ ID NO: 2, and has $O^6$-alkylguanine-DNA alkyltransferase activity as defined above.

Said homologous polypeptides having $O^6$-alkylguanine-DNA alkyltransferase activity can be produced using protein engineering techniques known to the skilled person and/or using molecular evolution to generate and select new $O^6$-alkylguanine-DNA alkyltransferases. Such techniques are e.g. targeted mutagenesis, phage display methods, saturation mutagenesis, error prone PCR to introduce variations anywhere in the sequence, DNA shuffling used after saturation mutagenesis and/or error prone PCR, or family shuffling using genes from several species.

In the most preferred embodiment, the AGT polypeptide used in the method of the invention is the SNAP mutant of SEQ ID NO: 2.

The AGT enzyme irreversibly transfers the alkyl group from its substrate, $O^6$-alkylguanine-DNA, to one of its cysteine residues. However, substitutions of $O^6$-benzylguanine at the C4 of the benzyl ring do not significantly affect the reactivity of AGT against $O^6$-benzylguanine derivatives. This property has been used to transfer a label attached to the C4 of the benzyl ring to AGT (see WO 2004/031404 and WO 2005/085470).

A number of $O^6$-benzylguanine derivatives have been shown to react with the AGT enzyme by transferring their benzyl group to the active site cysteine of the AGT enzyme (cf. Damoiseaux et al., *ChemBiochem.*, 2001, WO 2004/031404 and WO 2005/085470).

In a preferred embodiment, the AGT substrates used in the method of the invention are $O^6$ benzyl guanine derivatives having the formula I:

$$R1\text{-}X—CH_2—R3\text{-}R4\text{-}Y$$

wherein:

R1 is a group recognized by said AGT polypeptide as a substrate, such as a heteroaromatic group containing 1 to 5 nitrogen atoms, and preferably a purine radical of the formula:

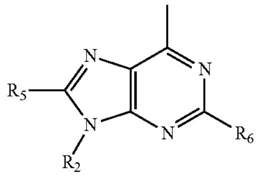

wherein R5 is hydrogen, halogen, e.g. chloro or bromo, trifluoromethyl, or hydroxy; R6 is hydrogen, hydroxy or unsubstituted or substituted amino; and R2 is hydrogen, an alkyl of 1 to 10 carbon atoms, or a saccharide moiety;

X is an oxygen or sulfur atom; preferably an oxygen atom;

R3 is an aromatic or a heteroaromatic group, or an optionally substituted unsaturated alkyl, cycloalkyl or heterocyclyl group with the double bond connected to $CH_2$; preferably a phenyl, e.g. a phenyl substituted by R4 in para or meta position, R4 is a linker moiety, Y is a reactive group, preferably an amino group.

In a preferred embodiment, said linker moiety $R_4$ is a flexible linker. Linker units are chosen in the context of the envisioned application, i.e. in the transfer of the substrate to a fusion protein comprising AGT. The linker does not interfere with the reaction with AGT nor with the target antibody.

For example, it can be a straight or branched chain alkylene group with 1 to 20 carbon atoms, preferably 5 to 15 carbon atoms, wherein:

(a) one or more carbon atoms are replaced by oxygen, in particular wherein every third carbon atom is replaced by oxygen, e.g. a poylethyleneoxy group with 1 to 5 ethyleneoxy units;

(b) one or more carbon atoms are replaced by nitrogen carrying a hydrogen atom, and the adjacent carbon atoms are substituted by oxo, representing an amide function —NH—CO—;

(c) one or more carbon atoms are replaced by oxygen, and the adjacent carbon atoms are substituted by oxo, representing an ester function —O—CO—;

(d) the bond between two adjacent carbon atoms is a double or a triple bond, representing a function —CH═CH— or —C≡C—;

(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;

(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

In a preferred embodiment, R4 is a polyethyleneoxy group with 1 to 8 ethyleneoxy units, further comprising one to four nitrogen atoms carrying a hydrogen atom, which adjacent carbon atoms are substituted by oxo, representing an amide function —NH—CO—.

In a more preferred embodiment, R4 is $—CH_2—NH—CO—NH—[C_2H_4—O]_n—$, wherein n is comprised between 1 to 8, preferably 2 to 6, and is most preferably 3.

In a preferred embodiment, said reactive group is a functional group that facilitates the attachment and bonding of the substrate on the solid support. Such functional groups are well-known in the art. They include amine, activated esters, acrylamides, acyl azides, acyl halides, acyl nitriles, aldehydes, ketones, alkyl halides, anhydrides, aryl halides, aziridines, boronates, activated carnoxylic acids, carbodiimides, diazoalkanes, epoxides, haloacetamides, haloplatinate, halotriazines, imido esters, isocyanates, isothiocyanates, maleimides, phosphoramidites, solyl halides, sulfonate esters and sulfonyl halides. It is preferably the amine group $—NH_2$.

On the opposite side, the solid support should be functionalized by complementary groups corresponding to such reactive groups. The complementary groups corresponding to each of these reactive groups are well-known in the art. They are given for example on the table I of WO 2010/107433.

In a preferred embodiment, the AGT substrate used in the method of the invention is:

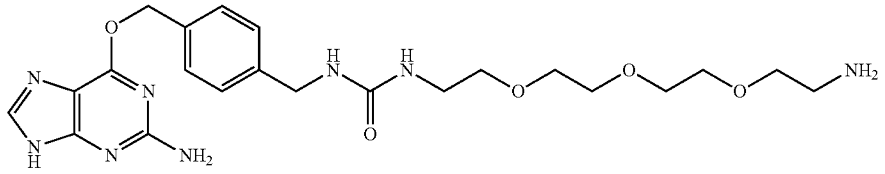 [SMILES: NCCOCCOCCOCCNC(=O)NCc1ccc(COc2nc(N)nc3[nH]cnc23)cc1]

In another preferred embodiment, the AGT substrate used in the method of the invention is the fluorescent linker designated "SNAP-cell® 505", having the following formula:

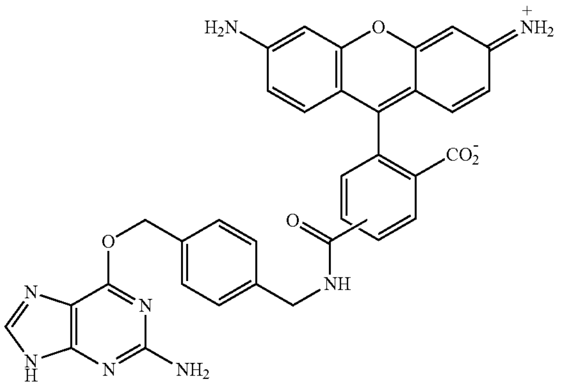

This benzylguanine derivative possesses one benzyl purine group (guanine) for the specific interaction with the SNAP domain, as well as one free amine group for the covalent coupling to the microsphere surface. It is commercialized by New England BioLaps and has been successfully coupled to the surface of the microparticles of the invention.

Substrates of the invention are generally prepared by standard methods known in the art. Particular methods are explained e.g. in patent application WO 2005/085470.

The methods of the invention require that the AGT substrates be covalently coupled to the solid supports. In the context of the present invention, an AGT substrate is "covalently coupled" to a solid support if it is permanently attached to the said solid support, and will not desorb or leach over time. According to the invention, an AGT substrate is permanently attached to the said solid support if it stays attached for a long period of storage, e.g., typically, at least 6 months of storage. A number of coupling proceedings have been described so far. Any of these coupling proceedings can be used in the immunoassay of the invention, provided that the AGT substrate becomes permanently attached to the solid support.

In the immunoassay of the invention, the covalent coupling is preferably performed by contacting the AGT substrates (with contain a reactive group Y, as mentioned above) with solid supports which have been previously functionalized with a complementary group such as those disclosed in table I of WO 2010/107433, the disclosure of which is incorporated herein by reference.

Thus, in a preferred embodiment, the methods of the invention use solid supports that have been functionalized with a group which is complementary to the reactive group of the AGT substrate, before being contacted with the AGT substrate.

A preferred and conventional procedure for covalently coupling an AGT substrate to the surface of solid supports is based on the carbodiimide reaction and uses water-soluble carbodiimide. According to this procedure, solid supports have surface carboxyl groups available for attachment of the reactive amine- or sulfhydryl-containing AGT substrate. Thus, in this preferred embodiment, the methods of the invention use solid supports that have been functionalized with surface carboxyl groups prior to be contacted with the AGT substrate.

In this case, the first step of the method of the invention is to activate the carboxyl groups coating the solid supports. This activation is usually performed by adding a so-called "activation buffer", for example a 50 mg/mL EDAC solution or a 50 mg/mL S-NHS solution. These solutions are commercially available. Activation of the solid supports is typically performed by incubating said supports with the activation buffer at room temperature for a few minutes (e.g. 5 minutes to 30 minutes), according to the manufacturer's instructions.

Importantly, covalent coupling of the AGT substrate to the solid support has to be performed under particular conditions, so as to preserve the AGT substrate solubility and the integrity of the bead (internal fluorochrome). The inventors have observed that the AGT substrates should be suspended in a "covalent coupling" buffer containing between 0 and 20% of dimethylsulfoxide (DMSO). In particular, the inventors have observed that concentrations of DMSO above 20% may affect the detection step of the methods of the invention. Preferably, said buffer is a PBS buffer containing between 0 and 20% of DMSO, more preferably between 10% and 20% of DMSO.

Advantageously, the unspecific sites on the solid supports that have not been covalently attached to the AGT substrate can be further blocked by any conventional means, for example, by using a blocking buffer containing 1% of bovine serum albumin (BSA) or any saturating protein (e.g. casein).

Once the solid supports of the invention have been covalently coupled with the AGT substrate (preferably through a carbodiimide covalent linkage), the solid supports are then contacted by the fusion proteins of the invention, so as to couple the epitopes that are specifically recognized by the target antibodies to said supports.

Again, this coupling step has to be performed under particular conditions. As a matter of fact, the catalytic site of the AGT enzyme and the conformational structure of the antigens/epitopes which are carried by the fusion proteins have to be conserved during the coupling proceedings. The inventors identified that the fusion protein should be suspended in a dithiothreitol (DTT)-containing buffer, preferably a PBS/DTT buffer, for the coupling to be efficient. Advantageously, the said coupling buffer contains TWEEN 20; indeed, it has been observed by the present inventors that addition of TWEEN 20 to the coupling medium helps avoiding bead aggregation. Preferably, the coupling buffer contains 0.02% TWEEN 20. More preferably, the covalent coupling buffer of the invention is a PBS buffer of pH 7.4, containing 0.02% TWEEN 20, and 1 mM DTT.

Other coupling conditions are usual ones. Preferably, the covalent coupling of the AGT substrate and the coupling of the fusion protein to the solid supports are performed at room temperature. If the solid supports are fluorescently labeled, said proceedings are more preferably performed in darkness.

In a second aspect, the present invention is thus drawn to a method for covalently coupling a AGT polypeptide having $O^6$-alkylguanine-DNA alkyltransferase activity, on a functionalized solid support, comprising the following steps:

a) activating the said functionalized solid support,
b) adding a substrate of said AGT polypeptide, said substrate being suspended in a buffer containing between 0 and 20% of DMSO, in appropriate conditions so that the substrate is covalently attached to said support,
c) contacting the said AGT polypeptide with the substrate-coated support of step b) in a PBS/DTT buffer, wherein unbound molecules are washed out after steps b) and c).

Washings can be performed by using any kind of appropriate washing buffers. Such buffers are routinely used by the person of skills in the art and need not be further detailed here. Preferably, a PBS buffer is used.

As used herein, "appropriate conditions" are usual ones. Preferably, the covalent coupling of the AGT substrate is performed at room temperature and, if the solid supports are fluorescently labeled, in darkness.

The functionalization of the solid support can be performed by any conventional means (as those reminded above). The activation of said functionalized solid support is performed accordingly. In a preferred embodiment, the said solid supports are functionalized with surface carboxyl groups and further activated with a classical activation buffer, for example a 50 mg/mL EDAC solution or a 50 mg/mL S-NHS solution.

In a preferred embodiment, DTT is at a concentration of 1 mM in the PBS/DTT buffer.

The present invention is also drawn to a solid support which has been obtained by the said method, and to the use of said solid support in the immunoassay of the invention.

Said solid supports can then be stored in conventional storage buffers, for example containing 0.5 g/L sodium azide, 0.1% BSA, 0.02% TWEEN 20, and/or 1 mM DTT.

All these coupling steps are preferably performed in vitro, in buffers which are devoid of living cells, so that there is no need to take into account the reaction with endogenous AGT enzymes, and the reaction of the (exogenous) AGT fusion protein is therefore highly specific.

The solid supports that can be used in the methods of the invention can be of any kind, e.g. test tubes, microtiter wells, sheets, beads, chips, and/or microparticles, provided that they can be specifically identified from each other. Such identification is possible for example when they are separately located in space (e.g. the wells in a microtiter plate, or different locations on a chip) or when they are differently labeled. A "solid support" has therefore to be understood in a broad meaning, that is, by designating either discrete small parts of a whole solid supports (in case of a plate or a biochip) or a large number of identical microparticles that share common detectable characteristics (hereafter referred to as microparticles "subset").

In a preferred embodiment, the solid supports used in this invention can be specifically identified by their specific location, size, diameter, weight, granulometry, and/or labeling. Such labeling is for example a fluorochrome, a fluorophore, a chromophore, a radioisotope, a mass tag, or any kind of detectable tag which is known in the art.

The solid supports used in the invention can be made of any material, for example in polystyrene, cellulose, nitrocellulose, glass, ceramic, resin, rubber, plastic, silica, silicone, metal, and/or polymer. Polymeric materials include brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, polysulfone, or combinations thereof, that are acceptable as well. Most of these supports are commercially available. For example, beads from synthetic polymers such as polystyrene, polyacrylamide, polyacrylate, or latex are commercially available from numerous sources such as Bio-Rad Laboratories (Richmond, Calif.) and LKB Produkter (Stockholm, Sweden). Beads formed from natural macromolecules and particles such as agarose, cross-linked agarose, globulin, deoxyribose nucleic acid, and liposomes are commercially available from sources such as Bio-Rad Laboratories, Pharmacia (Piscataway, N.J.), and IBF (France). Beads formed from copolymers of polyacrylamide and agarose are commercially available from sources such as IBF and Pharmacia.

When polymeric supports were used, carboxyl groups can be added to the surface of the solid support by incorporating monomers containing such groups into the polymers (for example, acrylic acid, methacrylic acid, itaconic acid, and the like). Alternatively, they can be added to the support by further chemical reaction of a polymer having other precursor reactive groups which can be converted to carboxyl groups (for example, by hydrolysis of anhydrides, such as maleic anhydride, or by oxidation of surface methylol or aldehyde end groups), as already described.

In a preferred embodiment, the solid supports used in the invention are microparticles. Said microparticles have preferably a diameter of less than one millimeter, preferably a diameter ranging from about 0.1 to about 1,000 micrometers (μm). Even though the microparticles can be of any size, the preferred size is 1-100 μm, more preferably 2-50 μm, more preferably 3-25 μm, and even more preferably about 6-12 μm. Microparticles are made of any regularly shaped material. The preferred shape is spherical; however, particles of any other shape can be employed since this parameter is immaterial to the nature of the invention. The shape of the particle can serve as an additional distinction parameter, which is discriminated by flow cytometry, e.g., by a high-resolution slit-scanning method.

As used hereinafter the terms “microparticles”, “microspheres”, or “microbeads” are used interchangeably and bear equivalent meanings as they refer to small particles with overall diameter that falls essentially in the micrometer range. The terms “nanospheres”, “nanoparticles”, or “nanobeads” refer to smaller particles with overall size that falls essentially in the nanometer range. As used hereinafter the general term particles, spheres, or “beads” refers both to microparticles and nanoparticles, which can effectively serve as solid supports in the methods of the invention.

In the context of the present invention, a “subset” of microparticles corresponds to numerous identical microparticles having the same characteristics and that have been coated with the same epitope. Importantly, each subset of microparticles should be distinguishable from other subsets of the population by at least one characteristic (e.g. location, size, diameter, weight, granulometry, and/or labeling).

In a preferred embodiment, the different subsets of microparticles can be distinguished as they are differently labeled (e.g. with a fluorochrome, a fluorophore, a chromophore, a radioisotope, a mass tag, or any kind of detectable tag which is known in the art).

In a more preferred embodiment, the different subsets of microparticles can be distinguished as they are differently fluorescently labeled, as proposed in U.S. Pat. No. 5,736,330, U.S. Pat. No. 5,981,180, U.S. Pat. No. 6,057,107, U.S. Pat. No. 6,268,222, U.S. Pat. No. 6,449,562, U.S. Pat. No. 6,514,295, U.S. Pat. No. 6,524,793 and U.S. Pat. No. 6,528,165. More precisely, these different subsets can be dyed with different fluorescent dyes, and/or different concentrations of one or more fluorescent dyes. As such, the different subsets can have different fluorescent signatures (e.g. different fluorescent wavelength(s), different fluorescent intensities, etc.) that can be measured and used by a measurement system to determine the subset that individual microparticles belong to (i.e., to classify the microparticles according to the subset).

In a preferred embodiment, the microparticles used in the invention are internally labeled with fluorescent dyes, as proposed in EP 1 204 869.

These microparticles may also incorporate magnet or magnetically responsive metal oxides selected from the group consisting of superparamagnetic, paramagnetic, and ferromagnetic metal oxide. Magnetic beads are for example commercially available from sources such as Dynal Inc. (Great Neck, N.Y.) or can be prepared using known in the art methods as disclosed for example in U.S. Pat. No. 4,358,388; U.S. Pat. No. 4,654,267; U.S. Pat. No. 4,774,265; U.S. Pat. No. 5,320,944; and U.S. Pat. No. 5,356,713. In a preferred embodiment, the solid supports used in the invention are therefore magnetic.

In a more preferred embodiment, the solid supports used in the invention are microparticles internally labeled with fluorescent dyes with magnetite encapsulated in a functional polymer outer coat containing surface carboxyl groups for covalent coupling of ligands, such as those marketed by Luminex Corp under the trade name MagPlex.

It is also possible to use MicroPlex microspheres (sold by Luminex) that are carboxylated polystyrene micro-particles that have been color coded into spectrally distinct regions. These regions can be quickly distinguished by an xMAP Instrument allowing for the interrogation of up to 100 different analytes simultaneously from one single sample volume.

It is also possible to use SeroMAP microspheres (sold by Luminex) which are a special formulation of MicroPlex microspheres which have been optimized to reduce non-specific binding in serology assays.

The last step of the method of the invention consists in detecting the presence of the antibodies that are bound to the epitopes and therefore to the detectable solid support. By analyzing to which subset of microparticles antibodies are bound, it can be easily inferred which antibodies were present in the biological sample, and therefore by which pathogen the tested subject was infected.

Any known technology can be used to detect the presence of the antibodies that are bound to the solid supports. For example, labeled secondary antibodies recognizing specifically the constant part of the subject immunoglobulins can be used, as shown in the experimental part below. It is important to note that the labeling of the detecting-antibodies should be different from the one of the solid support, so as to distinguish between the solid supports that are coupled to antibodies, and those that are not.

Alternatively, immunoglobulins present in sera from infected animals or humans can be directly conjugated to R-phycoerythrin (R-PE), using a one-step antibody labeling protocol (Lightning-Link™ R-Phycoerythrin Conjugation Kit—Innova Biosciences). The hands-on time for the entire procedure is usually 20-30 seconds, and allows the labeling of small quantities of immunoglobulins with 100% recovery. This procedure eliminates the need for secondary reagents, such as conjugated anti-species antibodies and streptavidin-R-phycoerythrin, in multiplex-immunoassay experiments.

When microparticles internally labeled with fluorescent dyes are used, the fluorescent detection instrument should be equipped with a first laser for detecting the type of microsphere, and a second laser to ensure the quantification of captured IgM or IgG by exciting the fluorophore which is conjugated to the specific detection antibody.

With its extensive multiplexing capabilities and lower limit of detection, this approach offers substantial cost and sample savings over traditional ELISA measurements. Moreover, the selected sets of microspheres are adaptable to an affordable, compact, and robust fluorescent detection system such as the MagPix (Luminex Corporation).

In this embodiment, the method of the invention makes it possible to simultaneously analyze up to 100 types of coupled microspheres per well by using a flow analysis tool, and affords greatly enhanced sensitivity that is expected to be on the order of several orders of magnitude larger than that of currently used systems and methods.

Interestingly, the method of the invention enables to perform high throughput serological screening to diagnose multiple infections in an individual, either a human or an animal.

In a third aspect, the present invention provides a kit which is suitable for use in the detection of antibodies according to the method of the invention.

This kit comprises at least two solid supports as defined above, more precisely:

- a first solid support as obtained in step (c) of the method of the invention, said support being covalently coupled with a first epitope that is recognized by a first target antibody, and
- a second solid support as obtained in step (f) of the method of the invention, said support being covalently coupled with a second epitope that is recognized by a second target antibody, and not by said first target antibody, wherein the at least two solid supports can be specifically identified from each other and enable to detect two different target antibodies.

In other terms, the present invention relates to a kit for the detection of at least two target antibodies in a biological sample comprising:

(a) a first solid support comprising an AGT substrate covalently coupled to a first fusion protein comprising an AGT polypeptide having a O6-alkylguanine-DNA alkyltransferase activity and a first epitope that is recognized by a first target antibody; and b) a second solid support comprising an AGT substrate covalently coupled to a second fusion protein comprising an AGT polypeptide having a O6-alkylguanine-DNA alkyltransferase activity and a second epitope that is recognized by a second target antibody, but not by said first target antibody.

In a preferred embodiment, said first and/or second epitope is present on a viral protein chosen in the group consisting of: the EDIII protein of the dengue virus 1 of SEQ ID NO:3, the EDIII protein of the dengue virus 2 of SEQ ID NO:4, the EDIII protein of the dengue virus 3 of SEQ ID NO:5, the EDIII protein of the dengue virus 4 of SEQ ID NO:6, the EDIII protein of the West Nile virus of SEQ ID NO:7, the EDIII protein of the Yellow Fever virus of SEQ ID NO:8, the EDIII protein of the Japanese encephalitis virus of SEQ ID NO:9, the EDIII protein of the Zika virus of SEQ ID NO:10, the EDIII protein of the Wesselbron virus of SEQ ID NO:11, the EDIII protein of the Rocio virus of SEQ ID NO:12, the EDIII protein of the Murray encephalitis virus of SEQ ID NO:13, and the EDIII protein of the Saint-Louis encephalitis virus of SEQ ID NO:14, the EDIII protein of the Japanese encephalitis virus of genotype 1 encoded by SEQ ID NO:54, the EDIII protein of the Japanese encephalitis virus of genotype 2 encoded by SEQ ID NO:55, the EDIII protein of the Japanese encephalitis virus of genotype 4 encoded by SEQ ID NO:56, the EDIII protein of the Japanese encephalitis virus of genotype 5 encoded by SEQ ID NO:57, the EDIII protein of the Rabensburg virus encoded by SEQ ID NO:58, and the viral protein of HIV1, of HIV2, of the Hepatitis B virus, of the Hepatitis C virus, of the Hepatitis E virus, of the West-Nile virus and of oncogenic HPV strains such as HPV 16, 18, 31, 33, 35, 39, 45, 51, 52, 56, 58, 59, 66 and 68.

Preferably, this kit also contains the means to detect the at least two target antibodies which are bound to the solid supports. Said means are more preferably secondary antibodies recognizing the constant part of the target antibodies. Said secondary antibodies can be labeled, provided that the labeling is not the same as the ones that are present on the solid support. However, it is possible to use the same labeling for all the secondary antibodies that are used for detecting the antibodies bound to solid support(s), since the information concerning the infectious pathogen(s) are given only by the identification of the solid support which is bound to the antibodies.

The kit of the invention may contain other ingredients that are accepted as standard reagents such as a wash buffer, necessary plasticware, and the like.

In a preferred embodiment, the kit of the invention comprises at least 10, preferably at least 50, more preferably at least 100 differently coupled-solid supports, said solid supports being for example subsets of microparticles as defined above.

In a more preferred embodiment, the said solid supports are microspheres, for example those which are internally labeled with a fluorescent dye with magnetite encapsulated in a functional polymer outer coat containing surface carboxyl groups.

In another preferred embodiment, in the kit of the invention, the said solid supports are mixed together in at least one single compartment.

Advantageously, the kit of the invention contains conventional support(s), e.g., microtiter plates, containing the different antigen-coated microparticles subsets defined above. In a preferred embodiment, the said microparticles subsets are mixed together in at least one single compartment (e.g. a well or a tube). Such a device is disclosed on FIG. 11.

The kit of the invention may also contain recipients (e.g., tubes) containing the said subsets of antigen-coated microparticles.

The present invention also targets the use of the kit of the invention for detecting at least two, preferably at least 10, more preferably at least 50 and even more preferably at least 100 target antibodies in a biological sample from a subject.

In a preferred embodiment, the kit of the invention is used for detecting at least two, preferably at least 10, and more preferably at least 20 target antibodies that are generated upon infection by endemic viruses or parasites of the same geographic region. For example, the kit of the invention could contain microparticles that are coated with antigens of viruses or parasites that are specific of Africa regions, such as the Dengue virus type 1, type 2, type 3, type 4, the Yellow fever virus, the West-Nile virus, the Usutu virus, the Zika virus, the Wesselsbron virus, the Shamonda virus, the Rift Valley fever virus, the Chikungunya virus, the Crimean-Congo hemorrhagic fever virus, the Ebola virus, the Marburg virus, the Lassa virus, the Hepatitis C virus, the Hepatitis E virus, the Enterovirus 71, *Plasmodium falciparum*, or *Leptospira interrogans.*

Table 1 below discloses examples of antigen-coupled microspheres combinations which can be included in the kit of the invention depending on the geographic region it is intended for (Asia, Europa, America, Oceania, or Africa).

The kit of the invention may alternatively contain antigen-coupled microspheres that enable the diagnosis of viruses or parasites inducing specific symptoms (flu-like, encephalitis, or hemorrhagic fever) or infecting specific animals, so that it can be adapted to each patient/animal.

Table 1 below discloses examples of antigen-coupled microspheres combinations which can be included in the kit of the invention depending on the symptoms of the patient or of the animal.

Finally, kits containing antigen combinations that are proposed by national sanitary agencies are obviously also encompassed in the present invention.

In particular, the kit of the invention comprises at least two solid supports coated with at least two fusion proteins that are selected in the group consisting of: SEQ ID NO:21, SEQ ID NO:42, SEQ ID NO:49, SEQ ID NO:51, SEQ ID NO:53, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149 and SEQ ID NO:151.

In a preferred embodiment, the kit of the invention contains a combination of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen or at least twenty solid supports coated with said fusion proteins.

In a more preferred embodiment, the kit of the invention contains a combination of at least five solid supports (e.g., microsphere subsets) that are coated with at least five different fusion proteins containing antigens as recommended by the Food and Drug Administration, namely, antigens from the HBV, HCV, HIV1, HIV2 and West Nile viruses.

TABLE 1

Advantageous combinations of antigen-coupled microspheres to be included in the kit of the invention

| Agent | | Antigen-coupled microspheres | | Microsphere panels Geographical | | |
|---|---|---|---|---|---|---|
| Genus | Species | Abbreviation | Description | Africa | Asia | Europe |
| Flavivirus | Dengue virus type 1 | SNAP + DEN1.EDIII | Domain III of envelope E protein | x | x | x |
| | Dengue virus type 2 | SNAP + DEN2.EDIII | Domain III of envelope E protein | x | x | x |
| | Dengue virus type 3 | SNAP + DEN3.EDIII | Domain III of envelope E protein | x | x | x |
| | Dengue virus type 4 | SNAP + DEN4.EDIII | Domain III of envelope E protein | x | x | x |
| | Yellow fever virus | SNAP + YF.EDIII | Domain III of envelope E protein | x | | |
| | West Nile virus | SNAP + WNV.EDIII | Domain III of envelope E protein | x | x | x |
| | | WNV.prM- sE + SNAP | secreted soluble form of envelope E protein | x | x | x |
| | Usutu virus | SNAP + USU.EDIII | Domain III of envelope E protein | x | | x |
| | Japanese encephalitis virus genotype 3 | JE.prM-sE + SNAP | secreted soluble form of envelope E protein | | x | |
| | Japanese encephalitis virus genotype 1 | SNAP + JE-1. EDIII | Domain III of envelope E protein | | x | |
| | Japanese encephalitis virus genotype 2 | SNAP + JE-2. EDIII | Domain III of envelope E protein | | x | |
| | Japanese encephalitis virus genotype 3 | SNAP + JE-3. EDIII | Domain III of envelope E protein | | x | |
| | Japanese encephalitis virus genotype 4 | SNAP + JE-4. EDIII | Domain III of envelope E protein | | x | |
| | Japanese encephalitis virus genotype 5 | SNAP + JE-5. EDIII | Domain III of envelope E protein | | x | |
| | Murray Valley encephalitis virus | SNAP + MVE. EDIII | Domain III of envelope E protein | | x | |
| | Saint-Louis encephalitis virus | SNAP + SLE. EDIII | Domain III of envelope E protein | | | |
| | Zika virus | SNAP + ZIKV. EDIII | Domain III of envelope E protein | x | x | |
| | Wesselsbron virus | SNAP + WSL. EDIII | Domain III of envelope E protein | x | | |
| | Rocio virus | SNAP + ROCV. EDIII | Domain III of envelope E protein | | | |
| | Rabensburg virus | SNAP + RabV.EDIII | Domain III of envelope E protein | | | x |
| | Insectivore flavivirus (coll, La Timone) | SNAP + Insectflavi. EDIII | Domain III of envelope E protein | | | x |
| | Tickborne encephalitis virus | SNAP + TBE.EDIII | Domain III of envelope E protein | | | x |
| | Omsk Hemorrhagic Fever virus | SNAP + OMSK.EDIII | Domain III of envelope E protein | | x | |
| | Kyasanur forest Disease virus | SNAP + KAS.EDIII | Domain III of envelope E protein | | x | |
| | Akhumra virus | SNAP + ALK.EDIII | Domain III of envelope E protein | | x | |
| Orthobunyavirus | Schmallenberg virus | SNAP + AKA.N | Nucleoprotein N | | | x |
| | Akabane virus | SNAP + AKA.N | Nucleoprotein N | | | x |
| | Aino virus | SNAP + AIN.N | Nucleoprotein N | | | x |
| | Shamonda virus | SNAP + SHA.N | Nucleoprotein N | x | | x |
| Bunyavirus | Rift Valley fever virus | SNAP + RVF.N | Nucleoprotein N | x | | x |
| Alphavirus | Chikungunya virus | CHIK.sE2 + SNAP | secreted soluble form of envelope E2 protein | x | x | x |

TABLE 1-continued

Advantageous combinations of antigen-coupled microspheres to be included in the kit of the invention

| | | | | | | |
|---|---|---|---|---|---|---|
| | Ross River virus | RR.sE2 + SNAP | secreted soluble form of envelope E2 protein | | | |
| | Mayaro virus | MAY.sE2 + SNAP | secreted soluble form of envelope E2 protein | | | |
| | Eastern equine encephalitis virus | EEE.sE2 + SNAP | secreted soluble form of envelope E2 protein | | | |
| | Western equine encephalitis virus | WEE.sE2 + SNAP | secreted soluble form of envelope E2 protein | | | |
| | Venezuelan equine encephalitis | VEE.sE2 + SNAP | secreted soluble form of envelope E2 protein | | | |
| Nairovirus | Crimean-Congo hemorrhagic fever virus | SNAP + CCHF.N | Nucleoprotein N | x | x | x |
| Ebolavirus | Ebola virus (Zaire) | SNAP + EBO.N | Nucleoprotein N | x | | |
| Marburgvirus | Marburg virus | SNAP + MAR.N | Nucleoprotein N | x | | |
| Arenavirus | Lassa virus | LAS.ectoGP1 + SNAP | Ectodomain of Glycoprotein1 | x | | |
| | | LAS.ectoGP2 + SNAP | Ectodomain of Glycoprotein2 | x | | |
| | | SNAP + LAS.N | Nucleoprotein N | x | | |
| | Junin virus | JUN.ectoGP1 + SNAP | Ectodomain of Glycoprotein1 | | | |
| | | JUN.ectoGP2 + SNAP | Ectodomain of Glycoprotein2 | | | |
| | | SNAP + JUN.N | Nucleoprotein N | | | |
| | Machupo virus | MAC .ectoG1 + SNAP | Ectodomain of Glycoprotein1 | | | |
| | | MAC .ectoGP2 + SNAP | Ectodomain of Glycoprotein2 | | | |
| | | SNAP + MAC.N | Nucleoprotein N | | | |
| | Sabia virus | SAB .ectoGP1 + SNAP | Ectodomain of Glycoprotein1 | | | |
| | | SAB .ectoGP2 + SNAP | Ectodomain of Glycoprotein2 | | | |
| | | SNAP + SAB.N | Nucleoprotein N | | | |
| | Guanarito virus | GUA .ectoGP1 + SNAP | Ectodomain of Glycoprotein1 | | | |
| | | GUA .ectoGP2 + SNAP | Ectodomain of Glycoprotein2 | | | |
| | | SNAP + GUA.N | Nucleoprotein N | | | |
| Betacoronavirus | Human betacoronavirus (2cEMC/2012) | SNAP + huCOV.N | Nucleoprotein N | | x | |
| | | huCOV.S + SNAP | Soluble form of spike S protein | | x | |
| Hepacivirus | Hepatitis C virus genotype 1b (strain TCHM-R2/03) | SNAP + HCV.C | Capsid protein C | x | x | x |
| Hepevirus | Hepatitis E virus | SNAP + HEV.C | Capsid protein C | x | x | x |
| Enterovirus | Enterovirus 71 (strain JL-AFP-EV71-07-03) | SNAP + EV71.VP1 | Capsid protein VP1 | x | x | x |
| *Plasmodium* | *Plasmodium falciparum* | SNAP + MSP-1(19) + AMA-1 (III) | Proteins MSP-1(19) + AMA-1(III) in tandem | x | x | x |
| *Leptospira* | *Leptospira interrogans* serovar Lai str.56601 | SNAP + HbpA | The 55 kDa-form of protein HbpA | x | x | x |

| Agent | | Microsphere panels | | | | | | |
|---|---|---|---|---|---|---|---|---|
| | | Geographical | | Syndromic | | | Veterinary | |
| Genus | Species | Americas | Oceania | Flu-like | Encephalitis | Hemorrhagic fever | Bovine disease | Equine disease |
| Flavivirus | Dengue virus type 1 | x | x | x | | x | | |
| | Dengue virus type 2 | x | x | x | | x | | |
| | Dengue virus type 3 | x | x | x | | x | | |
| | Dengue virus type 4 | x | x | x | | x | | |
| | Yellow fever virus | x | | x | | x | | |
| | West-Nile virus | x | x | x | x | | | x |
| | | x | x | x | x | | | x |
| | Usutu virus | | | | x | | | x |
| | Japanese encephalitis virus genotype 3 | | x | x | x | | | |
| | Japanese encephalitis virus genotype 1 | | x | x | x | | | |
| | Japanese encephalitis virus genotype 2 | | x | x | x | | | |
| | Japanese encephalitis virus genotype 3 | | x | x | x | | | |
| | Japanese encephalitis virus genotype 4 | | x | x | x | | | |
| | Japanese encephalitis virus genotype 5 | | x | x | x | | | |
| | Murray Valley encephalitis virus | | x | x | x | | | |
| | Saint-Louis encephalitis virus | x | | x | x | | | x |
| | Zika virus | | x | x | | | | |
| | Wesselsbron virus | | | x | | | x | |
| | Rocio virus | x | | x | | | | |
| | Rabensburg virus | | | | | | | |
| | Insectivore flavivirus (coll, La Timone) | | | | | | | |
| | Tickborne encephalitis virus | | | | | | x | x |
| | Omsk Hemorrhagic Fever virus | | | | | x | | |
| | Kyasanur forest Disease virus | | | | | x | | |
| | Akhumra virus | | | | | x | | |
| Orthobunyavirus | Schmallenberg virus | | | | | | x | |
| | Akabane virus | | x | | | | x | |
| | Aino virus | | x | | | | x | |
| | Shamonda virus | | | | | | x | |

TABLE 1-continued

Advantageous combinations of antigen-coupled microspheres to be included in the kit of the invention

| | | | | | | | | |
|---|---|---|---|---|---|---|---|---|
| Bunyavirus | Rift Valley fever virus | | | x | | x | x | |
| Alphavirus | Chikungunya virus | x | x | x | | | | |
| | Ross River virus | | x | x | | | | x |
| | Mayaro virus | x | | x | | | | |
| | Eastern equine encephalitis virus | x | | x | | | | x |
| | Western equine encephalitis virus | x | | x | | | | x |
| | Venezuelan equine encephalitis | x | | x | | | | x |
| Nairovirus | Crimean-Congo hemorrhagic fever virus | | | | | x | x | |
| Ebolavirus | Ebola virus (Zaire) | | | | | x | | |
| Marburgvirus | Marburg virus | | | | | x | | |
| Arenavirus | Lassa virus | | | | | x | | |
| | | | | | | x | | |
| | | | | | | x | | |
| | Junin virus | x | | | | x | | |
| | | x | | | | x | | |
| | | x | | | | x | | |
| | Machupo virus | x | | | | x | | |
| | | x | | | | x | | |
| | | x | | | | x | | |
| | Sabia virus | x | | | | x | | |
| | | x | | | | x | | |
| | | x | | | | x | | |
| | Guanarito virus | x | | | | x | | |
| | | x | | | | x | | |
| | | x | | | | x | | |
| Betacoronavirus | Human betacoronavirus (2cEMC/2012) | | | | | | | |
| Hepacivirus | Hepatitis C virus genotype 1b (strain TCHM-R2/03) | x | x | | | | | |
| Hepevirus | Hepatitis E virus | x | x | | | | | |
| Enterovirus | Enterovirus 71 (strain JL-AFP-EV71-07-03) | x | x | | x | | | |
| *Plasmodium* | *Plasmodium falciparum* | x | x | x | x | | | |
| *Leptospira* | *Leptospira interrogans* serovar Lai str.56601 | x | x | x | | x | x | |

In another aspect, the present invention relates to a method for manufacturing the kit of the invention as defined above, said method comprising the steps of:

(a) providing a least a first fusion protein comprising:
  - a polypeptide comprising a first epitope that is recognized by a first target antibody and
  - a AGT polypeptide having a O6-alkylguanine-DNA alkyltransferase activity, (b) contacting said first fusion protein with a first solid support, said support being covalently coupled with a substrate of said AGT polypeptide, (c) obtaining a first solid support covalently coupled with a first epitope that is recognized by the first target antibody, (d) providing at least a second fusion protein comprising:
  - a polypeptide comprising a second epitope, said second epitope being recognized by a second target antibody but not by said first target antibody, and
  - a AGT polypeptide having a O6-alkylguanine-DNA alkyltransferase activity, (e) contacting said second fusion protein with a second solid support, said support being covalently coupled with a substrate of said AGT polypeptide, (f) obtaining a second solid support covalently coupled with a second epitope that is recognized by the second target antibody, but not by said first target antibody, wherein said at least first and at least second solid supports can be specifically identified from each other, the kit of the invention comprising at least said first and second supports.

In another aspect, the present invention relates to a multiplex immuno screening assay comprising at least 2, 25, 50, 96 solid supports as defined above and wherein each of said solid supports emits a different and distinguishable wave length after excitation.

In another aspect, the present invention relates to a multiplex immuno screening assay method comprising:

a) contacting one or several biological sample(s) with at least 2, 25, 50, 96 solid supports as defined above and wherein each of the solid supports emits a different and distinguishable wave length after excitation, and b) detecting the presence or absence of target antibodies.

In a preferred embodiment, said target antibodies are specific to antigen from viruses to be detected in blood bank according to WHO or FDA guidelines, such as for example viruses selected from HBV, HCV, HIV1, HIV2, and WNV.

In another preferred embodiment, said target antibodies are specific to oncogenic HPV strains such as HPV 16, 18, 31, 33, 35, 39, 45, 51, 52, 56, 58, 59, 66 and 68.

In another preferred embodiment, each of said target antibodies are labeled with a detectable label.

In another aspect, the present invention relates to an apparatus for carrying out the method for manufacturing the kit of the invention as defined above, comprising a technical device for detecting the light sources emitted from the solid supports and the light source emitted from the target antibodies or labeled antibodies binding to the target antibodies, and a calculating or computer device for identifying which solid supports are bound with target antibodies, thereby indicating the presence or absence of antigens, bacteria, virus, or parasites in the analyzed sample.

In another aspect, the present invention relates to an in vitro method for diagnosing at least one target disease in a subject, said target disease being known to induce the synthesis of at least one target antibody in said subject, comprising performing the immunoassay of the invention, wherein said subject is diagnosed to be suffering from said at least one target disease if the amount of said at least one target antibody is higher than a control value.

This diagnosing method preferably enables to diagnose two, preferably three, and more preferably four target diseases in a subject in need thereof. This number is however not limiting: it is indeed possible to diagnose until 100 target diseases in so far as it is possible to detect until 100 different antibodies with the detecting method of the invention.

In a preferred embodiment, said at least one target disease is a viral, a bacterial, a yeast or a fungi-mediated infection, preferably a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum.*

In a preferred embodiment, said in vitro method is used to diagnose at least 5, more preferably at least 15, more preferably at least 50, and even more preferably at least 100 viral and/or bacterial and/or parasite infections in said subject.

In a preferred embodiment, the control value used in said method represents the amount of said target antibody in a sample from a subject which is not suffering from said target disease, preferably, a healthy subject.

The methods of the invention can be used to diagnose infections in animals.

In particular, they can be used for the diagnosis of animal diseases, as well as a DIVA (Differentiating Infected from Vaccinated Animals) approach to differentiate naturally infected animals from vaccinated animals. The use of a DIVA strategy complementing novel vaccines would allow the implementation of vaccination as targeted control strategy alongside conventional strategies (test, slaughter and meat inspection). Moreover, increased test specificity would have a major economic benefit by reducing the numbers of false-positive animals that may be slaughtered needlessly. Lastly, improved sensitivity, particularly when novel diagnostic assays are used, would have a further benefit in reducing the economic burden of disease control even in the absence of vaccination In a preferred embodiment, the methods of the invention are applied to human individuals.

The present invention finally relates to the use of the kit of the invention for diagnosing at least two target diseases in a subject, wherein said target disease is a viral infection caused by a Papillomavirus or a RNA virus from the family of the Flaviviridae (Dengue, Yellow fever, West Nile, Japanese encephalitis, Tick-Borne Encephalitis, Hepatitis C viruses), the Togaviridae (Chikungunya, Ross River, Mayaro, Western Equine encephalitis, Eastern Equine Encephalitis, Venezuela Equine Encephalitis viruses), the Bunyaviridae (Crimean-Congo hemorrhagic fever, Rift Valley Fever, Schmallenberg viruses), the Caliciviridae (Hepatitis E virus), the Arenaviridae (Lassa) or the Filoviridae (Ebola, Marburg), a bacterial infection caused by *Leptospirosa Interrogans*, or an infection caused by *Plasmodium falciparum.*

A new emerging arbovirus has been recently sequenced and affects cattle in Germany, Benelux and France. This virus is called Schmallenberg virus (SBV), and is related to the Akabane virus belonging to the Simbu serogroup of the Orthobunyavirus genus of the Bunyaviridae family. The viral genome of the Schmallenberg virus comprises three single-stranded RNA segments known as S, L and M. The S segment encodes the N nucleoprotein and the NSs non-structural protein. The N nucleoprotein shares antigenic determinants with different Bunyaviruses. The three RNA viral sequences of the BH80/11-4 strain of the Schmallenberg virus are available under the numbers HE649913.1, HE649914.1, and HE649912.1.

The present inventors observed that the fusion as a chimeric protein of the 6-alkylguanine-DNA-alkyltransferase enzyme (AGT) with the SBV N protein greatly improves the production of recombinant N protein, in particular in invertebrate cells such as S2 cells.

The present inventors propose here for the first time to use the AGT enzyme (EC 2.1.1.63), a mutant thereof, a catalytic domain thereof or sub-fragments thereof, for enhancing the production of the N nucleoprotein from SBV in host cells, in particular in non-vertebrate cells. The enhancing effect is observed when the host cells express a fusion polypeptide comprising at least i) a secretion signal peptide which is functional in said host cells, ii) the AGT enzyme, mutant, catalytic domain or sub-fragments thereof, and iii) the N nucleoprotein of SBV. For the enhancing effect to occur, the AGT enzyme has to be physically linked, directly or indirectly (spacers and other amino acids might be introduced), to the protein of interest. Without being bound by theory, it is contemplated that the AGT enzyme acts as a chaperone protein, for example by facilitating the secretion from the host cell and stabilising the synthesised fusion polypeptide in the supernatant of the host cells, or for preventing it to be metabolised during and after its synthesis and secretion from the host cells. In addition, it has been observed that AGT has a 3D globular structure comprising α helix (Wibley J. E. A. et al, 2000), which is compatible with a scaffolding role of AGT.

In the context of the present invention, "host" cells are any cells which can be used for producing recombinant proteins, such as "non-vertebrate" (or invertebrate) cells, vertebrate cells, plant cells, yeast cells, or prokaryote cells. They are preferably non-vertebrate and vertebrate cells.

Non-vertebrate (also known as invertebrate) comprises different phyla, the most famous being the Insect, Arachnida, Crustacea, Mollusca, Annelida, Cirripedia, Radiata, Coelenterata and Infusoria. They are now classified into over 30 phyla, from simple organisms such as sea sponges and flatworms to complex animals such as arthropods and molluscs. In the context of the invention, non-vertebrate cells are preferably insect cells, such as *Drosophila* or Mosquito cells, more preferably *Drosophila* S2 cells.

Examples of cells derived from vertebrate organisms that are useful as host cell lines include non-human embryonic stem cells or derivative thereof, for example avian EBX cells; monkey kidney CVI line transformed by SV40 sequences (COS-7, ATCC CRL 1651); a human embryonic kidney line (293); baby hamster kidney cells (BHK, ATCC CCL 10); Chinese hamster ovary cells (CHO); mouse sertoli cells [TM4]; monkey kidney cells (CVI, ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); rat hepatoma cells [HTC, MI.5]; YB2/O (ATCC no CRL1662); NIH3T3; HEK and TRI cells. In the context of the invention, vertebrate cells are preferably EBX, CHO, YB2/O, COS, HEK, NIH3T3 cells or derivatives thereof.

Plant cells which can be used in the context of the invention are the tobacco cultivars Bright Yellow 2 (BY2) and *Nicotiana tabaccum* 1 (NT-1).

Yeast cells which can be used in the context of the invention are: *Saccharomyces cerevisiae, Schizosaccharomyces pombe*, and *Hansenula polymolpha*, as well as methylotropic yeasts like *Pichia pastoris* and *Pichia methanolica.*

Prokaryote cells which can be used in the context of the invention are typically *E. coli* bacteria or *Bacillus subtilis* bacteria.

In another aspect, the present invention is thus drawn to a vector for expressing the N nucleoprotein from SBV in an host cell (SBV.N), comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the N nucleoprotein of SBV of SEQ ID NO: 16.

The N nucleoprotein from SBV will be referred to hereafter as the "heterologous protein", the "protein of interest", "chimeric protein", or the "recombinant protein".

The term "vector" herein means the vehicle by which a DNA or RNA sequence of a foreign gene can be introduced into a host cell so as to transform it and promote expression of the introduced sequence. As understood herein, a vector is a nucleic acid molecule, such as, for example, plasmids, phages, and viruses. They are discussed in greater detail below. Any type of plasmid, cosmid, YAC or viral vector may be used to prepare a recombinant nucleic acid construct which can be introduced to a host cell where expression of the protein of interest is desired. When expression of the protein of interest in a particular type of host cell is desired, viral vectors that selectively infect the desired cell type or tissue type can be used. Also important in the context of the invention are vectors for use in gene therapy (i.e. which are capable of delivering the nucleic acid molecule to a host organism).

For example, viral vectors, such as lentiviruses, retroviruses, herpes viruses, adenoviruses, adeno-associated viruses, vaccinia virus, baculovirus, and other recombinant viruses with desirable cellular tropism. Methods for constructing and using viral vectors are known in the art (see, Miller and Rosman, *BioTechniques,* 7:980-990, 1992).

Viral vectors that are actually preferred in the present invention are those that are well suited for use in vertebrate and non-vertebrate cells.

For non-vertebrate cells, preferred vectors are the arboviruses, the West Nile virus being particularly preferred, which are arthropod vectors. Other vectors that are known to efficiently be expressed in non-vertebrate cells are the baculoviruses.

For vertebrate cells, lentiviral, AAV, baculoviral and adenoviral vectors are preferred. The vectors suited for expression in mammalian host cells can also be of non-viral (e.g. plasmid DNA) origin. Suitable plasmid vectors include, without limitation, pREP4, pCEP4 (Invitrogen), pCI (Promega), pCDM8 and pMT2PC, pVAX and pgWiz.

For prokaryotic cells, plasmid, bacteriophage and cosmid vectors are preferred. Suitable vectors for use in prokaryotic systems include without limitation pBR322 (Gibco BRL), pUC (Gibco BRL), pBluescript (Stratagene), p Poly, pTrc; pET 11d; pIN; and pGEX vectors.

For plant cells, plasmid expression vectors such as Ti plasmids, and virus expression vectors such as Cauliflower mosaic virus (CaMV) and tobacco mosaic virus TMV are preferred.

Expression of recombinant proteins in yeast cells can be performed using three types of vectors: integration vectors (YIp), episomal plasmids (YEp), and centromeric plasmids (YCp): Suitable vectors for expression in yeast (e.g. *S. cerevisiae*) include, but are not limited to pYepSec1, pMFa, pJRY88, pYES2 (Invitrogen Corporation, San Diego, Calif.) and pTEF-MF (Dualsystems Biotech Product code: P03303).

Vectors which can be used for gene therapy are well-known in the art. They are for example lentivirus, retrovirus, adenovirus, poxvirus, herpes virus, measles virus, foamy virus or adeno-associated virus (AAV). Viral vectors can be replication-competent, or can be genetically disabled so as to be replication-defective or replication-impaired. Preferred gene therapy vector are the DNA Flap vectors as described in WO 99/055892, U.S. Pat. No. 6,682,507 and WO 01/27300.

A sequence "encoding" an expression product, such as a RNA, polypeptide, protein or enzyme, is a nucleotide sequence that, when expressed, results in the production of that RNA, polypeptide, protein or enzyme; i.e., the nucleotide sequence "encodes" that RNA or it encodes the amino acid sequence for that polypeptide, protein or enzyme.

The vector of the invention contains a nucleotide sequence encoding a 6-alkylguanine-DNA-alkyltransferase enzyme (AGT), a mutant, a fragment or a catalytic domain thereof. These polypeptides have been defined above. Preferably, said AGT mutant is the SNAP enzyme of SEQ ID NO: 2, and is encoded for example by SEQ ID NO:15 or SEQ ID NO: 31, the latter having a G/C content of 51%.

Preferably, the nucleotide expression vector of the invention further comprises cloning sites enabling the in-frame insertion of a heterologous DNA sequence encoding the protein of interest.

As meant in the present invention, the term "secretion signal peptide" designates a short (3-60 amino acids long) peptide chain that directs the transport of the N nucleoprotein outside the host cells.

Examples of secretion signals appropriate for the present invention include, but are not limited to, the signal peptide sequences of the mating factor (MF) alpha (U.S. Pat. No. 5,879,926); invertase (WO 84/01153); PHO5 (DK 3614/83); YAP3 (yeast aspartic protease 3; WO 95/02059); and BAR1 (WO 87/02670).

In the context of the invention, this secretion signal peptide is preferably functional either in non-vertebrate cells or in vertebrate cells, or both.

Examples of secretion signal peptides which are functional in insect cells are: the insect ssBiP (SEQ ID NO: 37, for example encoded by the DNA sequence SEQ ID NO: 22), the BiP-like peptide signal of SEQ ID NO: 24 (for example encoded by the DNA sequence SEQ ID NO: 23), the BiP-like peptide signal of SEQ ID NO:153 (for example encoded by the DNA sequence SEQ ID NO:152) and any peptide signal present in an arbovirus, for example the envelop E protein of the West-Nile virus (SEQ ID NO: 38).

Interestingly, the above-mentioned BiP-like peptide signal of SEQ ID NO:24 is functional in both non-vertebrate and vertebrate cells. This BiP-like signal corresponds to the BiP peptide signal of SEQ ID NO: 37 in which the last Glycine amino acid has been replaced by the amino acid sequence Pro Thr Ala Leu Ala (SEQ ID NO: 39) which corresponds to the cleavage site of the E protein of the Dengue virus. Accordingly, the BiP-like signal will be advantageously cleaved once the protein will be translated and secreted in the supernatant of the host cells.

A variety of secretion signals is also available for expression in yeast host cells, e.g. in *S. cerevisiae*. These include the prepro-alpha factor, HSp150, PHO1, SUC2, KILM1 (killer toxin type 1), and GGP1.

A cloning site is a sequence which facilitates cloning of a gene encoding a protein of interest into the expression system. It contains restriction sites, or restriction recognition sites, i.e. locations on a DNA molecule containing specific sequences of nucleotides, which are recognized by restriction enzymes (see for example in the figures). These are generally palindromic sequences (because restriction enzymes usually bind as homodimers), and a particular restriction enzyme may cut the sequence between two nucleotides within its recognition site, or somewhere nearby. The cloning sites are well known for the man skilled in the art.

In a preferred embodiment of the invention, the DNA sequence encoding said AGT enzyme is located in 5' or in 3' of the DNA sequence encoding said heterologous protein of interest, preferably in 5'. Therefore, the AGT enzyme is directly or indirectly linked to the heterologous protein/polypeptide of interest, and preferably located at the N-terminal end of the heterologous protein/polypeptide of interest. The DNA sequence encoding the fusion polypeptide comprising said peptide signal, said AGT enzyme, mutant or catalytic domain, and said recombinant protein of interest, can be operatively associated with an inducible promoter which is functional in the same host cells as the peptide signal is.

More preferably, in the vector of the invention, said open reading frame is operatively associated with an inducible promoter which is functional in the same host cell as the peptide signal is.

A coding sequence is "operatively associated with" an expression control sequence (i.e. transcriptional and translational control sequences) in a cell, when RNA polymerase transcribes the coding sequence into RNA, which is then trans-RNA spliced (if it contains introns) and, if the sequence encodes a protein, is translated into that protein.

A "promoter" is a sequence of nucleotides from which transcription may be initiated of DNA operably linked downstream (i.e. in the 3' direction on the sense strand of double-stranded DNA). Within the promoter sequence will be found a transcription initiation site (conveniently found, for example, by mapping with nuclease S1), as well as protein binding domains (consensus sequences) responsible for the binding of RNA polymerase.

Promoters which may be used to control gene expression in the context of the present invention are for example the one that are functional in non-vertebrate cells or in vertebrate cells. For example, for non-vertebrate cells, the regulatory sequences of the metallothionein gene can be used (Brinster et al., *Nature,* 296:39-42, 1982).

Preferably, the inducible promoter which is present in the vector of the invention has a promoter activity in an insect cell, and more preferably in a *Drosophila* cell. It is for example the *Drosophila metallothionein* promoter pMT (Lastowski-Perry et al, *J. Biol. Chem.* 260:1527 (1985)), which directs high level transcription of the gene in the presence of metals, e.g. $CuSO_4$. Alternatively, the *Drosophila* actin 5C gene promoter, which is a constitutive promoter and does not require addition of a metal, can be used (B. J. Bond et al, *Mol. Cell. Biol.* 6:2080 (1986)). Examples of other known *Drosophila* promoters include, e.g. the inducible heatshock (Hsp70) and COPIA LTR promoters. The SV40 early promoter gives lower level of expression than the *Drosophila* metallothionein promoter.

Preferably, the inducible promoter which is present in the vector of the invention has a promoter activity in a *Drosophila melanogaster* cell, preferably in *Drosophila* S2 cells. It is for example the metallothionein promoter which is thoroughly described in Lastowski-Perry et al, *J. Biol. Chem.* 260: 1527 (1985).

Promoters suitable for constitutive expression in mammalian cells include the cytomegalovirus (CMV) immediate early promoter, the adenovirus major late promoter, the phosphoglycero kinase (PGK) promoter, and the thymidine kinase (TK) promoter of herpes simplex virus (HSV)-1. Inducible eukaryotic promoters regulated by exogenously supplied compounds, include without limitation, the zinc-inducible metallothionein (MT) promoter, the dexamethasone (Dex)-inducible mouse mammary tumor virus (MMTV) promoter, the T7 polymerase promoter system (WO 98/10088), the ecdysone insect promoter, the tetracycline-repressible promoter, the tetracycline-inducible promoter, the RU486-inducible promoter and the rapamycin-inducible promoter.

Preferably, the promoter which is present in the vector of the invention has a promoter activity in a mammal cell, preferably in HeLa cells. It is for example the SV 40 promoter.

A range of yeast promoters is available for protein expression in yeast host cells. Some like ADH2, SUC2 are inducible and others like GAPDH are constitutive in expression. Other promoters suitable for expression in yeast include the TEF, PGK, MF alpha, CYC-1, GAL-1, GAL4, GAL10, PHO5, glyceraldehyde-3-phosphate dehydrogenase (GAP or GAPDH), and alcohol dehydrogenase (ADH) promoters.

For use in plant cells, the most commonly used promoter is the cauliflower mosaic virus (CaMV) 35S promoter or its enhanced version, but a number of alternative promoter can be used, such as the hybrid (ocs)3mas promoter or the ubiquitin promoter from maize and *Arabidospsis thaliana*. In contrast to these constitutive promoters, the rice α-amylase RAmy3D promoter is induced by sugar deprivation (Hellwig S et al., *Nat. Biotechnol.* 2004; 22(11):1415-22).

Promoters suitable for expression in *E. coli* host cell include, but are not limited to, the bacteriophage lamba pL promoter, the lac, TRP and IPTG-inducible pTAC promoters.

It is preferred that the secretion signal peptide and the inducible promoter are functional in the same host cell.

More preferably, the secretion signal peptide and the inducible promoter are functional in both *Drosophila* S2 cells and vertebrate cells.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Once an appropriate vector has been constructed and transfected into the selected host cell, preferably a *Drosophila* cell line, the expression of a heterologous protein is induced by the addition of an appropriate inducing agent for the inducible promoter. For example cadmium or copper are inducing agents for the Hsp70 promoter. For constitutive promoters, such as the actin 5C promoter, no inducing agent is required for expression.

In another embodiment of the invention, the nucleotide expression vector encodes at least one peptide cleavage site, which is preferably located between the AGT enzyme or its catalytic domain and the recombinant protein of interest.

A peptide cleavage site (also called "peptide cleavage site") is an amino acid sequence which is recognized by at least one protease enzyme (for example serine protease, cysteine protease, among others). An example of a peptide cleavage site is the enterokinase cleavage site of SEQ ID NO: 40 (AspAspAspAspLys/Asp). The enterokinase is a serine protease enzyme (EC 3.4.21.9) which is known to convert inactive trypsinogen into active trypsin by cleavage at the C-terminal end of the sequence: Val-$(Asp)_4$-Lys-Ile-Val~ (trypsinogen)→Val-$(Asp)_4$-Lys (hexapeptide)+Ile-Val~ (trypsin). Enterokinase cleaves after lysine if the Lys is preceded by four Asp and not followed by a proline residue.

Another useful peptide cleavage site is the cleavage site of the so-called "TEV protease", having the amino acid sequence SEQ ID NO: 32 (pro-TEV1) or SEQ ID NO: 33 (pro-TEV2) (Glu Asn Leu Tyr Phe Gln Ser or Gly respectively). Such cleavage sites can be encoded for example by SEQ ID NO:29 and 30. TEV protease is the common name for the 27 kDa catalytic domain of the nuclear inclusion protein encoded by the tobacco etch virus. It is commercially available (Invitrogen).

The cleavage site from the membrane precursor prM from Dengue virus serotype 1 (SEQ ID NO: 39) may also be used in the vector of the invention.

In another embodiment, the nucleotide expression vector of the invention further encodes a label, preferably located at the C-terminal end of the recombinant protein in the fusion polypeptide of the invention (comprising the peptide signal, the AGT protein or homologous thereof, and the recombinant protein). In the context of the invention, a "label" is dedicated to facilitate the recovery of the polypeptide from the crude lysate of the host cell, and is preferably selected from the group comprising: fluorescent proteins, poly-histidine (poly-his) or poly-histidine-glycine (poly-his-gly) tags; flu HA tags; c-myc tag Herpes simplex virus glycoprotein D (gD) tags, Flag-peptides, alpha-tubulin epitopes, or T7 gene 10 protein peptide tags. However, any other label might be used. In a preferred embodiment of the invention, the vectors comprise the DNA of SEQ ID NO: 28 encoding a hexa-histidine tag which has the SEQ ID NO: 27.

In another embodiment, the nucleotide expression vector of the invention further encodes spacer sequence(s), located preferably between the AGT enzyme (or its catalytic domain) and the recombinant protein of interest and/or between the recombinant protein of interest and the label. In the context of the invention, a spacer sequence is an amino acid sequence comprising at least three amino acids, dedicated to spatially separate two linked polypeptides (these polypeptides being then indirectly linked). Such spacer can be for example the amino acid sequence Glycine-Glycine-Glycine-Serine (GGGS, SEQ ID NO: 25) and the DNA spacer sequence encoding it can be SEQ ID NO: 26. In the context of this invention, this DNA sequence is hereafter designated as "DNA spacer sequence" and is located between the DNA encoding AGT or its catalytic domain, and the recombinant DNA sequence, preferably upstream from the DNA sequence encoding the peptide cleavage site.

As used herein, the term "pDeSNAPUniv" designates a DNA cassette encoding, in a single open reading frame, from 5' to 3':

a) a secretion signal peptide,
b) an AGT protein of SEQ ID NO:1, a mutant, a fragment or a catalytic domain thereof, in particular the SNAP mutant of SEQ ID NO:2,
c) at least one peptide cleavage site,
d) at least one label, and
e) at least one spacer sequence.

This pDeSNAPUniv DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

More preferably, the pDeSNAPUniv DNA cassette comprises, from 5' to 3', the sequence SEQ ID NO:23 encoding the BiP-like secretion signal, the SEQ ID NO:15 or 31 encoding the SNAP mutant, the spacer sequence of SEQ ID NO:26, the peptide cleavage site pro-TEV of SEQ ID NO:29, the peptide cleavage site pro-TEV of SEQ ID NO:30, the spacer sequence of SEQ ID NO:26 and the sequence SEQ ID NO:28 encoding the His-tag label (see FIG. 8, showing the structure of the pDeSNAPUniv cassette). Such a pDeSNAPUniv DNA cassette is for example SEQ ID NO:34.

This "pDeSNAPUniv" cassette is held as "universal" since it can be inserted in any kind of vectors dedicated to transfect host cells in order to produce heterologous proteins, namely vertebrate vectors (such as pcDNA3 or pCI-neo vectors) as well as non-vertebrate vectors (such as pMT/BiP/V5-HisA which is useful in the DES system from Invitrogen). Examples of plasmid comprising said universal sequence is SEQ ID NO:43 (pMT/BiP/V5-HisA from Invitrogen comprising the pDeSNAP Univ cassette), SEQ ID NO:44 (pUC57 from Invitrogen comprising the pDeSNAP Univ cassette) or SEQ ID NO:45 (pcDNA3 from Invitrogen comprising the pDeSNAP Univ cassette).

Another example of plasmid comprising said universal sequence is SEQ ID NO:105 which is a pUC57 plasmid comprising, from 5' to 3', the constitutive promoter of *Orgyia pseudotsugata* multicapsid nucleoprotein virus-immediate-early 2 promoter (OpIE2SP) the BiPlike signal peptide of SEQ ID NO:152, the SNAP-like sequence of SEQ ID NO:31, the spacer sequence of SEQ ID NO:26, the pro-TEV1 sequence SEQ ID NO:29, and the C-term peptide tag of SEQ ID NO:106.

Once the heterologous sequence of a protein of interest such as SBV.N is cloned herein, such a vector can be advantageously transfected in either vertebrate or non-vertebrate host cells, so as to produce the protein of interest in high amounts.

In a preferred embodiment, the vector of the invention comprises a so-called "pDeSNAP Univ/SBV.N cassette" i.e., a pDeSNAPUniv DNA cassette in which the sequence of the N nucleoprotein of SBV has been inserted, said pDeSNAP Univ/SBV.N cassette comprising a nucleotide sequence encoding, in a single open reading frame, from 5' to 3':

a) a secretion signal peptide,
b) an AGT protein of SEQ ID NO:1, a mutant, a fragment or a catalytic domain thereof, in particular the SNAP mutant of SEQ ID NO:2, c) at least one peptide cleavage site, d) the N nucleoprotein of SBV of SEQ ID NO: 16, e) at least one label, and f) at least one spacer sequence.

This pDeSNAP Univ/SBV.N DNA cassette encodes a secretion signal peptide which is advantageously the BiP-like peptide signal of SEQ ID NO:24 or the ssBiP peptide signal of SEQ ID NO:37, the SNAP mutant of SEQ ID NO:2, the N nucleoprotein of SBV of SEQ ID NO:16, a label which is advantageously a His-tag of SEQ ID NO:27, a peptide cleavage site which is advantageously either the pro-TEV of SEQ ID NO:32 or the pro-TEV of SEQ ID NO:33, and/or a spacer sequence which has advantageously the amino acid sequence SEQ ID NO:25.

More preferably, the pDeSNAP Univ/SBV.N DNA cassette comprises, from 5' to 3', the sequence SEQ ID NO:23 encoding the BiP-like secretion signal or the SEQ ID NO:22 encoding the ssBiP secretion signal, the SEQ ID NO:15 or 31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label.

Even more preferably, the pDeSNAP Univ/SBV.N DNA cassette comprises, from 5' to 3', the sequence SEQ ID NO:22 encoding the ssBiP secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:35.

Alternatively, the pDeSNAP Univ/SBV.N DNA cassette can comprise, from 5' to 3', the sequence SEQ ID NO:23 encoding the BiP-like secretion signal, the SEQ ID NO:31 encoding the SNAP mutant, the spacer sequence of SEQ ID NO:26, the peptide cleavage site pro-TEV1 of SEQ ID NO:29, the sequence SEQ ID NO: 17 encoding the N nucleoprotein of SBV, the peptide cleavage site pro-TEV2 of SEQ ID NO:30, the spacer sequence of SEQ ID NO:26 and the sequence SEQ ID NO:28 encoding the His-tag label. Such a pDeSNAP Univ/SBV.N cassette is for example SEQ ID NO:36 (whose structure is shown on FIG. 9).

Thus, in a preferred embodiment, the vector of the invention comprises the pDeSNAP Univ/SBV.N cassette having the nucleotide sequence SEQ ID NO: 35 or the nucleotide sequence SEQ ID NO:36.

More precisely, the pDeSNAP Univ/SBV.N cassette nucleotide sequence of SEQ ID NO:35 comprises:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

And the pDeSNAP Univ/SBV.N cassette nucleotide sequence SEQ ID NO:36 comprises (see also FIG. 9):

- an insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

Interestingly, the pDeSNAP Univ/SBV.N cassette nucleotide sequence of SEQ ID NO:36 cassette also comprises in addition an NheI site upstream of the ATG, a BglII site between the BiP-like sequence and the SNAP-like sequence, and an AgeI site and a HindIII site which are both located downstream of the stop codon.

Vectors of the invention are for example SEQ ID NO:43 (which is the pMT/BiP/V5-HisA plasmid from Invitrogen comprising the pDeSNAP Univ cassette) in which the SBV.N DNA sequence SEQ ID NO: 17 has been inserted, SEQ ID NO:44 (which is the pUC57 plasmid from Invitrogen comprising the pDeSNAP Univ cassette) in which the SBV.N DNA sequence SEQ ID NO: 17 has been inserted or SEQ ID NO:45 (which is the pcDNA3 plasmid from Invitrogen comprising the pDeSNAP Univ cassette) in which the SBV.N DNA sequence SEQ ID NO: 17 has been inserted.

Vectors of the invention are also provided in the S2 cells which have been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another aspect, the present invention targets a recombinant cell which is stably transfected by a vector of the invention, preferably a vector comprising the nucleotide sequence SEQ ID NO: 35 or SEQ ID NO: 36.

Preferably, in this aspect of the invention, said recombinant cell is a non-vertebrate cell, preferably an insect cell, and more preferably a S2 cell.

Non-vertebrate cells can be any cells from the Insect, Arachnida, Crustacea, Mollusca, Annelida, Cirripedia, Radiata, Coelenterata and Infusoria. In the context of the invention, non-vertebrate cells are preferably insect cells, such as *Drosophila* or Mosquito cells. They are more preferably a *Drosophila* S2 cells. In this case, the expression vector of the invention comprises for example SEQ ID NO: 35.

*Drosophila* S2 cells have been widely described. They are especially suited to high-yield production of protein, because they can be maintained in suspension cultures at room temperature (24±1° C.). Culture medium is $M_3$ supplemented with between 5 and 10% (v/v) heat-inactivated fetal bovine serum (FBS). In the preferred embodiment of the invention, the culture medium contains 5% FBS. After induction, the cells are cultured in serum-free media. In this media, the S2 cells can be grown in suspension cultures, for example in 250 mL to 2000 mL spinner flasks, with stirring at 50-60 rpm. Cells densities are typically maintained between $10^6$ and $10^7$ cells per mL.

In a preferred embodiment, the recombinant cell of the invention is the S2 cell which has been deposited at the Centre National de Culture et de Microorganismes (CNCM), Institut Pasteur (25 rue du Docteur Roux, 75724 Paris cedex 15, France) on Apr. 24, 2012, under the number CNCM I-4616.

In another preferred embodiment, said recombinant cell is a vertebrate cell.

Preferably, said vertebrate recombinant cell is a mammal cell, a preferably CHO, YB2/O, COS, HEK, NIH3T3, HeLa cell or derivatives thereof. More preferably, in this case, the expression vector of the invention comprises SEQ ID NO: 36.

In another aspect of the present invention, the said recombinant cell is used to amplify and purify the expression vectors of the invention, preferably those comprising SEQ ID NO: 35 or 36.

In this aim, the nucleotide expression vectors of the invention may also comprise a gene encoding a selection marker, and/or a terminator sequence. Selection markers genes that can be included in the construct are typically those that confer selectable phenotypes such as resistance to antibiotics (e.g. blasticidin, ampicillin, kanamycin, hygromycin, puromycin, chloramphenicol).

Methods for producing expression vectors are well-known in the art.

In another aspect, the recombinant cell of the invention is used so as to produce the N nucleoprotein of the Schmallenberg virus in high amounts.

Thus, in a particular embodiment, the present invention is also drawn to a method for the production of the N nucleoprotein of the Schmallenberg virus, the method comprising the steps of:

(a) obtaining the vector of the invention, said vector comprising for example the DNA sequence SEQ ID NO:35 or SEQ ID NO:36,
(b) transfecting an host cell (preferably an insect cell or a mammal cell) with the polynucleotide obtained under step (a);
(c) allowing for the expression of said polynucleotide obtained under step (b) to produce the N nucleoprotein of the Schmallenberg virus;
(d) optionally, cleaving the AGT polypeptide, (e) recovering the N nucleoprotein of the Schmallenberg virus,
(f) optionally, purifying the N nucleoprotein of the Schmallenberg virus.

For performing the different steps of the method of the present invention, there may be employed conventional molecular biology, microbiology and recombinant DNA techniques within the skills of the person of the art. Such techniques are fully explained in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

The term "transfection" means the introduction of a foreign nucleic acid into a eukaryotic host cell so that the host cell will express the introduced gene or sequence to produce the N nucleoprotein of Schmallenberg virus. A host cell that receives and expresses introduced DNA or RNA has been "transfected" and is a "transfectant" or a "clone". The DNA or RNA introduced to a host cell can come from any source, including cells of the same genus or species as the host cell or cells of a different genus or species.

In the context of the invention, the transfection of the host cells with the polynucleotides can be performed by a classical method in the art, for example by transfection, infection, or electroporation. In another embodiment, the vector of the invention can be introduced in vivo by lipofection (as naked DNA), or with other transfection facilitating agents (peptides, polymers, etc.). Synthetic cationic lipids can be used to prepare liposomes for in vivo transfection of a gene encoding a marker (Felgner et al., *Proc. Natl. Acad. Sci. U.S.A.,* 84:7413-7417, 1987). Useful lipid compounds and compositions for transfer of nucleic acids are described in WO 95/18863 and WO 96/17823, and in U.S. Pat. No. 5,459,127. Lipids may be chemically coupled to other molecules for the purpose of targeting (see, Mackey et al., *Proc. Natl. Acad. Sci. U.S.A.,* 85:8027-8031, 1988). Targeted peptides, such as hormones or neurotransmitters, and proteins such as antibodies, or non-peptide molecules could be coupled to liposomes chemically. Other molecules are also useful for facilitating transfection of a nucleic acid in vivo, such as a cationic oligopeptides (see WO 95/21931), peptides derived from DNA binding proteins (see WO 96/25508), or a cationic polymer (see WO 95/21931). It is also possible to introduce the vector in vivo as a naked DNA plasmid. Naked DNA vectors for gene therapy can be introduced into the desired host cells by methods known in the art, such as electroporation, microinjection, cell fusion, DEAE dextran, calcium phosphate precipitation, use of a gene gun, or use of a DNA vector transporter (see, Wu et al., *J. Biol. Chem.,* 267:963-967, 1992; Wu and Wu, *J. Biol. Chem.,* 263:14621-14624, 1988; Williams et al., *Proc. Natl. Acad. Sci. U.S.A.,* 88:2726-2730, 1991).

The term "allowing for the expression" of a polynucleotide herein means that the stimulus of the regulatory sequences that are present in the vector (e.g. the stimulus activating the inducible promoter), and all the required components are present in a sufficient amount for the translation of the polynucleotide to occur.

If need be, the AGT/SNAP polypeptide can be cleaved off the produced fusion protein by adding a protease having a defined cleavage site to the supernatant of or into the recombinant cells. For example, when a vector comprising the pDeSNAP Univ cassette of SEQ ID NO: 35 or 36 is used, the cleavage of the pro-TEV cleavage site ENLKYFQ/G(S) is obtained by adding the TEV protease to the supernatant of the recombinant cells. Alternatively, the AGT/SNAP polypeptide can be maintained so as to enhance the life-span of the N nucleoprotein from SBV.

Moreover, the skilled artisan will appreciate that an expressed or secreted protein or polypeptide can be detected in the culture medium used to maintain or grow the present host cells. The culture medium can be separated from the host cells by known procedures, such as centrifugation or filtration. The protein or polypeptide can then be detected in the cell-free culture medium by taking advantage of known properties characteristic of the protein or polypeptide. Such properties can include the distinct immunological, enzymatic or physical properties of the protein or polypeptide. For example, if a protein or polypeptide has a unique enzyme activity an assay for that activity can be performed on the culture medium used by the host cells. Moreover, when antibodies reactive against a given protein or polypeptide are available, such antibodies can be used to detect the protein or polypeptide in any known immunological assay (for example as in Harlowe, et al., 1988, Antibodies: A Laboratory Manual, Cold Spring Harbor Laboratory Press).

Recovery of the nucleoprotein N from SBV is mediated by the means well-known in the art, including, but not limited to, preparative disc-gel electrophoresis, isoelectric focusing, HPLC, reversed-phase HPLC, gel filtration, ion exchange and partition chromatography, precipitation and salting-out chromatography, extraction, and countercurrent distribution, and the like. As it is preferable to produce the protein of interest in the recombinant system of the invention linked with a label, said label will facilitate the recovery of the polypeptide from the crude lysate of the host cell by chromatography on an appropriate solid-phase matrix. Alternatively, antibodies produced against the protein or against peptides derived therefrom can be used as recovery reagents.

The present Inventors discovered that the fusion proteins generated with the method of the invention generally do not need to be further purified. However, a further step (g) of purification may be performed, if required.

A purified material may contain less than about 50%, preferably less than about 75%, and most preferably less than about 90%, of the cellular components with which it was originally associated. The term "substantially pure" indicates the highest degree of purity which can be achieved using conventional purification techniques known in the art.

In an embodiment of the invention, the methods of the invention enable to obtain at least 40 mg/L, preferably at least 50 mg/L, more preferably at least 60 mg/L of the substantially pure N nucleoprotein of the Schmallenberg virus in the recovered cell culture supernatant.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein of Schmallenberg virus of SEQ ID NO: 16.

In this fusion polypeptide, said AGT enzyme is preferably the protein of SEQ ID NO: 2, or a homologue thereof (said homologous being as defined above).

This fusion polypeptide preferably further comprises a label, as defined above. This label is preferably a polyhistidine label, and is preferably located at the C terminal end of the N nucleoprotein of the Schmallenberg virus.

The fusion polypeptide of the invention is for example the amino acid sequence of SEQ ID NO: 41 (corresponding to the BiPlike/SNAP/SBV.N/Histag fusion protein) or SEQ ID NO: 46 (corresponding to the ssBiP/SNAP/SBV.N/Histag fusion protein) or SEQ ID NO:42 (corresponding to the SNAP/SBV.N fusion protein).

Finally, the chimeric protein SNAP-SBV. N may be useful as a diagnostic agent for the detection of the viral infection by the Schmallenberg virus, or for the detection of antibodies specific of the said virus in biological fluids, such as blood, serum, saliva, and the like.

Thus, in another aspect, the present invention is also drawn to the use of the fusion protein [SNAP-SBV. N] obtained by any method of the invention for identifying the presence of said pathogenic or non-pathogenic microorganisms in a biological sample, for example thanks to the immunoassay of the present invention.

In other aspects, the present invention also relates to vectors expressing fusion proteins of particular interest, said fusion proteins comprising a 6-alkylguanine-DNA-alkyltransferase enzyme (AGT), a mutant, a fragment or a catalytic domain thereof, that is fused in frame with interesting antigens, such as viral or bacterial antigens, microbial peptides and/or polypeptides of interest. These vectors are detailed below.

Echovirus Antigen

In another aspect, the present invention relates to a vector for expressing an echovirus antigen, for example the VP1 protein of the enterovirus 71 (Picornaviridae), in a host cell. In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VP1 protein of the enterovirus 71 (EV71, see for example Kolpe A. B. et al, *Virus Research* 2012).

In a preferred embodiment, this vector comprises a so-called "pDeSNAP Univ/EV71.VP1 cassette" i.e., a pDeSNAPUniv DNA cassette as defined above, in which the sequence SEQ ID NO:47 encoding the VP1 protein from the EV71 virus strain JL-AFP-EV71-07-03 (Genebank#JQ715713) has been inserted.

In a preferred embodiment, this vector comprises the pDeSNAP Univ/EV71.VP1 cassette having the nucleotide sequence SEQ ID NO: 48 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence SEQ ID NO:47 encoding the VP1 protein from the EV71 virus strain JL-AFP-EV71-07-03 (Genebank#JQ715713),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VP1 protein from the EV71 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 49 (corresponding to the SNAP-like/proTEV1/EV71.VP1/proTEV2/Histag fusion protein).

Thus, in another aspect, the present invention is also drawn to the use of this fusion protein [SNAP-EV71.VP1] for identifying the presence of the enterovirus 71 in a biological sample, for example thanks to the immunoassay of the present invention.

Flavivirus Antigens

In another aspect, the present invention relates to vectors for expressing particular Flavivirus antigens in a host cell.

In a preferred embodiment, said Flavivirus antigen is the soluble E protein (sE) from the Japanese Encephalitis virus (JEV.sE). More particularly, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE protein from the Japanese Encephalitis virus.

In a preferred embodiment, this vector comprises a so-called "pDeSNAP Univ/JEV.sE cassette" i.e., a pDeSNAPUniv DNA cassette as defined above, in which the sequences of gene encoding the soluble E protein (sE) from the Japanese Encephalitis virus (JEV) have been inserted.

In a preferred embodiment, this vector comprises the pDeSNAP Univ/JEV.sE cassette having the nucleotide sequence SEQ ID NO: 50 comprising, from 5' to 3':

- an insect BiP sequence of SEQ ID NO: 22,
- the DNA sequence encoding the prM/M sequence from JEV strain SA-14 (Genbank#M55506),
- the DNA sequence encoding the E[1-395] sequence from JEV strain SA-14 (Genbank#M55506),
- a DNA sequence SEQ ID NO: 26 encoding the spacer sequence GGGS (SEQ ID NO: 25),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble E protein (sE) from the Japanese Encephalitis virus (JEV.sE). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 51 (corresponding to the JEV.sE/SNAP-like/Histag fusion protein).

Thus, in another aspect, the present invention is also drawn to the use of this fusion protein [SNAP-JEV.sE] for identifying the presence of the Japanese Encephalitis virus (JEV) in a biological sample, for example thanks to the immunoassay of the present invention.

In a preferred embodiment, said Flavivirus antigen is the domain III of the envelope E protein (EDIII protein) from the Japanese encephalitis virus of genotype 1 (JE-1.EDIII), of genotype 2 (JE-3.EDIII), of genotype 4 (JE-4.EDIII), or of genotype 5 (JE-5.EDIII).

In another aspect, the present invention therefore relates to a vector for expressing the domain III of the envelope E protein (EDIII protein) from the Japanese encephalitis virus of genotype I (JE-I.EDIII), of genotype 2 (JE-2.EDIII), of genotype 4 (JE-4.EDIII), or of genotype 5 (JE-5.EDIII) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the EDIII protein from the Japanese encephalitis virus of genotype 1 (JE-I.EDIII), of genotype 2 (JE-2.EDIII), of genotype 4 (JE-4.EDIII), or of genotype 5 (JE-5.EDIII).

In a preferred embodiment, this vector comprises a so-called "pDeSNAP Univ/JE-I.EDIII cassette" i.e., a pDeSNAPUniv DNA cassette as defined above, in which the sequence of gene encoding the domain III of the envelope E protein (EDIII protein) from the Japanese encephalitis virus of genotype 1 (JE-1.EDIII) has been inserted.

In a preferred embodiment, this vector comprises the pDeSNAP Univ/JE-1.EDIII cassette having the nucleotide sequence SEQ ID NO: 52 comprising:

- an insect BiP-like sequence of SEQ ID NO: 23,
- the SNAP-like sequence of SEQ ID NO: 31,
- the DNA sequence SEQ ID NO:54 encoding the domain III of the envelope E protein (EDIII protein) from the Japanese encephalitis virus of genotype 1 (Genebank#AY377577),
- a DNA sequence SEQ ID NO: 28 encoding a HisTag sequence.

In a preferred embodiment, this vector comprises a so-called "pDeSNAP Univ/JE-2.EDIII cassette" i.e., a pDeSNAPUniv DNA cassette as defined above, in which the sequence of the domain III of the envelope E protein (EDIII protein) from the Japanese encephalitis virus of genotype 2 (JE-2.EDIII) has been inserted.

In a preferred embodiment, this vector comprises the pDeSNAP Univ/JE-2.EDIII cassette having the nucleotide sequence SEQ ID NO: 59 comprising:

- an insect BiP-like sequence of SEQ ID NO: 23,
- the SNAP-like sequence of SEQ ID NO: 31,
- the DNA sequence SEQ ID NO:55 encoding the domain III of the envelope E protein (EDIII protein) from the Japanese encephalitis virus of genotype 2 (Genebank#L-43566),
- a DNA sequence SEQ ID NO: 28 encoding a HisTag sequence.

In a preferred embodiment, this vector comprises a so-called "pDeSNAP Univ/JE-4.EDIII cassette" i.e., a pDeSNAPUniv DNA cassette as defined above, in which the sequence of the domain III of the envelope E protein (EDIII protein) from the Japanese encephalitis virus of genotype 4 (JE-4.EDIII) has been inserted.

In a preferred embodiment, this vector comprises the pDeSNAP Univ/JE-4.EDIII cassette having the nucleotide sequence SEQ ID NO: 61 comprising:

- an insect BiP-like sequence of SEQ ID NO: 23,
- the SNAP-like sequence of SEQ ID NO: 31,
- the DNA sequence SEQ ID NO:56 encoding the domain III of the envelope E protein (EDIII protein) from the Japanese encephalitis virus of genotype 4 (Genebank#U70408),
- a DNA sequence SEQ ID NO: 28 encoding a HisTag sequence.

In a preferred embodiment, this vector comprises a so-called "pDeSNAP Univ/JE-5.EDIII cassette" i.e., a pDeSNAPUniv DNA cassette as defined above, in which the sequence of the gene encoding the domain III of the envelope E protein (EDIII protein) from the Japanese encephalitis virus of genotype 5 (JE-5.EDIII) has been inserted.

In a preferred embodiment, this vector comprises the pDeSNAP Univ/JE-5.EDIII cassette having the nucleotide sequence SEQ ID NO: 63 comprising:

- an insect BiP-like sequence of SEQ ID NO: 23,
- the SNAP-like sequence of SEQ ID NO: 31,
- the DNA sequence SEQ ID NO:57 encoding the domain III of the envelope E protein (EDIII protein) from the Japanese encephalitis virus of genotype 5 (Genebank#JN587258),
- a DNA sequence SEQ ID NO: 28 encoding a HisTag sequence.

In another aspect, the present invention relates to recombinant cells which are stably transfected by said vectors.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the JE-1, JE-2, JE-4, or JE-5 virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 53 (corresponding to the SNAP-like/JE-1.EDIII/Histag fusion protein), SEQ ID NO: 60 (corresponding to the SNAP-like/JE-2.EDIII/Histag fusion protein) SEQ ID NO: 62 (corresponding to the SNAP-like/JE-4.EDIII/Histag fusion protein) or SEQ ID NO: 64 (corresponding to the SNAP-like/JE-5.EDIII/Histag fusion protein).

Thus, in another aspect, the present invention is also drawn to the use of any of these fusion proteins [SNAP-JE-1.EDIII], [SNAP-JE-2.EDIII], [SNAP-JE-4.EDIII] or [SNAP-JE-5.EDIII] for identifying the presence of the Japanese encephalitis virus of genotype 1, 2, 4 or 5 respectively in a biological sample, for example thanks to the immunoassay of the present invention.

In another aspect, the present invention is drawn to a vector for expressing the domain III of the envelope E protein (EDIII protein) from the Rabensburg virus (RabV) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the envelope E protein (EDIII protein) from the Rabensburg virus (RabV).

In a preferred embodiment, this vector comprises a so-called "pDeSNAP Univ/RabV.EDIII cassette" i.e., a pDeSNAPUniv DNA cassette as defined above, in which the sequence of the EDIII protein from the Rabensburg virus has been inserted.

In a preferred embodiment, this vector comprises the pDeSNAP Univ/RabV.EDIII cassette having the nucleotide sequence SEQ ID NO: 65 comprising:

- an insect BiP-like sequence of SEQ ID NO: 23,
- the SNAP-like sequence of SEQ ID NO: 31,
- the DNA sequence SEQ ID NO:58 encoding the domain III of the envelope E protein (EDIII protein) from the Rabensburg virus (Genebank#AY65264),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Rabensburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 66 (corresponding to the SNAP-like/RabV.EDIII/Histag fusion protein).

Thus, in another aspect, the present invention is also drawn to the use of this fusion protein [SNAP-RabV.EDIII] for identifying the presence of the Rabensburg virus in a biological sample, for example thanks to the immunoassay of the present invention.

Alphavirus Antigens

In another aspect, the present invention is relates to vectors for expressing particular alphavirus antigens, for example the soluble E2 protein from the Ross River virus (RR.sE2) or from the Mayaro virus (MAY.sE2), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Ross River virus.

In a preferred embodiment, this vector comprises a so-called "pDeSNAP Univ/RR.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/RR.sE2 cassette having the nucleotide sequence SEQ ID NO: 69 comprising:

- an insect BiP sequence of SEQ ID NO: 22,
- the DNA sequence encoding the sE2 protein of the Ross River virus strain QML1 (Genbank#GQ433354),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Ross River virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 70 (corresponding to the RR.sE2/SNAP-like/Histag fusion protein).

Thus, in another aspect, the present invention is also drawn to the use of this fusion protein [SNAP-RR.sE2] for identifying the presence of the Ross River virus in a biological sample, for example thanks to the immunoassay of the present invention.

The present invention is also drawn to a vector for expressing the soluble E2 protein from the Mayaro virus (MAY.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the sE2 protein from the Mayaro virus.

In a preferred embodiment, this vector comprises a so-called "pDeSNAP Univ/MAY.sE2 cassette" i.e., a pDeSNAPUniv DNA cassette as defined above, in which the sequence of the sE2 gene from the Ross River virus has been inserted.

In a preferred embodiment, this vector comprises the pDeSNAP Univ/MAY.sE2 cassette having the nucleotide sequence SEQ ID NO: 71 comprising:

- an insect BiP sequence of SEQ ID NO: 22,
- the DNA sequence encoding the corrected sE2 protein (E2-S203C) of the Mayaro virus strain IQD2668 (Genbank#DQ487429.1),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the Mayaro virus (MAY.sE2). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 72 (corresponding to the MAY.sE2/SNAP-like/Histag fusion protein).

Thus, in another aspect, the present invention is also drawn to the use of this fusion protein [SNAP-MAY.sE2] for identifying the presence of the Mayaro virus in a biological sample, for example thanks to the immunoassay of the present invention.

Equine Encephalitis Virus Antigens

In another aspect, the present invention relates to vectors for expressing particular Equine Encephalitis virus antigens, for example the soluble E2 protein from the Western Equine Encephalitis virus (WEE.sE2), the Eastern Equine Encephalitis virus (EEE.sE2) or the Venezuelan Equine Encephalitis virus (VEE.sE2) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Western Equine Encephalitis virus.

In a preferred embodiment, this vector comprises a so-called "pDeSNAP Univ/WEE.sE2 cassette" i.e., a pDeSNAPUniv DNA cassette as defined above, in which the sequence of the sE2 gene from the Western Equine Encephalitis virus has been inserted.

In a preferred embodiment, this vector comprises the pDeSNAP Univ/WEE.sE2 cassette having the nucleotide sequence SEQ ID NO: 73 comprising:

an insect BiP sequence of SEQ ID NO: 22, the DNA sequence encoding the sE2 protein from Western Equine Encephalitis virus strain (Genbank#NC00390808), the SNAP-like sequence of SEQ ID NO: 31, a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the WEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 74 (corresponding to the WEE.sE2/SNAP-like/Histag fusion protein).

Thus, in another aspect, the present invention is also drawn to the use of this fusion protein [SNAP-WEE.sE2] for identifying the presence of the Western Equine Encephalitis virus in a biological sample, for example thanks to the immunoassay of the present invention.

In another embodiment, the present invention is also drawn to a vector for expressing the soluble E2 protein from the Eastern Equine Encephalitis virus (EEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Eastern Equine Encephalitis virus.

In a preferred embodiment, this vector comprises a so-called "pDeSNAP Univ/EEE.sE2 cassette" i.e., a pDeSNAPUniv DNA cassette as defined above, in which the sequence of the sE2 gene from the Eastern Equine Encephalitis virus has been inserted.

In a preferred embodiment, this vector comprises the pDeSNAP Univ/EEE.sE2 cassette having the nucleotide sequence SEQ ID NO: 75 comprising:

an insect BiP sequence of SEQ ID NO: 22, the DNA sequence encoding the sE2 protein from Eastern Equine Encephalitis virus strain (Genbank#EF151502), the SNAP-like sequence of SEQ ID NO: 31, a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the EEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 76 (corresponding to the EEE.sE2/SNAP-like/Histag fusion protein).

Thus, in another aspect, the present invention is also drawn to the use of this fusion protein [SNAP-EEE.sE2] for identifying the presence of the Eastern Equine Encephalitis virus in a biological sample, for example thanks to the immunoassay of the present invention.

In another embodiment, the present invention is also drawn to a vector for expressing the soluble E2 protein from the Venezuelan Equine Encephalitis virus (VEE.sE2) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble E2 protein from the Venezuelan Equine Encephalitis virus.

In a preferred embodiment, this vector comprises a so-called "pDeSNAP Univ/VEE.sE2 cassette" i.e., a pDeSNAPUniv DNA cassette as defined above, in which the sequence of the sE2 gene from the Venezuelan Equine Encephalitis virus has been inserted.

In a preferred embodiment, this vector comprises the pDeSNAP Univ/VEE.sE2 cassette having the nucleotide sequence SEQ ID NO: 77 comprising:

an insect BiP sequence of SEQ ID NO: 22, the DNA sequence encoding the sE2 protein from Venezuelan Equine Encephalitis virus strain (Genbank#AY973944), the SNAP-like sequence of SEQ ID NO: 31, a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the sE2 protein from the VEE virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 78 (corresponding to the VEE.sE2/SNAP-like/Histag fusion protein).

Thus, in another aspect, the present invention is also drawn to the use of this fusion protein [SNAP-VEE.sE2] for identifying the presence of the Venezuelan Equine Encephalitis virus in a biological sample, for example thanks to the immunoassay of the present invention.

Orthobunyavirus Antigens

In another aspect, the present invention relates to vectors for expressing particular orthobunyavirus antigens, for example the Nucleoprotein N from the Akabane virus (AKA.N), from the Aino virus (AIN.N) or from the Shamonda virus (SHA.N), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Akabane virus.

In a preferred embodiment, this vector comprises a so-called "pDeSNAP Univ/AKA.N cassette" i.e., a pDeSNAPUniv DNA cassette as defined above, in which the sequence of the gene encoding the Nucleoprotein N from the Akabane virus has been inserted.

In a preferred embodiment, this vector comprises the pDeSNAP Univ/AKA.N cassette having the nucleotide sequence SEQ ID NO: 79 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Akabane virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Akabane virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 80 (corresponding to the SNAP-like/proTEV1/AKA.N/pro-TEV2/Histag fusion protein).

Thus, in another aspect, the present invention is also drawn to the use of this fusion protein [SNAP-AKA.N] for identifying the presence of the Akabane virus in a biological sample, for example thanks to the immunoassay of the present invention.

In another embodiment, the present invention is drawn to a vector for expressing the Nucleoprotein N from the Aino virus (AIN.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Aino virus.

In a preferred embodiment, this vector comprises a so-called "pDeSNAP Univ/AIN.N cassette" i.e., a pDeSNAPUniv DNA cassette as defined above, in which the sequence of the gene encoding the Nucleoprotein N from the Aino virus has been inserted.

In a preferred embodiment, this vector comprises the pDeSNAP Univ/AIN.N cassette having the nucleotide sequence SEQ ID NO: 81 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Aino virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Aino virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 82 (corresponding to the SNAP-like/proTEV1/AIN.N/pro-TEV2/Histag fusion protein).

Thus, in another aspect, the present invention is also drawn to the use of this fusion protein [SNAP-AIN.N] for identifying the presence of the Aino virus in a biological sample, for example thanks to the immunoassay of the present invention.

In another embodiment, the present invention is drawn to a vector for expressing the Nucleoprotein N from the Shamonda virus (SHA.N) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Shamonda virus.

In a preferred embodiment, this vector comprises a so-called "pDeSNAP Univ/SHA.N cassette" i.e., a pDeSNAPUniv DNA cassette as defined above, in which the sequence of the gene encoding the Nucleoprotein N from the Shamonda virus has been inserted.

In a preferred embodiment, this vector comprises the pDeSNAP Univ/SHA.N cassette having the nucleotide sequence SEQ ID NO: 83 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the natural N nucleoprotein of the Shamonda virus,
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the N nucleoprotein from the Shamonda virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 84 (corresponding to the SNAP-like/proTEV1/SHA.N/pro-TEV2/Histag fusion protein).

Thus, in another aspect, the present invention is also drawn to the use of this fusion protein [SNAP-SHA.N] for identifying the presence of the Shamonda virus in a biological sample, for example thanks to the immunoassay of the present invention.

Betacoronavirus Antigens

In another aspect, the present invention relates to vectors for expressing particular betacoronavirus antigens, for example the Nucleoprotein N from human betacoronavirus (huCOV.N) or the protein S of the human betacoronavirus (huCOV.S), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from human betacoronavirus.

In a preferred embodiment, this vector comprises a so-called "pDeSNAP Univ/huCOV.N cassette" i.e., a pDeSNAPUniv DNA cassette as defined above, in which the sequence of the gene encoding the Nucleoprotein N from human betacoronavirus has been inserted.

In a preferred embodiment, this vector comprises the pDeSNAP Univ/huCOV.N cassette having the nucleotide sequence SEQ ID NO: 85 comprising:

- an insect BiP sequence of SEQ ID NO: 22,
- the SNAP-like sequence of SEQ ID NO: 31,
- a DNA sequence SEQ ID NO: 29 encoding a pro-TEV1 cleavage site of sequence ENLYFQS (SEQ ID NO: 32),
- the DNA sequence encoding the gene N from human betacoronavirus 2cEMC/2012 (Genbank#JX869059),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 86 (corresponding to the SNAP-like/proTEV1/huCOV.N/proTEV2/Histag fusion protein).

Thus, in another aspect, the present invention is also drawn to the use of this fusion protein [SNAP-huCOV.N] for identifying the presence of the human betacoronavirus in a biological sample, for example thanks to the immunoassay of the present invention.

In another embodiment, the present invention is drawn to a vector for expressing the soluble form of the spike S protein from human betacoronavirus (huCOV.S) in an host cell, comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the soluble form of the spike S protein from human betacoronavirus.

In a preferred embodiment, this vector comprises a so-called "pDeSNAP Univ/huCOV.S cassette" i.e., a pDeSNAPUniv DNA cassette as defined above, in which the sequence of the gene S from human betacoronavirus has been inserted.

In a preferred embodiment, this vector comprises the pDeSNAP Univ/huCOV.S cassette having the nucleotide sequence SEQ ID NO: 87 comprising:

- an insect BiP sequence of SEQ ID NO: 22,
- the DNA sequence encoding the gene S from human betacoronavirus 2cEMC/2012 (Genbank#JX869059),
- a DNA sequence SEQ ID NO: 26 encoding the spacer sequence GGGS (SEQ ID NO: 25),
- the SNAP-like sequence of SEQ ID NO: 31,
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the soluble form of the spike S protein from human betacoronavirus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 88 (corresponding to the huCOV.S/SNAP-like/Histag fusion protein).

Thus, in another aspect, the present invention is also drawn to the use of this fusion protein [SNAP-huCOV.S] for identifying the presence of the human betacoronavirus in a biological sample, for example thanks to the immunoassay of the present invention.

Hepacivirus Antigen

In another aspect, the present invention relates to vectors for expressing particular hepacivirus antigens, for example the protein C from Hepatitis C virus (HCV.C) or from Hepatitis E virus (HEV.C), in a host cell.

In one embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis C virus.

In a preferred embodiment, this vector comprises a so-called "pDeSNAP Univ/HCV.C cassette" i.e., a pDeSNAPUniv DNA cassette as defined above, in which the sequence of the gene of the protein C from Hepatitis C virus has been inserted.

In a preferred embodiment, this vector comprises the pDeSNAP Univ/HCV.C cassette having the nucleotide sequence SEQ ID NO: 89 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the C protein from hepatitis C virus genotype 1b (strain TCHM-R2/03),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis C virus (HCV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 90 (corresponding to the SNAP-like/proTEV1/HCV.C/proTEV2/Histag fusion protein).

Thus, in another aspect, the present invention is also drawn to the use of this fusion protein [SNAP-HCV.C] for identifying the presence of the Hepatitis C virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the protein C from Hepatitis E virus (HEV.C).

In a preferred embodiment, this vector comprises a so-called "pDeSNAP Univ/HEV.C cassette" i.e., a pDeSNAPUniv DNA cassette as defined above, in which the sequence of the gene of the protein C from Hepatitis E virus has been inserted.

In a preferred embodiment, this vector comprises the pDeSNAP Univ/HEV.C cassette having the nucleotide sequence SEQ ID NO: 150 comprising:

- an insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the C protein from hepatitis E virus (Genbank#AB29196),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the protein C from Hepatitis E virus (HEV.C). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 151 (corresponding to the SNAP-like/proTEV1/HEV.C/proTEV2/Histag fusion protein).

Thus, in another aspect, the present invention is also drawn to the use of this fusion protein [SNAP-HEV.C] for identifying the presence of the Hepatitis E virus in a biological sample, for example thanks to the immunoassay of the present invention.

Malaria Antigens

In another aspect, the present invention is drawn to a vector for expressing particular Malaria antigens, for example, the MSP-1 and the AMA-1 proteins from *Plasmodium falciparum* (MSP-1+AMA-1) (see Pan W. et al, *The Journal of Immunology,* 2004), in an host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MSP-1 and the AMA-1 proteins from the parasite *Plasmodium falciparum.*

In a preferred embodiment, this vector comprises a so-called "pDeSNAP Univ/MSP-1+AMA-1cassette" i.e., a pDeSNAPUniv DNA cassette as defined above, in which the sequence encoding the MSP-1 and the AMA-1 proteins from the parasite *Plasmodium falciparum* has been inserted.

In a preferred embodiment, this vector comprises the pDeSNAP Univ/MSP-1+AMA-1cassette having the nucleotide sequence SEQ ID NO: 91 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- the DNA sequence encoding the MSP-1 (19) sequence (50% G+C) from *Plasmodium falciparum,*
- a DNA sequence SEQ ID NO: 30 encoding a pro-TEV2 cleavage site of sequence ENLYFQG (SEQ ID NO: 33),
- the DNA sequence encoding the AMA-1 (III) sequence (50% G+C) from *Plasmodium falciparum,*
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MSP-1+AMA-1 protein from *Plasmodium falciparum*. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 92 (corresponding to the SNAP-like/MSP-1/proTEV2/AMA-1/Histag fusion protein).

Thus, in another aspect, the present invention is also drawn to the use of this fusion protein [SNAP-MSP-1+AMA-1] for identifying the presence of the parasite *Plasmodium falciparum* in a biological sample, for example thanks to the immunoassay of the present invention.

Leptospirosis Antigens

In another aspect, the present invention is drawn to a vector for expressing a particular leptospirosis antigen, such as the HbpA protein of *Leptospira* bacteria (see Sivakolundu S. et al, *Journal of Medical Microbiology,* 2012), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the HbpA protein from *Leptospira interrogans* bacteria.

In a preferred embodiment, this vector comprises a so-called "pDeSNAP Univ/HbpA cassette" i.e., a pDeSNAPUniv DNA cassette as defined above, in which the sequence encoding the HbpA protein from *Leptospira* bacteria has been inserted.

In a preferred embodiment, this vector comprises the pDeSNAP Univ/HbpA cassette having the nucleotide sequence SEQ ID NO: 93 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the modified short form of HbpA (TonB-dependent outer membrane receptor or LB191) from *Leptospira interrogans* serovar Lai str.56601 (Genbank#AA51750.1),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the HbpA protein from *Leptospira interrogans* bacteria. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 94 (corresponding to the SNAP-like/proTEV1/HbpA/proTEV2/Histag fusion protein).

Thus, in another aspect, the present invention is also drawn to the use of this fusion protein [SNAP-HbpA] for identifying the presence of the *Leptospira* bacteria in a biological sample, for example thanks to the immunoassay of the present invention.

Microbial Peptides

In another aspect, the present invention is drawn to a vector for expressing a microbial peptide, for example the microbial peptide MUB-40, in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the MUB-40 peptide.

In a preferred embodiment, this vector comprises a so-called "pDeSNAP Univ/MUB40 cassette" i.e., a pDeSNAPUniv DNA cassette as defined above, in which the sequence encoding the MUB40 peptide has been inserted.

In a preferred embodiment, this vector comprises the pDeSNAP Univ/MUB40 cassette having the nucleotide sequence SEQ ID NO: 95 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the MUB-40 peptide,
- a DNA sequence SEQ ID NO: 30 encoding a pro-TEV2 cleavage site of sequence ENLYFQG (SEQ ID NO: 33), and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the MUB 40 peptide. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 96 (corresponding to the SNAP-like/proTEV1/MUB40/pro-TEV2/Histag fusion protein).

Thus, in another aspect, the present invention is also drawn to the use of this fusion protein [SNAP-MUB40] for identifying the presence of a ligand in a biological sample, for example thanks to the immunoassay of the present invention.

Lectins Involved in Flavivirus Pathogenesis

In another aspect, the present invention is drawn to vectors for expressing particular lectins involved in Flavivirus pathogenesis, for example the mouse or the human soluble form of C-type like lectin (CLEC5A), in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the mouse CLEC5A (mo-CLEC5A) or the human CLEC5A (hu-CLEC5A).

In a preferred embodiment, this vector comprises a so-called "pDeSNAP Univ/mo-CLEC5A cassette" i.e., a pDeSNAPUniv DNA cassette as defined above, in which the sequence encoding the mouse soluble form of C-type like lectin has been inserted.

In a preferred embodiment, this vector comprises the pDeSNAP Univ/mo-CLEC5A cassette having the nucleotide sequence SEQ ID NO: 97 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the mouse soluble form of C-type like lectin (CLEC5A),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25), and
- a DNA sequence SEQ ID NO: 28 encoding a HisTag sequence.

In another aspect, the present invention relates to a recombinant cell which is stably transfected by said vector.

In another preferred embodiment, this vector comprises a so-called "pDeSNAP Univ/hu-CLEC5A cassette" i.e., a pDeSNAPUniv DNA cassette as defined above, in which the sequence encoding the human soluble form of C-type like lectin has been inserted.

In a preferred embodiment, this vector comprises the pDeSNAP Univ/hu-CLEC5A cassette having the nucleotide sequence SEQ ID NO: 99 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32), the DNA sequence encoding the human soluble form of C-type like lectin (CLEC5A), a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), and a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the mouse or the human soluble form of C-type like lectin (CLEC5A). In this fusion polypeptide, said AGT enzyme is preferably the protein of SEQ ID NO: 2, or a homologue thereof (said homologous being as defined above). This fusion polypeptide is for example the amino acid sequence of SEQ ID NO: 98 (corresponding to the SNAP-like/proTEV1/mo-CLEC5A/proTEV2/Histag fusion protein) or the amino acid sequence of SEQ ID NO: 100 (corresponding to the SNAP-like/proTEV1/hu-CLEC5A/proTEV2/Histag fusion protein).

Thus, in another aspect, the present invention is also drawn to the use of this fusion protein [SNAP-mo-CLEC5A] or [SNAP-hu-CLEC5A] for detection of presence of flaviviruses in a biological sample, for example thanks to the immunoassay of the present invention.

Anti-Flaviviral Mosquito Proteins

In another aspect, the present invention is drawn to vectors for expressing particular antiviral mosquito proteins, for example the VAGO protein from the *Culex* species (cxVAGO) or from the *Aedes* species (aaVAGO) in a host cell.

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Aedes albopictus* mosquito.

In a preferred embodiment, this vector comprises a so-called "pDeSNAP Univ/aaVAGO cassette" i.e., a pDeSNAPUniv DNA cassette as defined above, in which the sequence encoding the VAGO protein from the *Aedes albopictus* mosquito has been inserted.

In a preferred embodiment, this vector comprises the pDeSNAP Univ/aaVAGO cassette having the nucleotide sequence SEQ ID NO: 103 comprising:

an insect BiP-like sequence of SEQ ID NO: 152, the SNAP-like sequence of SEQ ID NO: 31, a DNA sequence SEQ ID NO: 26 encoding the spacer sequence GGGS (SEQ ID NO: 25), the DNA sequence encoding the VAGO protein from the *Aedes albopictus* mosquito, and a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Aedes albopictus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 104 (corresponding to the SNAP-like/aaVAGO/Histag fusion protein).

Thus, in another aspect, the present invention is also drawn to the use of this fusion protein [SNAP-aaVAGO] for identifying the presence of a ligand in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the VAGO protein from the *Culex quinquefasciatus* mosquito.

In a preferred embodiment, this vector comprises a so-called "pDeSNAP Univ/cxVAGO cassette" i.e., a pDeSNAPUniv DNA cassette as defined above, in which the sequence encoding the VAGO protein from the *Culex quinquefasciatus* mosquito has been inserted.

In a preferred embodiment, this vector comprises the pDeSNAP Univ/cxVAGO cassette having the nucleotide sequence SEQ ID NO: 101 comprising:

an insect BiP-like sequence of SEQ ID NO: 152, the SNAP-like sequence of SEQ ID NO: 31, a DNA sequence SEQ ID NO: 26 encoding the spacer sequence GGGS (SEQ ID NO: 25), the DNA sequence encoding the VAGO protein from the *Culex quinquefasciatus* mosquito, and a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the VAGO protein from the *Culex quinquefasciatus* mosquito. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 102 (corresponding to the SNAP-like/cxVAGO/Histag fusion protein).

Thus, in another aspect, the present invention is also drawn to the use of this fusion protein [SNAP-cxVAGO] for identifying the presence of a ligand in a biological sample, for example thanks to the immunoassay of the present invention.

Viral Hemorragic Fever Antigens

In another aspect, the present invention is drawn to vectors for expressing particular viral hemorragic fever antigens such as:

the Nucleoprotein N from the Crimean-Congo virus (CCHF.N), from the Ebola virus (EBO.N), from the Marburg virus (MAR.N), from the Lassa virus (LAS.N), from the Junin virus (JUN.N), from the Machupo virus (MAC.N), from the Sabia virus (SAB.N), or from the Guanarito virus (GUA.N), the Ectodomain of GP1 from the Lassa virus (LAS.ectoGP1), from the Junin virus (JUN.ectoGP1), from the Machupo virus (MAC.ectoGP1), from the Sabia virus (SAB.ectoGP1), or from the Guanarito virus (GUA.ectoGP1), the Ectodomain of GP2 from the Lassa virus (LAS.ectoGP2), from the Junin virus (JUN.ectoGP2), from the Machupo virus (MAC.ectoGP2), from the Sabia virus (SAB.ectoGP2), or from the Guanarito virus (GUA.ectoGP2), the domain III of the envelope E protein from the Omsk virus (OMSK.EDIII), from the Kasyanur virus (KAS.EDIII), or from the Alkhurma virus (ALK. EDIII).

In particular, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Crimean-Congo virus (CCHF.N).

In a preferred embodiment, this vector comprises a so-called "pDeSNAP Univ/CCHF.N cassette" i.e., a pDeSNAPUniv DNA cassette as defined above, in which the sequence encoding the Nucleoprotein N from the Crimean-Congo virus has been inserted.

In a preferred embodiment, this vector comprises the pDeSNAP Univ/CCHF.N cassette having the nucleotide sequence SEQ ID NO: 108 comprising:

an insect BiP sequence of SEQ ID NO: 22, the SNAP-like sequence of SEQ ID NO: 31, a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32), the DNA sequence encoding the Nucleoprotein N from the Crimean-Congo virus, a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Crimean-Congo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 109 (corresponding to the SNAP-like/proTEV1/CCHF.N/proTEV2/Histag fusion protein).

Thus, in another aspect, the present invention is also drawn to the use of this fusion protein [SNAP-CCHF.N] for identifying the presence of the Crimean-Congo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Ebola virus (EBO.N).

In a preferred embodiment, this vector comprises a so-called "pDeSNAP Univ/EBO.N cassette" i.e., a pDeSNAPUniv DNA cassette as defined above, in which the sequence encoding the Nucleoprotein N from the Ebola virus has been inserted.

In a preferred embodiment, this vector comprises the pDeSNAP Univ/EBO.N cassette having the nucleotide sequence SEQ ID NO: 110 comprising:

an insect BiP sequence of SEQ ID NO: 22, the SNAP-like sequence of SEQ ID NO: 31, a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32), the DNA sequence encoding the Nucleoprotein N from the Ebola virus (Genbank#NC_002549), a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Ebola virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 111 (corresponding to the SNAP-like/proTEV1/EBO.N/proTEV2/Histag fusion protein).

Thus, in another aspect, the present invention is also drawn to the use of this fusion protein [SNAP-EBO.N] for identifying the presence of the Ebola virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Marburg virus (MAR.N).

In a preferred embodiment, this vector comprises a so-called "pDeSNAP Univ/MAR.N cassette" i.e., a pDeSNAPUniv DNA cassette as defined above, in which the sequence encoding the Nucleoprotein N from the Marburg virus has been inserted.

In a preferred embodiment, this vector comprises the pDeSNAP Univ/MAR.N cassette having the nucleotide sequence SEQ ID NO: 112 comprising:

an insect BiP sequence of SEQ ID NO: 22, the SNAP-like sequence of SEQ ID NO: 31, a first DNA sequence SEQ ID NO: 26 encoding the spacer sequence GGGS (SEQ ID NO: 25), a DNA sequence SEQ ID NO: 29 encoding a pro-TEV1 cleavage site of sequence ENLYFQS (SEQ ID NO: 32), the DNA sequence encoding the Nucleoprotein N from the Marburg virus (Genbank#NC_001608), a DNA sequence SEQ ID NO: 30 encoding a pro-TEV2 cleavage site of sequence ENLYFQG (SEQ ID NO: 33), a second DNA sequence SEQ ID NO: 26 encoding the spacer sequence GGGS (SEQ ID NO: 25), a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Marburg virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 113 (corresponding to the SNAP-like/proTEV1/MAR.N/proTEV2/Histag fusion protein).

Thus, in another aspect, the present invention is also drawn to the use of this fusion protein [SNAP-MAR.N] for identifying the presence of the Marburg virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Lassa virus (LAS.N).

In a preferred embodiment, this vector comprises a so-called “pDeSNAP Univ/LAS.N cassette” i.e., a pDeSNAPUniv DNA cassette as defined above, in which the sequence encoding the Nucleoprotein N from the Lassa virus has been inserted.

In a preferred embodiment, this vector comprises the pDeSNAP Univ/LAS.N cassette having the nucleotide sequence SEQ ID NO: 114 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Lassa virus (Genbank#NC_004296),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 115 (corresponding to the SNAP-like/proTEV1/LAS.N/proTEV2/Histag fusion protein).

Thus, in another aspect, the present invention is also drawn to the use of this fusion protein [SNAP-LAS.N] for identifying the presence of the Lassa virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Junin virus (JUN.N).

In a preferred embodiment, this vector comprises a so-called “pDeSNAP Univ/JUN.N cassette” i.e., a pDeSNAPUniv DNA cassette as defined above, in which the sequence encoding the Nucleoprotein N from the Junin virus has been inserted.

In a preferred embodiment, this vector comprises the pDeSNAP Univ/JUN.N cassette having the nucleotide sequence SEQ ID NO: 116 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Junin virus (Genbank#NC_005081),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 117 (corresponding to the SNAP-like/proTEV1/JUN.N/proTEV2/Histag fusion protein).

Thus, in another aspect, the present invention is also drawn to the use of this fusion protein [SNAP-JUN.N] for identifying the presence of the Junin virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Machupo virus (MAC.N).

In a preferred embodiment, this vector comprises a so-called “pDeSNAP Univ/MAC.N cassette” i.e., a pDeSNAPUniv DNA cassette as defined above, in which the sequence encoding the Nucleoprotein N from the Machupo virus has been inserted.

In a preferred embodiment, this vector comprises the pDeSNAP Univ/MAC.N cassette having the nucleotide sequence SEQ ID NO: 118 comprising:

- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32), the DNA sequence encoding the Nucleoprotein N from the Machupo virus (Genbank#NC_005078),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 119 (corresponding to the SNAP-like/proTEV1/MAC.N/proTEV2/Histag fusion protein).

Thus, in another aspect, the present invention is also drawn to the use of this fusion protein [SNAP-MAC.N] for identifying the presence of the Machupo virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Guanarito virus (GUA.N).

In a preferred embodiment, this vector comprises a so-called "pDeSNAP Univ/GUA.N cassette" i.e., a pDeSNAPUniv DNA cassette as defined above, in which the sequence encoding the Nucleoprotein N from the Guanarito virus has been inserted.

In a preferred embodiment, this vector comprises the pDeSNAP Univ/GUA.N cassette having the nucleotide sequence SEQ ID NO: 120 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Guanarito virus (Genbank#NC_005077),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 121 (corresponding to the SNAP-like/proTEV1/GUA.N/proTEV2/Histag fusion protein).

Thus, in another aspect, the present invention is also drawn to the use of this fusion protein [SNAP-GUA.N] for identifying the presence of the Guanarito virus in a biological sample, for example thanks to the immunoassay of the present invention.

In another embodiment, the present invention relates to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Nucleoprotein N from the Sabia virus (SAB.N).

In a preferred embodiment, this vector comprises a so-called "pDeSNAP Univ/SAB.N cassette" i.e., a pDeSNAPUniv DNA cassette as defined above, in which the sequence encoding the Nucleoprotein N from the Sabia virus has been inserted.

In a preferred embodiment, this vector comprises the pDeSNAP Univ/SAB.N cassette having the nucleotide sequence SEQ ID NO: 122 comprising:
- an insect BiP sequence of SEQ ID NO: 22,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the DNA sequence encoding the Nucleoprotein N from the Sabia virus (Genbank#NC_006317),
- a DNA sequence SEQ ID NO: 30 encoding a pro-TEV2 cleavage site of sequence ENLYFQG (SEQ ID NO: 33),
- a second DNA sequence SEQ ID NO: 26 encoding the spacer sequence GGGS (SEQ ID NO: 25),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Nucleoprotein N from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 123 (corresponding to the SNAP-like/proTEV1/SAB.N/proTEV2/Histag fusion protein).

Thus, in another aspect, the present invention is also drawn to the use of this fusion protein [SNAP-SAB.N] for identifying the presence of the Sabia virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Omsk virus (OMSK.EDIII).

In a preferred embodiment, this vector comprises a so-called "pDeSNAP Univ/OMSK.EDIII cassette" i.e., a pDeSNAPUniv DNA cassette as defined above, in which the sequence encoding the EDIII protein from the Omsk virus has been inserted.

In a preferred embodiment, this vector comprises the pDeSNAP Univ/OMSK.EDIII cassette having the nucleotide sequence SEQ ID NO: 124 comprising:

- an insect BiP-like sequence of SEQ ID NO: 152,
- the SNAP-like sequence of SEQ ID NO: 31,
- the DNA sequence encoding the EDIII protein of the Omsk virus (Genbank#NC_005062),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Omsk virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 125 (corresponding to the SNAP-like/OMSK.EDIII/Histag fusion protein).

Thus, in another aspect, the present invention is also drawn to the use of this fusion protein [SNAP-OMSK.EDIII] for identifying the presence of the Omsk virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Kyasanur Forest Disease virus (KYA.EDIII).

In a preferred embodiment, this vector comprises a so-called "pDeSNAP Univ/KYA.EDIII cassette" i.e., a pDeSNAPUniv DNA cassette as defined above, in which the sequence encoding the EDIII protein from the Kyasanur Forest Disease virus has been inserted.

In a preferred embodiment, this vector comprises the pDeSNAP Univ/KYA.EDIII cassette having the nucleotide sequence SEQ ID NO: 126 comprising:

- an insect BiP-like sequence of SEQ ID NO: 152,
- the SNAP-like sequence of SEQ ID NO: 31,
- the DNA sequence encoding the EDIII protein of the Kyasanur Forest Disease virus (Genbank#JF416958),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Kyasanur Forest Disease virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 127 (corresponding to the SNAP-like/KYA.EDIII/Histag fusion protein).

Thus, in another aspect, the present invention is also drawn to the use of this fusion protein [SNAP-KYA.EDIII] for identifying the presence of the Kyasanur Forest Disease virus in a biological sample, for example thanks to the immunoassay of the present invention.

In another embodiment, the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the domain III of the Envelop protein E from the Alkhurma virus (ALK.EDIII).

In a preferred embodiment, this vector comprises a so-called "pDeSNAP Univ/ALK.EDIII cassette" i.e., a pDeSNAPUniv DNA cassette as defined above, in which the sequence encoding the EDIII protein from the Alkhurma virus has been inserted.

In a preferred embodiment, this vector comprises the pDeSNAP Univ/ALK.EDIII cassette having the nucleotide sequence SEQ ID NO: 128 comprising:

- an insect BiP-like sequence of SEQ ID NO: 152,
- the SNAP-like sequence of SEQ ID NO: 31,
- the DNA sequence encoding the EDIII protein of the Alkhurma virus (Genbank#NC_004355),
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the EDIII protein from the Alkhurma virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 129 (corresponding to the SNAP-like/ALK.EDIII/Histag fusion protein).

Thus, in another aspect, the present invention is also drawn to the use of this fusion protein [SNAP-ALK.EDIII] for identifying the presence of the Alkhurma virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Lassa virus (LAS.ectoGP1).

In a preferred embodiment, this vector comprises a so-called "pDeSNAP Univ/LAS.ectoGP1 cassette" i.e., a pDeSNAPUniv DNA cassette as defined above, in which the sequence encoding the Glycoprotein GP1 ectodomain from the Lassa virus has been inserted.

In a preferred embodiment, this vector comprises the pDeSNAP Univ/LAS.ectoGP1 cassette having the nucleotide sequence SEQ ID NO: 130 comprising:

- an insect BiP sequence of SEQ ID NO: 22,
- the DNA sequence encoding the Glycoprotein GP1 ectodomain from the Lassa virus (Genbank#NC_004296),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 131 (corresponding to the SNAP-like/LAS.ectoGP1/Histag fusion protein).

Thus, in another aspect, the present invention is also drawn to the use of this fusion protein [SNAP-LAS.ectoGP1] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Junin virus (JUN.ectoGP1).

In a preferred embodiment, this vector comprises a so-called "pDeSNAP Univ/JUN.ectoGP1 cassette" i.e., a pDeSNAPUniv DNA cassette as defined above, in which the sequence encoding the Glycoprotein GP1 ectodomain from the Junin virus has been inserted.

In a preferred embodiment, this vector comprises the pDeSNAP Univ/JUN.ectoGP1 cassette having the nucleotide sequence SEQ ID NO: 132 comprising:

- an insect BiP sequence of SEQ ID NO: 22,
- the DNA sequence encoding the Glycoprotein GP1 ectodomain from the Junin virus (Genbank#NC_005081),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 133 (corresponding to the SNAP-like/JUN.ectoGP1/Histag fusion protein).

Thus, in another aspect, the present invention is also drawn to the use of this fusion protein [SNAP-JUN.ectoGP1] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Machupo virus (MAC.ectoGP1).

In a preferred embodiment, this vector comprises a so-called "pDeSNAP Univ/MAC.ectoGP1 cassette" i.e., a pDeSNAPUniv DNA cassette as defined above, in which the sequence encoding the Glycoprotein GP1 ectodomain from the Machupo virus has been inserted.

In a preferred embodiment, this vector comprises the pDeSNAP Univ/MAC.ectoGP1 cassette having the nucleotide sequence SEQ ID NO: 134 comprising:

- an insect BiP sequence of SEQ ID NO: 22,
- the DNA sequence encoding the Glycoprotein GP1 ectodomain from the Machupo virus (Genbank#NC_005078),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 135 (corresponding to the SNAP-like/MAC.ectoGP1/Histag fusion protein).

Thus, in another aspect, the present invention is also drawn to the use of this fusion protein [SNAP-MAC.ectoGP1] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Guanarito virus (GUA.ectoGP1).

In a preferred embodiment, this vector comprises a so-called "pDeSNAP Univ/GUA.ectoGP1 cassette" i.e., a pDeSNAPUniv DNA cassette as defined above, in which the sequence encoding the Glycoprotein GP1 ectodomain from the Guanarito virus has been inserted.

In a preferred embodiment, this vector comprises the pDeSNAP Univ/GUA.ectoGP1 cassette having the nucleotide sequence SEQ ID NO: 136 comprising:

- an insect BiP sequence of SEQ ID NO: 22,
- the DNA sequence encoding the Glycoprotein GP1 ectodomain from the Guanarito virus (Genbank#NC_005077),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 137 (corresponding to the SNAP-like/GUA.ectoGP1/Histag fusion protein).

Thus, in another aspect, the present invention is also drawn to the use of this fusion protein [SNAP-GUA.ectoGP1] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP1 ectodomain from the Sabia virus (SAB.ectoGP1).

In a preferred embodiment, this vector comprises a so-called "pDeSNAP Univ/SAB.ectoGP1 cassette" i.e., a pDeSNAPUniv DNA cassette as defined above, in which the sequence encoding the Glycoprotein GP1 ectodomain from the Sabia virus has been inserted.

In a preferred embodiment, this vector comprises the pDeSNAP Univ/SAB.ectoGP1 cassette having the nucleotide sequence SEQ ID NO: 138 comprising:

- an insect BiP sequence of SEQ ID NO: 22,
- the DNA sequence encoding the Glycoprotein GP1 ectodomain from the Guanarito virus (Genbank#NC_006317),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP1 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 139 (corresponding to the SNAP-like/SAB.ectoGP1/Histag fusion protein).

Thus, in another aspect, the present invention is also drawn to the use of this fusion protein [SNAP-SAB.ectoGP1] for identifying the presence of the Sabia virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Lassa virus (LAS.ectoGP2).

In a preferred embodiment, this vector comprises a so-called "pDeSNAP Univ/LAS.ectoGP2 cassette" i.e., a pDeSNAPUniv DNA cassette as defined above, in which the sequence encoding the Glycoprotein GP2 ectodomain from the Lassa virus has been inserted.

In a preferred embodiment, this vector comprises the pDeSNAP Univ/LAS.ectoGP2 cassette having the nucleotide sequence SEQ ID NO: 140 comprising:

- an insect BiP sequence of SEQ ID NO: 22,
- the DNA sequence encoding the Glycoprotein GP2 ectodomain from the Lassa virus (Genbank#NC_004296),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Lassa virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 141 (corresponding to the SNAP-like/LAS.ectoGP2/Histag fusion protein).

Thus, in another aspect, the present invention is also drawn to the use of this fusion protein [SNAP-LAS.ectoGP2] for identifying the presence of the Lassa virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Junin virus (JUN.ectoGP2).

In a preferred embodiment, this vector comprises a so-called "pDeSNAP Univ/JUN.ectoGP2 cassette" i.e., a pDeSNAPUniv DNA cassette as defined above, in which the sequence encoding the Glycoprotein GP2 ectodomain from the Junin virus has been inserted.

In a preferred embodiment, this vector comprises the pDeSNAP Univ/JUN.ectoGP2 cassette having the nucleotide sequence SEQ ID NO: 142 comprising:

- an insect BiP sequence of SEQ ID NO: 22,
- the DNA sequence encoding the Glycoprotein GP2 ectodomain from the Junin virus (Genbank#NC_005081),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Junin virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 143 (corresponding to the SNAP-like/JUN.ectoGP2/Histag fusion protein).

Thus, in another aspect, the present invention is also drawn to the use of this fusion protein [SNAP-JUN.ectoGP2] for identifying the presence of the Junin virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Machupo virus (MAC.ectoGP2).

In a preferred embodiment, this vector comprises a so-called "pDeSNAP Univ/MAC.ectoGP2 cassette" i.e., a pDeSNAPUniv DNA cassette as defined above, in which the sequence encoding the Glycoprotein GP2 ectodomain from the Machupo virus has been inserted.

In a preferred embodiment, this vector comprises the pDeSNAP Univ/MAC.ectoGP2 cassette having the nucleotide sequence SEQ ID NO: 144 comprising:

- an insect BiP sequence of SEQ ID NO: 22,
- the DNA sequence encoding the Glycoprotein GP2 ectodomain from the Machupo virus (Genbank#NC_005078),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Machupo virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 145 (corresponding to the SNAP-like/MAC.ectoGP2/Histag fusion protein).

Thus, in another aspect, the present invention is also drawn to the use of this fusion protein [SNAP-MAC.ectoGP2] for identifying the presence of the Machupo virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Guanarito virus (GUA.ectoGP2).

In a preferred embodiment, this vector comprises a so-called "pDeSNAP Univ/GUA.ectoGP2 cassette" i.e., a pDeSNAPUniv DNA cassette as defined above, in which the sequence encoding the Glycoprotein GP2 ectodomain from the Guanarito virus has been inserted.

In a preferred embodiment, this vector comprises the pDeSNAP Univ/GUA.ectoGP2 cassette having the nucleotide sequence SEQ ID NO: 146 comprising:

- an insect BiP sequence of SEQ ID NO: 22,
- the DNA sequence encoding the Glycoprotein GP2 ectodomain from the Guanarito virus (Genbank#NC_005077),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Guanarito virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 147 (corresponding to the SNAP-like/GUA.ectoGP2/Histag fusion protein).

Thus, in another aspect, the present invention is also drawn to the use of this fusion protein [SNAP-GUA.ectoGP2] for identifying the presence of the Guanarito virus in a biological sample, for example thanks to the immunoassay of the present invention.

In another embodiment the present invention is drawn to a vector comprising the nucleotide sequence encoding a) a secretion signal peptide which is functional in said host cells, and b) a 6-alkylguanine-DNA-alkyltransferase enzyme (AGT), a mutant, a fragment or a catalytic domain thereof, and c) the Glycoprotein GP2 ectodomain from the Sabia virus (SAB.ectoGP2).

In a preferred embodiment, this vector comprises a so-called "pDeSNAP Univ/SAB.ectoGP2 cassette" i.e., a pDeSNAPUniv DNA cassette as defined above, in which the sequence encoding the Glycoprotein GP2 ectodomain from the Sabia virus has been inserted.

In a preferred embodiment, this vector comprises the pDeSNAP Univ/MAC.ectoGP2 cassette having the nucleotide sequence SEQ ID NO: 148 comprising:

- an insect BiP sequence of SEQ ID NO: 22,
- the DNA sequence encoding the Glycoprotein GP2 ectodomain from the Sabia virus (Genbank#NC_006317),
- the SNAP-like sequence of SEQ ID NO: 31, and
- a DNA sequence SEQ ID NO: 28 encoding a HisTag sequence.

In another aspect, the present invention relates to a recombinant cell which is stably transfected by said vector.

In another aspect, the present invention is drawn to a fusion polypeptide comprising a) a 6-alkylguanine-DNA-alkyltransferase enzyme (AGT) (EC 2.1.1.63), a mutant or a catalytic domain thereof and b) the Glycoprotein GP2 ectodomain from the Sabia virus. In this fusion polypeptide, said AGT enzyme is preferably the protein of SEQ ID NO: 2, or a homologue thereof (said homologous being as defined above). This fusion polypeptide is for example the amino acid sequence of SEQ ID NO: 149 (corresponding to the SNAP-like/SAB.ectoGP2/Histag fusion protein).

Thus, in another aspect, the present invention is also drawn to the use of this fusion protein [SNAP-SAB.ectoGP2] for identifying the presence of the Sabia virus in a biological sample, for example thanks to the immunoassay of the present invention.

Examples

In the context of the invention, a multiplex bead-based immunoassay was developed for rapid and simultaneous detection of antibodies to arboviruses in biological fluids.

The system is based on the xMAP technology (Luminex corporation) and uses a mixture of antigen-coated microspheres as capture reagents for specific human immunoglobulins. Distinct sets of microspheres (Magplex, Luminex corporation) were coupled with purified AGT fusion proteins, namely the SNAP-tagged viral recombinant proteins: sSNAP-DV1.EDIII, sSNAP-DV2.EDIII, sSNAP-DV3.EDIII, sSNAP-DV4.EDIII, sSNAP-WN.EDIII, sSNAP-JE.EDIII, sSNAP-USU.EDIII, sSNAP-TBE.EDIII, sSNAP-YF.EDIII, sSNAP-MVE.EDIII, sSNAP-Rocio.EDIII, sSNAP-WSL.EDIII, sSNAP-ZIKA.EDIII, SNAP-DV1ectoM, sSNAP-N.RVF, sSNAP-N.TOS, and CHIK.sE2-SNAP. Recombinant antigens were covalently coupled to the carboxyl microsphere surface using a substrate of the AGT protein as linker (BG-PEG-NH2, New England Biolabs), thereby enhancing antibody capture efficiency as compared to standard amine coupling procedures.

Technical validation using anti-SNAP-tag antibodies and specific mouse monoclonal antibodies confirmed coupling efficiency and demonstrated long-term antigen stability (up to six month). This application is not limited to viral antigens as any peptide or polypeptide can be used for bead coating and subsequent antibody capture.

I. Material and Methods

1. The following buffers and solutions are used:

a) PBS buffer: 100 mL of 10×PBS, pH 7.4 in 1 L H2O sterile b) SNAP coupling buffer (PBS-DTT): 100 mL of 10×PBS, pH 7.4, 0.5 mL 10% TWEEN 20, 1 mL of 1.0 M DTT, in 1 L $H_2O$ sterile c) blocking/assay buffer (PBS-B): PBS, 1% BSA, pH 7.4 in 1 L $H_2O$ sterile d) storage buffer (PBS-TBN): 100 mL of 10×PBS, 1 g of BSA, 2 mL of 10% TWEEN 20, 500 mg of sodium azide, 1 mL of 1.0M DTT, in 1 L $H_2O$ sterile e) Substrate solution (4 mg/mL): 2 mg of BG-PEG-$NH_2$, DMSO 500 μL.

f) Activation solution (EDAC/SNHS): 50 mg/mL of EDAC solution or 50 mg/mL of SNSHS in distilled water 2. The following materials were used:

2.1. MagPlex Luminex microspheres: MC 100XX-ID (where XX is the fluorescence region), XX can be e.g. 26, 27, 28, 29, 34, 35, 36, 37, 45, 52, 53, 63, 64, as mentioned on FIG. 7B 2.2. hAGT substrate: PEG-BG-NH, (NEB S9150S)

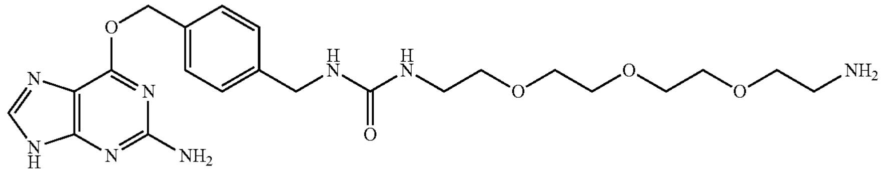 [SMILES: NCCOCCOCCOCCNC(=O)NCc1ccc(COc2nc(N)nc3[nH]cnc23)cc1]

2.3. Fusion Proteins SNAP-Viral EDIII:

The generation of a fusion protein comprising AGT and viral EDIII moieties is well-known to the skilled person. Every known synthesis process can be used for this purpose, provided that the AGT enzyme remains active in the fusion protein.

In the present case, the AGT mutant SNAP of SEQ ID NO: 2 has been used and SNAP-viral EDIII fusion proteins have been generated.

The *Drosophila* S2 inducible expression system (DES, Invitrogen), has been chosen for the mass production of individual EDIII from flaviviruses in non-vertebrate cells and the plasmid pMT/BiP/V5-HisA from Invitrogen has been used.

This plasmid contains:

The metallothionein promoter pMT,

An insect ssBiP sequence of SEQ ID NO: 22,

Bgl II and Age I restriction sites, the DNA of SEQ ID NO: 28 encoding a $His_6$tag located downstream of the AgeI restriction site, and the DNA spacer sequence of SEQ ID NO: 26 located between the AgeI restriction site and the DNA encoding a $His_6$tag.

The synthetic genes coding for the full-length domain III of the E proteins from flaviviruses WN, USU, JE, TBE, DEN-1 to DEN-4, YF, Rocio, MVE, Zika, SLE, and WSL are listed in SEQ ID NO: 3 to SEQ ID NO: 14. The ED III amino acid sequences were fused in frame to the C-terminus of the SNAP protein, with both moieties being separated by a linker GGGS (SEQ ID NO: 25). The DNA sequences encoding SNAP-EDIII were inserted in the plasmid pMT/BiP/V5-Histag (Invitrogen) to generate the plasmids pMT/BiP/SNAP/EDIII/Histag.

The resulting plasmids pMT/BiP/SNAP-EDIII-Histag, which can drive the expression of secreted SNAP-EDIII-$His_6$ fusion proteins, were co-transfected with selection marker pCo-Blast into S2 cells to generate the stable S2/sSNAP-ED III-Histag cell line showing resistance to blasticidine.

Stable S2 cell lines grown in spinner (1000 ml) were stimulated 10 days with heavy metal cadmium ($Cd^{2+}$) and proteins from extracellular medium were concentrated and purified.

Accumulation of secreted SNAP-tagged EDIII protein was observed in the supernatants of stable S2/sSNAP-EDIII-Histag cells after 10 days of induction with heavy metal cadmium.

The proteins SNAP-DEN1.EDIII of SEQ ID NO: 21, SNAP-DEN2.EDIII of SEQ ID NO:X, SNAP-DEN3.EDIII of SEQ ID NO:X, SNAP-DEN4.EDIII of SEQ ID NO:X, SNAP-WN.EDIII of SEQ ID NO:X, SNAP-JE.EDIII of SEQ ID NO:X, SNAP-YF.EDIII of SEQ ID NO:X, SNAP-MVE.EDIII of SEQ ID NO:X, SNAP-Rocio.EDIII of SEQ ID NO:X, SNAP-WSL.EDIII of SEQ ID NO:X, SNAP-ZIKA.EDIII of SEQ ID NO:X, SNAP-SLE.EDIII of SEQ ID NO:X have been produced accordingly.

3. Preparation of the Antigen-Coupled Beads

The production of antigen-coupled beads comprised two steps: functionalization of microsphere surfaces with an $O^6$-benzylguanine derivative (BG-PEG-amino), and covalent immobilization of the chimeric SNAP-viral Ags proteins using the BG-PEG-amino as an anchor (FIG. 1). The carboxyl microsphere surfaces were covalently coated with BG-PEG-amino substrate using an optimized two-step carbodiimide process (Wong et al *Journal of Clinical Microbiology* 42(1): 65-72, 2004). Subsequently, coupled BG-PEG-amino compounds were irreversibly linked to the chimeric SNAP-viral Ags proteins by transfer of the benzyl group to the active site cysteine of the SNAP protein. Due to the high specificity of this reaction, the fusion protein is exclusively coupled via the SNAP domain, leaving the viral antigen accessible for interactions with antibodies.

3.1. First, the commercial beads were activated as per the manufacturer instructions (by using the EDAC and SNHS activation solutions), and washed in a PBS buffer. All the steps were performed in darkness so as to prevent the fluorescent quenching of the beads, according to the manufacturer instructions.

About $1.25 \times 10^6$ beads were used for each coupling process.

3.2. The AGT substrate PEG-BG-$NH_2$ in the DMSO solution was then added for 6 hours at room temperature or overnight at 4° C. on the activated beads, and subsequently washed with PBS buffer.

3.3. The unbound carboxylic sites were then blocked with the blocking buffer for 30 minutes at room temperature, and the beads subsequently washed with the SNAP coupling buffer.

3.4. SNAP-EDIII proteins resuspended in the SNAP coupling buffer (1 mg/mL) were incubated with the thus obtained beads for two hours at room temperature, and then washed once with the SNAP coupling buffer, and three times with the storage buffer (PBS-TBN).

4. Microsphere Fluorescence Immunoassays

The bead sets, conjugated with different SNAP-viral Ags, were mixed by vortex to ensure total bead dispersal. After adjusting the bead density to 100 beads/µL, 25 µl of each of the bead sets (containing 2500 microspheres) were transferred to a 96-well microtiter plate (Bio-Plex Pro flat bottom plate, BioRad) in separate wells for singleplex assays, or mixed in the same wells for multiplex assays. The microspheres were washed 3 times with 100 µL washing buffer (BioPlex Wash buffer, BioRad) using a microplate wash station for magnetic beads (BioPlex Pro Wash Station, BioRad). The samples (antibodies or sera) were diluted in assay buffer (PBS-BSA) and 50 μL of the resulting solutions were added to the test wells containing the conjugated beads. After incubation in darkness on a plate shaker for 30 min, the plate was washed as previously. Subsequently, a fluorochrome-labeled secondary antibody was diluted in assay buffer (PBS-BSA) at 2 μg/mL, and 50 μL of the resulting solutions were added to the test wells containing the conjugated beads. After incubation in darkness on a plate shaker for 30 min, the plate was washed as previously. Finally, streptavidin-phycoerythrin (SAPE, Invitrogen Molecular Probes) was diluted in assay buffer (PBS-BSA) at 2 μg/ml, and 50 μL of the resulting solution was added to the microplate wells. The plate was incubated in darkness on a plate shaker for 10 min and washed as previously, before resuspending the contents of the wells in 125 μl of assay buffer. The median fluorescence intensity (MFI) of the detection antibody bound to the individual microspheres was evaluated from flow analysis of 50 microspheres per well using a dual-laser flow analyzer (BioPlex 200 instrument, BioRad). The fluorescent detection instrument is equipped with a first laser for detecting the type of bead, and a second to ensure the quantification of captured IgM or IgG by exciting the fluorophore (red-phycoerythrin) conjugated to the specific detection antibody.

4.1 Confirmation of Antigen Coupling

Antigen coupling was confirmed by testing the antigen-coupled microspheres with dilutions of rabbit anti-SNAP-tag polyclonal antibody (GenScript). The fluorescence immunoassays were performed in singleplex format, as described above. A two-fold dilution series of anti-SNAP antibody starting at 4000 ng/mL and ending at 3.9 ng/mL was performed in PBS-BSA, and volumes of each dilution were added to the test wells containing the beads. A biotin-conjugated goat anti-rabbit IgG (2 μg/mL in 50 μL PBS-BSA) was used as secondary antibody to detect bound anti-SNAP antibodies.

FIG. 2 shows the fluorescence results observed for the detection of anti-SNAP antibody on 8 different sets of microspheres coupled to chimeric SNAP-viral antigens proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE).

4.2 Detection of Specific Antibodies

The capture and detection of specific antibodies by the antigen-conjugated microspheres was assessed using purified monoclonal mouse antibodies (anti-WNV, anti-DV1 and anti-DV2) and polyclonal mouse sera (anti-DV3, anti-DV4, anti-YF and anti-JE) or human sera (anti-DV1). The fluorescence immunoassays were performed in singleplex and multiplex format, as described above. A four-fold dilution series of purified mouse monoclonal antibodies starting at 400 ng/mL and ending at 0.1 ng/mL, and of mouse and human sera starting at 1:25 and ending at 1:102400, was performed in PBS-BSA, and volumes of each dilution were added to the test wells containing the beads. A biotin-conjugated goat anti-mouse IgG (2 μg/mL in 50 μL PBS-BSA), was used as secondary antibody to detect bound monoclonal and polyclonal mouse antibodies. A biotin-conjugated goat anti-human IgM (2 μg/mL in 50 μL PBS-BSA) or a biotin-conjugated goat anti-human IgG (2 μg/mL in 50 μL PBS-BSA), was used to detect bound IgM or IgG antibodies in human serum, respectively.

FIG. 3 compares the sensitivity of the immunoassay experiment for the detection of purified monoclonal anti-DV2 antibody on chimeric SNAP-DV2.EDIII protein conjugated to microspheres via the substrate of the hAGT protein (coupling of the invention) or coupled through Bio-Plex Amine Coupling Kit, BIORAD.

FIG. 4 compares the sensitivity of the immunoassay experiment for the detection of purified monoclonal anti-DV1 antibody on chimeric SNAP-DV1.EDIII protein conjugated to microspheres, either in a singleplex or in a multiplex format with other chimeric SNAP-viral Ags proteins (SNAP-DV2.EDIII, SNAP.DV3.EDIII, SNAP.DV4.EDIII, SNAP-WNV, SNAP-YF, SNAP-JE, SNAP-TBE) coupled to microspheres.

FIG. 5 shows the reactivity and specificity of the multiplex immunoassay experiment for the detection of dilutions of purified monoclonal anti-WNV antibody on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-TBE) coupled to microspheres.

FIG. 6 shows the reactivity and specificity of anti-DV3 IgG detection in mouse polyclonal serum against DV3 (A) and anti-YF IgG detection in mouse polyclonal serum against YF (B) in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA) coupled to microspheres.

FIG. 7 shows the reactivity and specificity of anti-DV1 IgM detection (A) and anti-DV1 IgG detection (B) in DV1-infected serum of a human patient in multiplex immunoassays on chimeric SNAP-viral Ags proteins (SNAP-DV1.EDIII, SNAP-DV2.EDIII, SNAP.DV3.EDIII, SNAP.DV4.EDIII, SNAP-WNV, SNAP-YF, SNAP-JE, SNAP-WSL, SNAP-ROCIO, SNAP-MVE, SNAP-SLE, SNAP-ZIKA, SNAP-TBE) coupled to microspheres.

II. Results

The system of the invention uses a mixture of antigen-coated Magplex microspheres (Luminex Corporation) as capture reagents for specific human immunoglobulins. Each set of internally color-coded microspheres have been coupled to a specific recombinant antigen and mixed with other types of microspheres in a small sample volume. The power of this system lies in the fact that it is possible to simultaneously analyze up to 100 types of coupled microspheres per well using a flow analysis tool. The fluorescent detection instrument is equipped with a first laser for detecting the type of bead, and a second to ensure the quantification of captured IgM or IgG by exciting the fluorophore (phycoerythrin) conjugated to the specific detection antibody. With its extensive multiplexing capabilities and lower limit of detection, this approach offers substantial cost and sample savings over traditional ELISA measurements.

Presently, 16 distinct sets of microspheres have been coupled with purified chimeric SNAP-viral Ags proteins, allowing titration of serum antibodies specific to dengue serotypes 1 to 4, West Nile, Yellow fever, Japanese encephalitis, tick-borne encephalitis, Saint-Louis encephalitis, Murray Valley encephalitis, Wesselsbron, Zika, Rocio, Usutu, Rift Valley fever, and Chikungunya virus. The production of the system is highly time- and cost-effective, as only a very small amount of recombinant antigen (<50 μg) is required to produce one set of antigen-coupled microspheres (~$1.25\times10^6$ microspheres), sufficient to perform 500 individual assays. Moreover, the selected sets of microspheres are adaptable to an affordable, compact, and robust fluorescent detection system such as the MagPix (Luminex Corporation).

The evaluation of antigen coupling using an anti-SNAP antibody (FIG. 2) confirmed the coupling efficiency and demonstrated that the relative quantities of bound antigens are comparable between the different coupled microsphere sets. The assessment of antibody capture and detection using purified mouse antibodies showed enhanced capture of specific antibodies by the produced antigen-coupled microspheres as compared to antigen-coupled microspheres obtained by standard amine coupling procedures (FIG. 3). In addition, it demonstrated the low detection limit of the method and confirmed that multiplexing does not affect antibody detection (FIG. 4). Additionally, the antigen-conjugated microspheres exhibited long-term stability when stored at 4° C. (>6 months). Finally, the specificity of each set of coupled microspheres in multiplex immunoassays was demonstrated for purified mouse monoclonal antibodies (FIG. 5), for IgG antibodies in polyclonal mouse sera (FIG. 6A-B) and for both IgM and IgG antibodies in polyclonal sera from infected humans (FIG. 7).

With its extensive multiplexing capabilities (up to 100 types of coupled microspheres per well) and lower limit of detection, this approach offers substantial cost and sample savings over traditional ELISA measurements.

III. Generation of a Fusion Protein Comprising SNAP and the N Nucleoprotein of the Schmallenberg Virus 1. Construction of the Vectors Encoding the Fusion Protein SNAP-SBV.N The chimeric fusion protein comprising SNAP and the N nucleoprotein of the Schmallenberg virus has been obtained as follows:

In a first step, the sequence of the open reading frame of the S segment encoding the N nucleoprotein and the NSs protein of the BH80/11-4 strain was mutated by inserting an EcoRV restriction site at its 5' terminus and an XmaI restriction site at its 3' terminus. In addition, the internal EcoRV restriction site was removed by mutating the 294T nucleotide into 294A. This mutated sequence is shown on SEQ ID NO: 17.

This mutated sequence was then inserted into the EcoRV and XmaI restriction sites of the pDeSNAP Univ cassette of SEQ ID NO: 34, generating the "pDeSNAP Univ/SBV.N" DNA cassette of SEQ ID NO: 36.

The so-called "pDeSNAP Univ/SBV.N" DNA cassette comprises (see FIG. 9 and SEQ ID NO: 36):

- the insect BiP-like sequence of SEQ ID NO: 23,
- the SNAP-like sequence of SEQ ID NO: 31,
- a first DNA sequence SEQ ID NO: 26 encoding the spacer sequence GGGS (SEQ ID NO: 25),
- a DNA sequence SEQ ID NO: 29 encoding a pro-TEV1 cleavage site of sequence ENLYFQS (SEQ ID NO: 32),
- the SBV.N DNA sequence SEQ ID NO: 17 (which corresponds to the natural SBV.N sequence, in which the internal EcoRV site has been deleted and two EcoRV and XmaI sites have been added at the extremities),
- a DNA sequence SEQ ID NO: 30 encoding a pro-TEV2 cleavage site of sequence ENLYFQG (SEQ ID NO: 33),
- a DNA sequence SEQ ID NO: 28 encoding a HisTag sequence.

Note that this cassette comprises in addition an NheI site upstream of the ATG, a BglII site between the BiP-like sequence and the SNAP-like sequence, and an AgeI site and a HindIII site which are both located downstream of the stop codon.

The sequence comprised between the BglII and AgeI restriction sites of the pDeSNAPUniv/SBV.N cassette (see FIG. 9) was excised by enzymatic digestion, then cloned into the pMT/BiP/V5-A plasmid (Invitrogen) to generate the pMT/BiP/SNAP-SBV.N vector. This vector has been used to generate stable S2 cells secreting the SNAP-SBV.N fusion protein.

The sequence comprised between the NheI and NotI restriction sites of the pDeSNAPUniv/SBV.N cassette is then cloned into the pcDNA3 plasmid (Invitrogen) to generate the pcDNA3/SNAP-SBV.N vector. This vector is then used to generate stable mammalian cells secreting the SNAP-SBV.N fusion protein.

2. Production of the Fusion Protein SNAP-SBV.N

The resulting plasmids pMT/BiP/SNAP-SBV.N that allow the production of SNAP-tagged SBV.N proteins as secreted fusion proteins, were co-transfected with selection marker pCo-Blast into S2 cells to generate the stable S2/SNAP-SBV.N cell line showing resistance to blasticidine.

This cell line has been deposited to the Collection Nationale de Cultures de Microorganismes (CNCM) of the Institut Pasteur, 25, rue du Docteur Roux, 75724 PARIS CEDEX 15, under the number CNCM I-4616.

Stable S2 cell lines grown in spinner (1000 ml) were stimulated 10 days with heavy metal cadmium ($Cd^{2+}$).

Accumulation of secreted SNAP-SBV.N protein was observed in the supernatants of the S2/SNAP-SBV.N cells after 10 days of induction with heavy metal cadmium.

0.01 mL from 4 mL of supernatant of S2/SNAP-SBV.N cells induced 10 days with $Cd^{2+}$ were tested by immunoblot assay using anti-Histag antibody (dilution 1:1,000) (see FIG. 10).

The chimeric protein SNAP-SBV.N was compared with defined amounts of the SNAP-TOS.N chimeric protein (corresponding to the fusion protein comprising SNAP and the N nucleoprotein from the Toscana virus, which is a phlebovirus).

The production of purified SNAP-SBV.N from induced S2/SNAP+SBV.N cells for 10 days is 18 mg per liter of cell culture (FIG. 10B).

BIBLIOGRAPHIC REFERENCES

Avrameas S. *Immunol. Today* 1991 May; 12(5):154-9.
Zimmerman C W, *Electrophoresis* 1995; June; 16(6):941-7.
Kim H-J. *The Journal of Veterinary Medical Science,* 2011
Damoiseaux et al., *ChemBiochem.* 4:285-287, 2001
Xu-Welliver et al., *Biochemical Pharmacology* 58: 1279-85, 1999
Lim A. et al, *EMBO J.* 15: 4050-4060, 1996;
Daniels D. S. et al, *EMBO J.* 19: 1719-1730, 2000;
Juillerat A. et al, *Chemistry & Biology*, vol. 10, 313-317, 2003
Wong et al Journal of Clinical Microbiology 42, no. 1 (January 2004): 65-72
Wibley J. E. A. et al, 2000
Felgner et al., *Proc. Natl. Acad. Sci. U.S.A.,* 84:7413-7417, 1987
Mackey et al., *Proc. Natl. Acad. Sci. U.S.A.,* 85:8027-8031, 1988
Wu et al., *J. Biol. Chem.,* 267:963-967, 1992;
Wu and Wu, *J. Biol. Chem.,* 263:14621-14624, 1988;

Williams et al., *Proc. Natl. Acad. Sci. U.S.A.,* 88:2726-2730, 1991
Kolpe A. B. et al, *Virus Research* 2012; 168:64-72
Pan W. et al, *The Journal of Immunology,* 2004), 172:6167-6174
Sivakolundu S. et al, *Journal of Medical Microbiology,* 2012

The invention claimed is:

1. A method for detecting at least two target antibodies in a biological sample comprising:

(a) contacting said biological sample with at least one first solid support bound to a 6-alkylguanine-DNA-alkyltransferase (AGT) substrate covalently coupled to a first fusion protein comprising a 6-alkylguanine-DNA-alkyltransferase (AGT) polypeptide comprising SEQ ID NO:2 having a O6-alkylguanine-DNA alkyltransferase activity and a first epitope that is recognized by a first target antibody;

(b) contacting said biological sample with at least one second solid support bound to a 6-alkylguanine-DNA-alkyltransferase (AGT) substrate covalently coupled to a second fusion protein comprising a 6-alkylguanine-DNA-alkyltransferase (AGT) polypeptide having a O6-alkylguanine-DNA alkyltransferase activity and a second epitope that is recognized by a second target antibody, but not by said first target antibody; and (c) detecting the presence or absence of the two target antibodies by detecting the binding or lack of binding of the two target antibodies to the two fusion proteins.

2. The method of claim 1, wherein each of said solid supports is covalently coupled to said substrate of 6-alkylguanine-DNA-alkyltransferase (AGT) polypeptide.

3. The method of claim 2, wherein each of the said solid supports is a magnetic microparticle internally labeled with a fluorescent dye.

4. The method of claim 3, wherein said biological sample is selected from the group consisting of whole blood, serum, plasma, urine, seminal fluid, cerebrospinal fluid and saliva.

5. The method of claim 1, wherein each of said solid supports is selected from the group consisting of test tubes, microtiter wells, sheets, beads, chips, and microparticles.

6. The method of claim 1, wherein each of the said solid supports is magnetic.

7. The method of claim 1, wherein each of the said solid supports is a microparticle.

8. The method of claim 1, wherein each of said solid supports is labeled with a label selected from the group consisting of a fluorochrome, a chromophore, a radioisotope, and a mass tag.

9. The method of claim 1, wherein each of the said solid supports is a microparticle internally labeled with a fluorescent dye with magnetite encapsulated in a functional polymer outer coat containing surface carboxyl groups for covalent coupling of ligands.

10. The method of claim 1, comprising contacting said biological sample with at least 10 differently coupled-solid supports.

11. The method of claim 1, further comprising detecting the presence or absence of the two target antibodies with secondary antibodies recognizing the constant part of the target antibodies.

12. The method of claim 1, wherein said first or second epitope is selected from the group consisting of the amino acid sequences encoded by: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:54, SEQ ID NO:55, SEQ ID NO:56, SEQ ID NO:57, and SEQ ID NO:58.

13. The method of claim 1, wherein said first and second fusion proteins that are coupled with said first and second solid supports are selected from the group consisting of: SEQ ID NO:21, SEQ ID NO:42, SEQ ID NO:49, SEQ ID NO:51, SEQ ID NO:53, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:109, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149 and SEQ ID NO:151.

* * * * *